US009738693B2

(12) United States Patent
Telford et al.

(10) Patent No.: US 9,738,693 B2
(45) Date of Patent: Aug. 22, 2017

(54) NUCLEIC ACIDS AND PROTEINS FROM STREPTOCOCCUS GROUPS A AND B

(71) Applicants: Novartis AG, Basel (CH); J. Craig Venter Institute, Inc., Rockville, MD (US)

(72) Inventors: John Telford, Monteriggioni (IT); Vega Masignani, Siena (IT); Maria Scarselli, Siena (IT); Guido Grandi, Segrate (IT); Herve Tettelin, Rockville, MD (US); Claire Fraser, Clarksville, MD (US)

(73) Assignees: Novartis AG, Basel (CH); J. Craig Venter Institute, Inc., Rockville, MD (US)

( * ) Notice: Subject to any disclaimer, the term of this patent is extended or adjusted under 35 U.S.C. 154(b) by 0 days.

(21) Appl. No.: 15/166,010

(22) Filed: May 26, 2016

(65) Prior Publication Data
US 2016/0264632 A1 Sep. 15, 2016

Related U.S. Application Data

(60) Continuation of application No. 14/751,790, filed on Jun. 26, 2015, which is a continuation of application No. 14/615,108, filed on Feb. 5, 2015, now abandoned, which is a continuation of application No. 13/598,657, filed on Aug. 30, 2012, now abandoned, which is a division of application No. 11/434,203, filed on May 16, 2006, now Pat. No. 8,431,139, which is a continuation of application No. 10/415,182, filed as application No. PCT/GB01/04789 on Oct. 29, 2001, now Pat. No. 7,939,087.

(30) Foreign Application Priority Data

Oct. 27, 2000 (GB) .................................. 0026333.5
Nov. 24, 2000 (GB) .................................. 0028727.6
Mar. 7, 2001 (GB) .................................. 0105640.7

(51) Int. Cl.
C07K 14/315 (2006.01)
A61K 39/09 (2006.01)
C07K 16/12 (2006.01)
C07K 16/40 (2006.01)
C12N 9/10 (2006.01)
A61K 38/00 (2006.01)
A61K 39/00 (2006.01)

(52) U.S. Cl.
CPC .......... C07K 14/315 (2013.01); A61K 39/092 (2013.01); C07K 16/1275 (2013.01); C07K 16/40 (2013.01); C12N 9/1088 (2013.01); A61K 38/00 (2013.01); A61K 39/00 (2013.01); A61K 2039/505 (2013.01); A61K 2039/53 (2013.01); C07K 2319/00 (2013.01); C12Y 205/01018 (2013.01)

(58) Field of Classification Search
CPC .......... A61K 2039/505; A61K 2039/53; A61K 38/00; A61K 39/00; C07K 14/315; C07K 16/1275; C07K 16/40; C07K 2319/00
See application file for complete search history.

(56) References Cited

U.S. PATENT DOCUMENTS

| | | | |
|---|---|---|---|
| 4,454,121 A | 6/1984 | Beachey |
| 5,098,827 A | 3/1992 | Boyle et al. |
| 5,354,846 A | 10/1994 | Kehoe |
| 5,378,620 A | 1/1995 | Adams et al. |
| 5,391,712 A | 2/1995 | Adams |
| 5,445,820 A | 8/1995 | Seidel et al. |
| 5,585,098 A | 12/1996 | Coleman |
| 5,700,648 A | 12/1997 | Kehoe et al. |
| 5,821,088 A | 10/1998 | Darzins et al. |
| 5,846,547 A | 12/1998 | Cleary |
| 5,968,763 A | 10/1999 | Fischetti et al. |
| 6,174,528 B1 | 1/2001 | Cooper et al. |
| 6,372,222 B1 | 4/2002 | Michon et al. |
| 6,406,883 B1 | 6/2002 | Lutticken et al. |
| 6,420,152 B1 | 7/2002 | Adams et al. |
| 6,579,711 B1 | 6/2003 | Gaier et al. |
| 6,635,623 B1 | 10/2003 | Hoogeveen et al. |
| 6,669,703 B2 | 12/2003 | Shue |
| 6,737,521 B1 | 5/2004 | Fischetti et al. |
| 6,747,437 B2 | 6/2004 | Chiu |
| 6,777,547 B1 | 8/2004 | Podbielski |
| 6,833,356 B1 | 12/2004 | Koenig et al. |

(Continued)

FOREIGN PATENT DOCUMENTS

EP 0369825 A2 5/1990
EP 555438 A1 8/1993

(Continued)

OTHER PUBLICATIONS

UniProt data base ; Accession No. Q99ZW2 (Jun. 1, 2001).*

(Continued)

Primary Examiner — Padma V Baskar
(74) Attorney, Agent, or Firm — Clark & Elbing LLP

(57) ABSTRACT

The invention provides proteins from group B *streptococcus* (*Streptococcus agalactiae*) and group A *streptococcus* (*Streptococcus pyogenes*), including amino acid sequences and the corresponding nucleotide sequences. Data are given to show that the proteins are useful antigens for vaccines, immunogenic compositions, and/or diagnostics. The proteins are also targets for antibiotics.

5 Claims, 95 Drawing Sheets

(56) References Cited

U.S. PATENT DOCUMENTS

| | | |
|---|---|---|
| 7,041,814 B1 | 5/2006 | Weinstock et al. |
| 7,098,182 B2 | 8/2006 | Le Page et al. |
| 7,101,692 B2 | 9/2006 | Schneewind et al. |
| 7,128,918 B1 | 10/2006 | Hamel et al. |
| 7,128,919 B2 | 10/2006 | Adderson et al. |
| 7,169,902 B2 | 1/2007 | Podbielski |
| 7,247,308 B2 | 7/2007 | Martin et al. |
| 7,348,006 B2 | 3/2008 | Contorni et al. |
| 7,407,664 B2 | 8/2008 | Beall et al. |
| 7,438,912 B2 | 10/2008 | Meinke et al. |
| 7,485,710 B2 | 2/2009 | Reinscheid et al. |
| 2002/0061569 A1 | 5/2002 | Haselbeck et al. |
| 2002/0086023 A1 | 7/2002 | Dale |
| 2003/0035805 A1 | 2/2003 | Michel et al. |
| 2003/0109690 A1 | 6/2003 | Ruben et al. |
| 2003/0157122 A1 | 8/2003 | Dale |
| 2003/0171337 A1 | 9/2003 | Aylward et al. |
| 2004/0101536 A1 | 5/2004 | Teti et al. |
| 2004/0219639 A1 | 11/2004 | Potter et al. |
| 2005/0019345 A1 | 1/2005 | Podbielski |
| 2005/0020813 A1 | 1/2005 | Masignani et al. |
| 2005/0181388 A1 | 8/2005 | Edwards et al. |
| 2005/0214918 A1 | 9/2005 | Edwards et al. |
| 2005/0288866 A1 | 12/2005 | Sachdeva et al. |
| 2006/0039922 A1 | 2/2006 | Mizzen et al. |
| 2006/0041961 A1 | 2/2006 | Abad et al. |
| 2006/0073530 A1 | 4/2006 | Schneewind et al. |
| 2006/0115479 A1 | 6/2006 | Reinscheid et al. |
| 2006/0160121 A1 | 7/2006 | Mounts et al. |
| 2006/0165716 A1 | 7/2006 | Telford et al. |
| 2006/0210579 A1 | 9/2006 | Telford et al. |
| 2006/0210580 A1 | 9/2006 | Telford et al. |
| 2006/0210581 A1 | 9/2006 | Telford et al. |
| 2006/0210582 A1 | 9/2006 | Telford et al. |
| 2006/0258849 A1 | 11/2006 | Telford et al. |
| 2006/0269541 A1 | 11/2006 | Meinke et al. |
| 2006/0275315 A1 | 12/2006 | Telford et al. |
| 2007/0036828 A1 | 2/2007 | Rappuoli et al. |
| 2007/0053924 A1 | 3/2007 | Tettelin et al. |
| 2007/0098737 A1 | 5/2007 | Dale |
| 2007/0116712 A1 | 5/2007 | Hamel et al. |
| 2007/0128210 A1 | 6/2007 | Olmsted et al. |
| 2007/0128211 A1 | 6/2007 | Olmsted et al. |
| 2007/0128229 A1 | 6/2007 | Olmsted et al. |
| 2007/0141635 A1 | 6/2007 | James |
| 2008/0038268 A1 | 2/2008 | Martin et al. |
| 2008/0220010 A1 | 9/2008 | Telford et al. |
| 2009/0022753 A1 | 1/2009 | Olmsted et al. |

FOREIGN PATENT DOCUMENTS

| | | |
|---|---|---|
| EP | 555439 A1 | 8/1993 |
| EP | 0613947 A2 | 9/1994 |
| EP | 1770171 A1 | 4/2007 |
| GB | 2233977 A | 1/1991 |
| WO | WO-90/06951 A1 | 6/1990 |
| WO | WO-93/05155 A1 | 3/1993 |
| WO | WO-93/05156 A1 | 3/1993 |
| WO | WO-98/18931 A2 | 5/1998 |
| WO | WO-98/19689 A1 | 5/1998 |
| WO | WO-99/13084 A1 | 3/1999 |
| WO | WO-99/26969 A1 | 6/1999 |
| WO | WO-99/42588 A2 | 8/1999 |
| WO | WO-99/54457 A1 | 10/1999 |
| WO | WO-00/06736 A2 | 2/2000 |
| WO | WO-00/06737 A2 | 2/2000 |
| WO | WO-00/23456 A1 | 4/2000 |
| WO | WO-00/62804 A2 | 10/2000 |
| WO | WO-00/78787 A1 | 12/2000 |
| WO | WO-02/12294 A2 | 2/2002 |
| WO | WO-02/28891 A2 | 4/2002 |
| WO | WO-02/075507 A2 | 9/2002 |
| WO | WO-02/092818 A2 | 11/2002 |
| WO | WO-03/068813 A2 | 8/2003 |
| WO | WO-03/087353 A2 | 10/2003 |
| WO | WO-03/093306 A2 | 11/2003 |
| WO | WO-2004/018646 A2 | 3/2004 |
| WO | WO-2004/035618 A2 | 4/2004 |
| WO | WO-2004/041157 A2 | 5/2004 |
| WO | WO-2004/099242 A2 | 11/2004 |
| WO | WO-2005/013666 A2 | 2/2005 |
| WO | WO-2005/028618 A2 | 3/2005 |
| WO | WO-2005/076010 A2 | 8/2005 |
| WO | WO-2005/108419 A1 | 11/2005 |
| WO | WO-2006/035311 A1 | 4/2006 |
| WO | WO-2006/042027 A2 | 4/2006 |
| WO | WO-2006/069200 A2 | 6/2006 |
| WO | WO-2006/078318 A2 | 7/2006 |
| WO | WO-2006/082527 A2 | 8/2006 |
| WO | WO-2006/082530 A2 | 8/2006 |
| WO | WO-2006/130328 A2 | 12/2006 |
| WO | WO-2008/003515 A1 | 1/2008 |
| WO | WO-2008/020335 A2 | 2/2008 |
| WO | WO-2008/108830 A2 | 9/2008 |

OTHER PUBLICATIONS

Abbas et al., Cellular and Molecular Immunology, 4th ed., Chapter 15, pp. 360-362, 2000.

Amara et al., "Molecular detection of methionine in rat brain using specific antibodies," Neurosci. Lett. 185, 147-50, Feb. 13, 1995.

Areschoug et al., "Group B streptococcal surface proteins as targets for protective antibodies: identification of two novel proteins in strains of serotype V.," Inf. Immun. 67(12), 6350-57, Dec. 1999.

Banks et al., "Progress toward characterization of the Group A Streptococcus metagenome: Complete genome sequence of a macrolide-resistant serotype M6 strain," J. Infectious Diseases 190, 727-38, Aug. 15, 2004.

Barnett & Scott, "Differential recognition of surface proteins in Streptococcus pyogenes by two sortase gene homologs," J. Bacteriol. 184, 2181-91, 2002.

Barnett et al., "A Novel Sortase, SrtC2, from Streptococcus pyogenes Anchors a Surface Protein Containing a QVPTGV Motif to the Cell Wall," Journal of Bacteriology, vol. 186, No. 17, pp. 5865-5875, Sep. 2004.

Beckmann et al., "Identification of Novel Adhesins from Group B Streptococci by Use of Phage Display Reveals that C5a Peptidase Mediates Fibronectin Binding," Inf. Immun. 70, 2869-76, Jun. 2002.

Bessen et al., "Genomic Localization of a T Serotype Locus to a Recombinatorial Zone Ending Extracellular Matrix-Binding Proteins in Streptococcus pyogenes," Infection and Immunity, vol. 70, No. 3, pp. 1159-1167, Mar. 2002.

Blackburn et al., "The end of the (DNA) line," Nature Structural Biology 7, 847-49, Oct. 2000.

Bork et al., "Powers and pitfalls in sequence analysis: the 70% hurdle," Genome Research 10, 398-400, 2000.

Borovec et al., "Synthesis and assembly of hepatitis A virus-specific proteins in BS-C-1 cells," J. Virol. 67, 3095-301, Jun. 1993.

Bowie et al., "Deciphering the message in protein sequences: tolerance to amino acid substitution," Science 257, 1306-10, 1990.

Brodeur et al., "Identification of group B streptococcal Sip protein, which elicits cross-protective immunity," Inf. Immun. 68(10), 5610-8, Oct. 2000.

Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.

Chung et al., "chlorosome protein," NCBI Accession No. 2115394F, Jul. 10, 1992.

Clancy et al., "Cloning and Characterization of a Novel Macrolide Efflux Gene, mreA, from Streptococcus agalactiae," Antimicrobial Agents and Chemotherapy 41, 2719-23, 1997.

Collins et al., "Mutation of the principal sigma factor causes loss of virulence in a strain of the Mycobacterium tuberculosis complex," Proc. Natl. Acad. Sci. USA 92, 8036-40, 1995.

Dale, "Group A Streptococcal Vaccines," Infectious Disease Clinics of North America 13, 227-43, Mar. 1999.

(56) References Cited

OTHER PUBLICATIONS

Database EMBL, Accession No. AAX13129, *Enterococcus faecalis* genome contig SEQ ID No. 192, Mar. 19, 1999.
Database EPO Proteins, EBI Accession No. AX605513, "Sequence 3442 from WO0209818," Feb. 17, 2003.
Database Geneseq, "Fibrinogen-binding polypeptide, SEQ ID No. 17," EBI Accession No. GSP: ADS93952, Dec. 2, 2004; revised in 2007.
Database Geneseq, "Group B Streptococcus protein sequence SEQ ID No. 49," EBI Accession No. GSP:AAY91320, May 30, 2000.
Database Geneseq, "*Streptococcus agalactiae* protein, SEQ ID 2382," EBI Accession No. GSP:ADV81242, Feb. 24, 2005.
Database Geneseq, EBI Accession No. GSP: ABP30134, "Streptococcus polypeptide SEQ ID No. 9444," Jul. 2, 2002.
Database Geneseq, EBI Accession No. GSP: ABP27285, "Streptococcus polypeptide SEQ ID No. 3746," Jul. 2, 2002; revised in 2007.
Database Genseq, "Protein encoded by Prokaryotic essential gene #319788," Accession No. ABU46451, Jun. 13, 2003.
Database JPO Proteins, "Nucleic acid and protein originating in group B Streptococcus," EBI Accession No. JPOP:BD629260, Jul. 17, 2003.
Database Swissprot[Online] Oct. 1, 2002, accession No. EBI, Database accession No. Q9PGX9, Hypothetical protein XF0167.
Database UniProt [Online] Mar. 1, 2003, "Cell wall surface anchor family protein," retrieved from EBI accession No. UNIPROT: Q8DYR5, Database accession No. Q8DYR5, 87.2% identity with SEQ ID No. 20906.
Database UniProt [Online], Nov. 22, 2005, "Cell wall surface anchor family protein," retrieved from EBI accession No. UNIPROT: Q3D2D6; 100% identity with SEQ ID No. 20906; abstract.
Dittmer et al., "Treatment of infectious diseases with immunostimulatory oligodeoxynucleotides containing CpG motifs," Curr Opinion Microbiol. 6, 472-77, Oct. 2003.
Ellis, Vaccines, Chapter 29, Plotkin et al., eds., W.B. Saunders Company (Philadelphia), pp. 568-575, 1988.
Examination Report for New Zealand Application No. 560966, dated Mar. 4, 2009 (2 pages).
Ferretti et al., "Putative surface exclusion protein," GENBANK Accession No. Q9A1H3, Oct. 31, 2006.
Glaser et al., "Genome sequence of *Streptococcus agalactiae*, a pathogen causing invasive neonatal disease," Mol. Moicrobiol. 45, 1499-1513, 2002.
Grandi & Zagursky, "The impact of genomics in vaccine discovery: achievements and lessons," Expert. Rev. Vaccines 3, 621-23, 2004.
Greenspan et al., "Defining epitopes: It's not as easy as it seems," Nature Biotechnol. 7, 936-37, 1999.
Gutekunst et al., "Analysis of RogB-Controlled Virulence Mechanisms and Gene Expression in *Streptococcus agalactiae*," Inf. Immun. 71, 5056-64, Sep. 2003.
Gutierrez et al., "Insertional Mutagenesis and Recovery of Interrupted Genes of *Streptococcus* mutans by Using Transposon Tn917: Preliminary Characterization of Mutants Displaying Acid Sensitivity and Nutritional Requirements," J. Bacteriol. 178, 4166-75, Jul. 1996.
Guzman et al., "Protective immune response against *Streptococcus pyogenes* in mice after intranasal vaccination with the fibronectin-binding protein SfbI," J. Infectious Disease 179, 901-06, 1999.
Holmes, "PSMA specific antibodies and their diagnostic and therapeutic use," Exp. Opin. Invest. Drugs 10, 511-10, 2001.
Hong, "unnamed protein product [*Streptococcus pyogenes*]," NCBI Accession No. BAB1603, one page, Oct. 3, 2000.
Horvath et al., "Toward the development of a synthetic group a streptococcal vaccine of high purity and broad protective coverage," J Med Chem. Jul. 29, 2004;47(16):4100-4.
Hughs et al., "Identification of Major Outer surface Proteins of *Streptococcus agalactiae*," Inf. Immun. 70, 1254-59, Mar. 2002.
International Preliminary Examination Report for PCT/GB01/04789 (published as WO02/34771) dated Feb. 17, 2003.
International Preliminary Examination Report for PCT/GB2003/001882 (published as WO03/093306) dated Aug. 18, 2004.
International Preliminary Examination Report for PCT/IB2005/036009 (published as WO06/042027) dated Apr. 11, 2007.
International Preliminary Examination Report for PCT/US2003/029167 (published as WO04/041157) dated Mar. 5, 2005.
International Preliminary Examination Report for PCT/US2004/024868 (published as WO05/032582) dated Feb. 6, 2006.
International Preliminary Examination Report for PCT/US2004/030032 (published as WO05/028618) dated Mar. 16, 2006.
International Search Report for PCT/GB01/04789 (published as WO 02/34771) dated Aug. 27, 2002.
International Search Report for PCT/GB2003/001882 (published as WO 03/093306) dated Nov. 14, 2003.
International Search Report for PCT/IB2005/036009 (published as WO 06/042027) dated Jun. 20, 2006.
International Search Report for PCT/US05/046491 (published as WO 2006/069200) dated Jun. 26, 2007.
International Search Report for PCT/US2003/029167 (published as WO 04/041157) dated Aug. 2, 2004.
International Search Report for PCT/US2004/024868 (published as WO 05/032582) dated Oct. 28, 2005.
International Search Report for PCT/US2004/030032 (published as WO 05/028618) dated Dec. 6, 2005.
International Search Report for PCT/US2005/027239 (published as WO 06/078318) dated Aug. 25, 2008.
International Search Report for PCT/US2007/022838 (published as WO 08/108830) dated Oct. 9, 2008.
Jobling et al., "Analysis of structure and function of the B subunit of cholera toxin by the use of site-directed mutagenesis," Mol. Microbiol. 5, 1755-67, 1991.
Kalman et al., "Comparative genomes of *Chlamydia pneumoniae* and *C. trachomatis*," Nature Genetics 21, 385-89, Apr. 1999.
Kehoe et al., "Nucleotide Sequence of the Streptolysin O (SLO) Gene: Structural Homologies between SLO and Other Membrane-Damaging, Thiol-Activated Toxins," Inf. Immun. 55, 3228-32, Dec. 1987.
Koch et al., "Complexity and expression patterns of the desmosomal adherins," Proc. Natl. Acad. Sci. USA 89, 353-57, Jan. 1992.
Kunst et al., "The complete genome sequence of the Gram positive bacterium *Bacillus subtilis*," NCBI Accession No. CAB14964, Nov. 20, 1997.
Lachenauer et al., "A protective surface protein from the Type V Group B Streptococcus shares N-terminal sequence homology with the Alpha C Protein," Inf. Immun. 64, 4255-60, Oct. 1996.
Larsson et al., "Protection against experimental infection with group B streptococcus by immunization with a bivalent protein vaccine," Vaccine 17, 454-58, 1999.
Lauer et al., "Genome Analysis Reveals Pili in Group B Streptococcus," Science 309, 105, Jul. 1, 2005.
Lazar et al., "Transforming growth factor alpha: mutation of aspartic acid 47 and leucine 48 results in different biological activities," Mol Cell Biol. 8(3):1247-52 (1998).
Lei et al., "Identification and immunogenicity of group A streptococcus culture supernatant proteins," Inf. Immunity 68, 6807-18, 2000.
Lewis, "Riddle of Biofilm Resistance," Antimicrobial Agents and Chemotherapy, vol. 45, No. 4, pp. 999-1007, Apr. 2001.
Lindahl et al., "Surface proteins of *Streptococcus agalactiae* and related proteins in other bacterial pathogens," Clinical Microbiol. Rev. 18(1), 102-07, Jan. 2005.
Madoff et al., "Maternal Immunization of Mice with Group B Streptococcal Type III Polysaccharide-Beta C Protein Conjugate Elicits Protective Antibody to Multiple Serotypes," J. Clinical Invest. 94, 286-92, 1994.
Maione et al., "Identification of a Universal Group B Streptococcus Vaccine by Multiple Genome Screen," Science 309, 148-50, Jul. 1, 2005.
McMillan et al., "Identification and assessment of new vaccine candidates for group A streptococcal infections," Vaccine 22, 2783-90, 2004.

(56) References Cited

OTHER PUBLICATIONS

McMillan et al., "Prospecting for new group A streptococcal vaccine candidates," Indian J. Med. Res. 119, 121-25, May 2004.
Meinke et al., "*S. pyogenes* hyperimmune system reactive antigen Spy0269," EBI Accession No. ADR83896, Dec. 2, 2004; revised Jun. 15, 2007.
Michel et al., "Cloned alpha and beta C-protein antigens of group B Streptococci elicit protective immunity", Infection and Immunity, American Society for Microbiology, US, 59(6):2023-2028, Jun. 1, 1991.
Molling et al., "Naked DNA for vaccine or therapy," J. Mol. Med. 75, 242-46, 1997.
Mora et al., "Group A Streptococcus produce pilus-like structures containing protective antigens and Lancefield T antigens," Proc. Natl. Acad. Sci. USA 102, 15641-46, Oct. 25, 2005.
Nakagawa et al., "Genome sequence of an M3 strain of *Streptococcus pyogenes* reveals a large-scale genomic rearrangement in invasive strains and new insights into phage evolution," Genome Res. 13, 1042-55, Jun. 2003.
Nakata et al., "MsmR, a specific positive regulator of the *Streptococcus pyogenes* FCT pathogenicity region and cytolysin-mediated translocation system genes," Mol. Microbiol. 57, 786-803, 2005.
Navarre et al., "Surface Proteins of Gram-Positive Bacteria and Mechanisms of Their Targeting to the Cell Wall Envelope," Microbiology and Molecular Biology Reviews, vol. 63, No. 1, pp. 174-229, Mar. 1999.
Olive et al., "Protection of mice from group A streptococcal infection by intranasal immunization with a peptide vaccine that contains a conserved M protein B cell epitope and lacks a T cell autoepitope," Vaccine 20, 2816-25, 2002.
Orefici et al., "Possible virulence marker for *Streptococcus agalactiae* (Lancefiled Group B)," J Clin Microbiol. Infectious Diseases 7, 302-05, 1988.
Paoletti et al., "Neonatal mouse protection against infection with multiple group B streptococcal (GBS) serotypes by maternal immunization with a tetravalent GBS polysaccharide-tetanus toxoid conjugate vaccine," Inf. Immun. 62, 3236-43, 1994.
Paoletti, "Surface structure of group B streptoccoccus important in human immunity," in Gram Positive Pathogens, Fischetti et al., eds., Chapter 14, pp. 137-153, 2000.
Quinn, "The response of rheumatic and non-rheumatic children to streptolysin O concentrate," J. Clin. Invest. 36, 793-802, Jun. 1957.
Ramachandran et al., "Two Distinct Genotypes of prtF2, Encoding a Fibronectin Binding Protein, and Evolution of the Gene Family in *Streptococcus pyogenes*," Journal of Bacteriology, vol. 186, No. 22, pp. 7601-7609, Nov. 2004.
Rodewald et al., "Neonatal mouse model of group B streptococcal infection," J. Infectious Diseases 166, 635-39, 1992.
Roitt et al., Structure of Antigens, Immunology, 4th ed., Mosby, London, pp. 7.7 and 7.8, 1998.
Rosini et al., "Identification of novel genomic islands coding for antigenic pilus-like structures in *Streptococcus agalactiae*," Mol. Microbiol. 61, 126-41, 2006.
Rudenko et al., "Selection for activation of a new variant surface glycoprotein gene expression site in Trypanosoma brucei can result in deletion of the old one," Mol. Biochem. Parisitol. 95, 97-109, 1998; NCBI Accession No. CAD21770.
Rudinger et al., "Characteristics of the amino acids as components of a peptide hormone sequence," in Peptide Hormones, Parsons, ed., University Park Press, Jun. 1976, pp. 1-7.
Schneewind et al., "Sequence and Structural Characteristics of the Trypsin-Resistant T6 Surface Protein of Group A Streptococci," Journal of Bacteriology, vol. 172, No. 6, pp. 3310-3317, Jun. 1990.
Schneewind, "Structure of the Cell Wall anchor of Surface Proteins in *Staphylococcus aureus*," Science 268, 103-06, Apr. 7, 1995.
Segura et al., "*Streptococcus suis* and group B Streptococcus differ in their interactions with murine macrophages," FEMS Immunol. Med. Microbiol. 21, 189-95, 1998.
Seizen, "Multi-domain, cell envelope proteases of lactic acid bacteria," Antonie von Leeuwenhoek 76, 139-55, 1999.
Smoot et al., "Genome sequence and comparative microarray analysis of serotype M18 group A Streptococcus strains associated with acute rheumatic fever outbreaks," Proc. Natl. Acad. Sci. USA 99, 4668-73, Apr. 2, 2002.
Stalhammar-Carlemalm M et al., "The R28 protein of *streptococcus pyogenes* is related to several group B Streptococcal surface proteins, confers protective immunity and promotes binding to human epithelial cells", Molecular Microbiology, 33(1):208-219, Jul. 1,1999.
Stephenson et al., "The Fap1 fimbrial adhesin is a glycoprotein: antibodies specific for the glycan moiety block the adhesion of *Streptococcus parasanguis* in an in vitro tooth model," Mol. Microbiol. 43, 147-57, 2002.
Su et al., "Identification of a Xenopus cDNA that prevents mitotic catastrophe in the fission yeast Schizosaccharomyces pombe," Gene 145, 155-56, 1994.
Supplementary Search report for EP 03799822 (corresponding to WO 04/041157) dated Jan. 21, 2008.
Surovov & Ferretti, "Physical and Genetic Chromosomal Map of an M Type 1 Strain of *Streptococcus pyogenes*," J. Bacteriol. 178, 5546-49, Sep. 1996.
Takami et al., "Two component sensor histidine kinase involved in phosphate regulation," NCBI Accession No. NP.244022.1, Sep. 10, 2001.
Telford et al., Sequence 7466 from WO 02/34771, EBI Accession No. CQ650509, Feb. 2, 2004; modified May 31, 2006.
Telford et al., "Streptococcus polypeptide SEQ ID No. 9188" of WO 02/34771, EBI Accession No. ABP300006, Jul. 2, 2002; revised Jun. 15, 2007.
Tettelin et al., "Complete genome sequence and comparative genomic analysis of an emerging human pathogen, serotype V *Streptococcus agalactiae*," Proc. Natl. Acad. Sci. USA 99, 12391-96, Sep. 17, 2002.
Tettelin et al., "Complete genome sequence of a virulent isolate of *Streptococcus pneumoniae*," Science 293, 498-506, 2001.
Tettelin et al., Database EMBL, Accession No. AE014193, *Streptococcus agalactiae* 2603V/R section 3 of 100 of the complete genome, Sep. 2, 2002.
Tettelin et al., Swiss-Prot Accession No. Q3DV91 for *Streptococcus agalactiae* strain 18R21, Nov. 22, 2005.
Tighe et al., "Gene vaccination: plasmid DNA is more than just a blueprint," Immunology Today 19, 89-97, Feb. 1998.
Todd, "Antigenic Streptococcal Hemolysin," J. Exp. Med. 55, 267-80, 1932.
Ton-That & Schneewind, "Assembly of pili on the surface of *Corynebacterium diphtheriae*," Mol. Microbiol. 50, 1429-38, 2003.
Ton-That et al., "Sortases and pilin elements involved in pilus assembly of *Corynebacterium diphtheriae*," Mol. Microbiol. 53, 251-61, 2004.
UniProt Accession No. A7CNQ7, Jul. 5, 2004.
UniProt Accession No. Q5XEL1, Nov. 23, 2004.
UniProt Accession No. Q8P318, Oct. 1, 2002.
Vallet et al., "The chaperone/usher pathways of *Pseudomonas aeruginosa*: Identification of fimbrial gene clusters (cup) and their involvement in biofilm formation," PNAS, vol. 98, No. 12, pp. 6911-6916, Jun. 2001.
Wang et al., "Protein encoded by prokaryotic essential gene #31978," EBI Accession No. ABU46451, Jun. 19, 2003; revised Jun. 15, 2007.
Watnick et al., "Steps in the development of a Vibrio cholerae El Tor biofilm," Molecular Microbiology, vol. 34, No. 3, pp. 586-595, 1999.
Wessels et al., "Stimulation of protective antibodies against type 1a and 1b group B streptococci by a type 1a polysaccharide-tetanus toxoid conjugate vaccine," Inf. Immun. 61, 4760-66, 1993.
Woodson et al., "Analysis of a ribose transport operon from *Bacillus subtilis*," Microbiology 140, 1829-38, 1994.
Zhong et al., "Hypothetical protein of Arabidopsis thaliana," NCBI Accession No. AAD29767, May 11, 1999.
GenBank Accession No. B79568, dated Oct. 24, 1998 (1 page).
Ferretti et al., "Complete genome sequence of an M1 strain of *Streptococcus pyogenes*," Proc Natl Acad Sci U.S.A. 98(8):4658-63 (2001).

(56) References Cited

OTHER PUBLICATIONS

Third Party Observations dated Oct. 24, 2016 for European Patent Application No. 15154238.8, Publication No. 2896629, "Nucleic Acids and Proteins from Streptococcus Group A&B," Teleford et al., filed Oct. 28, 2001 (3 pages).

* cited by examiner

FIGURE 87
FIGURE 87A
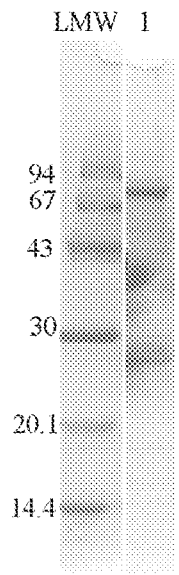
FIGURE 87B
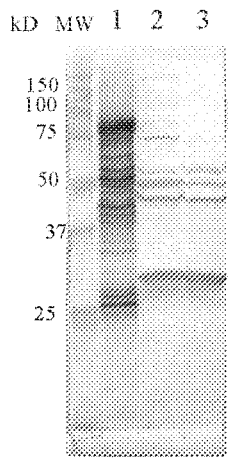
FIGURE 88
FIGURE 88A
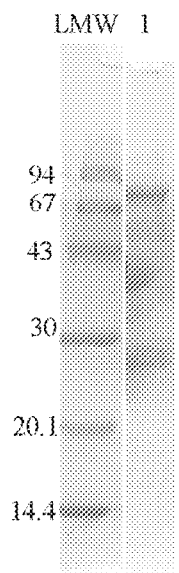
FIGURE 88B
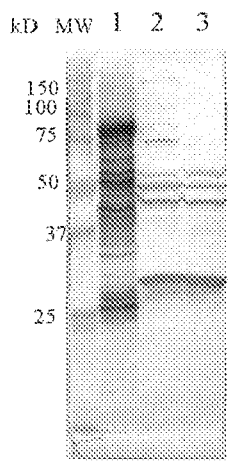

FIGURE 89
FIGURE 89A
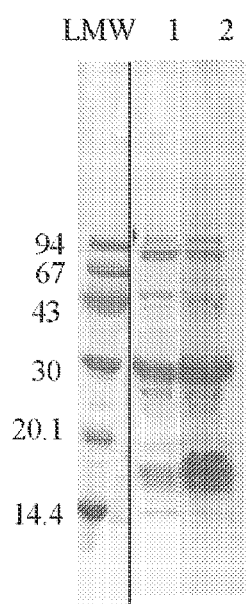
FIGURE 89B
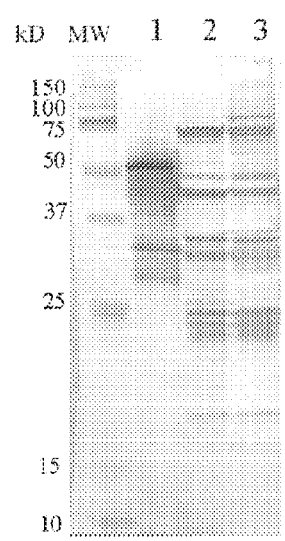

FIGURE 90
FIGURE 90A
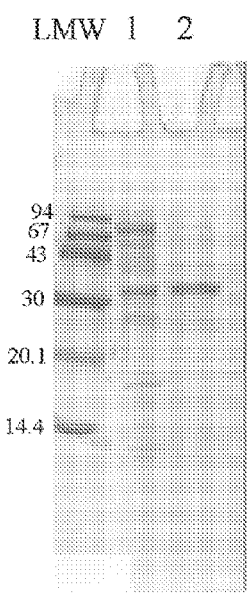
FIGURE 90B
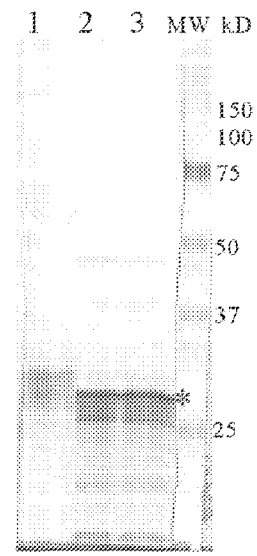
FIGURE 90C
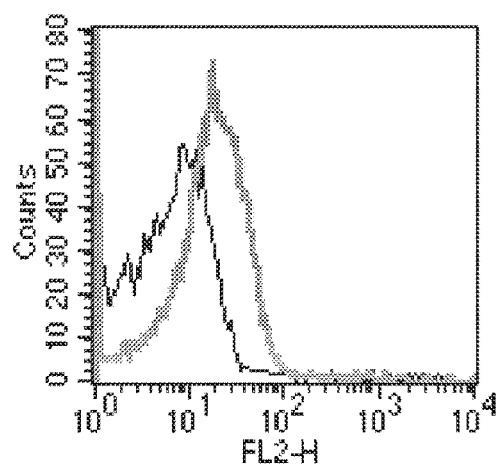

FIGURE 91
FIGURE 91A
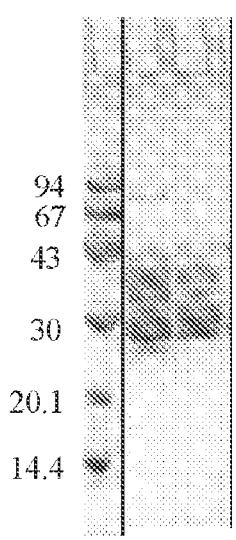
FIGURE 91B
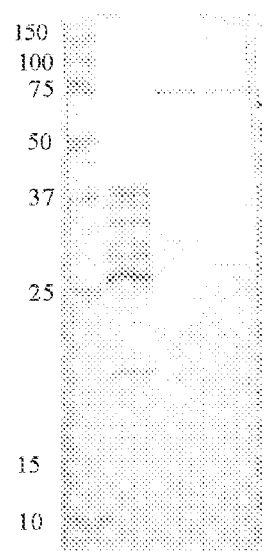
FIGURE 91C
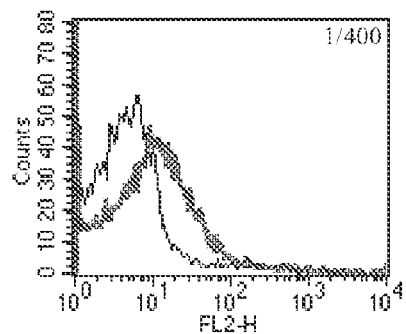

FIGURE 92
FIGURE 92A
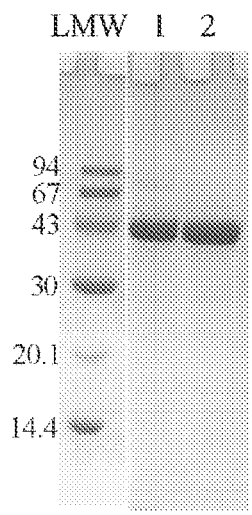
FIGURE 92B
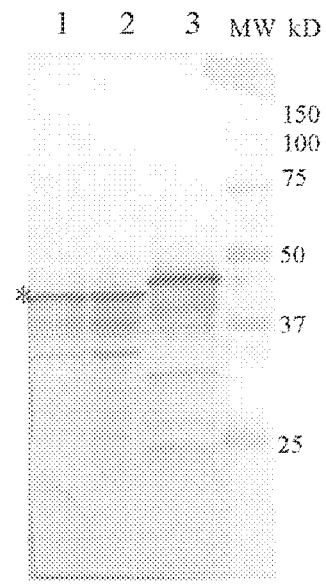
FIGURE 92C
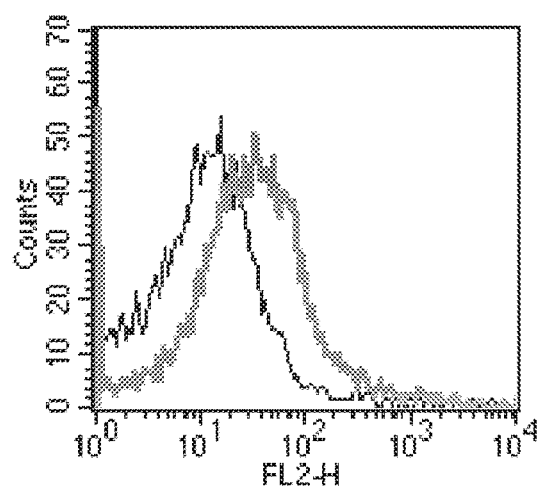

FIGURE 93
FIGURE 93A
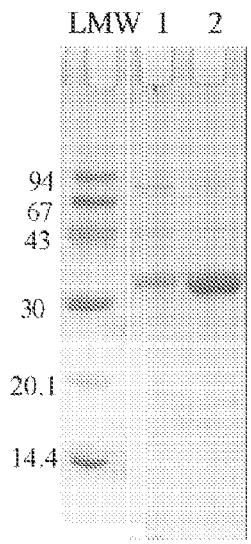
FIGURE 93B
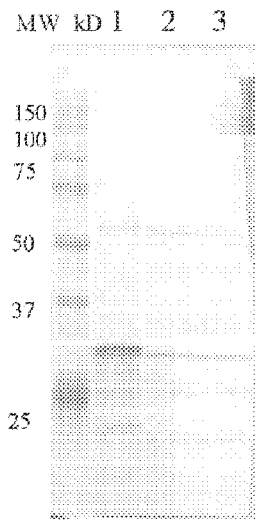
FIGURE 93C
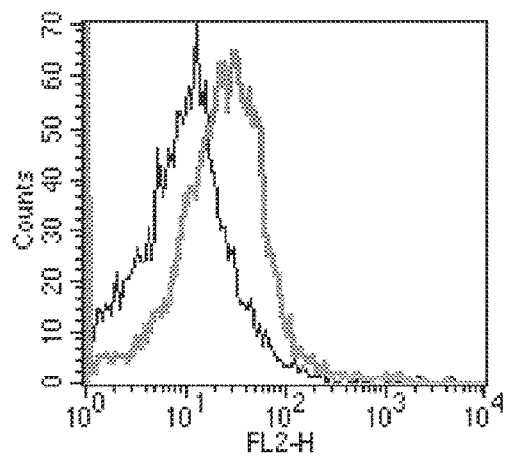

FIGURE 94
FIGURE 94A
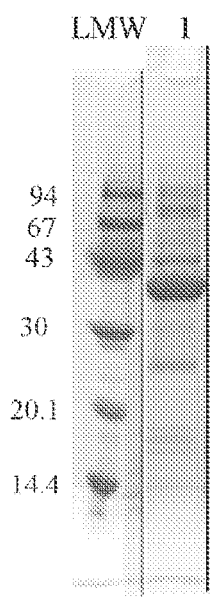
FIGURE 94B
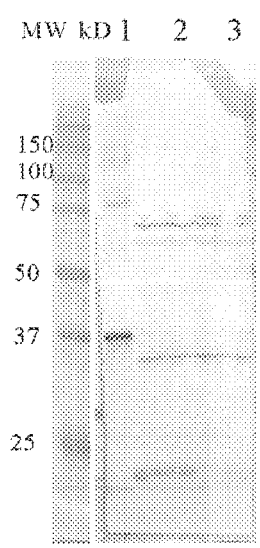
FIGURE 94C
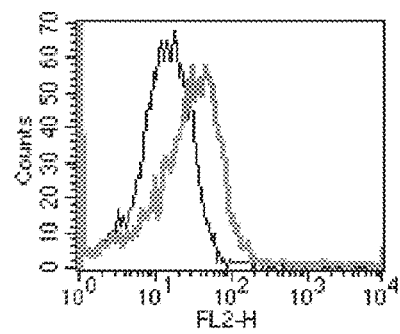

FIGURE 95
FIGURE 95A
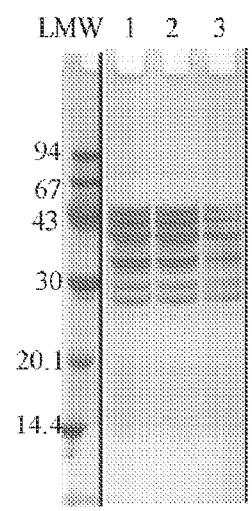
FIGURE 95B
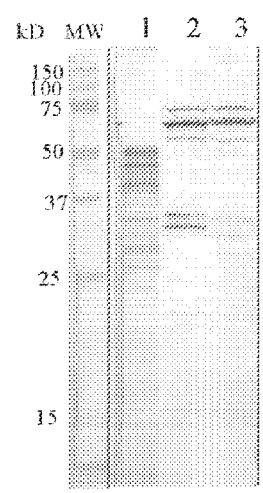
FIGURE 95C
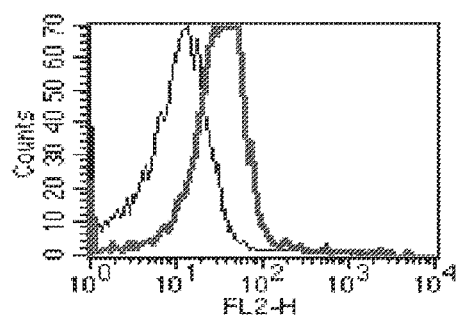

FIGURE 96
FIGURE 96A
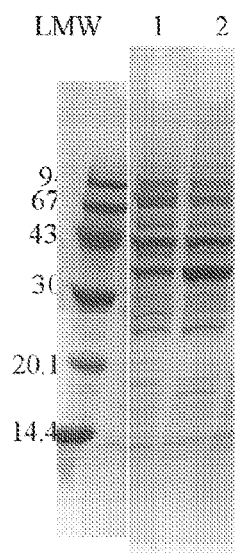
FIGURE 96B
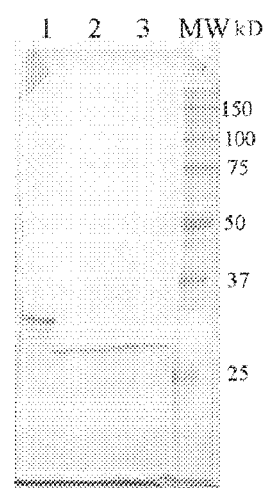
FIGURE 96C
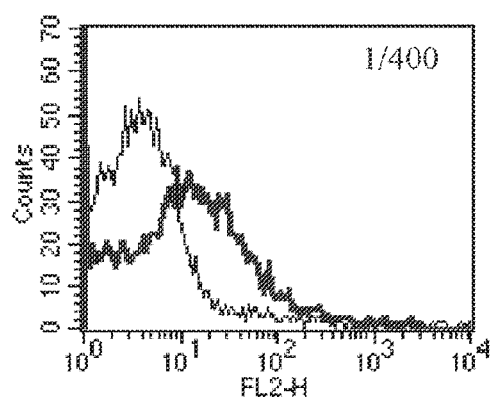

FIGURE 97
FIGURE 97A
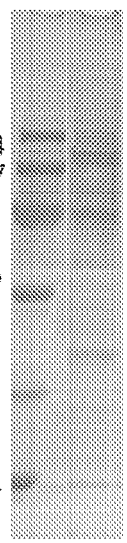
FIGURE 97B
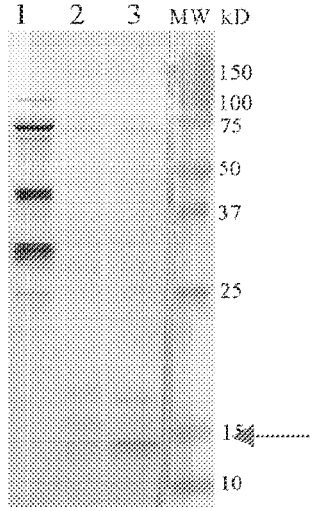
FIGURE 97C
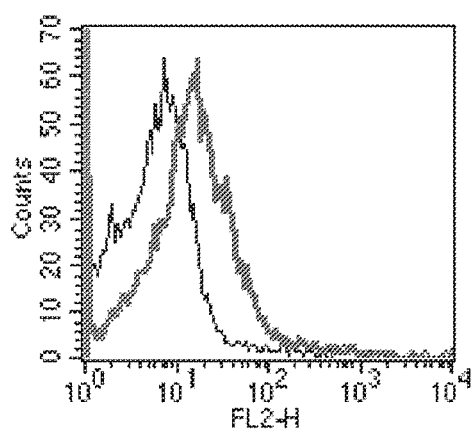

FIGURE 98
FIGURE 98A
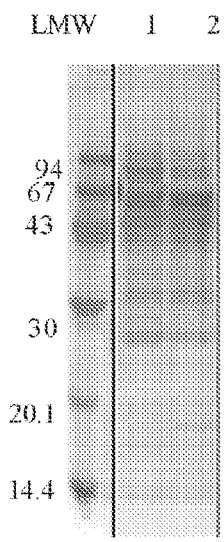
FIGURE 98B
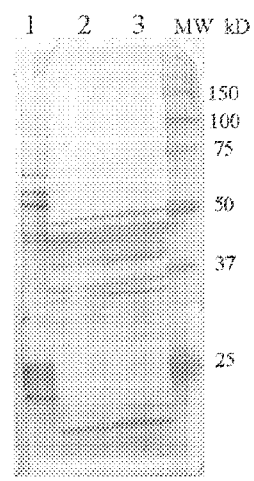
FIGURE 98C
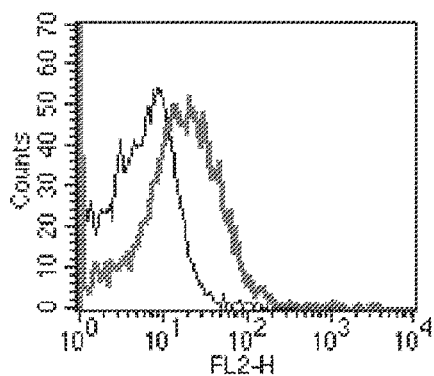

FIGURE 99
FIGURE 99A
FIGURE 99B
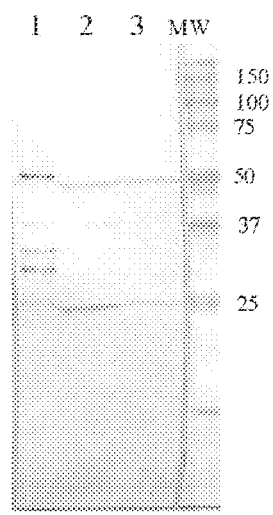
FIGURE 99C
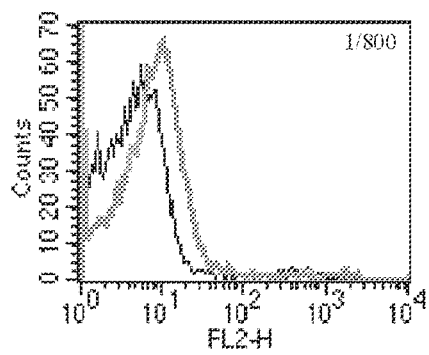

FIGURE 100
FIGURE 100A
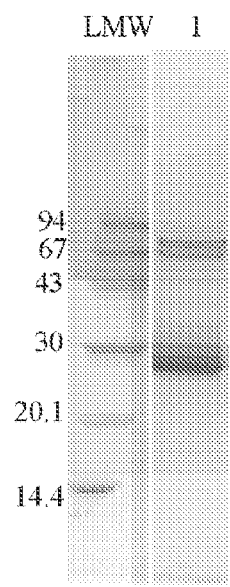
FIGURE 100B
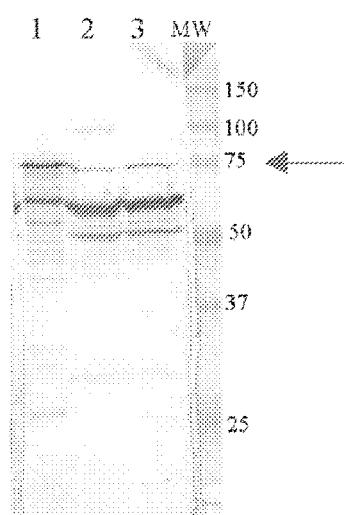
FIGURE 100C
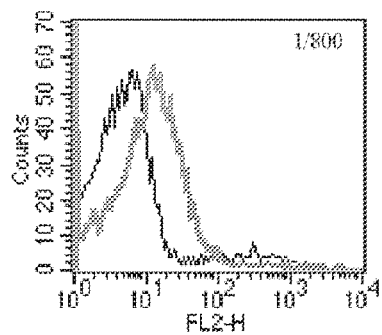

FIGURE 101
FIGURE 101A
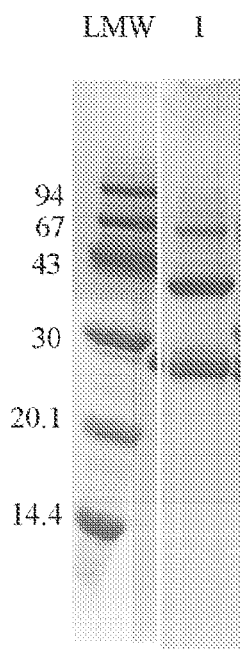
FIGURE 101B
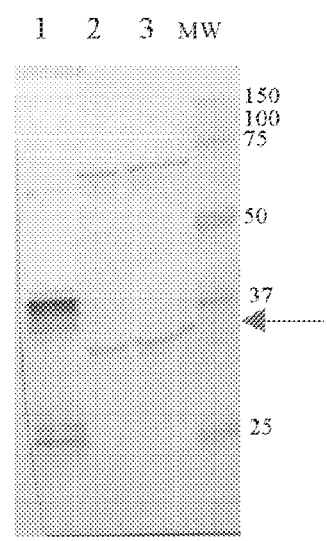
FIGURE 101C
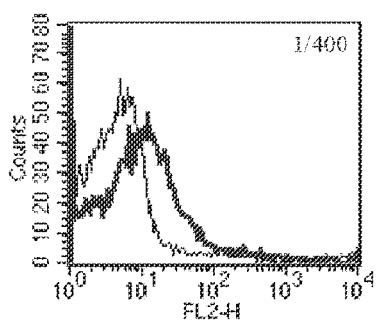

FIGURE 102
FIGURE 102A
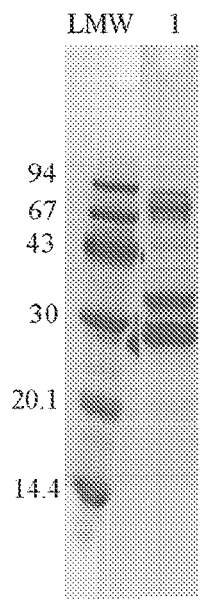
FIGURE 102B
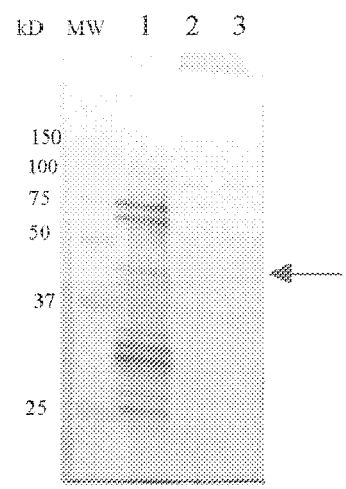
FIGURE 103
FIGURE 103A
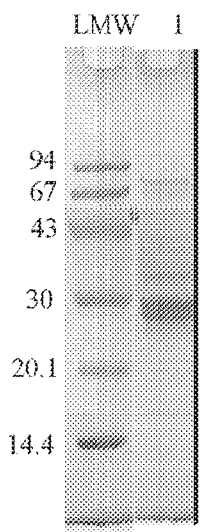
FIGURE 103B
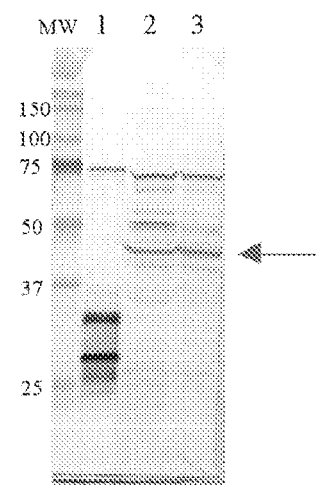

FIGURE 103C
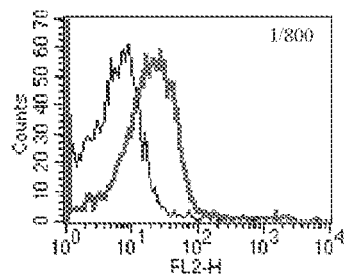
FIGURE 104
FIGURE 104A
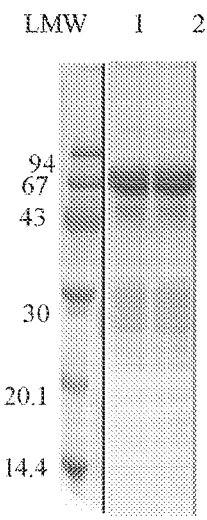
FIGURE 104B
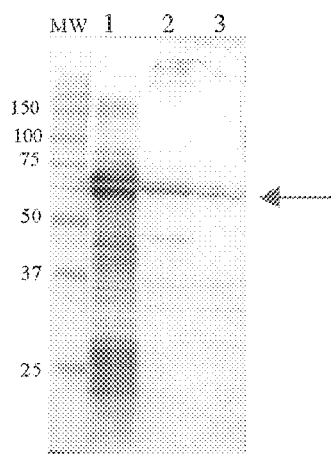
FIGURE 104C
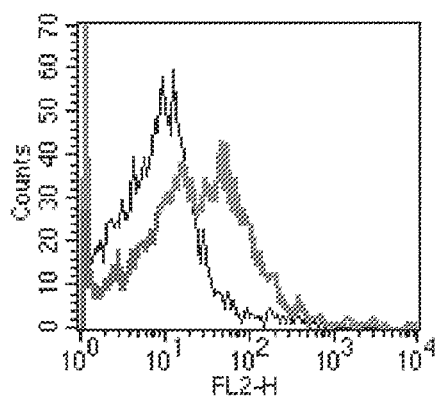

FIGURE 105
FIGURE 105A
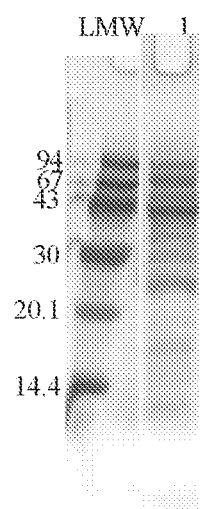
FIGURE 105B
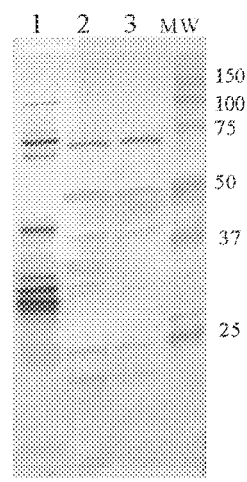
FIGURE 105C
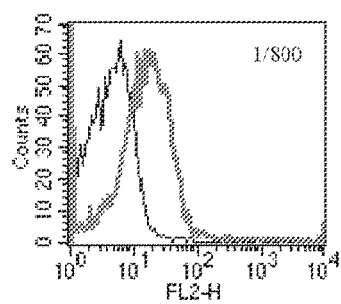

FIGURE 106
FIGURE 106A
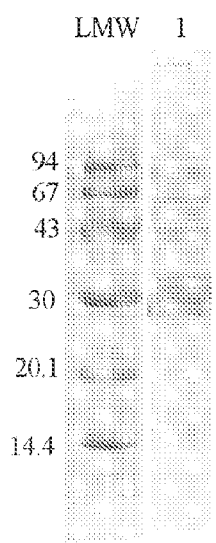
FIGURE 106B
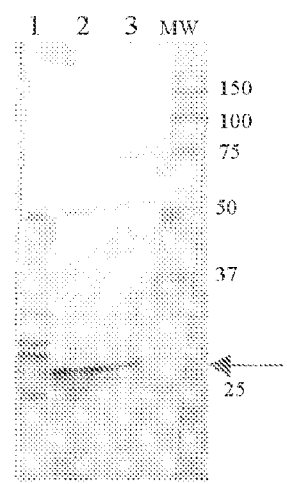
FIGURE 106C
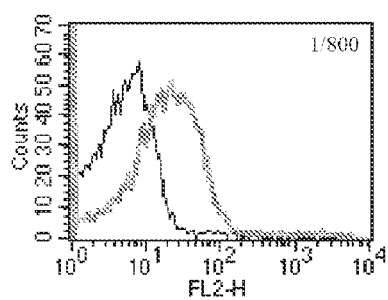

FIGURE 107
FIGURE 107A
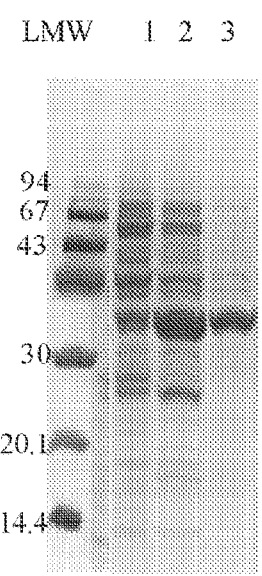
FIGURE 107B
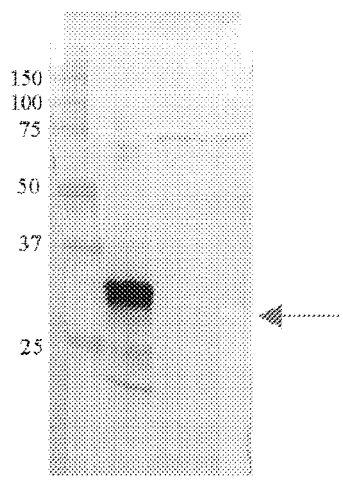
FIGURE 107C
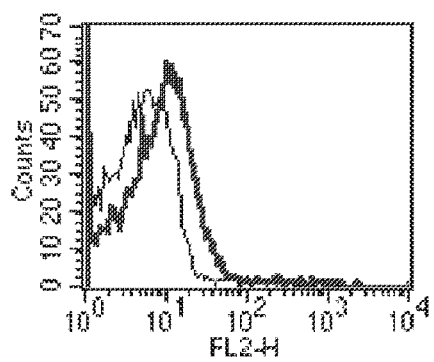

FIGURE 108
FIGURE 108A
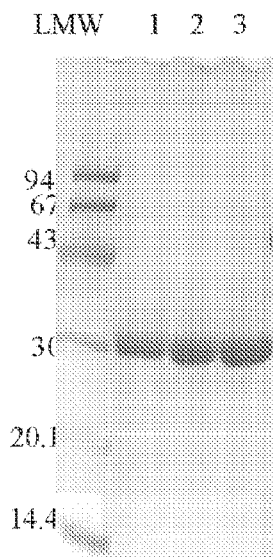
FIGURE 108B
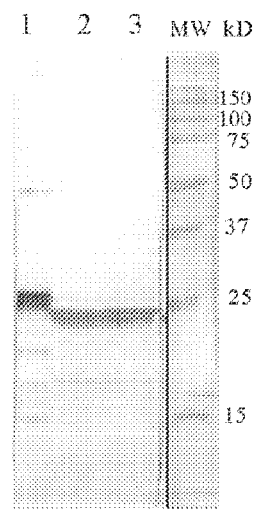
FIGURE 108C
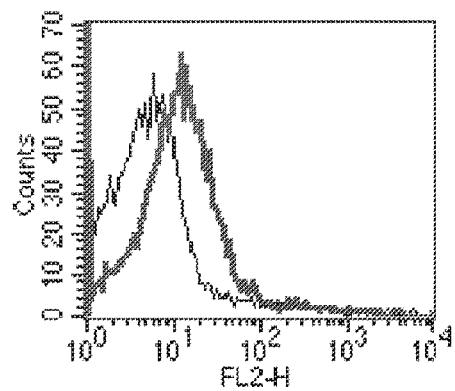

FIGURE 109
FIGURE 109A
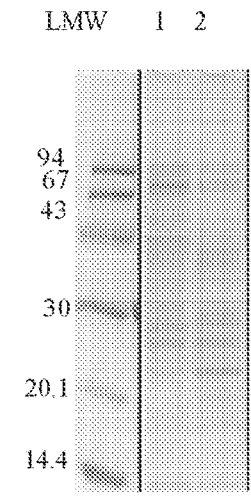
FIGURE 109B
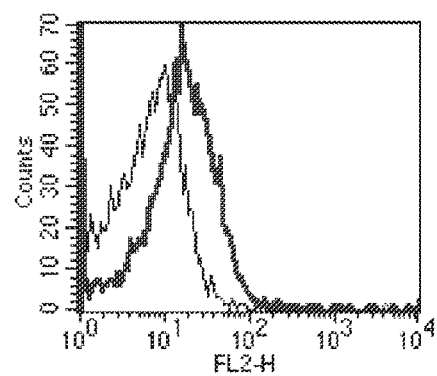
FIGURE 110
FIGURE 110A
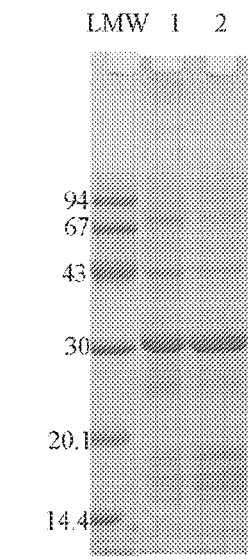
FIGURE 110B
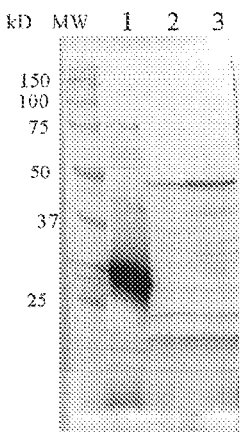

FIGURE 112
FIGURE 112A
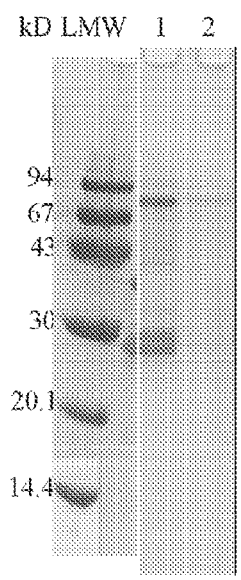
FIGURE 112B
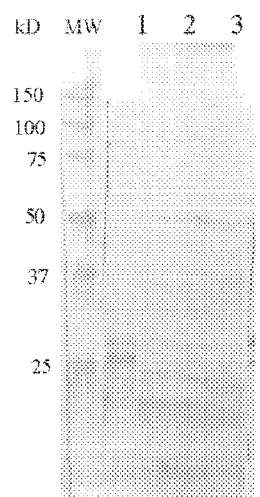
FIGURE 114
FIGURE 114A
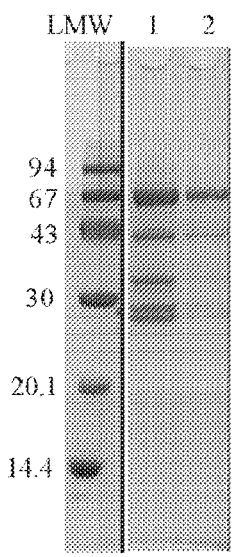
FIGURE 114B
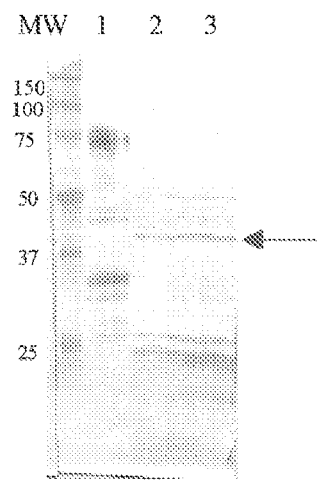

FIGURE 115
FIGURE 115A
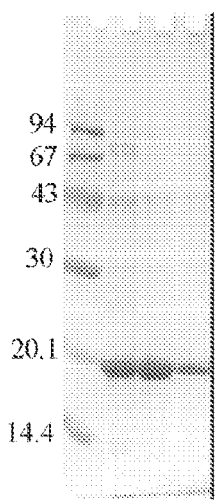
FIGURE 115B
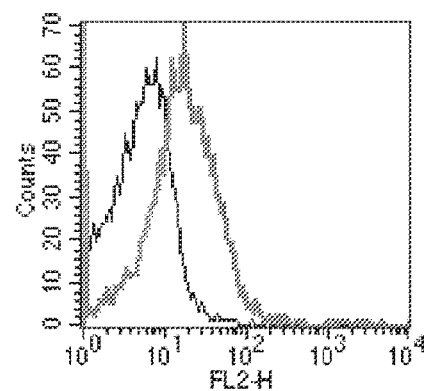
FIGURE 116
FIGURE 116A
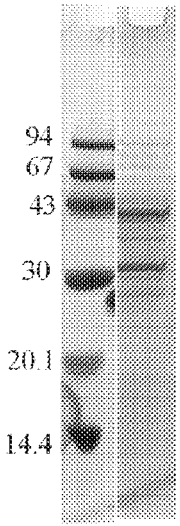

FIGURE 117
FIGURE 117A
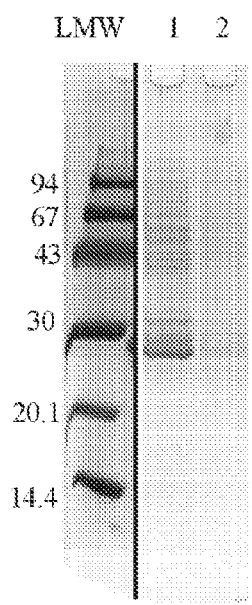
FIGURE 117B
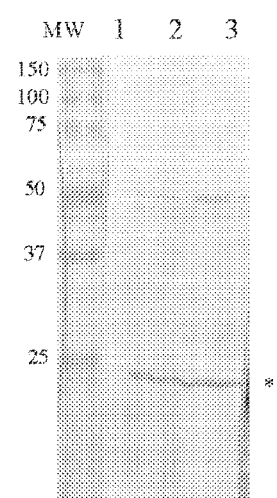
FIGURE 117C
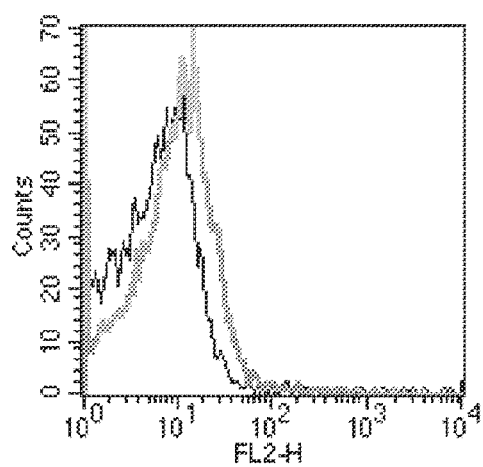

FIGURE 248
FIGURE 248A
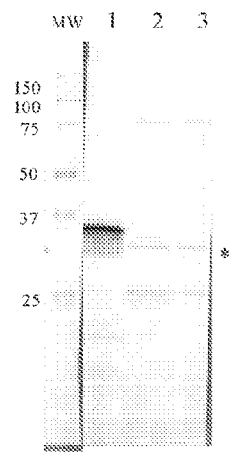
FIGURE 248B
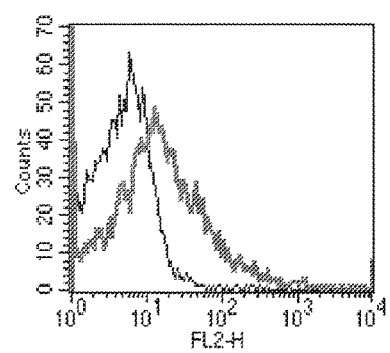
FIGURE 249
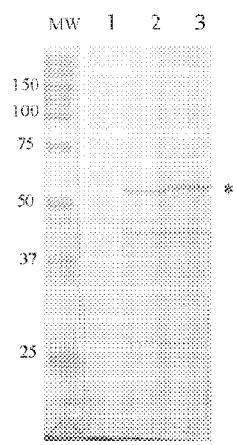
FIGURE 250
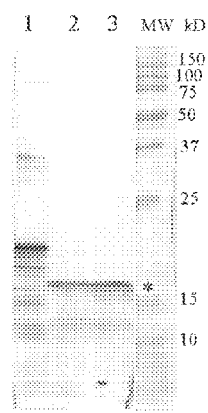
FIGURE 251
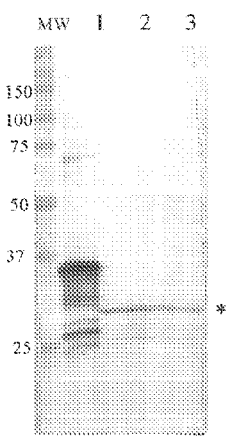

FIGURE 252
FIGURE 252A
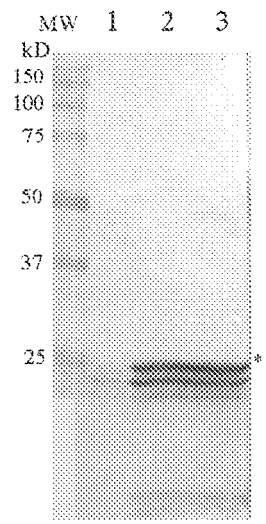
FIGURE 252B
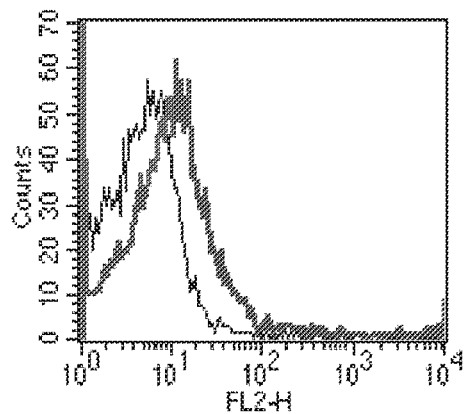
FIGURE 253
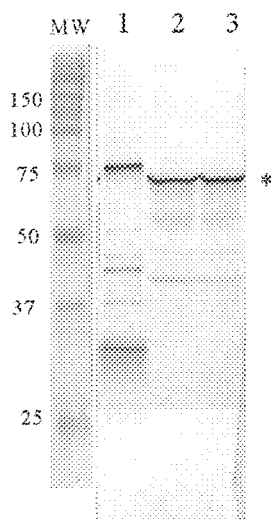

FIGURE 254
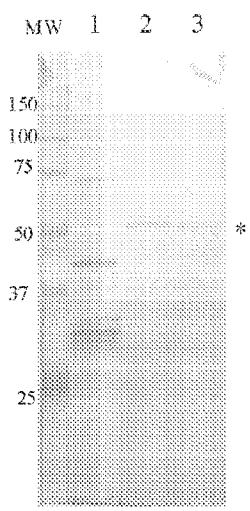
FIGURE 255
FIGURE 255A
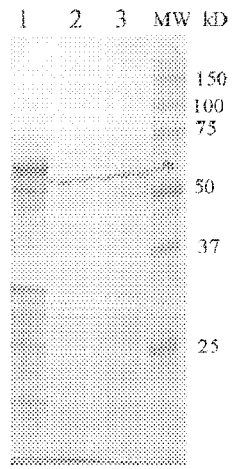
FIGURE 255B
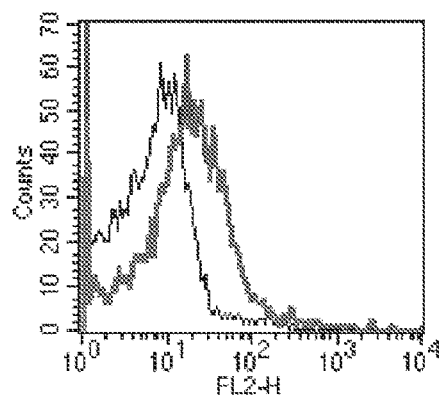

FIGURE 256
FIGURE 256A
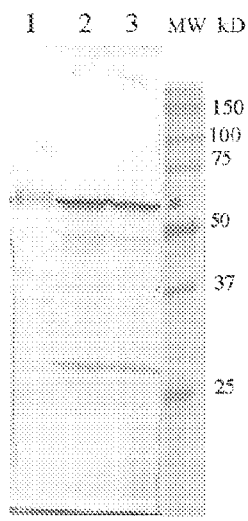
FIGURE 256B
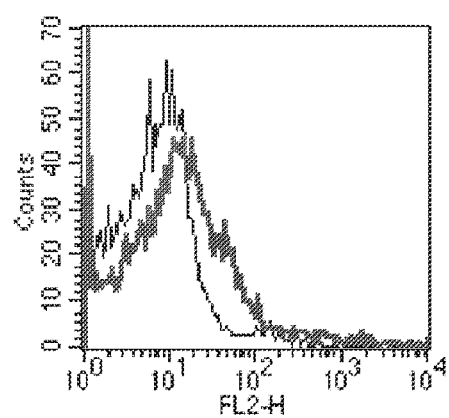
FIGURE 257
FIGURE 258
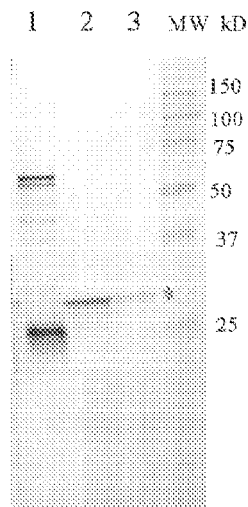

NUCLEIC ACIDS AND PROTEINS FROM STREPTOCOCCUS GROUPS A AND B

This application is a continuation of Ser. No. 14/615,108 filed Feb. 5, 2015. Ser. No. 14/615,108 is a continuation of Ser. No. 13/598,657 filed on Aug. 30, 2012, now abandoned. Ser. No. 13/598,657 is a division of Ser. No. 11/434,203 filed on May 16, 2006, now issued as U.S. Pat. No. 8,431,139, which is a continuation of Ser. No. 10/415,182 filed Apr. 28, 2003, now issued as U.S. Pat. No. 7,939,087. Ser. No. 10/415,182 is a National Stage application of PCT application PCT/GB01/04789, which was filed Oct. 29, 2001 and published in English under PCT Article 21(2) on May 2, 2002. PCT/GB01/04789 claims the benefit of Serial No. GB0026333.5 filed Oct. 27, 2000, Serial No. GB0028727.6 filed Nov. 24, 2000, and Serial No. GB0105640.7 filed Mar. 7, 2001. Each of these applications and all the other documents cited herein are incorporated by reference in their entireties.

This application incorporates by reference the contents of a 22.0 MB file created on Jun. 25, 2015 and submitted herewith, which is the sequence listing for this application.

TECHNICAL FIELD

This invention relates to nucleic acid and proteins from the bacteria *Streptococcus agalactiae* (GBS) and *Streptococcus pyogenes* (GAS).

BACKGROUND ART

Once thought to infect only cows, the Gram-positive bacterium *Streptococcus agalactiae* (or "group B *streptococcus*", abbreviated to "GBS") is now known to cause serious disease, bacteremia and meningitis, in immunocompromised individuals and in neonates. There are two types of neonatal infection. The first (early onset, usually within 5 days of birth) is manifested by bacteremia and pneumonia. It is contracted vertically as a baby passes through the birth canal. GBS colonises the vagina of about 25% of young women, and approximately 1% of infants born via a vaginal birth to colonised mothers will become infected. Mortality is between 50-70%. The second is a meningitis that occurs 10 to 60 days after birth. If pregnant women are vaccinated with type III capsule so that the infants are passively immunised, the incidence of the late onset meningitis is reduced but is not entirely eliminated.

The "B" in "GBS" refers to the Lancefield classification, which is based on the antigenicity of a carbohydrate which is soluble in dilute acid and called the C carbohydrate. Lancefield identified 13 types of C carbohydrate, designated A to O, that could be serologically differentiated. The organisms that most commonly infect humans are found in groups A, B, D, and G. Within group B, strains can be divided into 8 serotypes (Ia, Ib, Ia/c, II, III, IV, V, and VI) based on the structure of their polysaccharide capsule.

Group A *streptococcus* ("GAS", *S. pyogenes*) is a frequent human pathogen, estimated to be present in between 5-15% of normal individuals without signs of disease. When host defences are compromised, or when the organism is able to exert its virulence, or when it is introduced to vulnerable tissues or hosts, however, an acute infection occurs. Diseases include puerperal fever, scarlet fever, erysipelas, pharyngitis, impetigo, necrotising fasciitis, myositis and streptococcal toxic shock syndrome.

*S. pyogenes* is typically treated using antibiotics. Although *S. agalactiae* is inhibited by antibiotics, however, it is not killed by penicillin as easily as GAS. Prophylactic vaccination is thus preferable.

Current GBS vaccines are based on polysaccharide antigens, although these suffer from poor immunogenicity. Anti-idiotypic approaches have also been used (e.g. WO99/54457). There remains a need, however, for effective adult vaccines against *S. agalactiae* infection. There also remains a need for vaccines against *S. pyogenes* infection.

It is an object of the invention to provide proteins which can be used in the development of such vaccines. The proteins may also be useful for diagnostic purposes, and as targets for antibiotics.

BRIEF DESCRIPTION OF DRAWINGS

FIGS. 87 to 118 and 247 to 319 show protein characterization data for various proteins of the invention.

DETAILED DESCRIPTION

Figure 1:
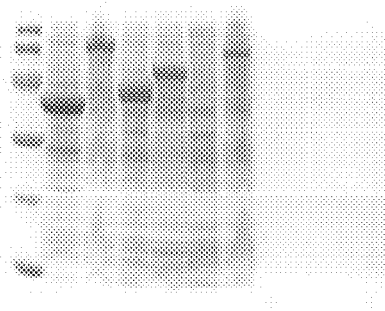
FIGS. 1 to 85, 119-188, 238, and 239 show SDS-PAGE analysis of total cell extracts from cultures of recombinant *E. coli* expressing GBS proteins of the invention. Lane 1 in each gel (except for FIG. 185) contains molecular weight markers. These are 94, 67, 43, 30, 20.1, and 14.4 kDa (except for FIGS. 7, 8, 10, 11, 13, 14, 15, and 119-170, which use 250, 150, 100, 75, 50, 37, 25, 15 & 10 kDa).
Figure 2:
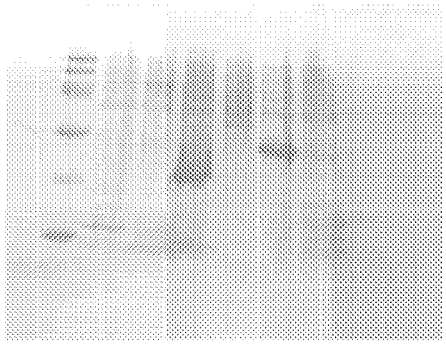
Figure 3:
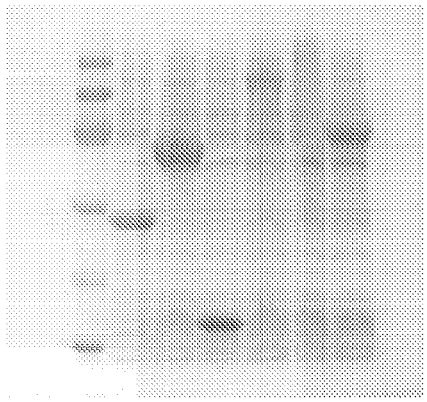

The invention provides proteins comprising the *S. agalactiae* amino acid sequences disclosed herein, and proteins comprising the *S. pyogenes* amino acid sequences disclosed herein. These amino acid sequences are the even SEQ ID NOS: between 1 and 10960.

The invention provides proteins comprising the *S. agalactiae* amino acid sequence disclosed in the example, and proteins comprising the *S. pyogenes* amino acid sequence disclosed in the example. These amino acid sequences are SEQ ID NOS: 4210 and 4212, respectively.

It also provides proteins comprising amino acid sequences having sequence identity to the *S. agalactiae* amino acid sequence disclosed in the example, and proteins comprising amino acid sequences having sequence identity to the *S. pyogenes* amino acid sequence disclosed in the example. Depending on the particular sequence, the degree of sequence identity is preferably greater than 50% (e.g. 60%, 70%, 80%, 90%, 95%, 99% or more). These proteins include homologs, orthologs, allelic variants and functional mutants. Typically, 50% identity or more between two proteins is considered to be an indication of functional equivalence. Identity between proteins is preferably determined by the Smith-Waterman homology search algorithm as implemented in the MPSRCH program (Oxford Molecular), using an affine gap search with parameters gap open penalty=12 and gap extension penalty=1.

Preferred proteins of the invention are GBS1 to GBS689 (see Table IV).

The invention further provides proteins comprising fragments of the *S. agalactiae* amino acid sequence disclosed in the example, and proteins comprising fragments of the *S. pyogenes* amino acid sequence disclosed in the example. The fragments should comprise at least n consecutive amino acids from the sequences and, depending on the particular sequence, n is 7 or more (e.g. 8, 10, 12, 14, 16, 18, 20, 30, 40, 50, 60, 70, 80, 90, 100 or more). Preferably the fragments comprise one or more epitopes from the sequence. Other preferred fragments are (a) the N-terminal signal peptides of the proteins disclosed in the example, (b) the proteins disclosed in the example, but without their N-terminal signal peptides, (c) fragments common to the related GAS and GBS proteins disclosed in the example, and (d) the proteins disclosed in the example, but without their N-terminal amino acid residue.

The proteins of the invention can, of course, be prepared by various means (e.g. recombinant expression, purification from GAS or GBS, chemical synthesis etc.) and in various forms (e.g. native, fusions, glycosylated, non-glycosylated etc.). They are preferably prepared in substantially pure form (i.e. substantially free from other streptococcal or host cell proteins) or substantially isolated form. Proteins of the invention are preferably streptococcal proteins.

According to a further aspect, the invention provides antibodies which bind to these proteins. These may be polyclonal or monoclonal and may be produced by any suitable means (e.g. by recombinant expression). To increase compatibility with the human immune system, the antibodies may be chimeric or humanised (e.g. Breedveld (2000) *Lancet* 355(9205):735-740; Gorman & Clark (1990) *Semin. Immunol.* 2:457-466), or fully human antibodies may be used. The antibodies may include a detectable label (e.g. for diagnostic assays).

According to a further aspect, the invention provides nucleic acid comprising the *S. agalactiae* nucleotide sequences disclosed herein, and nucleic acid comprising the *S. pyogenes* nucleotide sequences disclosed herein. These nucleic acid sequences are the odd SEQ ID NOS: between 1 and 10966.

According to a further aspect, the invention provides nucleic acid comprising the *S. agalactiae* nucleotide sequence disclosed in the example, and nucleic acid comprising the *S. pyogenes* nucleotide sequence disclosed in the example. These nucleic acid sequences are SEQ ID NOS: 4209 and 4211, respectively.

In addition, the invention provides nucleic acid comprising nucleotide sequences having sequence identity to the *S. agalactiae* nucleotide sequence disclosed in the example, and nucleic acid comprising nucleotide sequences having sequence identity to the *S. pyogenes* nucleotide sequence disclosed in the example. Identity between sequences is preferably determined by the Smith-Waterman homology search algorithm as described above.

Furthermore, the invention provides nucleic acid which can hybridise to the *S. agalactiae* nucleic acid disclosed in the example, and nucleic acid which can hybridise to the *S. pyogenes* nucleic acid disclosed in the example preferably under 'high stringency' conditions (e.g. 65° C. in 0.1×SSC, 0.5% SDS solution).

Nucleic acid comprising fragments of these sequences are also provided. These should comprise at least n consecutive nucleotides from the *S. agalactiae* or *S. pyogenes* sequences and, depending on the particular sequence, n is 10 or more (e.g. 12, 14, 15, 18, 20, 25, 30, 35, 40, 50, 60, 70, 80, 90, 100, 150, 200 or more). The fragments may comprise sequences which are common to the related GAS and GBS sequences disclosed in the examples.

According to a further aspect, the invention provides nucleic acid encoding the proteins and protein fragments of the invention.

The invention also provides: nucleic acid comprising nucleotide sequence SEQ ID NO:10967; nucleic acid comprising nucleotide sequences having sequence identity to SEQ ID NO: 10967; nucleic acid which can hybridise to SEQ ID NO: 10967 (preferably under 'high stringency' conditions); nucleic acid comprising a fragment of at least n consecutive nucleotides from SEQ ID NO: 10967, wherein n is 10 or more e.g. 12, 14, 15, 18, 20, 25, 30, 35, 40, 50, 60, 70, 80, 90, 100, 150, 200, 250, 300, 350, 400, 450, 500, 600, 700, 800, 900, 1000, 1500, 2000, 3000, 4000, 5000, 10000, 100000, 1000000 or more.

The invention also provides: nucleic acid comprising nucleotide sequence SEQ ID NO:10967, nucleic acid comprising nucleotide sequences having sequence identity to SEQ ID NO:10967; nucleic Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA etc.) and other nucleic acid techniques.

It should also be appreciated that the invention provides nucleic acid comprising sequences complementary to those described above (e.g. for antisense or probing, or for use as primers).

Nucleic acid according to the invention can, of course, be prepared in many ways (e.g. by chemical synthesis, from genomic or cDNA libraries, from the organism itself etc.) and can take various forms (e.g. single stranded, double stranded, vectors, primers, probes, labelled etc.). The nucleic acid is preferably in substantially isolated form.

Nucleic acid according to the invention may be labelled e.g. with a radioactive or fluorescent label. This is particularly useful where the nucleic acid is to be used in nucleic acid detection techniques e.g. where the nucleic acid is a primer or as a probe for use in techniques such as PCR, LCR, TMA, NASBA etc.

In addition, the term "nucleic acid" includes DNA and RNA, and also their analogues, such as those containing modified backbones, and also peptide nucleic acids (PNA) etc.

According to a further aspect, the invention provides vectors comprising nucleotide sequences of the invention (e.g. cloning or expression vectors) and host cells transformed with such vectors.

According to a further aspect, the invention provides compositions comprising protein, antibody, and/or nucleic acid according to the invention. These compositions may be suitable as immunogenic compositions, for instance, or as diagnostic reagents, or as vaccines.

The invention also provides nucleic acid, protein, or antibody according to the invention for use as medicaments (e.g. as immunogenic compositions or as vaccines) or as diagnostic reagents. It also provides the use of nucleic acid, protein, or antibody according to the invention in the manufacture of: (i) a medicament for treating or preventing disease and/or infection caused by *streptococcus*; (ii) a diagnostic reagent for detecting the presence of *streptococcus* or of antibodies raised against *streptococcus*; and/or (iii) a reagent which can raise antibodies against *streptococcus*. Said *streptococcus* may be any species, group or strain, but is preferably *S. agalactiae*, especially serotype III or V, or *S. pyogenes*. Said disease may be bacteremia, meningitis, puerperal fever, scarlet fever, erysipelas, pharyngitis, impetigo, necrotising fasciitis, myositis or toxic shock syndrome.

The invention also provides a method of treating a patient, comprising administering to the patient a therapeutically effective amount of nucleic acid, protein, and/or antibody of the invention. The patient may either be at risk from the disease themselves or may be a pregnant woman ('maternal immunisation' e.g. Glezen & Alpers (1999) *Clin. Infect. Dis.* 28:219-224).

Administration of protein antigens is a preferred method of treatment for inducing immunity.

Administration of antibodies of the invention is another preferred method of treatment. This method of passive immunisation is particularly useful for newborn children or for pregnant women. This method will typically use monoclonal antibodies, which will be humanised or fully human.

The invention also provides a kit comprising primers (e.g. PCR primers) for amplifying a template sequence contained within a *Streptococcus* (e.g. *S. pyogenes* or *S. agalactiae*) nucleic acid sequence, the kit comprising a first primer and a second primer, wherein the first primer is substantially complementary to said template sequence and the second primer is substantially complementary to a complement of said template sequence, wherein the parts of said primers which have substantial complementarity define the termini of the template sequence to be amplified. The first primer and/or the second primer may include a detectable label (e.g. a fluorescent label).

The invention also provides a kit comprising first and second single-stranded oligonucleotides which allow amplification of a *Streptococcus* template nucleic acid sequence contained in a single- or double-stranded nucleic acid (or mixture thereof), wherein: (a) the first oligonucleotide comprises a primer sequence which is substantially complementary to said template nucleic acid sequence; (b) the second oligonucleotide comprises a primer sequence which is substantially complementary to the complement of said template nucleic acid sequence; (c) the first oligonucleotide and/or the second oligonucleotide comprise(s) sequence which is not complementary to said template nucleic acid; and (d) said primer sequences define the termini of the template sequence to be amplified. The non-complementary sequence(s) of feature (c) are preferably upstream of (i.e. 5' to) the primer sequences. One or both of these (c) sequences may comprise a restriction site (e.g. EP-B-0509612) or a promoter sequence (e.g. EP-B-0505012). The first oligonucleotide and/or the second oligonucleotide may include a detectable label (e.g. a fluorescent label).

The template sequence may be any part of a genome sequence (e.g. SEQ ID NO:10967). For example, it could be a rRNA gene (e.g. Turenne et al. (2000) *J. Clin. Microbiol.* 38:513-520; SEQ ID NOS: 12018-12024 herein) or a protein-coding gene. The template sequence is preferably specific to GBS.

The invention also provides a computer-readable medium (e.g. a floppy disk, a hard disk, a CD-ROM, a DVD etc.) and/or a computer database containing one or more of the sequences in the sequence listing. The medium preferably contains one or both of SEQ ID NO:10967.

The invention also provides a hybrid protein represented by the formula $NH_2$-A-[-X-L-]$_n$-B—COOH, wherein X is a protein of the invention, L is an optional linker amino acid sequence, A is an optional N-terminal amino acid sequence, B is an optional C-terminal amino acid sequence, and n is an integer greater than 1. The value of n is between 2 and x, and the value of x is typically 3, 4, 5, 6, 7, 8, 9 or 10. Preferably n is 2, 3 or 4; it is more preferably 2 or 3; most preferably, n=2. For each n instances, —X— may be the same or different. For each n instances of [-X-L-], linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc Linker amino acid sequence(s) -L- will typically be short (e.g. 20 or fewer amino acids i.e. 19, 18, 17, 16, 15, 14, 13, 12, 11, 10, 9, 8, 7, 6, 5, 4, 3, 2, 1). Examples include short peptide sequences which facilitate cloning, poly-glycine linkers (i.e. Gly$_n$ where n=2, 3, 4, 5, 6, 7, 8, 9, 10 or more), and histidine tags (i.e. His$_n$ where n=3, 4, 5, 6, 7, 8, 9, 10 or more). Other suitable linker amino acid sequences will be apparent to those skilled in the art. -A- and —B— are optional sequences which will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. His$_n$ where n=3, 4, 5, 6, 7, 8, 9, 10 or more). Other suitable N-terminal and C-terminal amino acid sequences will be apparent to those skilled in the art. In some embodiments, each X will be a GBS sequence; in others, mixtures of GAS and GBS will be used.

According to further aspects, the invention provides various processes.

A process for producing proteins of the invention is provided, comprising the step of culturing a host cell of to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridising conditions to form duplexes; and (b) detecting said duplexes.

A process for detecting *Streptococcus* in a biological sample (e.g. blood) is also provided, comprising the step of contacting nucleic acid according to the invention with the biological sample under hybridising conditions. The process may involve nucleic acid amplification (e.g. PCR, SDA, SSSR, LCR, TMA, NASBA etc.) or hybridisation (e.g. microarrays, blots, hybridisation with a probe in solution etc.). PCR detection of *Streptococcus* in clinical samples, in particular *S. pyogenes*, has been reported [see e.g. Louie et al. (2000) *CMAJ* 163:301-309; Louie et al. (1998) *J. Clin. Microbiol.* 36:1769-1771]. Clinical assays based on nucleic acid are described in general in Tang et al. (1997) *Clin. Chem.* 43:2021-2038.

A process for detecting proteins of the invention is provided, comprising the steps of: (a) contacting an antibody of the invention with a biological sample under conditions suitable for the formation of an antibody-antigen complexes; and (b) detecting said complexes.

A process for identifying an amino acid sequence is provided, comprising the step of searching for putative open reading frames or protein-coding regions within a genome sequence of *S. agalactiae*. This will typically involve in silico searching the sequence for an initiation codon and for an in-frame termination codon in the downstream sequence. The region between these initiation and termination codons is a putative protein-coding sequence. Typically, all six possible reading frames will be searched. Suitable software for such analysis includes ORFFINDER (NCBI), GENEMARK [Borodovsky & McIninch (1993) *Computers Chem.* 17:122-133), GLIMMER [Salzberg et al. (1998) *Nucleic Acids Res.* 26:544-548; Salzberg et al. (1999) *Genomics* 59:24-31; Delcher et al. (1999) *Nucleic Acids Res.* 27:4636-4641], or other software which uses Markov models [e.g. Shmatkov et al. (1999) *Bioinformatics* 15:874-876]. The invention also provides a protein comprising the identified amino acid sequence. These proteins can then be expressed using conventional techniques.

The invention also provides a process for determining whether a test compound binds to a protein of the invention. If a test compound binds to a protein of the invention and this binding inhibits the life cycle of the GBS bacterium, then the test compound can be used as an antibiotic or as a lead compound for the design of antibiotics. The process will typically comprise the steps of contacting a test compound with a protein of the invention, and determining whether the test compound binds to said protein. Preferred proteins of the invention for use in these processes are enzymes (e.g. tRNA synthetases), membrane transporters and ribosomal proteins. Suitable test compounds include proteins, polypeptides, carbohydrates, lipids, nucleic acids (e.g. DNA, RNA, and modified forms thereof), as well as small organic compounds (e.g. MW between 200 and 2000 Da). The test compounds may be provided individually, but will typically be part of a library (e.g. a combinatorial library). Methods for detecting a binding interaction include NMR, filter-binding assays, gel-retardation assays, displacement assays, surface plasmon resonance, reverse two-hybrid etc. A compound which binds to a protein of the invention can be tested for antibiotic activity by contacting the compound with GBS bacteria and then monitoring for inhibition of growth. The invention also provides a compound identified using these methods.

The invention also provides a composition comprising a protein or the invention and one or more of the following antigens:

a protein antigen from *Helicobacter pylori* such as VacA, CagA, NAP, HopX, HopY [e.g. WO98/04702] and/or urease.

a protein antigen from *N. meningitidis* serogroup B, such as those in WO99/24578, WO99/36544, WO99/57280, WO00/22430, Tettelin et al. (2000) *Science* 287:1809-1815, Pizza et al. (2000) *Science* 287:1816-1820 and WO96/29412, with protein '287' and derivatives being particularly preferred.

an outer-membrane vesicle (OMV) preparation from *N. meningitidis* serogroup B, such as those disclosed in WO01/52885; Bjune et al. (1991) *Lancet* 338(8775): 1093-1096; Fukasawa et al. (1999) *Vaccine* 17:2951-2958; Rosenqvist et al. (1998) *Dev. Biol. Stand.* 92:323-333 etc.

a saccharide antigen from *N. meningitidis* serogroup A, C, W135 and/or Y, such as the oligosaccharide disclosed in Costantino et al. (1992) *Vaccine* 10:691-698 from serogroup C [see also Costantino et al. (1999) *Vaccine* 17:1251-1263].

a saccharide antigen from *Streptococcus pneumoniae* [e.g. Watson (2000) *Pediatr Infect Dis J* 19:331-332; Rubin (2000) *Pediatr Clin North Am* 47:269-285, v; Jedrzejas (2001) *Microbiol Mol Biol Rev* 65:187-207].

an antigen from hepatitis A virus, such as inactivated virus [e.g. Bell (2000) *Pediatr Infect Dis J* 19:1187-1188; Iwarson (1995) *APMIS* 103:321-326].

an antigen from hepatitis B virus, such as the surface and/or core antigens [e.g. Gerlich et al. (1990) *Vaccine* 8 Suppl:S63-68 & 79-80].

an antigen from hepatitis C virus [e.g. Hsu et al. (1999) *Clin Liver Dis* 3:901-915].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. Gustafsson et al. (1996) *N. Engl. J. Med.* 334:349-355; Rappuoli et al. (1991) *TIBTECH* 9:232-238].

a diphtheria antigen, such as a diphtheria toxoid [e.g. chapter 3 of *Vaccines* (1988) eds. Plotkin & Mortimer. ISBN 0-7216-1946-0]e.g. the $CRM_{197}$ mutant [e.g. Del Guidice et al. (1998) *Molecular Aspects of Medicine* 19:1-70].

a tetanus antigen, such as a tetanus toxoid [e.g. chapter 4 of Plotkin & Mortimer].

a saccharide antigen from *Haemophilus influenzae* B.

an antigen from *N. gonorrhoeae* [e.g. WO99/24578, WO99/36544, WO99/57280].

an antigen from *Chlamydia pneumoniae* [e.g. PCT/IB01/01445; Kalman et al. (1999) *Nature Genetics* 21:385-389; Read et al. (2000) *Nucleic Acids Res* 28:1397-406; Shirai et al. (2000) *J. Infect. Dis.* 181(Suppl 3):S524-S527; WO99/27105; WO00/27994; WO00/37494].

an antigen from *Chlamydia trachomatis* [e.g. WO99/28475].

an antigen from *Porphyromonas gingivalis* [e.g. Ross et al. (2001) *Vaccine* 19:4135-4142].

polio antigen(s) [e.g. Sutter et al. (2000) *Pediatr Clin North Am* 47:287-308; Zimmerman & Spann (1999) *Am Fam Physician* 59:113-118, 125-126] such as IPV or OPV.

rabies antigen(s) [e.g. Dreesen (1997) *Vaccine* 15 Suppl: S2-6] such as lyophilised inactivated virus [e.g. *MMWR Morb Mortal Wkly Rep* 1998 Jan. 16; 47(1):12, 19; RabAvert™]

measles, mumps and/or rubella antigens [e.g. chapters 9, 10 & 11 of Plotkin & Mortimer].

influenza antigen(s) [e.g. chapter 19 of Plotkin & Mortimer], such as the haemagglutinin and/or neuraminidase surface proteins.

an antigen from *Moraxella catarrhalis* [e.g. McMichael (2000) *Vaccine* 19 Suppl 1:S101-107].

an antigen from *Staphylococcus aureus* [e.g. Kuroda et al. (2001) *Lancet* 357(9264):1225-1240; see also pages 1218-1219].

Where a saccharide or carbohydrate antigen is included, it is preferably conjugated to a carrier protein in order to enhance immunogenicity [e.g. Ramsay et al. (2001) *Lancet* 357(9251):195-196; Lindberg (1999) *Vaccine* 17 Suppl 2:S28-36; *Conjugate Vaccines* (eds. Cruse et al.) ISBN 3805549326, particularly vol. 10:48-114 etc.]. Preferred carrier proteins are bacterial toxins or toxoids, such as diphtheria or tetanus toxoids. The $CRM_{197}$ diphtheria toxoid is particularly preferred. Other suitable carrier proteins include the *N. meningitidis* outer membrane protein [e.g. EP-0372501], synthetic peptides [e.g. EP-0378881, EP-0427347], heat shock proteins [e.g. WO93/17712], pertussis proteins [e.g. WO98/58668; EP-0471177], protein D from *H. influenzae* [e.g. WO00/56360], toxin A or B from *C. difficile* [e.g. WO00/61761], etc. Any suitable conjugation reaction can be used, with any suitable linker where necessary.

Toxic protein antigens may be detoxified where necessary (e.g. detoxification of pertussis toxin by chemical and/or genetic means).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens.

Antigens are preferably adsorbed to an aluminium salt.

Antigens in the composition will typically be present at a concentration of at least 1 µg/ml each. In general, the concentration of any given antigen will be sufficient to elicit an immune response against that antigen.

The invention also provides compositions comprising two or more proteins of the present invention. The two or more proteins may comprise GBS sequences or may comprise GAS and GBS sequences.

A summary of standard techniques and procedures which may be employed to perform the invention (e.g. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature e.g. Sambrook *Molecular Cloning; A Laboratory Manual*, Second Edition (1989); *DNA Cloning, Volumes I and II* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology*, Volumes I-IV (D. M. Weir and C. C. Blackwell eds 1986).

Standard abbreviations for nucleotides and amino acids are used in this specification.

Definitions

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" e.g. a composition "comprising" X may consist exclusively of X or may include something additional e.g. X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a *streptococcus* sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (e.g. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (e.g. see U.S. Pat. No. 5,753,235).

Expression Systems

The *streptococcus* nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (eg. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed.*].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionin gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236:1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus tripartite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminater/polyadenylation signals include those derived from SV40 [Sambrook et al (1989) "Expression of cloned genes in cultured mammalian cells." In *Molecular Cloning: A Laboratory Manual]*.

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin* No. 1555 (1987) (hereinafter "Summers and Smith").

Prior to inserting the DNA sequence encoding the protein into the baculovirus genome, the above described components, comprising a promoter, leader (if desired), coding sequence, and transcription termination sequence, are usually assembled into an intermediate transplacement construct (transfer vector). This may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extra-chromosomal element (e.g. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.,* 42:177) and a prokaryotic ampicillin-resistance (amp) gene and origin of replication for selection and propagation in *E. coli.*

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system; cell culture technology is generally known to those skilled in the art. See, eg. Summers and Smith supra.

The modified insect cells may then be grown in an appropriate nutrient medium, which allows for stable maintenance of the plasmid(s) present in the modified insect host.

Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, etc. As appropriate, the product may be further purified, as required, so as to remove substantially any insect proteins which are also present in the medium, so as to provide a product which is at least substantially free of host debris, e.g. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., *Nucleic Acids Research* 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*, Malcolm B. Wilkins, ed., 1984 Pitman Publishing Limited, London, pp. 21-52. References that describe other metabolically-regulated genes: Sheen, *Plant Cell*, 2:1027-1038 (1990); Maas et al., *EMBO J.* 9:3447-3452 (1990); Benkel and Hickey, *Proc. Natl. Acad. Sci.* 84:1337-1339 (1987).

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859-1863, 1982.

The vector may also be introduced into the plant cells by electroporation. (Fromm et al., *Proc. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. I. Gresser)], bacteriophage lambda PL [Shimatake et al. (1981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EP-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) *J. Biotechnol.* 5:93; Makoff et al. (1989) *J. Gen. Microbiol.* 135:11], and Chey [EP-A-0 324 647] genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus lactis* by electroporation, in: Streptococcal Genetics (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) *Proc. Natl. Acad. Sci. USA* 80:1].

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) *Proc. Natl. Acad. Sci. USA* 77:1078; Henikoff et al. (1981) *Nature* 283:835; Hollenberg et al. (1981) *Curr. Topics Microbiol. Immunol.* 96:119; Hollenberg et al. (1979) "The Expression of Bacterial Antibiotic Resistance Genes in the Yeast *Saccharomyces cerevisiae*," in: Plasmids of Medical, Environmental and Commercial Importance (eds. K. N. Timmis and A. Puhler); Mercereau-Puigalon et al. (1980) *Gene* 11:163; Panthier et al. (1980) *Curr. Genet.* 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (e.g. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) *Gene* 8:17-24], pCl/1 [Brake et al. (1984) *Proc. Natl. Acad. Sci USA* 81:4642-4646], and YRp17 [Stinchcomb et al. (1982) *J. Mol. Biol.* 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Gregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Gregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying *streptococcus* proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (eg. hypoxanthine, aminopterin, thymidine medium, "HAT"). The resulting hybridomas are plated by limiting dilution, and are assayed for production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}I$, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the molecule of the invention in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines according to the invention may either be prophylactic (i.e. to prevent infection) or therapeutic (i.e. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) oil-in-water emulsion formulations (with or without other specific immunostimulating agents such as muramyl peptides (see below) or bacterial cell wall components), such as for example (a) MF59™ (WO90/14837; Chapter 10 in *Vaccine Design—the subunit and adjuvant approach* (1995) ed. Powell & Newman), containing 5% Squalene, 0.5% TWEEN® 80 (polyoxyethylene sorbitan monoleate), and 0.5% SPAN® 85 (sorbitan trioleate) (optionally containing MTP-PE) formulated into submicron particles using a microfluidizer, (b) SAF, containing 10% Squalane, 0.4% TWEEN® 80, 5% pluronic-blocked polymer L121, and thr-MDP either microfluidized into a submicron emulsion or vortexed to generate a larger particle size emulsion, and (c) RIBI™ adjuvant system (RAS), (Bibi Immunochem, Hamilton, Mont.) containing 2% Squalene, 0.2% TWEEN® 80, and one or more bacterial cell wall components from the group consisting of monophosphorylipid A (MPL), trehalose dimycolate (TDM), and cell wall skeleton (CWS), preferably MPL+CWS (DETOX™); (2) saponin adjuvants, such as QS21 or STIMULON™ (Cambridge Bioscience, Worcester, Mass.) may be used or particles generated therefrom such as ISCOMs (immunostimulating complexes), which ISCOMS may be devoid of additional detergent e.g. WO00/07621; (3) Complete Freund's Adjuvant (CFA) and Incomplete Freund's Adjuvant (IFA); (4) cytokines, such as interleukins (e.g. IL-1, IL-2, IL-4, IL-5, IL-6, IL-7, IL-12 (WO99/44636), etc.), interferons (e.g. gamma interferon), macrophage colony stimulating factor (M-CSF), tumor necrosis factor (TNF), etc.; (5) monophosphoryl lipid A (MPL) or 3-O-deacylated MPL (3dMPL) e.g. GB-2220221, EP-A-0689454; (6) combinations of 3dMPL with, for example, QS21 and/or oil-in-water emulsions e.g. EP-A-0835318, EP-A-0735898, EP-A-0761231; (7) oligonucleotides comprising CpG motifs [Krieg *Vaccine* 2000, 19, 618-622; Krieg *Curr Opin Mol Ther* 2001 3:15-24; Roman et al., *Nat. Med.,* 1997, 3, 849-854; Weiner et al., *PNAS USA,* 1997, 94, 10833-10837; Davis et al., *J. Immunol.,* 1998, 160, 870-876; Chu et al., *J. Exp. Med.,* 1997, 186, 1623-1631; Lipford et al., *Eur. J. Immunol.,* 1997, 27, 2340-2344; Moldoveanu et al., *Vaccine,* 1988, 16, 1216-1224, Krieg et al., *Nature,* 1995, 374, 546-549; Klinman et al., *PNAS USA,* 1996, 93, 2879-2883; Ballas et al., *J. Immunol.,* 1996, 157, 1840-1845; Cowdery et al., *J. Immunol.,* 1996, 156, 4570-4575; Halpern et al., *Cell. Immunol.,* 1996, 167, 72-78; Yamamoto et al., *Jpn. J. Cancer Res.,* 1988, 79, 866-873; Stacey et al., *J. Immunol.,* 1996, 157, 2116-2122; Messina et al., *J. Immunol.,* 1991, 147, 1759-1764; Yi et al., *J. Immunol.,* 1996, 157, 4918-4925; Yi et al., *J. Immunol.,* 1996, 157, 5394-5402; Yi et al., *J. Immunol.,* 1998, 160, 4755-4761; and Yi et al., *J. Immunol.,* 1998, 160, 5898-5906; International patent applications WO96/02555, WO98/16247, WO98/18810, WO98/40100, WO98/55495, WO98/37919 and WO98/52581] i.e. containing at least one CG dinucleotide, with 5-methylcytosine optionally being used in place of cytosine; (8) a polyoxyethylene ether or a polyoxyethylene ester e.g. WO99/52549; (9) a polyoxyethylene sorbitan ester surfactant in combination with an octoxynol (e.g. WO01/21207) or a polyoxyethylene alkyl ether or ester surfactant in combination with at least one additional non-ionic surfactant such as an octoxynol (e.g. WO01/21152); (10) an immunostimulatory oligonucleotide (e.g. a CpG oligonucleotide) and a saponin e.g. WO00/62800; (11) an immunostimulant and a particle of metal salt e.g. WO00/23105; (12) a saponin and an oil-in-water emulsion e.g. WO99/11241; (13) a saponin (e.g. QS21)+3dMPL+IL-12 (optionally+a sterol) e.g. WO98/57659; (14) aluminium salts, preferably hydroxide or phosphate, but any other suitable salt may also be used (e.g. hydroxyphosphate, oxyhydroxide, orthophosphate, sulphate etc. [e.g. see chapters 8 & 9 of Powell & Newman]). Mixtures of different aluminium salts may also be used. The salt may take any suitable form (e.g. gel, crystalline, amorphous etc.); (15) other substances that act as immunostimulating agents to enhance the efficacy of the composition. Aluminium salts and/or MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphos-phoryloxy)-ethylamine (MTP-PE), etc.

The immunogenic compositions (eg. the immunising antigen/immuno-gen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, e.g. by injection, either subcutaneously, intramuscularly, or transdermally/transcutaneously (e.g. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be used [e.g. Robinson & Torres (1997) *Seminars in Immunol* 9:271-283; Donnelly et al. (1997) *Annu Rev Immunol* 15:617-648; later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) *Cancer Gene Therapy* 1:51-64; Kimura (1994) *Human Gene Therapy* 5:845-852; Connelly (1995) *Human Gene Therapy* 6:185-193; and Kaplitt (1994) *Nature Genetics* 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) *J. Virol.* 53:160) polytropic retroviruses eg. MCF and MCF-MLV (see Kelly (1983) *J. Virol.* 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-Inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) *J Virol* 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825, WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) *Human Gene* Therapy 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (i.e. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354, 678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC with accession numbers VR-977 and VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, *Nature* 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569:86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Phannacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, etc.

Other groups that can be included are, for example: hormones, steroids, androgens, estrogens, thyroid hormone, or vitamins, folic acid.

C. Polyalkylenes, Polysaccharides, etc.

Also, polyalkylene glycol can be included with the desired polynucleotides/polypeptides. In a preferred embodiment, the polyalkylene glycol is polyethlylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097: 1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem.* 265:10189-10192), in functional form.

Cationic liposomes are readily available. For example, NH-2,3-dioleyloxy)propyll-N,N,N-triethyl-ammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *Proc. Natl. Acad. Sci. USA* 75:4194-4198; WO90/11092 for a description of the synthesis of DOTAP (1,2-bis(oleoyloxy)-3-(trimethylammonio)propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C & E, over time these lipoproteins lose A and acquire C & E. VLDL comprises A, B, C & E apoproteins, LDL comprises apoprotein B; and HDL comprises apoproteins A, C, & E.

The amino acid of these apoproteins are known and are described in, for example, Breslow (1985) *Annu Rev. Biochem* 54:699; Law (1986) *Adv. Exp Med. Biol.* 151:162; Chen (1986) *J Biol Chem* 261:12918; Kane (1980) *Proc Natl Acad Sci USA* 77:2465; and Utermann (1984) *Hum Genet* 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids is chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in WO98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and LIPOFECTAMINE™ are monomers that form polycationic complexes when combined with polynucleotides/polypeptides.

Immunodiagnostic Assays

*Streptococcus* antigens of the invention can be used in immunoassays to detect antibody levels (or, conversely, anti-*streptococcus* antibodies can be used to detect antigen levels). Immunoassays based on well defined, recombinant antigens can be developed to replace invasive diagnostics methods. Antibodies to *streptococcus* proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment (s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm = 81 + 16.6(\log_{10} Ci) + 0.4[\%(G+C)] - 0.6(\% \text{ formamide}) - 600/n - 1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes this approach impractical, several hybridization and/or washing stringencies should be tested in parallel.

Nucleic Acid Probe Assays

Methods such as PCR, branched DNA probe assays, or blotting techniques utilizing nucleic acid probes according to the invention can determine the presence of cDNA or mRNA. A probe is said to "hybridize" with a sequence of the invention if it can form a duplex or double stranded complex, which is stable enough to be detected.

The nucleic acid probes will hybridize to the *streptococcus* nucleotide sequences of the invention (including both sense and antisense strands). Though many different nucleotide sequences will encode the amino acid sequence, the native *streptococcus* sequence is preferred because it is the actual sequence present in cells. mRNA represents a coding sequence and so a probe should be complementary to the coding sequence; single-stranded cDNA is complementary to mRNA, and so a cDNA probe should be complementary to the non-coding sequence.

The probe sequence need not be identical to the *streptococcus* sequence (or its complement)—some variation in the sequence and length can lead to increased assay sensitivity if the nucleic acid probe can form a duplex with target nucleotides, which can be detected. Also, the nucleic acid probe can include additional nucleotides to stabilize the formed duplex. Additional *streptococcus* sequence may also be helpful as a label to detect the formed duplex. For example, a non-complementary nucleotide sequence may be attached to the 5' end of the probe, with the remainder of the probe sequence being complementary to a *streptococcus* sequence. Alternatively, non-complementary bases or longer sequences can be interspersed into the probe, provided that the probe sequence has sufficient complementarity with the a *streptococcus* sequence in order to hybridize therewith and thereby form a duplex which can be detected.

The exact length and sequence of the probe will depend on the hybridization conditions (e.g. temperature, salt condition etc.). For example, for diagnostic applications, depending on the complexity of the analyte sequence, the nucleic acid probe typically contains at least 10-20 nucleotides, preferably 15-25, and more preferably at least 30 nucleotides, although it may be shorter than this. Short primers generally require cooler temperatures to form sufficiently stable hybrid complexes with the template.

Probes may be produced by synthetic procedures, such as the triester method of Matteucci et al. [*J. Am. Chem. Soc.* (1981) 103:3185], or according to Urdea et al. [*Proc. Natl. Acad. Sci. USA* (1983) 80: 7461], or using commercially available automated oligonucleotide synthesizers.

The chemical nature of the probe can be selected according to preference. For certain applications, DNA or RNA are appropriate. For other applications, modifications may be incorporated eg. backbone modifications, such as phosphorothioates or methylphosphonates, can be used to increase in vivo half-life, alter RNA affinity, increase nuclease resistance etc. [eg. see Agrawal & Iyer (1995) *Curr Opin Biotechnol* 6:12-19; Agrawal (1996) *TIBTECH* 14:376-387]; analogues such as peptide nucleic acids may also be used [eg. see Corey (1997) *TIBTECH* 15:224-229; Buchardt et al. (1993) *TIBTECH* 11:384-386].

Alternatively, the polymerase chain reaction (PCR) is another well-known means for detecting small amounts of target nucleic acid. The assay is described in Mullis et al. [*Meth. Enzymol.* (1987) 155:335-350] & U.S. Pat. No. 4,683,195 & 4,683,202. Two "primer" nucleotides hybridize with the target nucleic acids and are used to prime the reaction. The primers can comprise sequence that does not hybridize to the sequence of the amplification target (or its complement) to aid with duplex stability or, for example, to incorporate a convenient restriction site. Typically, such sequence will flank the desired *streptococcus* sequence.

A thermostable polymerase creates copies of target nucleic acids from the primers using the original target nucleic acids as a template. After a threshold amount of target nucleic acids are generated by the polymerase, they can be detected by more traditional methods, such as Southern blots. When using the Southern blot method, the labelled probe will hybridize to the *streptococcus* sequence (or its complement).

Also, mRNA or cDNA can be detected by traditional blotting techniques described in Sambrook et al [supra]. mRNA, or cDNA generated from mRNA using a polymerase enzyme, can be purified and separated using gel electrophoresis. The nucleic acids on the gel are then blotted onto a solid support, such as nitrocellulose. The solid support is exposed to a labelled probe and then washed to remove any unhybridized probe. Next, the duplexes containing the labeled probe are detected. Typically, the probe is labelled with a radioactive moiety.

EXAMPLE

The following example describes nucleic acid sequences which have been identified in *Streptococcus*, along with their inferred translation products. The example is generally in the following format:
 a nucleotide sequence which has been identified in *Streptococcus*
 the inferred translation product of this sequence
 a computer analysis (e.g. PSORT output) of the translation product, indicating antigenicity.

The example describes nucleotide sequences from *S. agalactiae*. The specific strain which was sequenced was from serotype V, and is a clinical strain isolated in Italy which expresses the R antigen (ISS/Rome/Italy collection, strain. 2603 V/R). The corresponding sequences from *S. pyogenes* are also given. Where GBS and GAS show homology in this way, there is conservation between species which suggests an essential function and also gives good cross-species reactivity.

The example includes details of homology to sequences in the public databases. Proteins that are similar in sequence are generally similar in both structure and function, and the homology often indicates a common evolutionary origin. Comparison with sequences of proteins of known function is widely used as a guide for the assignment of putative protein function to a new sequence and has proved particularly useful in whole-genome analyses.

Various tests can be used to assess the in vivo immunogenicity of the proteins identified in the example. For example, the proteins can be expressed recombinantly and used to screen patient sera by immunoblot. A positive reaction between the protein and patient serum indicates that the patient has previously mounted an immune response to the protein in question i.e. the protein is an immunogen. This method can also be used to identify immunodominant proteins. The mouse model used in the example can also be used.

The recombinant protein can also be conveniently used to prepare antibodies e.g. in a mouse. These can be used for direct confirmation that a protein is located on the cell-surface. Labelled antibody (e.g. fluorescent labelling for FACS) can be incubated with intact bacteria and the presence of label on the bacterial surface confirms the location of the protein.

For many GBS proteins, the following data are given:
 SDS-PAGE analysis of total recombinant *E. coli* cell extracts for GBS protein expression
 SDS-PAGE analysis after the protein purification
 Western-blot analysis of GBS total cell extract using antisera raised against recombinant proteins
 FACS and ELISA analysis against GBS using antisera raise against recombinant proteins
 Results of the in vivo passive protection assay
 Details of experimental techniques used are presented below:

Sequence Analysis

Open reading frames (ORFs) within nucleotide sequences were predicted using the GLIMMER program [Salzberg et al. (1998) *Nucleic Acids Res* 26:544-8]. Where necessary, start codons were modified and corrected manually on the basis of the presence of ribosome-binding sites and promoter regions on the upstream DNA sequence.

ORFs were then screened against the non-redundant protein databases using the programs BLASTp [Altschul et al. (1990) *J. Mol. Biol.* 215:403-410] and PRAZE, a modification of the Smith-Waterman algorithm [Smith & Waterman (1981) *J Mol Biol* 147:195-7; see Fleischmann et al (1995) *Science* 269:496-512].

Leader peptides within the ORFs were located using three different approaches: (i) PSORT [Nakai (1991) *Bull. Inst. Chem. Res., Kyoto Univ.* 69:269-291; Horton & Nakai (1996) *Intellig. Syst. Mol. Biol.* 4:109-115; Horton & Nakai (1997) *Intellig. Syst. Mol. Biol.* 5:147-152]; (ii) SignalP [Nielsen & Krogh (1998) in *Proceedings of the Sixth International Conference on Intelligent Systems for Molecular Biology* (ISMB 6), AAAI Press, Menlo Park, Calif., pp. 122-130; Nielsen et al. (1999) *Protein Engineering* 12:3-9; Nielsen et al. (1997). *Int. J. Neural Sys.* 8:581-599]; and (iii) visual inspection of the ORF sequences. Where a signal sequences is given a "possible site" value, the value represents the C-terminus residue of the signal peptide e.g. a "possible site" of 26 means that the signal sequence consists of amino acids 1-26.

Lipoprotein-specific signal peptides were located using three different approaches: (i) PSORT [see above]; (ii) the "prokaryotic membrane lipoprotein lipid attachment site" PROSITE motif [Hofmann et al. (1999) *Nucleic Acids Res.* 27:215-219; Bucher & Bairoch (1994) in *Proceedings 2nd International Conference on Intelligent Systems for Molecular Biology* (ISMB-94), AAAI Press, pages 53-61]; and (iii) the FINDPATTERNS program available in the GCG Wisconsin Package, using the pattern (M, L, V)x{9, 35}LxxCx.

Transmembrane domains were located using two approaches: (i) PSORT [see above]; (ii) TopPred [von Heijne (1992) *J. Mol. Biol.* 225:487-494].

LPXTG motifs, characteristic of cell-wall attached proteins in Gram-positive bacteria [Fischetti et al. (1990) *Mol Microbiol* 4:1603-5] were located with FINDPATTERNS using the pattern (L, I, V, M, Y, F)Px(T, A, S, G) (G, N, S, T, A, L).

RGD motifs, characteristic of cell-adhesion molecules [D'Souza et al. (1991) *Trends Biochem Sci* 16:246-50] were located using FINDPATTERNS.

Enzymes belonging to the glycolytic pathway were also selected as antigens, because these have been found experimentally expressed on the surface of *Streptococci* [e.g. Pancholi & Fischetti (1992) *J Exp Med* 176:415-26; Pancholi & Fischetti (1998) *J Biol Chem* 273:14503-15].

Cloning, Expression and Purification of Proteins

GBS genes were cloned to facilitate expression in *E. coli* as two different types of fusion proteins:
   a) proteins having a hexa-histidine tag at the amino-terminus (His-gbs)
   b) proteins having a GST fusion partner at the amino-terminus (Gst-gbs)

Cloning was performed using the Gateway™ technology (Life Technologies), which is based on the site-specific recombination reactions that mediate integration and excision of phage lambda into and from the *E. coli* genome. A single cloning experiment included the following steps:
   1—Amplification of GBS chromosomal DNA to obtain a PCR product coding for a single ORF flanked by attB recombination sites.
   2—Insertion of the PCR product into a pDONR vector (containing attP sites) through a BP reaction (attBxattP sites). This reaction gives a so called 'pEntry' vector, which now contains attL sites flanking the insert.
   3—Insertion of the GBS gene into *E. coli* expression vectors (pDestination vectors, containing attR sites) through a LR reaction between pEntry and pDestination plasmids (attLxattR sites).

A) Chromosomal DNA preparation

For chromosomal DNA preparation, GBS strain 2603 V/R (Istituto Superiore Sanità, Rome) was grown to exponential phase in 2 liters TH Broth (Difco) at 37° C., harvested by centrifugation, and dissolved in 40 ml TES (50 mM Tris pH 8, 5 mM EDTA pH 8, 20% sucrose). After addition of 2.5 ml lysozyme solution (25 mg/ml in TES) and 0.5 ml mutanolysin (Sigma M-9901, 25000 U/ml in $H_2O$), the suspension was incubated at 37° C. for 1 hour. 1 ml RNase (20 mg/ml) and 0.1 ml proteinase K (20 mg/ml) were added and incubation was continued for 30 min. at 37° C.

Cell lysis was obtained by adding 5 ml sarkosyl solution (10% N-laurylsarcosine in 250 mM EDTA pH 8.0), and incubating 1 hour at 37° C. with frequent inversion. After sequential extraction with phenol, phenol-chloroform and chloroform, DNA was precipitated with 0.3M sodium acetate pH 5.2 and 2 volumes of absolute ethanol. The DNA pellet was rinsed with 70% ethanol and dissolved in TE buffer (10 mM Tris-HCl, 1 mM EDTA, pH 8). DNA concentration was evaluated by $OD_{260}$.

B) Oligonucleotide Design

Synthetic oligonucleotide primers were designed on the basis of the coding sequence of each ORF. The aim was to express the protein's extracellular region. Accordingly, predicted signal peptides were omitted (by deducing the 5' end amplification primer sequence immediately downstream from the predicted leader sequence) and C-terminal cell-wall anchoring regions were removed (e.g. LPXTG motifs and downstream amino acids). Where additional nucleotides have been deleted, this is indicated by the suffix 'd' (e.g. 'GBS352d'). Conversely, a suffix 'L' refers to expression without these deletions. Deletions of C- or N-terminal residues were also sometimes made, as indicated by a 'C' or 'N' suffix.

The amino acid sequences of the expressed GBS proteins (including 'd' and 'L' forms etc.) are definitively defined by the sequences of the oligonucleotide primers.

5' tails of forward primers and 3' tails of reverse primers included attB1 and attB2 sites respectively:

Forward primers: 5'-GGGGACAAGTTTGTA-CAAAAAAGCAGGCTCT-ORF in frame-3' (nucleotides 1-31 of SEQ ID NO:11313; the TCT sequence preceding the ORF was omitted when the ORF's first coding triplet began with T).

Reverse primers: 5'-GGGGACCACTTTGTA-CAAGAAAGCTGGGTT-ORF reverse complement-3' (nucleotides 1-30 of SEQ ID NO:11838).

The primers for GBS317 are thus:

```
Fwd:
                                      (SEQ ID NO: 11313)
5'-ggggacaagtttgtacaaaaaagcaggctctaataagccatattcaa
tag-3'
Rev:
                                      (SEQ ID NO: 11838)
5'-ggggaccactttgtacaagaaagctgggttatcttctcctaacttac
cc-3'
```

The number of nucleotides which hybridized to the sequence to be amplified depended on the melting temperature of the primers, which was determined as described by Breslauer et al. [*PNAS USA* (1986) 83:3746-50]. The average melting temperature of the selected oligos was 50-55° C. for the hybridizing region and 80-85° C. for the whole oligos.

C) Amplification

The standard PCR protocol was as follows: 50 ng genomic DNA were used as template in the presence of 0.5 µM each primer, 200 µM each dNTP, 1.5 mM $MgCl_2$, 1× buffer minus $Mg^{++}$ (Gibco-BRL) and 2 units of Taq DNA polymerase (Platinum Taq, Gibco-BRL) in a final volume of 100 µl. Each sample underwent a double-step of amplification: 5 cycles performed using as the hybridizing temperature 50° C., followed by 25 cycles at 68° C.

The standard cycles were as follows:
Denaturation: 94° C., 2 min
5 cycles: Denaturation: 94° C., 30 seconds
Hybridization: 50° C., 50 seconds
Elongation: 72° C., 1 min. or 2 min. and 40 sec.
25 cycles: Denaturation: 94° C., 30 seconds
Hybridization: 68° C., 50 seconds
Elongation: 72° C., 1 min. or 2 min. and 40 sec.

Elongation time was 1 minute for ORFs shorter than 2000 bp and 2:40 minutes for ORFs longer than 2000 bp. Amplifications were performed using a Gene Amp PCR system 9600 (Perkin Elmer).

To check amplification results, 2 µl of each PCR product were loaded onto 1-1.5 agarose gel and the size of amplified fragments was compared with DNA molecular weight standards (DNA marker IX Roche, 1 kb DNA ladder Biolabs).

Single band PCR products were purified by PEG precipitation: 300 µl of TE buffer and 200 µl of 30% PEG 8000/30 mM MgCl$_2$ were added to 100 µl PCR reaction. After vortexing, the DNA was centrifuged for 20 min at 10000 g, washed with 1 vol. 70% ethanol and the pellet dissolved in 30 µl TE. PCR products smaller than 350 bp were purified using a PCR purification Kit (Qiagen) and eluted with 30 µl of the provided elution buffer.

In order to evaluate the yield, 2 µl of the purified DNA were subjected to agarose gel electrophoresis and compared to titrated molecular weight standards.

D) Cloning of PCR Products into Expression Vectors

Cloning was performed following the GATEWAY™ technology's "one-tube protocol", which consists of a two step reaction (BP and LR) for direct insertion of PCR products into expression vectors.

BP reaction (attB×attP sites): The reaction allowed insertion of the PCR product into a pDONR vector. The pDONR™ 201 vector we used contains the killer toxin gene ccdB between attP1 and attP2 sites to minimize background colonies lacking the PCR insert, and a selectable marker gene for kanamycin resistance. The reaction resulted in a so called pEntry vector, in which the GBS gene was located between attL1 and attL2 sites.

60 fmol of PCR product and 100 ng of pDONR™ 201 vector were incubated with 2.5 µl of BP CLONASE™ in a final volume of 12.5 µl for 4 hours at 25° C.

Figure 86A:
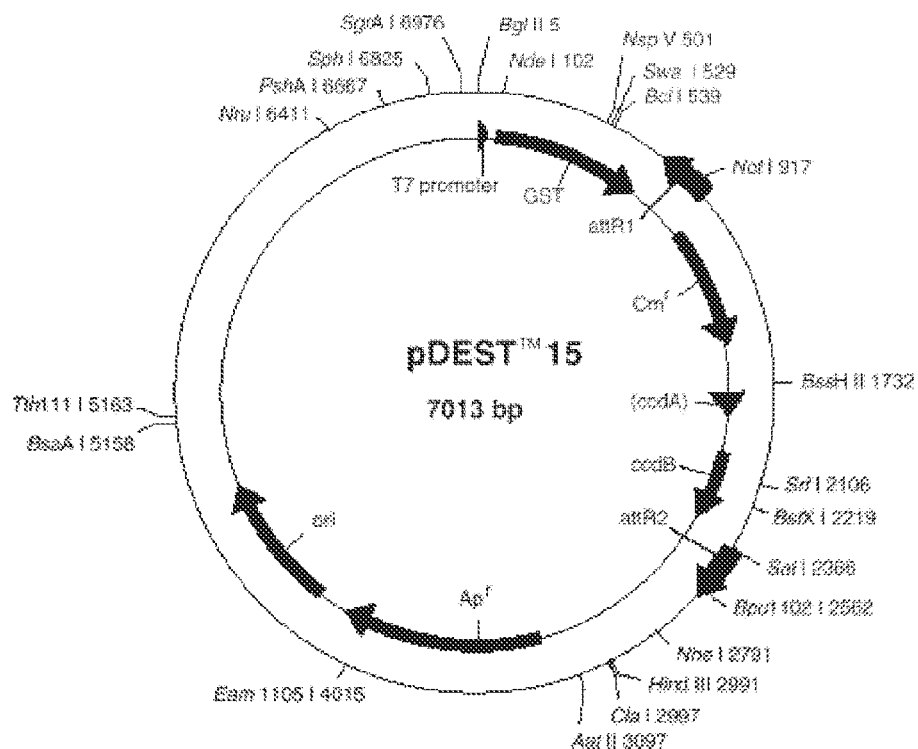
FIG. 86A shows the pDEST15 vector.
Figure 86B:
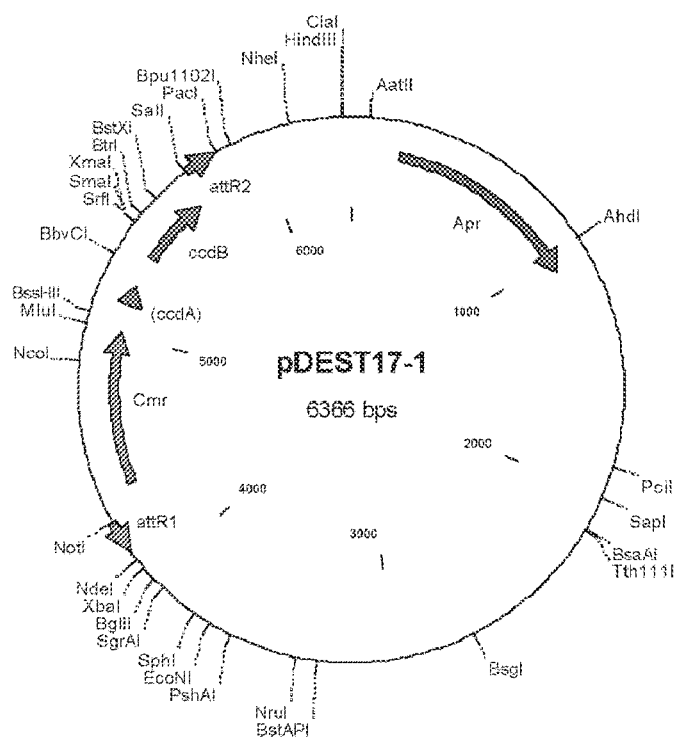
FIG. 86B shows the pDEST17-1 vector.
Figure 110C:
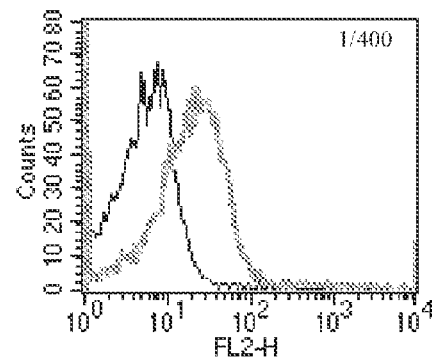
Figure 111:
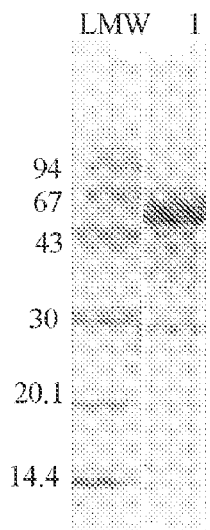
Figure 113:
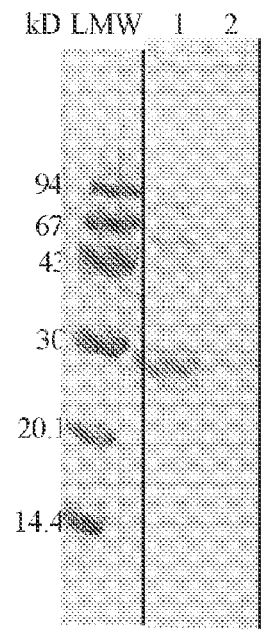
Figure 118:
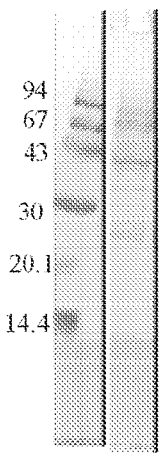
Figure 119:
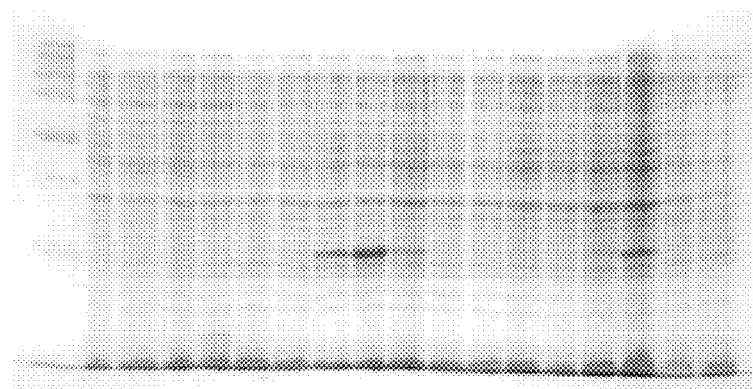
Figure 120:
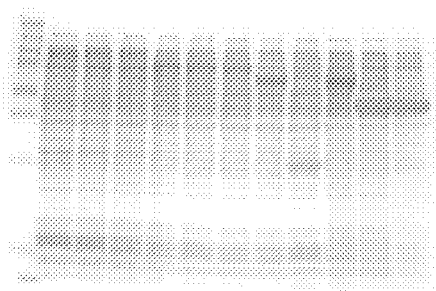
Figure 121:
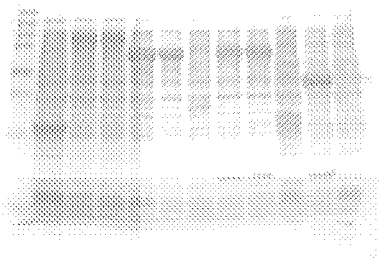
Figure 122:
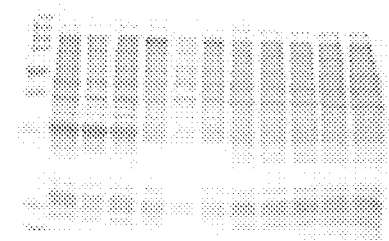
Figure 123:
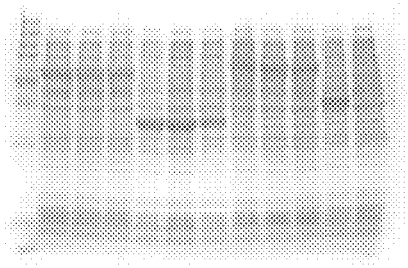
Figure 124:
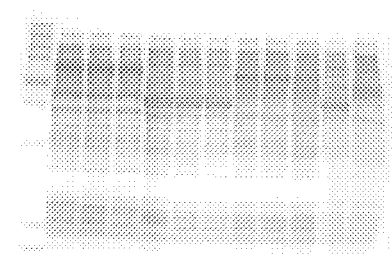
Figure 125:
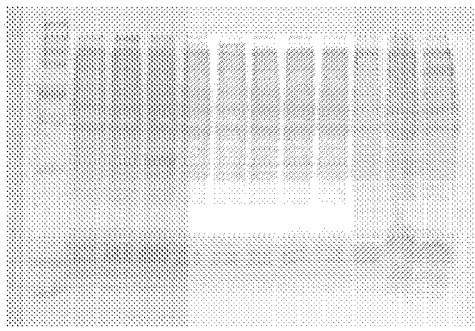
Figure 126:
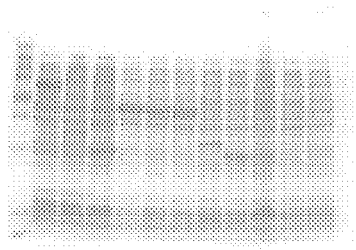
Figure 127:
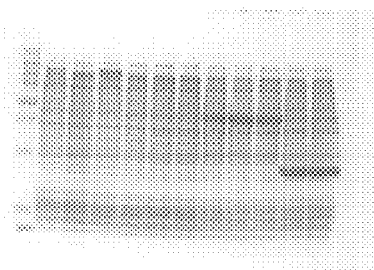
Figure 128:
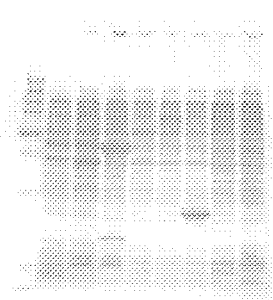
Figure 129:
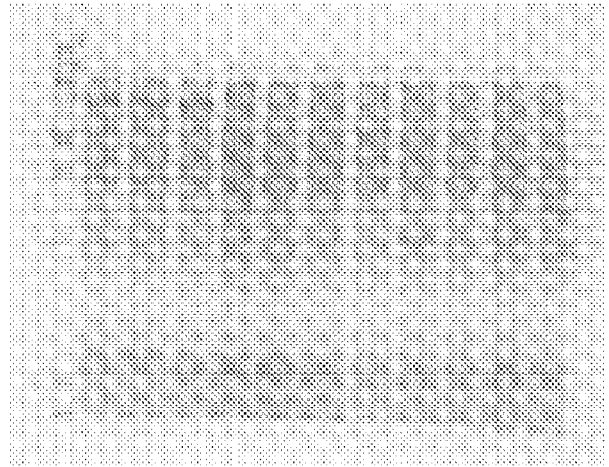
Figure 130:
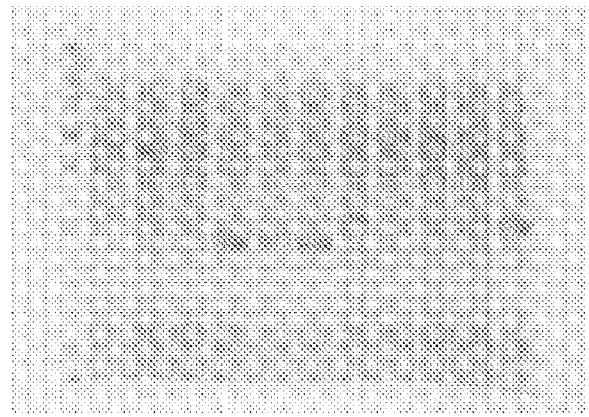
Figure 131:
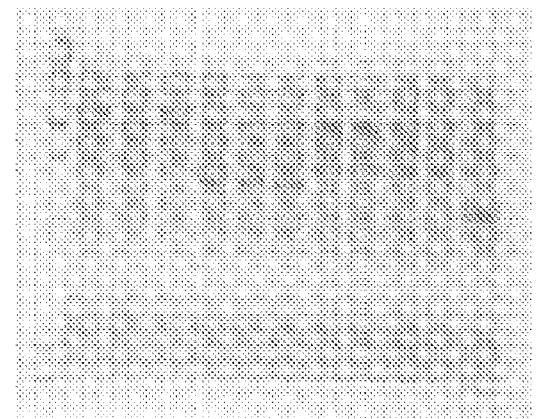
Figure 132:
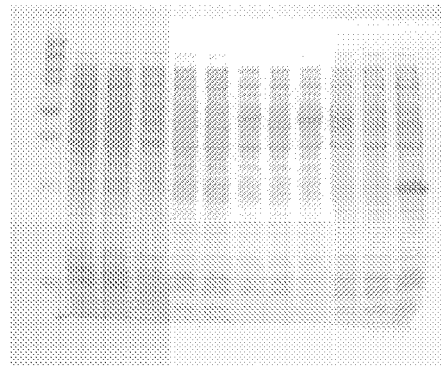
Figure 133:
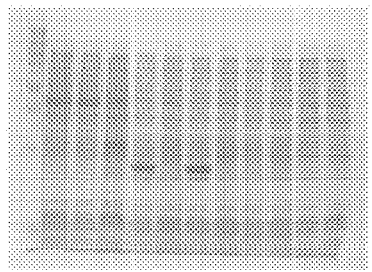
Figure 134:
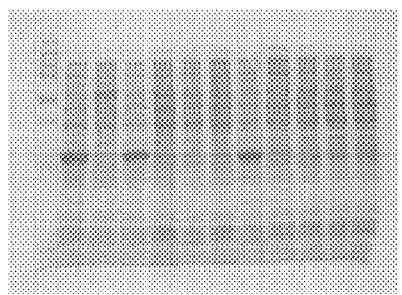
Figure 135:
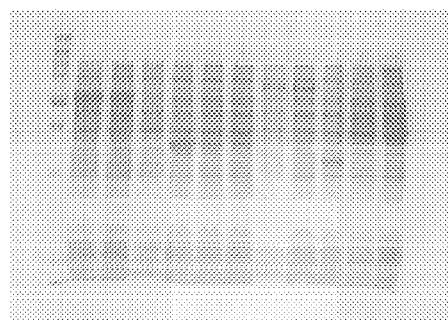
Figure 136:
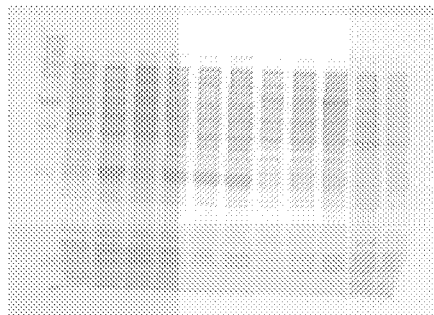
Figure 137:
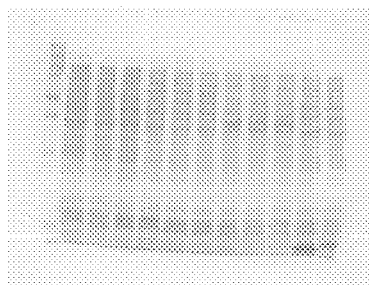
Figure 138:
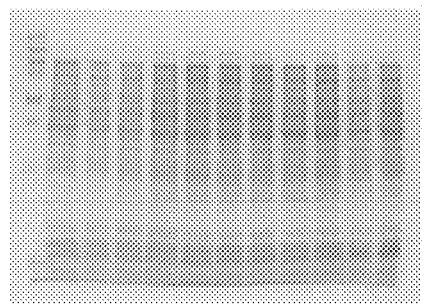
Figure 139:
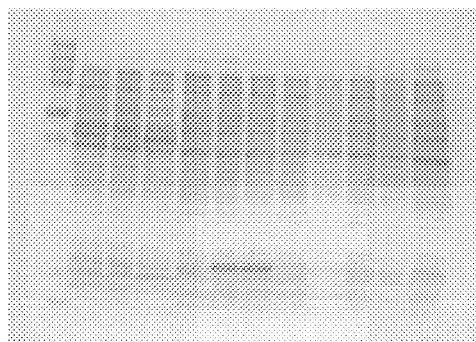
Figure 140:
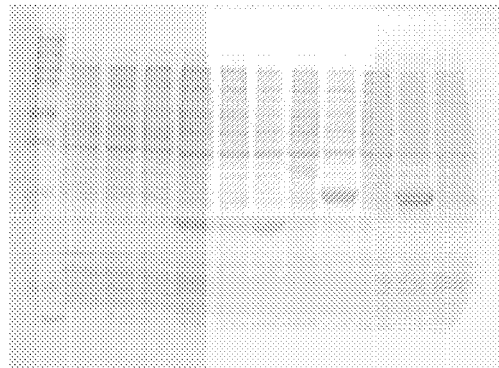
Figure 141:
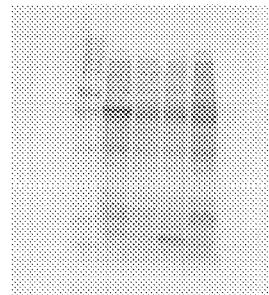
Figure 142:
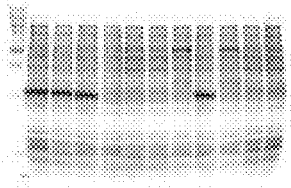
Figure 143:
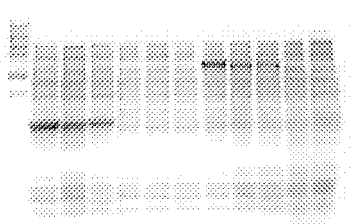
Figure 144:
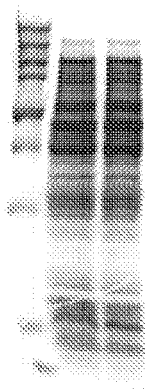
Figure 145:
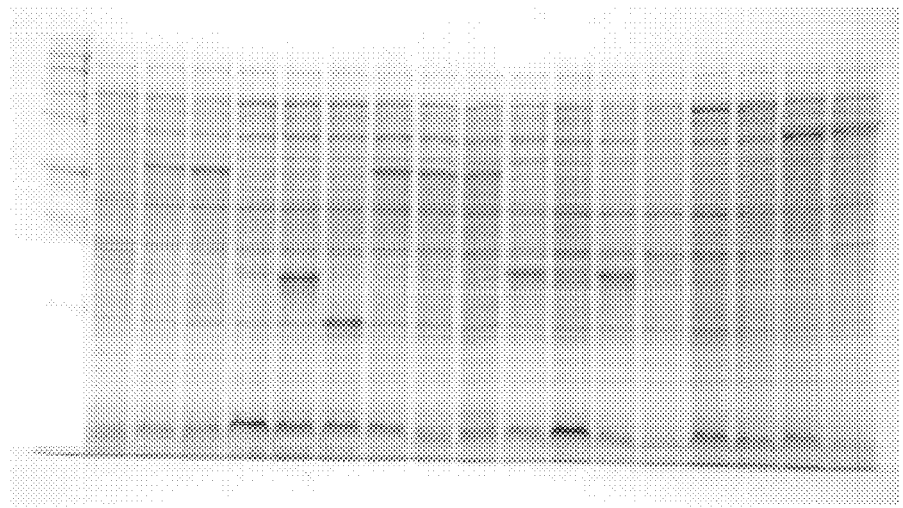
Figure 146:
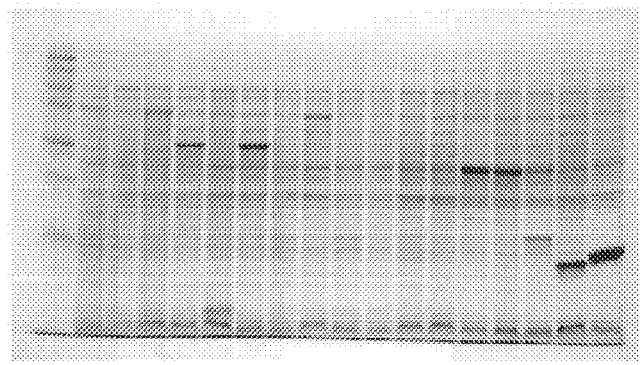
Figure 147:
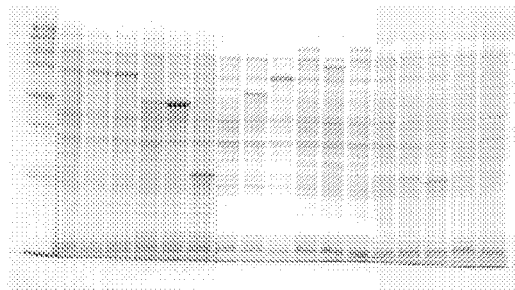
Figure 148:
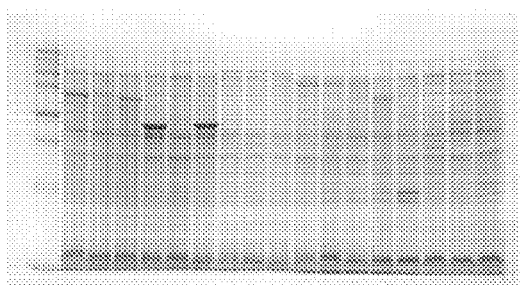

LR reaction (attL×attR sites): The reaction allowed the insertion of the GBS gene, now present in the pEntry vector, into *E. coli* expression vectors (pDestination vectors, containing attR sites). Two pDestination vectors were used (pDEST15 for N-terminal GST fusions—FIG. 86; and pDEST17-1 for N-terminal His-tagged fusions—FIG. 87). Both allow transcription of the ORF fusion coding mRNA under T7 RNA polymerase promoter [Studier et al (1990) *Meth. Enzymol* 185: 60ff].

To 5 µl of BP reaction were added 0.25 µl of 0.75 M NaCl, 100 ng of destination vector and 1.5 µl of LR CLONASE™. The reaction was incubated at 25° C. for 2 hours and stopped with 1 µl of 1 mg/ml proteinase K solution at 37° C. for 15 min.

1 µl of the completed reaction was used to transform 50 µl electrocompetent BL21-SI™ cells (0.1 cm, 200 ohms, 25 µF). BL21-SI cells contain an integrated T7 RNA polymerase gene under the control of the salt-inducible prU promoter [Gowrishankar (1985) *J. Bacteriol.* 164:434ff]. After electroporation cells were diluted in 1 ml SOC medium (20 g/l bacto-tryptone, 5 g/l yeast extract, 0.58 g/l NaCl, 0.186 g/l KCl, 20 mM glucose, 10 mM MgCl$_2$) and incubated at 37° C. for 1 hour. 200 µl cells were plated onto LBON plates (Luria Broth medium without NaCl) containing 100 µg/ml ampicillin. Plates were then incubated for 16 hours at 37° C.

Entry clones: In order to allow the future preparation of Gateway compatible pEntry plasmids containing genes which might turn out of interest after immunological assays, 2.5 µl of BP reaction were incubated for 15 min in the presence of 3 µl 0.15 mg/ml proteinase K solution and then kept at −20° C. The reaction was in this way available to transform *E. coli* competent cells so as to produce Entry clones for future introduction of the genes in other Destination vectors.

E) Protein Expression

Single colonies derived from the transformation of LR reactions were inoculated as small-scale cultures in 3 ml LBON 100 µg/ml ampicillin for overnight growth at 25° C. 50-200 µl of the culture was inoculated in 3 ml LBON/Amp to an initial OD600 of 0.1. The cultures were grown at 37° C. until OD600 0.4-0.6 and recombinant protein expression was induced by adding NaCl to a final concentration of 0.3 M. After 2 hour incubation the final OD was checked and the cultures were cooled on ice. 0.5 OD$_{600}$ of cells were harvested by centrifugation. The cell pellet was suspended in 50 µl of protein Loading Sample Buffer (50 mM TRIS-HCl pH 6.8, 0.5% w/v SDS, 2.5% v/v glycerin, 0.05% w/v Bromophenol Blue, 100 mM DTT) and incubated at 100° C. for 5 min. 10 µl of sample was analyzed by SDS-PAGE and Coomassie Blue staining to verify the presence of induced protein band.

F) Purification of the Recombinant Proteins

Single colonies were inoculated in 25 ml LBON 100 µg/ml ampicillin and grown at 25° C. overnight. The overnight culture was inoculated in 500 ml LBON/amp and grown under shaking at 25° C. until OD$_{600}$ values of 0.4-0.6. Protein expression was then induced by adding NaCl to a final concentration of 0.3 M. After 3 hours incubation at 25° C. the final OD$_{600}$ was checked and the cultures were cooled on ice. After centrifugation at 6000 rpm (JA10 rotor, Beckman) for 20 min., the cell pellet was processed for purification or frozen at −20° C.

Proteins were purified in 1 of 3 ways depending on the fusion partner and the protein's solubility:

Purification of Soluble his-Tagged Proteins from *E. coli*

1. Transfer pellets from −20° C. to ice bath and reconstitute each pellet with 10 ml B-PER™ solution (Bacterial-Protein Extraction Reagent, Pierce cat. 78266), 10 µl of a 100 mM MgCl$_2$ solution, 50 µl of DNAse I (Sigma D-4263, 100 K units in PBS) and 100 µl of 100 mg/ml lysozyme in PBS (Sigma L-7651, final concentration 1 mg/ml).
2. Transfer resuspended pellets in 50 ml centrifuge tubes and leave at room temperature for 30-40 minutes, vortexing 3-4 times.
3. Centrifuge 15-20 minutes at about 30-40000×g.
4. Prepare Poly-Prep (Bio-Rad) columns containing 1 ml of Fast Flow Ni-activated Chelating Sepharose (Pharmacia). Equilibrate with 50 mM phosphate buffer, 300 mM NaCl, pH 8.0.
5. Store the pellet at −20° C., and load the supernatant on to the columns.
6. Discard the flow through.
7. Wash with 10 ml 20 mM imidazole buffer, 50 mM phosphate, 300 mM NaCl, pH 8.0.
8. Elute the proteins bound to the columns with 4.5 ml (1.5 ml+1.5 ml+1.5 ml) 250 mM imidazole buffer, 50 mM phosphate, 300 mM NaCl, pH 8.0 and collect three fractions of ~1.5 ml each. Add to each tube 15 µl DTT 200 mM (final concentration 2 mM).
9. Measure the protein concentration of the collected fractions with the Bradford method and analyse the proteins by SDS-PAGE.
10. Store the collected fractions at +4° C. while waiting for the results of the SDS-PAGE analysis.
11. For immunisation prepare 4-5 aliquots of 20-100 µg each in 0.5 ml in 40% glycerol. The dilution buffer is the above elution buffer, plus 2 mM DTT. Store the aliquots at −20° C. until immunisation.

Purification of his-Tagged Proteins from Inclusion Bodies
1. Bacteria are collected from 500 ml cultures by centrifugation. If required store bacterial pellets at −20° C. Transfer the pellets from −20° C. to room temperature and reconstitute each pellet with 10 ml B-PER™ solution, 10 µl of a 100 mM $MgCl_2$ solution (final 1 mM), 50 µl of DNAse I equivalent to 100 K units in PBS and 100 µl of a 100 mg/ml lysozyme (Sigma L-7651) solution in PBS (equivalent to 10 mg, final concentration 1 mg/ml).
2. Transfer the resuspended pellets in 50 ml centrifuge tubes and let at room temperature for 30-40 minutes, vortexing 3-4 times.
3. Centrifuge 15 minutes at 30-4000×g and collect the pellets.
4. Dissolve the pellets with 50 mM TRIS-HCl, 1 mM TCEP {Tris(2-carboxyethyl)-phosphine hydrochloride, Pierce}, 6M guanidine hydrochloride, pH 8.5. Stir for ~10 min. with a magnetic bar.
5. Centrifuge as described above, and collect the supernatant.
6. Prepare Poly-Prep (Bio-Rad) columns containing 1 ml of Fast Flow Ni-activated Chelating Sepharose (Pharmacia). Wash the columns twice with 5 ml of $H_2O$ and equilibrate with 50 mM TRIS-HCl, 1 mM TCEP, 6M guanidine hydrochloride, pH 8.5.
7. Load the supernatants from step 5 onto the columns, and wash with 5 ml of 50 mM TRIS-HCl buffer, 1 mM TCEP, 6M urea, pH 8.5
8. Wash the columns with 10 ml of 20 mM imidazole, 50 mM TRIS-HCl, 6M urea, 1 mM TCEP, pH 8.5. Collect and set aside the first 5 ml for possible further controls.
9. Elute proteins bound to columns with 4.5 ml buffer containing 250 mM imidazole, 50 mM TRIS-HCl, 6M urea, 1 mM TCEP, pH 8.5. Add the elution buffer in three 1.5 ml aliquots, and collect the corresponding three fractions. Add to each fraction 15 µl DTT (final concentration 2 mM).
10. Measure eluted protein concentration with Bradford method and analyse proteins by SDS-PAGE.
11. Dialyse overnight the selected fraction against 50 mM Na phosphate buffer, pH 8.8, containing 10% glycerol, 0.5 M arginine, 5 mM reduced glutathione, 0.5 mM oxidized glutathione, 2 M urea.
12. Dialyse against 50 mM Na phosphate buffer, pH 8.8, containing 10% glycerol, 0.5 M arginine, 5 mM reduced glutathione, 0.5 mM oxidized glutathione.
13. Clarify the dialysed protein preparation by centrifugation and discard the non-soluble material and measure the protein concentration with the Bradford method.
14. For each protein destined to the immunization prepare 4-5 aliquot of 20-100 µg each in 0.5 ml after having adjusted the glycerol content up to 40%. Store the prepared aliquots at −20° C. until immunization.

Purification of GST-Fusion Proteins from E. coli
1. Bacteria are collected from 500 ml cultures by centrifugation. If required store bacterial pellets at −20° C. Transfer the pellets from −20° C. to room temperature and reconstitute each pellet with 10 ml B-PER™ solution, 10 µl of a 100 mM $MgCl_2$ solution (final 1 mM), 50 µl of DNAse I equivalent to 100 K units in PBS and 100 µl of a 100 mg/ml lysozyme (Sigma L-7651) solution in PBS (equivalent to 10 mg, final concentration 1 mg/ml).
2. Transfer the resuspended pellets in 50 ml centrifuge tubes and let at room temperature for 30-40 minutes, vortexing 3-4 times.
3. Centrifuge 15-20 minutes at about 30-40000×g.
4. Discard centrifugation pellets and load supernatants onto the chromatography columns, as follows.
5. Prepare Poly-Prep (Bio-Rad) columns containing 0.5 ml of Glutathione-Sepharose 4B resin. Wash the columns twice with 1 ml of $H_2O$ and equilibrate with 10 ml PBS, pH 7.4.
6. Load supernatants on to the columns and discard the flow through.
7. Wash the columns with 10 ml PBS, pH 7.4.
8. Elute proteins bound to columns with 4.5 ml of 50 mM TRIS buffer, 10 mM reduced glutathione, pH 8.0, adding 1.5 ml+1.5 ml+1.5 ml and collecting the respective 3 fractions of −1.5 ml each.
9. Measure protein concentration of the fractions with the Bradford method and analyse the proteins by SDS-PAGE.
10. Store the collected fractions at +4° C. while waiting for the results of the SDS-PAGE analysis.
11. For each protein destined for immunisation prepare 4-5 aliquots of 20-100 µg each in 0.5 ml of 40% glycerol. The dilution buffer is 50 mM TRIS-HCl, 2 mM DTT, pH 8.0. Store the aliquots at −20° C. until immunisation.

FIG. 4

Figure 4:
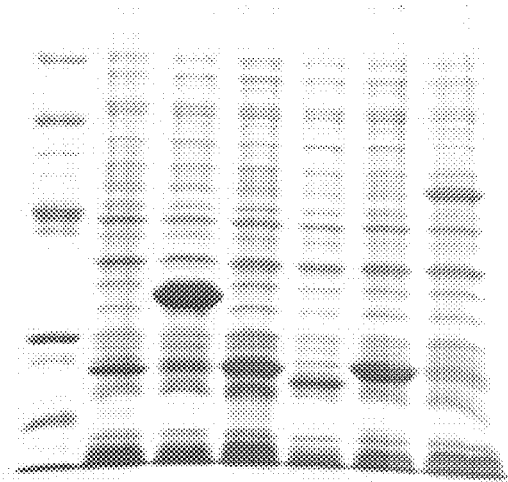
Figure 5:
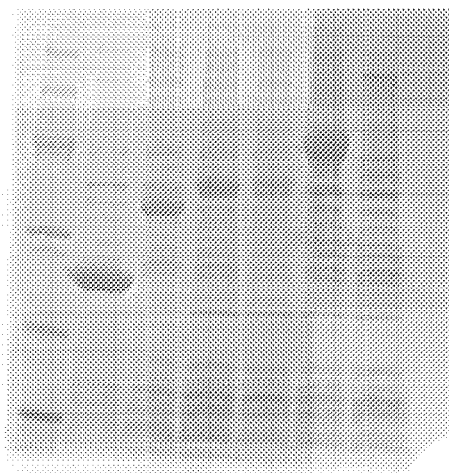
Figure 6:
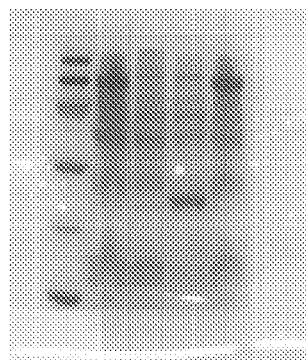
Figure 7:
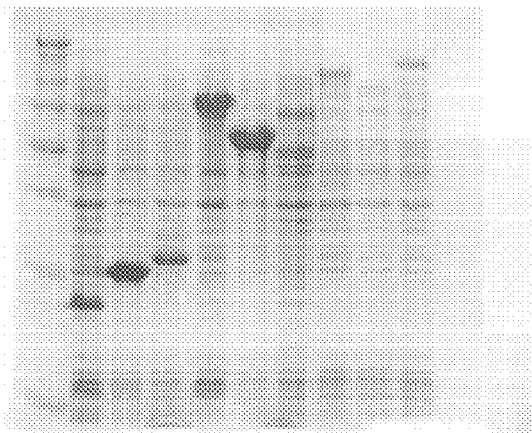
Figure 8:
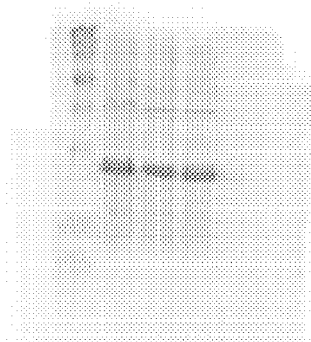
Figure 9:
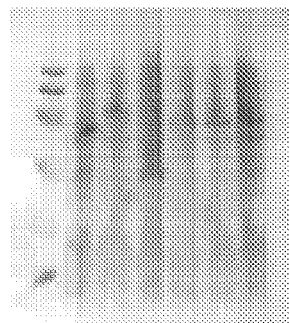
Figure 10:
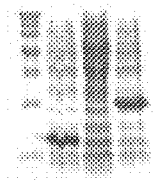
Figure 11:
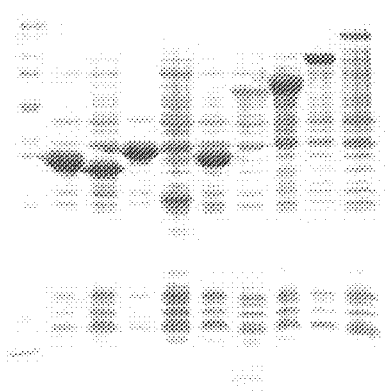
Figure 12:
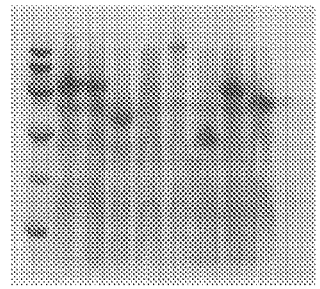
Figure 13:
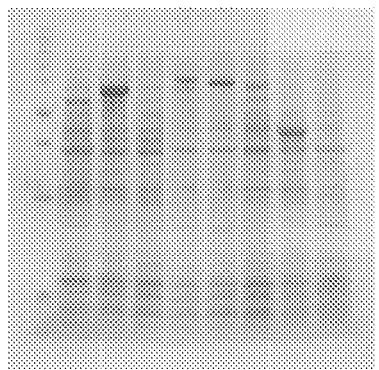
Figure 14:
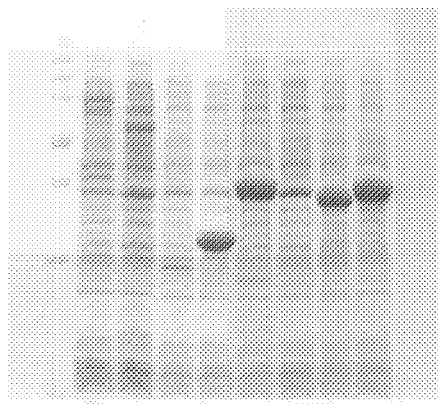
Figure 15:
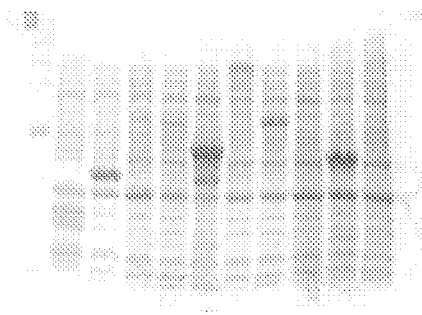
Figure 16:
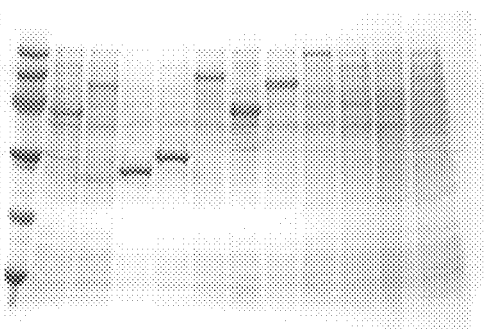
Figure 17:
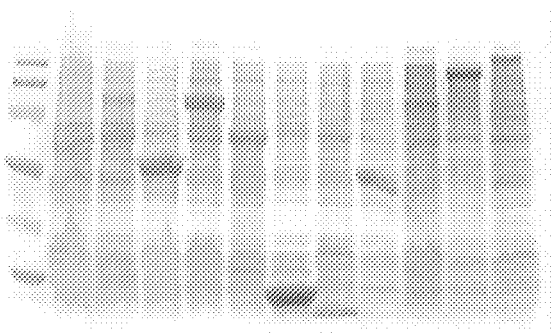
Figure 18:
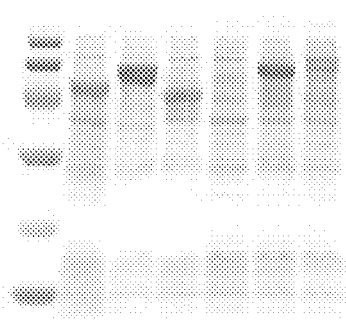
Figure 19:
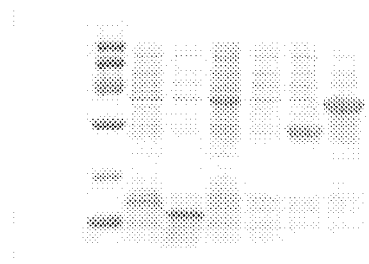
Figure 20:
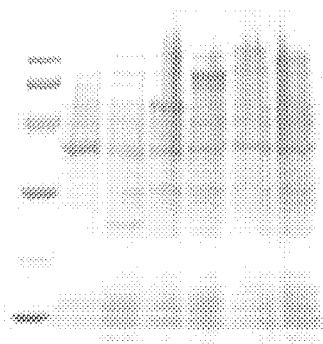
Figure 21:
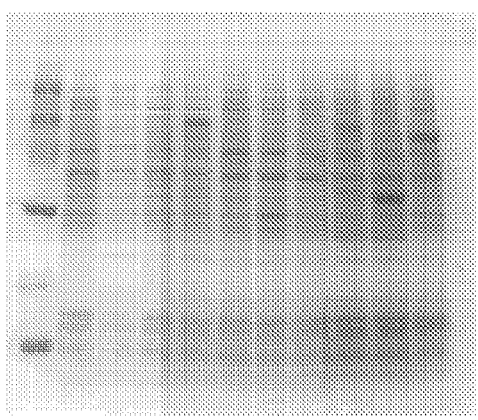
Figure 22:
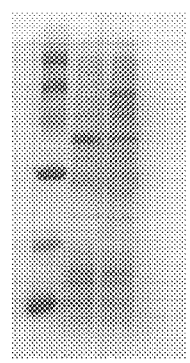
Figure 23:
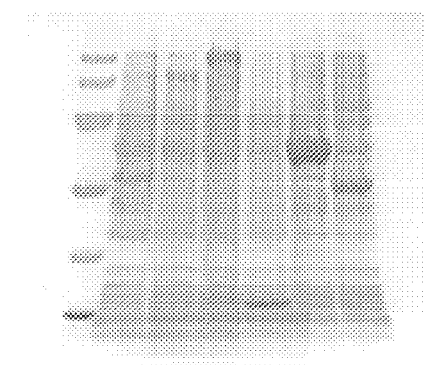
Figure 24:
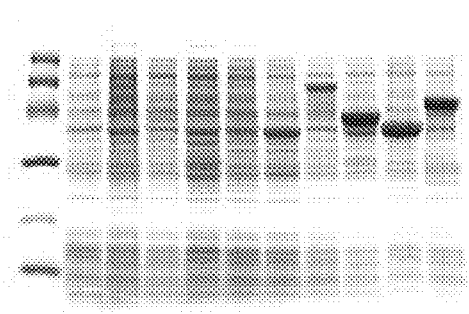
Figure 25:
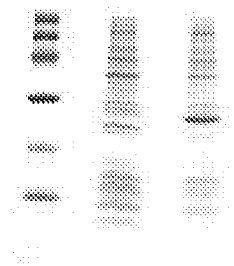
Figure 26:
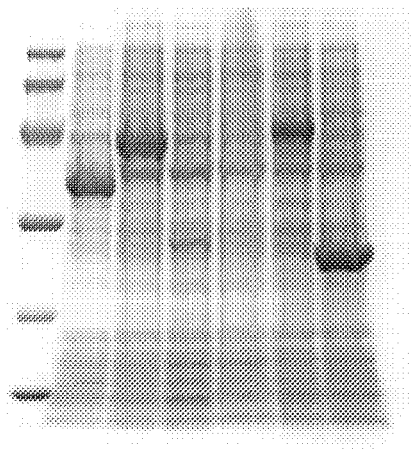

For the experiment shown in FIG. 4, the GBS proteins were fused at the N-terminus to thioredoxin and at C-terminus to a poly-His tail. The plasmid used for cloning is pBAD-DEST49 (Invitrogen Gateway™ technology) and expression is under the control of an L(+)-Arabinose dependent promoter. For the production of these GBS antigens, bacteria are grown on RM medium (6 g/l $Na_2HPO_4$, 3 g/l $KH_2PO_4$, 0.5 g/l NaCl, 1 g/l $NH_4Cl$, pH7.4, 2% casaminoacids, 0.2% glucose, 1 mM $MgCl_2$) containing 100 µg/ml ampicillin. After incubation at 37° C. until cells reach $OD_{600}$=0.5, protein expression is induced by adding 0.2% (v/v) L(+)Arabinose for 3 hours.

Immunisations with GBS Proteins

The purified proteins were used to immunise groups of four CD-1 mice intraperitoneally. 20 µg of each purified protein was injected in Freund's adjuvant at days 1, 21 & 35. Immune responses were monitored by using samples taken on day 0 & 49. Sera were analysed as pools of sera from each group of mice.

FACScan Bacteria Binding Assay Procedure.

GBS serotype V 2603 V/R strain was plated on TSA blood agar plates and incubated overnight at 37° C. Bacterial colonies were collected from the plates using a sterile dracon swab and inoculated into 100 ml Todd Hewitt Broth. Bacterial growth was monitored every 30 minutes by following $OD_{600}$. Bacteria were grown until $OD_{600}$=0.7-0.8. The culture was centrifuged for 20 minutes at 5000 rpm. The supernatant was discarded and bacteria were washed once with PBS, resuspended in ½ culture volume of PBS containing 0.05% paraformaldehyde, and incubated for 1 hour at 37° C. and then overnight at 4° C.

50 µl bacterial cells ($OD_{600}$ 0.1) were washed once with PBS and resuspended in 20 µl blocking serum (Newborn Calf Serum, Sigma) and incubated for 20 minutes at room temperature. The cells were then incubated with 100 µl diluted sera (1:200) in dilution buffer (20% Newborn Calf Serum 0.1% BSA in PBS) for 1 hour at 4° C. Cells were centrifuged at 5000 rpm, the supernatant aspirated and cells washed by adding 200 µl washing buffer (0.1% BSA in PBS). 50 µl R-Phicoerytrin conjugated F(ab)$_2$ goat anti-mouse, diluted 1:100 in dilution buffer, was added to each sample and incubated for 1 hour at 4° C. Cells were spun down by centrifugation at 5000 rpm and washed by adding 200 µl of washing buffer. The supernatant was aspirated and cells resuspended in 200 µl PBS. Samples were transferred to FACScan tubes and read. The condition for FACScan setting were: FL2 on; FSC-H threshold: 54; FSC PMT Voltage: E 02; SSC PMT: 516; Amp. Gains 2.63; FL-2 PMT: 728. Compensation values: 0.

Samples were considered as positive if they had a Δ mean values >50 channel values.

Whole Extracts Preparation

GBS serotype III COH1 strain and serotype V 2603 V/R strain cells were grown overnight in Todd Hewitt Broth. 1 ml of the culture was inoculated into 100 ml Todd Hewitt Broth. Bacterial growth was monitored every 30 minutes by following OD$_{600}$. The bacteria were grown until the OD reached 0.7-0.8. The culture was centrifuged for 20 minutes at 5000 rpm. The supernatant was discarded and bacteria were washed once with PBS, resuspended in 2 ml 50 mM Tris-HCl, pH 6.8 adding 400 units of Mutanolysin (Sigma-Aldrich) and incubated 3 hrs at 37° C. After 3 cycles of freeze/thaw, cellular debris were removed by centrifugation at 14000 g for 15 minutes and the protein concentration of the supernatant was measured by the Bio-Rad Protein assay, using BSA as a standard.

Western Blotting

Purified proteins (50 ng) and total cell extracts (25 µg) derived from GBS serotype III COH1 strain and serotype V 2603 V/R strain were loaded on 12% or 15% SDS-PAGE and transferred to a nitrocellulose membrane. The transfer was performed for 1 hours at 100V at 4° C., in transferring buffer (25 mM Tris base, 192 mM glycine, 20% methanol). The membrane was saturated by overnight incubation at 4° C. in saturation buffer (5% skimmed milk, 0.1% TWEEN® 20 (polyoxyethylene sorbitan monolaurate) in PBS). The membrane was incubated for 1 hour at room temperature with 1:1000 mouse sera diluted in saturation buffer. The membrane was washed twice with washing buffer (3% skimmed milk, 0.1% TWEEN® 20 in PBS) and incubated for 1 hour with a 1:5000 dilution of horseradish peroxidase labelled anti-mouse Ig (Bio-Rad). The membrane was washed twice with 0.1% TWEEN® 20 in PBS and developed with the Opti-4CN Substrate Kit (Bio-Rad). The reaction was stopped by adding water.

Unless otherwise indicated, lanes 1, 2 and 3 of blots in the drawings are: (1) the purified protein; (2) GBS-III extracts; and (3) GBS-V extracts. Molecular weight markers are also shown.

In Vivo Passive Protection Assay in Neonatal Sepsis Mouse Model.

The immune sera collected from the CD1 immunized mice were tested in a mouse neonatal sepsis model to verify their protective efficacy in mice challenged with GBS serotype III. Newborn Balb/C littermates were randomly divided in two groups within 24 hrs from birth and injected subcutaneously with 25 µl of diluted sera (1:15) from immunized CD1 adult mice. One group received preimmune sera, the other received immune sera. Four hours later all pups were challenged with a 75% lethal dose of the GBS serotype III COH1 strain. The challenge dose obtained diluting a mid log phase culture was administered subcutaneously in 25 µl of saline. The number of pups surviving GBS infection was assessed every 12 hours for 4 days.

The contents of PCT publication WO2002/034771, including Examples 1 to 1374, and 1376 to 3329, all Figures, and Tables I to VI, is hereby incorporated by reference in its entirety.

Identification of GBSx 1460

A DNA sequence (GBSx1460) was identified in *S. agalactiae* <SEQ ID 4209> which encodes the amino acid sequence <SEQ ID 4210>. Analysis of this protein sequence reveals the following:

---

Possible site: 59
>>> Seems to have no N-terminal signal sequence
---Final Results---
    bacterial cytoplasm---Certainty = 0.1109(Affirmative) < succ>
    bacterial membrane---Certainty = 0.0000(Not Clear) < succ>
    bacterial outside---Certainty = 0.0000(Not Clear) < succ>

---

The protein has homology with the following sequences in the GENPEPT database.

```
>GP: CAB73943 GB: AL139078 hyopthetical protein Cj1523c[Campylobacter
jejuni]
Identities = 165/746 (22%), Positives = 291/746 (38%), Gaps = 115/746 (15%)
Query:    318 LSASMIQRYDEHREDLKQLKQFVKASLPEKYQEI--FADSSKDGYAGYIEGKTNQEAFYK 375
              L+ S  +R     + L LK +        Y++    F +S    Y G +      E  ++
Sbjct:     50 LARSARKRLARRKARLNHLKHLIANEFKLNYEDYQSFDESLAKAYKGSLISP--YELRFR 107

Query:    376 YLSKLLTKQEDSENFLE--KIKNEDFLRKQRTFDNGSIPHQVHLTELKAIIRRQS----- 428
              L++LL+KQ+ +    L    K + D ++    + G+I   +   E K +   QS
Sbjct:    108 ALNELLSKQDFARVILHIAKRRGYDDIKNSDDKEKGAILKAIKQNEEK-LANYQSVGEYL 166

Query:    429 --EYYPFLKENQDRIEKILTFRIPYY-----------IGPLAREKSDFAW-MTRKTDDSI 474
                EY+   KEN      +    + Y            +  + +++ +F +  ++K ++ +
Sbjct:    167 YKEYFQKFKENSKEFTNVRNKKESYERCIAQSFLKDELKLIFKKQREFGFSFSKKFEEEV 226

Query:    475 RPWNFEDLVDKEKSAEAFIHRMINNDFYLPEEKVLPKHSLIYEKFIVYNELIKV--RYKN 532
                F      +++ +   F H + N F+   +EK  PK+S +       F    +   +   KN
Sbjct:    227 LSVAFY-----KRALKDFSHLVGNCSFFT-DEKRAPKNSPLAFMFVALTRIINLLNNLKN 280

Query:    533 EQGETYFFDSNIKQEIFDGVFKEHRKVSK--KKLLDFLAKEYEEFRIVDVIGLDKENKAF 590
              +G   Y     D        + + V K     K   KKLL   L+ +YE              E    +
Sbjct:    281 TEGILYTKDD--LNALLNEVLKNGTLTYKQTKKLLG-LSDDYE---------FKGEKGTY 328

Query:    591 NASLGTYHDLEKILDKDFLDNPDNESILEDIVQTLTLFEDREMIKKRLENYKDLFTESQL 650
                      Y +   KL +   L    D       L +I +  +TL +D    +KK L  Y        ++Q+
Sbjct:    329 FIEFKKYKEFIKALGEHNLSQDD----LNEIAKDIILIKDEIKLKKALAKYD--LNQNQI 382
```

```
Query:   651 KKLYRRHYTGWGRLSAKLINGIRDK--ESQKTILDYLIDDGRSNRNFMQLINDDGLSFKS 708
             L + +      +S K +  +     E +K      D+ +  N    IN+D    F
Sbjct:   383 DSLSKLEFKDHLNISFKALKLVTPLMLEGKK------YDEACNELNLKVAINEDKKDFLP 436

Query:   709 IISKAQAGSHSDNLKEVVGELAGSPAIKKGILQSLKIVDELVKVMGYEPEQIVVEMAREN 768
             ++        N           P + + I + K+++ L+K  G +  +I +E+ARE
Sbjct:   437 AFNETYYKDEVTN-----------PVVLRAIKEYRKVLNALLKKYG-KVHKINIELAREV 484

Query:   769 QIINQGR----RNSRQRYKLLDDG---VKNLASDLNG-NILKEYPIDNQALQNERLFLYY 820
               + R    +    + YK   D      + L  +N  NILK            L L+
Sbjct:   485 GKNHSQRAKIEKEQNENYKAKKDAELECEKLGLKINSKNILK------------LRLFK 531

Query:   821 LQNGRDMYTGEALDIDNLSQ---YDIDHIIPQAFIKDDSIDNRVLVSSAKNRGKSDDVPS 877
              Q    Y+GE + I  +L      +IDHI P +    DDS  N+VLV + +N+ K +  P
Sbjct:   532 EQKEFCAYSGEKIKISDLQDEKMLEIDHIYPYSRSFDDSYMNKVLVFTKQNQEKLNQTP- 590

Query:   878 LEIVKDCKVFWKKL--LDAKLMSQRKYDNLTKAERGGLTSDDKARFIQRQLVETRQITKH 935
              E    +  W+K+  L     L ++++    L K       ++  F  R L +TR I +
Sbjct:   591 FEAFGNDSAKWQKIEVLAKNLPTKKQKRILDK----NYKDKEQKNFKDRNLNDTRYIARL 646

Query:   936 VARI---------LDERFNNELDSKGRRIRKVKIVTLKSNLVSNFRKEFGFYKIREVNNY 986
             V           L +  N +L+     ++ KV +      L S R +GF         N+
Sbjct:   647 VLNYTKDYLDFLPLSDDENTKLNDT-QKGSKVHVEAKSGMLTSALRHTWGFSAKDRNNHL 705

Query:   987 HHAHDAYLNAVVAKAILTKYPQLEPE                                  1012
             HHA DA + A    +I+ +   + E
Sbjct:   706 HHAIDAVIIAYANNSIVKAFSDFKKE                                   731
```

A related DNA sequence was identified in *S. pyogenes* <SEQ ID 4211> which encodes the amino acid sequence <SEQ ID 4212>. Analysis of this protein sequence reveals the following:

Possible site: 61
>>> Seems to have no N-terminal signal sequence

---Final Results---
bacterial cytoplasm---Certainty = 0.0973(Affirmative) < succ>
bacterial membrane---Certainty = 0.0000(Not Clear) < succ>
bacterial outside---Certainty = 0.0000(Not Clear) < succ>

An alignment of the GAS and GBS proteins is shown below.

```
Identities = 881/1380 (63%), Positives = 1088/1380 (78%), Gaps = 22/1380 (1%)
Query:     1 MNKPYSIGLDIGTNSVGWSIITDDYKVPAKKMRVLGNTDKEYIKKNLIGALLFDGGNTAA 60
             M+K YSIGLDIGTNSVGW++ITD+YKVP+KK +VLGNTD+  IKKNLIGALLFD G TA
Sbjct:     1 MDKKYSIGLDIGTNSVGWAVITDEYKVPSKKFKVLGNTDRHSIKKNLIGALLFDSGETAE 60

Query:    61 DRRLKRTARRRYTRRRNRILYLQEIFAEEMSKVDDSFFHRLEDSFLVEEDKRGSKYPIFA 120
              RLKRTARRRYTRR+NRI YLQEIF+ EM+KVDDSFFHRLE+SFLVEEDK+  ++PIF
Sbjct:    61 ATRLKRTARRRYTRRKNRICYLQEIFSNEMAKVDDSFFHRLEESFLVEEDKKHERHPIFG 120

Query:   121 TLQEEKDYHEKFSTIYHLRKELADKKEKADLRLIYIALAHIIKFRGHFLIEDDSFDVRNT 180
              + +E  YHEK+ TIYHLRK+L D  +KADLRLIY+ALAH+IKFRGHFLIE D + N+
Sbjct:   121 NIVDEVAYHEKYPTIYHLRKKLVDSTDKADLRLIYLALAHMIKFRGHFLIEGD-LNPDNS 179

Query:   181 DISKQYQDFLEIFNTTFENNDLLSQNVDVEAILTDKISKSAKKDRILAQYPNQKSTGIFA 240
             D+ K +   ++ +N  FE N + +  VD +AIL+  ++SKS + + ++AQ P +K  G+F
Sbjct:   180 DVDKLFIQLVQTYNQLFEENPINASGVDAKAILSARLSKSRRLENLIAQLPGEKKNGLFG 239

Query:   241 EFLKLIVGNQADFKKYFNLEDKTPLQFAKDSYEDLENLLGQIGDEFADLFSAAKKLYDS 300
              + L +G  +FK  F+L +    LQ +KD+YD+DL+NLL QIGD++ADLF AAK L D+
Sbjct:   240 NLIALSLGLTPNFKSNFDLAEDAKLQLSKDTYDDDLDNLLAQIGDQYADLFLAAKNLSDA 299

Query:   301 VLLSGILTVIDLSTKAPLSASMIQRYDEHREDLKQLKQFVKASLPEKYQEIFADSSKDGY 360
             +LLS IL V    TKAPLSASMI+RYDEH +DL  LK  V+  LPEKY+EIF D SK+GY
Sbjct:   300 ILLSDILRVNTEITKAPLSASMIKRYDEHHQDLTLLKALVRQQLPEKYKEIFFDQSKNGY 359

Query:   361 AGYIEGKTNQEAFYKYLSKLLTKQEDSENFLEKIKNEDFLRKQRTFDNGSIPHQVHLTEL 420
             AGYI G +QE FYK++ +L K + +E  L K+  ED LRKQRTFDNGSIPHQ +HL EL
Sbjct:   360 AGYIDGGASQEEFYKFIKPILEKMDGTEELVKLNREDLLRKQRTFDNGSIPHQIHLGEL 419

Query:   421 KAIIRRQSEYYPFLKENQDRIEKILTFRIPYYIGPLAREKSDFAWMTRKTDDSIRPWNFE 480
              AI+RRQ ++YPFLK+N++ IEKILTFRIPYY+GPLAR  S FAWMTRK++++I PWNFE
Sbjct:   420 HAILRRQEDFYPFLKDNREKIEKILTFRIPYYVGPLARGNSRFAWMTRKSEETITPWNFE 479

Query:   481 DLVDKEKSAEAFIHRMTNNDFYLPEEKVLPKHSLIYEKFTVYNELTKVRYKNE-QGETYF 539
             ++VDK  SA++FI RMTN D LP EKVLPKHSL+YE FTVYNELTKV+Y  E +   F
Sbjct:   480 EVVDKGASAQSFIERMTNFDKNLPNEKVLPKHSLLYEYFTVYNELTKVKYVTEGMRKPAF 539

Query:   540 FDSNIKQEIFDGVFKEHRKVSKKKLLDFLAKEYEEFRIVDVIGLDKENKAFNASLGTYHD 599
                 K+  I D +FK +RKV+ K+L    K+ E F V++  G++           FNASLGTYHD
```

```
-continued
Sbjct:   540  LSGEQKKAIVDLLFKTNRKVTVKQLKEDYFKKIECFDSVEISGVEDR---FNASLGTYHD  596

Query:   600  LEKIL-DKDFLDNPDNESILEDIVQTLTLFEDREMIKKRLENYKDLFTESQLKKLYRRHY  658
              L KI+ DKDFLDN +NE ILEDIV TLTLFEDREMI++RL+ Y  LF +  +K+L RR Y
Sbjct:   597  LLKIIKDKDFLDNEENEDILEDIVLTLTLFEDREMIEERLKTYAHLFDDKVMKQLKRRRY  656

Query:   659  TGWGRLSAKLINGIRDKESQKTILDYLIDDGRSNRNFMQLINDDGLSFKSIISKAQAGSH  718
              TGWGRLS KLINGIRDK+S KTILD+L  DG +NRNFMQLI+DD L+FK  I KAQ
Sbjct:   657  TGWGRLSRKLINGIRDKQSGKTILDFLKSDGFANRNFMQLIHDDSLTFKEDIQKAQVSGQ  716

Query:   719  SDNLKEVVGELAGSPAIKKGILQSLKIVDELVKVMG-YEPEQIVVEMARENQTTNQGRRN  777
                D+L E +  LAGSPAIKKGILQ++K+VDELVKVMG ++PE IV+EMARENQTT +G++N
Sbjct:   717  GDSLHEHIANLAGSPAIKKGILQTVKVVDELVKVMGRHKPENIVIEMARENQTTQKGQKN  776

Query:   778  SRQRYKLLDDGVKNLASDLNGNILKEYPTDNQALQNERLFLYYLQNGRDMYTGEALDIDN  837
              SR+R K  +++G+K L S     ILKE+P +N  LQNE+L+YYLQNGRDMY  + LDI+
Sbjct:   777  SRERMKRIEEGIKELGS----QILKEHPVENTQLQNEKLYLYYLQNGRDMYVDQELDINR  832

Query:   838  LSQYDIDHIIPQAFIKDDSIDNRVLVSSAKNRGKSDDVPSLEIVKDCKVFWKKLLDAKLM  897
              LS YD+DHI+PQ+F+KDDSIDN+VL  S KNRGKSD+VPS E+VK  K +W++LL+AKL+
Sbjct:   833  LSDYDVDHIVPQSFLKDDSIDNKVLTRSDKNRGKSDNVPSEEVVKKMKNYWRQLLNAKLI  892

Query:   898  SQRKYDNLTKAERGGLTSDDKARFIQRQLVETRQITKHVARILDERFNNELDSKGRRIRK  957
              +QRK+DNLTKAERGGL+  DKA FI+RQLVETRQITKHVA+ILD R N + D   + IR+
Sbjct:   893  TQRKFDNLTKAERGGLSELDKAGFIKRQLVETRQITKHVAQILDSRMNTKYDENDKLIRE  952

Query:   958  VKIVTLKSNLVSNFRKEFGFYKIREVNNYHHAHDAYLNAVVAKAILTKYPQLEPEFVYGD  1017
              VK++TLKS LVS+FRK+F FYK+RE+NNYHHAHDAYLNAVV A++ KYP+LE EFVYGD
Sbjct:   953  VKVITLKSKLVSDFRKDFQFYKVREINNYHHAHDAYLNAVVGTALIKKYPKLESEFVYGD  1012

Query:  1018  YPKYN-------SYKTRKSATEKLFFYSNIMNFFKTKVTLADGTVVVKDDIEVNNDTGEI  1070
              Y Y+       S +    AT K FFYSNIMNFFKT++TLA+G +   IE N +TGEI
Sbjct:  1013  YKVYDVRKMIAKSEQEIGKATAKYFFYSNIMNFFKTEITLANGEIRKRPLIETNGETGEI  1072

Query:  1071  VWDKKKHFATVRKVLSYPQNNIVKKTEIQTGGFSKESILAHGNSDKLIPRKTKDIYLDPK  1130
              VWDK + FATVRKVLS PQ N+VKKTE+QTGGFSKESIL   NSDKLI RK  KD   DPK
Sbjct:  1073  VWDKGRDFATVRKVLSMPQVNIVKKTEVQTGGFSKESILPKRNSDKLIARK-KD--WDPK  1129

Query:  1131  KYGGFDSPIVAYSVLVVADIKKGKAQKLKTVTELLGITIMERSRFEKNPSAFLESKGYLN  1190
              KYGGFDSP VAYSVLVVA ++KGK++KLK+V ELLGITIMERS FEKNP  FLE+KGY
Sbjct:  1130  KYGGFDSPTVAYSVLVVAKVEKGKSKKLKSVKELLGITIMERSSFEKNPIDFLEAKGYKE  1189

Query:  1191  IRADKLIILPKYSLFELENGRRRLLASAGELQKGNELALPTQFMKFLYLASRYNESKGKP  1250
              ++ D +I LPKYSLFELENGR+R+LASAGELQKGNELALP++++ FLYLAS Y + KG P
Sbjct:  1190  VKKDLIIKLPKYSLFELENGRKRMLASAGELQKGNELALPSKYVNFLYLASHYEKLKGSP  1249

Query:  1251  EEIEKKQEFVNQHVSYFDDILQLINDFSKRVILADANLEKINKLYQDNKENISVDELANN  1310
              E+ E+KQ FV QH Y D+I++ I++FSKRVILADANL+K+   Y    +   + E AN
Sbjct:  1250  EDNEQKQLFVEQHKHYLDEIIEQISEFSKRVILADANLDKVLSAYNKHRDK-PIREQAEN  1308

Query:  1311  IINLFTFTSLGAPAAFKFFDKIVDRKRYTSTKEVLNSTLIHQSITGLYETRIDLGKLGED  1370
              II+LFT T+LGAPAAFK+FD  +DRKRYTSTKEVL++TLIHQSITGLYETRIDL +LG D
Sbjct:  1309  IIHLFTLTNLGAPAAFKYFDTTIDRKRYTSTKEVLDATLIHQSITGLYETRIDLSQLGGD  1368
```

Figure 27:
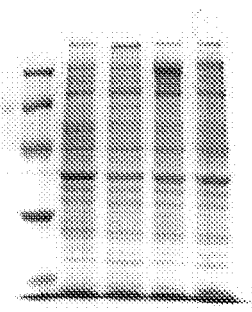
Figure 28:
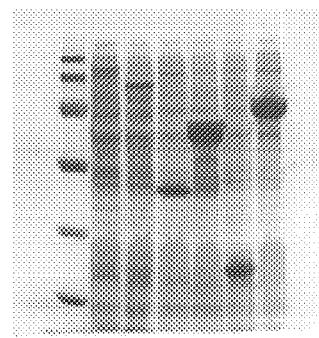
Figure 29:
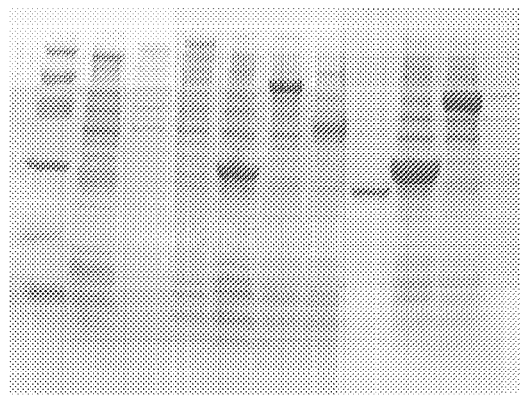
Figure 30:
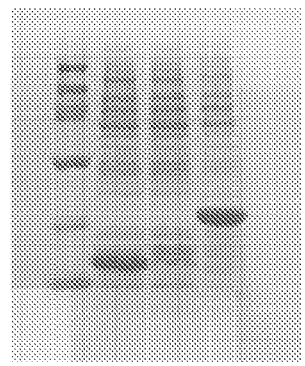
Figure 31:
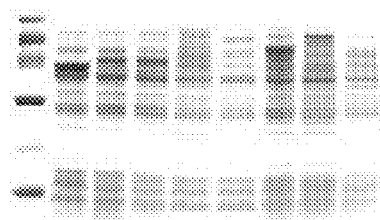
Figure 32:
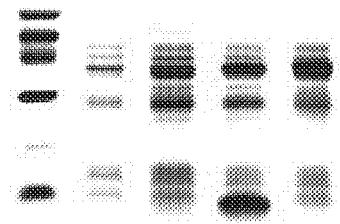
Figure 33:
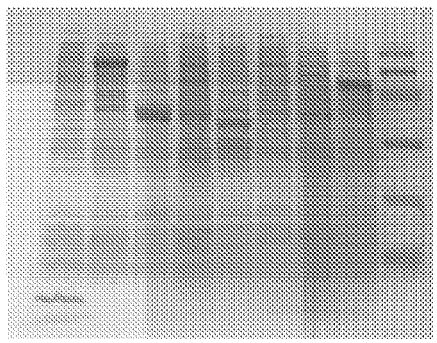
Figure 34:
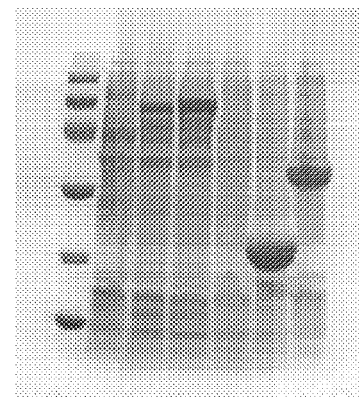
Figure 35:
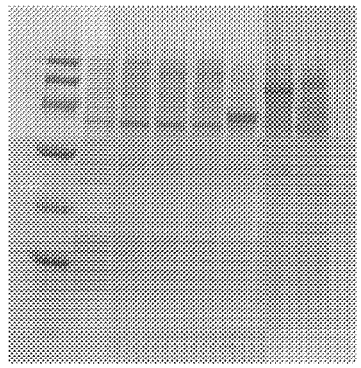
Figure 36:
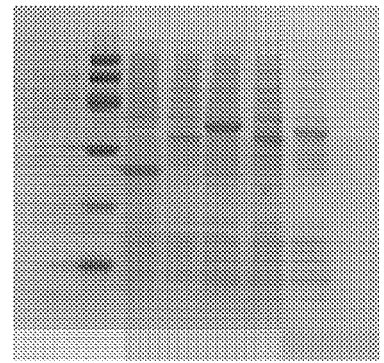
Figure 37:
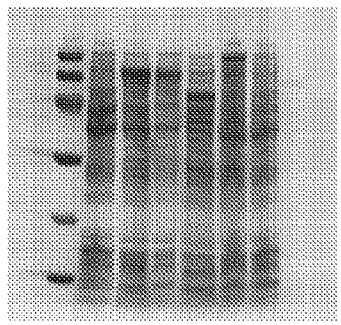
Figure 38:
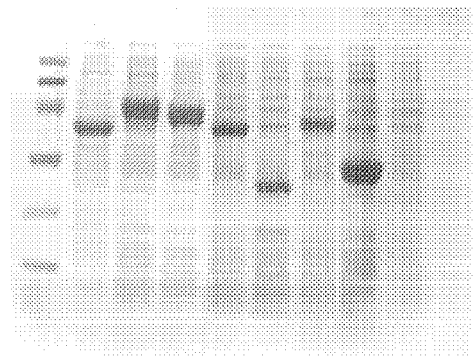
Figure 39:
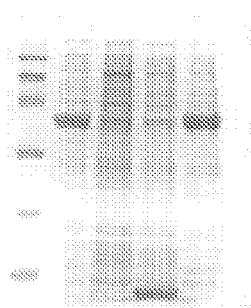
Figure 40:
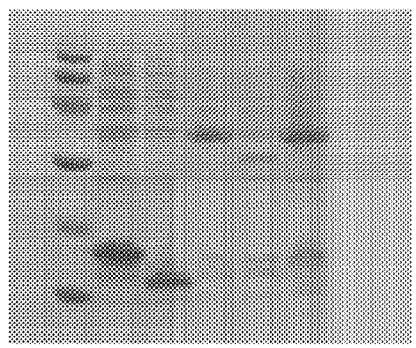
Figure 41:
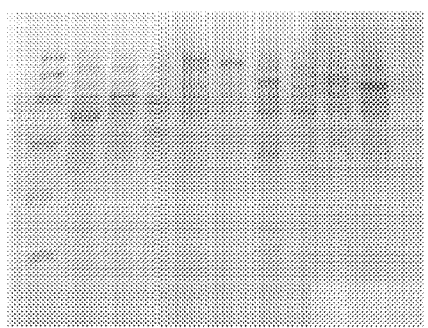
Figure 42:
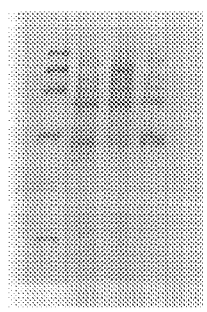
Figure 43:
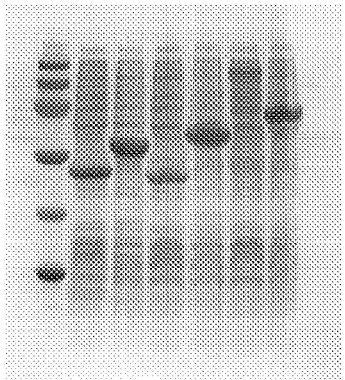
Figure 44:
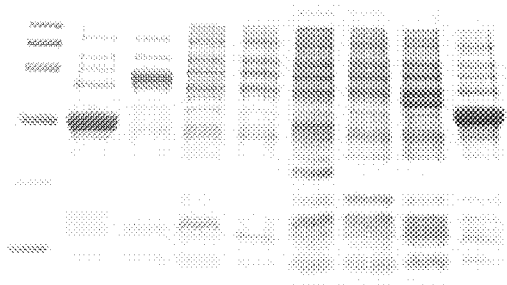
Figure 45:
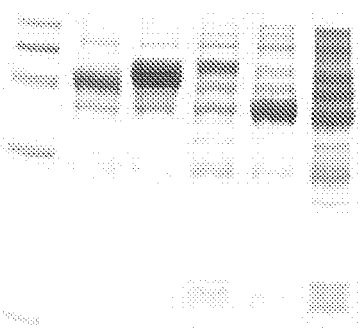
Figure 46:
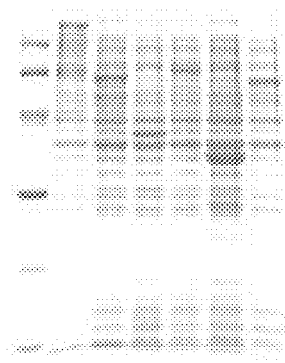
Figure 47:
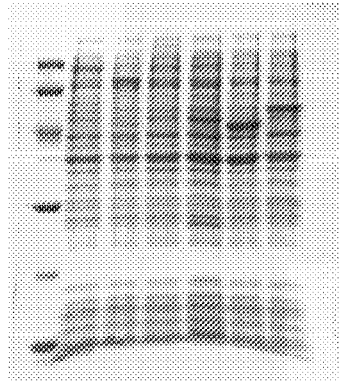
Figure 48:
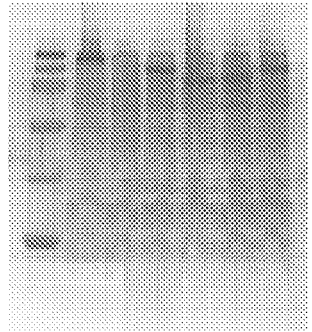
Figure 49:
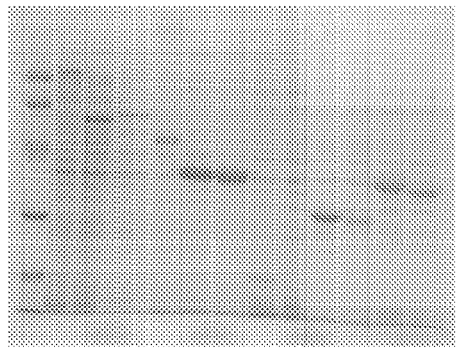
Figure 50:
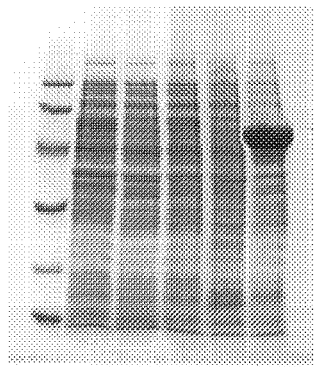
Figure 51:
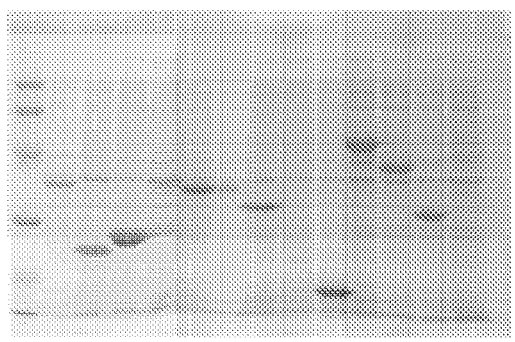
Figure 52:
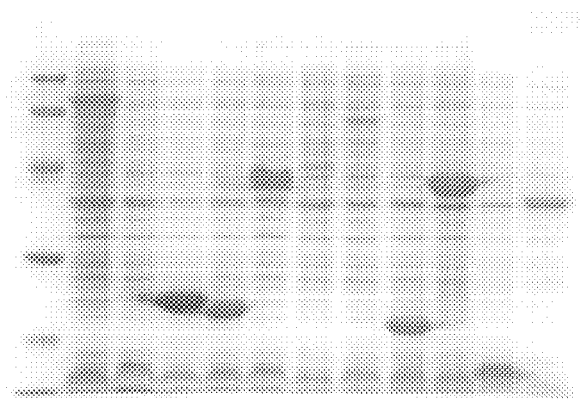
Figure 53:
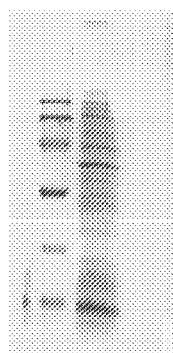
Figure 54:
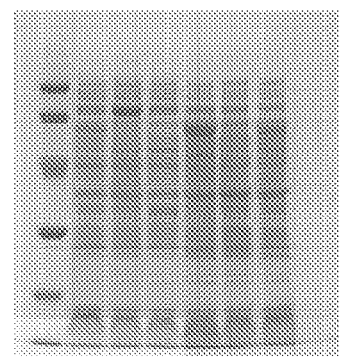
Figure 55:
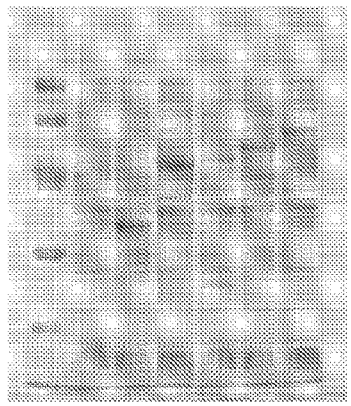
Figure 56:
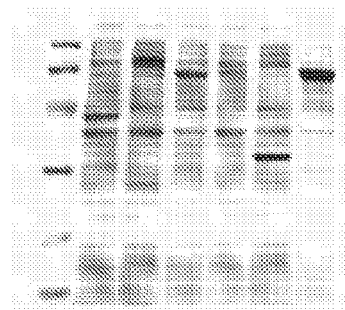
Figure 57:
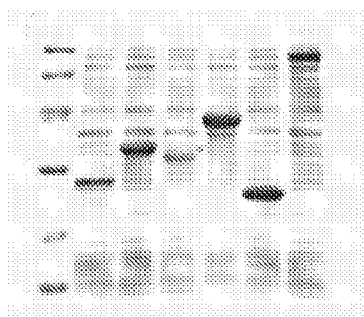
Figure 58:
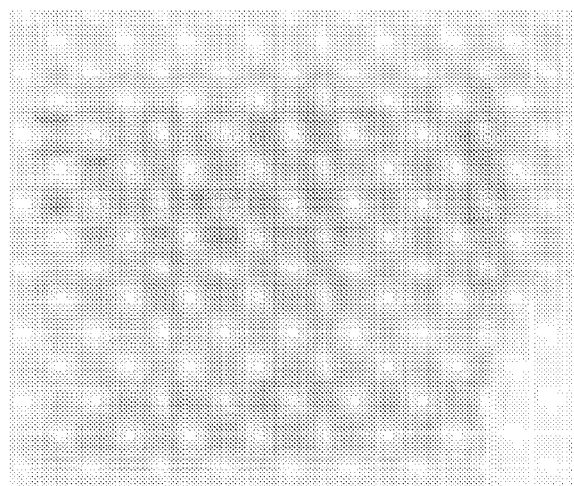
Figure 59:
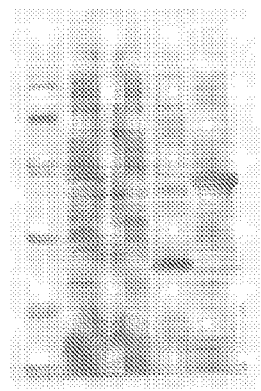
Figure 60:
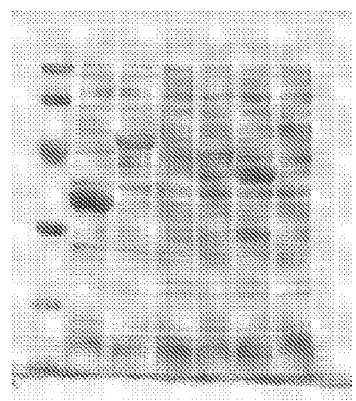
Figure 61:
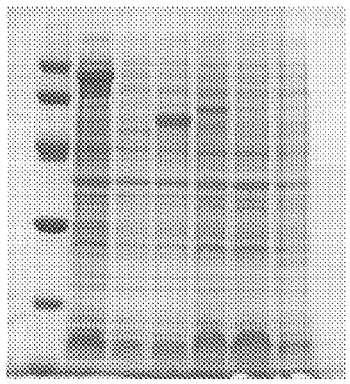
Figure 62:
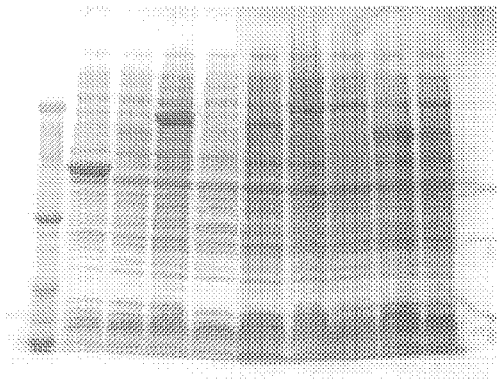
Figure 63:
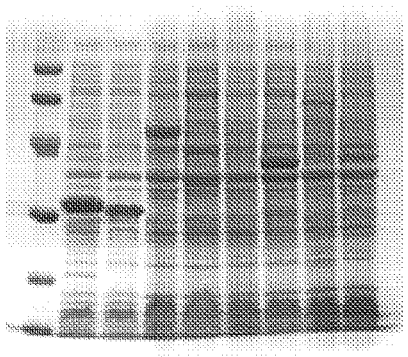
Figure 64:
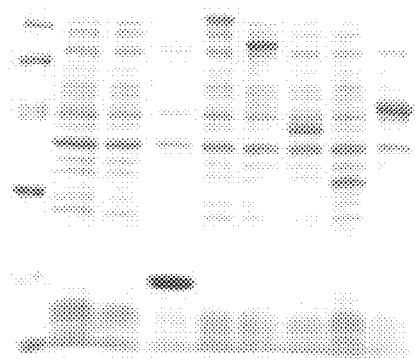
Figure 65:
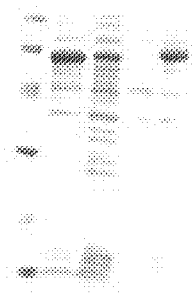
Figure 66:
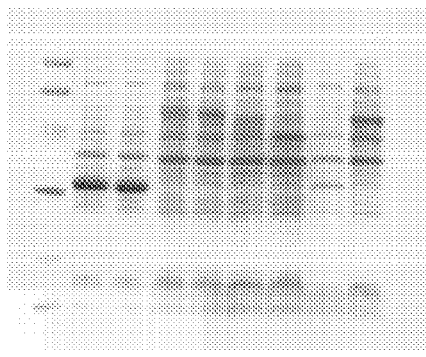
Figure 67:
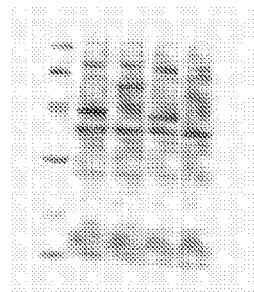
Figure 68:
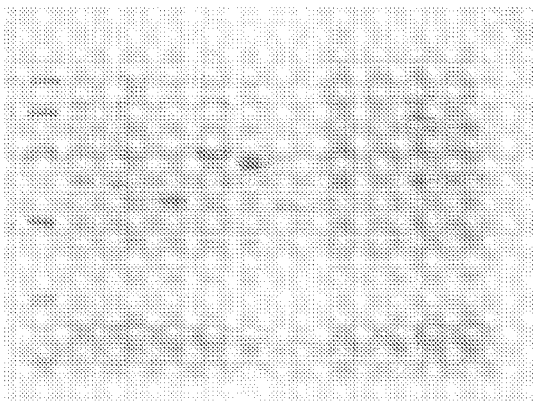
Figure 69:
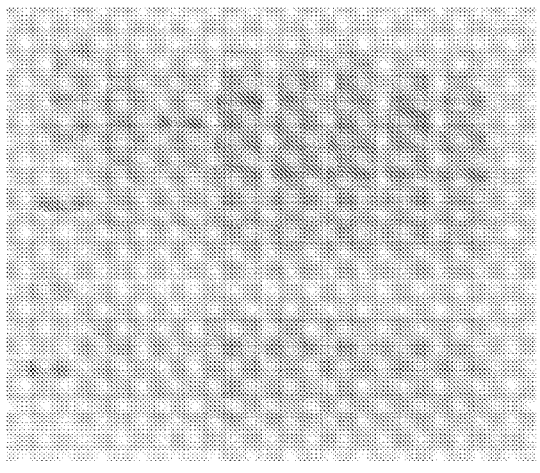
Figure 70:
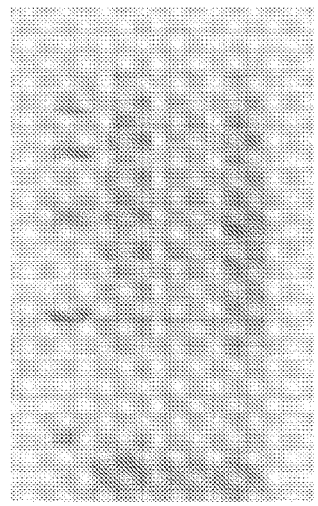
Figure 71:
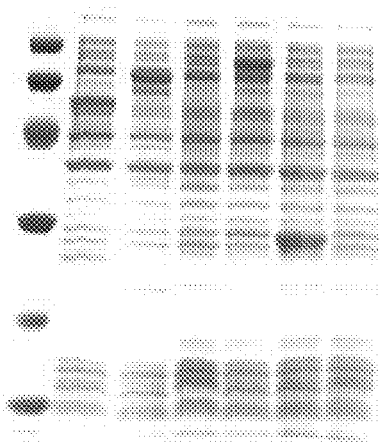
Figure 72:
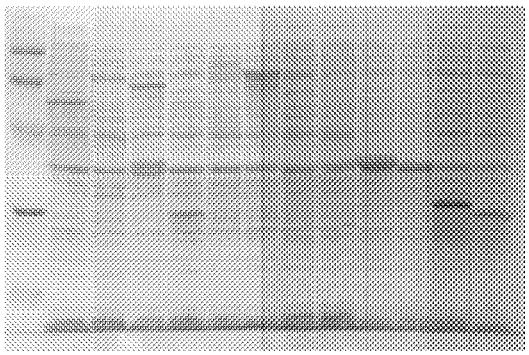
Figure 73:
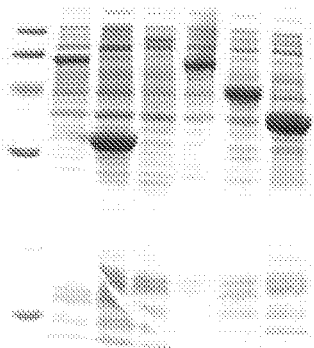
Figure 74:
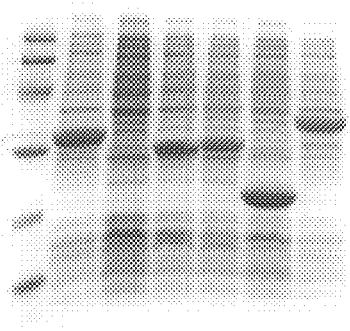
Figure 75:
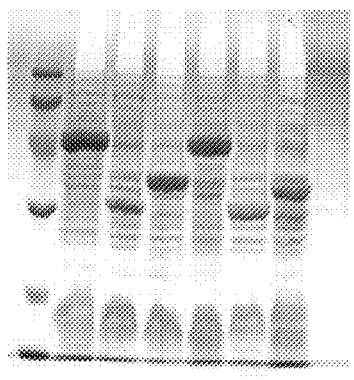
Figure 76:
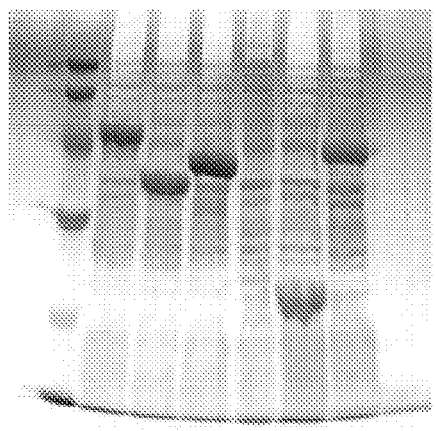
Figure 77:
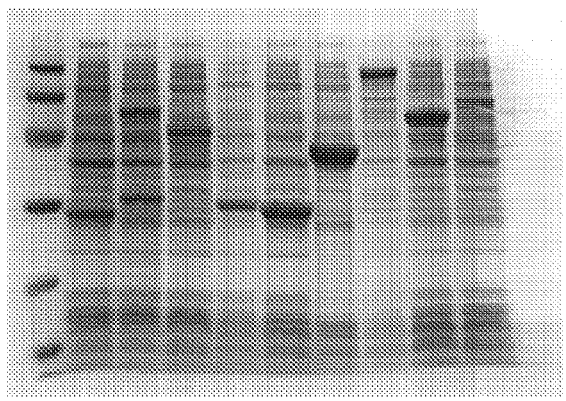
Figure 78:
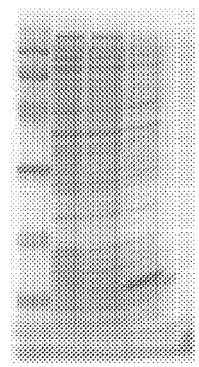
Figure 79:
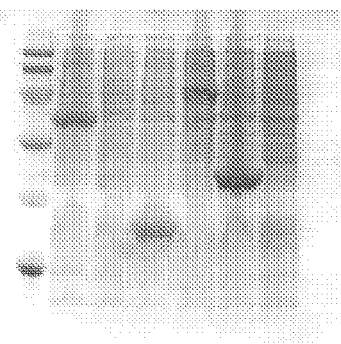
Figure 80:
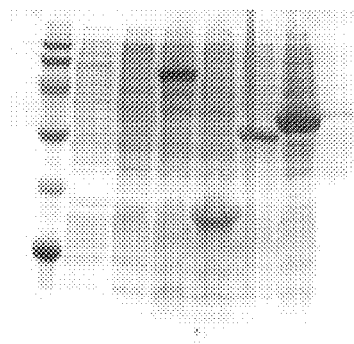
Figure 81:
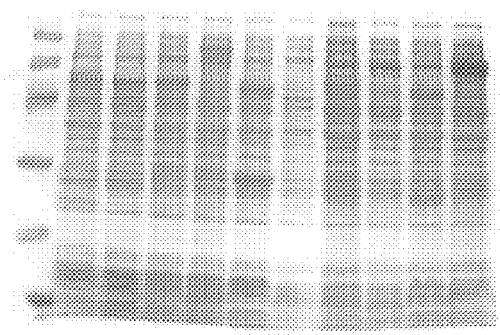
Figure 82:
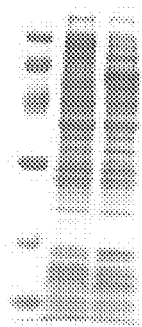
Figure 83:
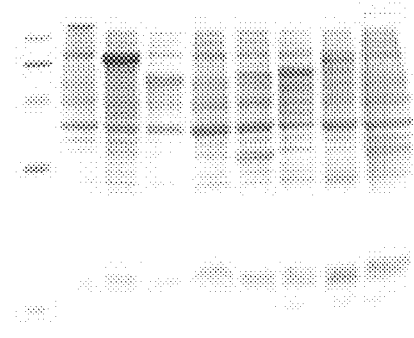
Figure 84:
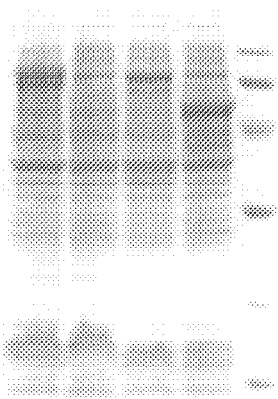
Figure 85:
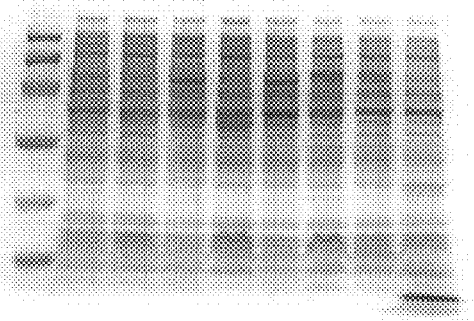
Figure 159:
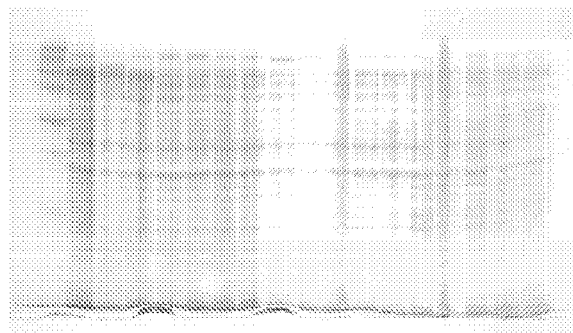
Figure 160:
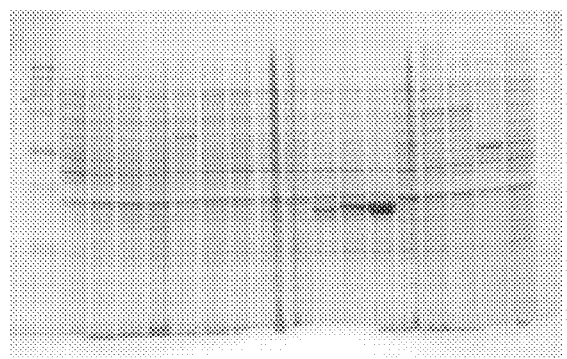
Figure 161:
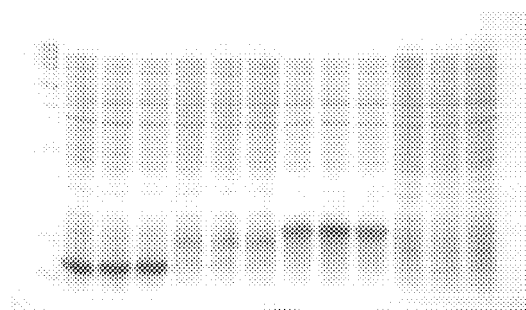
Figure 162:
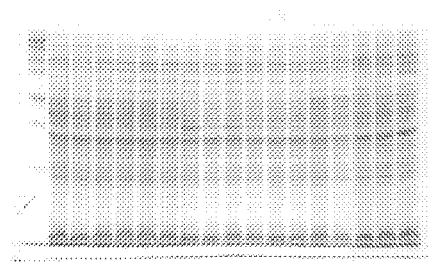
Figure 163:
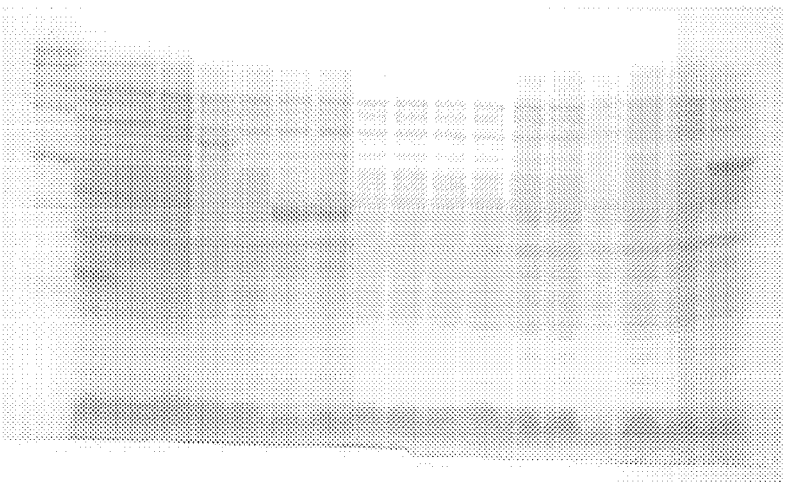
Figure 164:
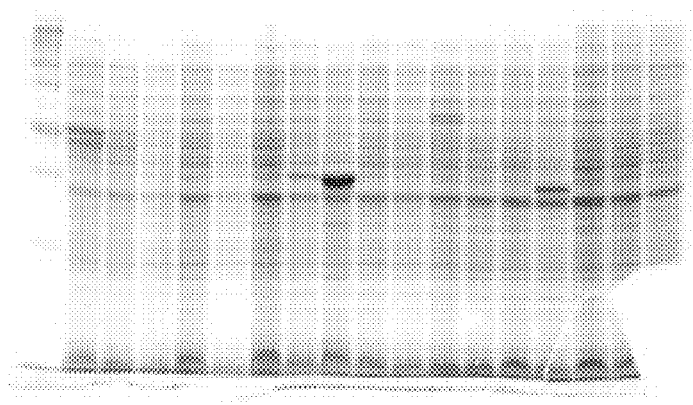
Figure 165:
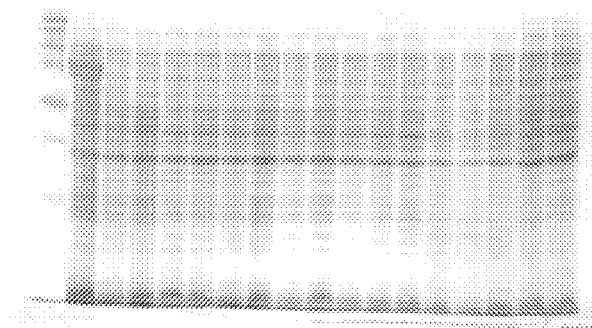

SEQ ID 4210 (GBS317) was expressed in *E. coli* as a GST-fusion product. SDS-PAGE analysis of total cell extract is shown in FIG. 27 (lane 2; MW 179.3 kDa) and in FIG. 159 (lane 5 & 6; MW 180 kDa). It was also expressed in *E. coli* as a His-fusion product. SDS-PAGE analysis of total cell extract is shown in FIG. 27 (lane 3; MW 154.3 kDa) and in FIG. 159 (lane 9 & 10; MW 154 kDa).

Figure 222:
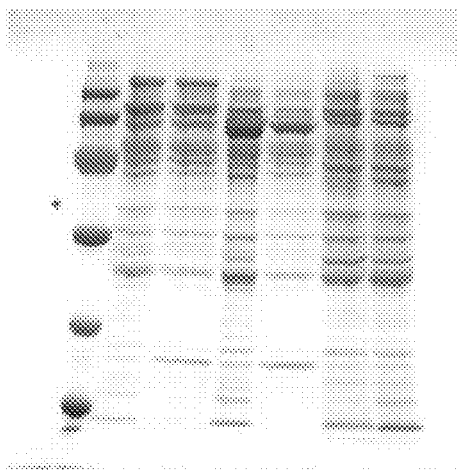
Figure 223:
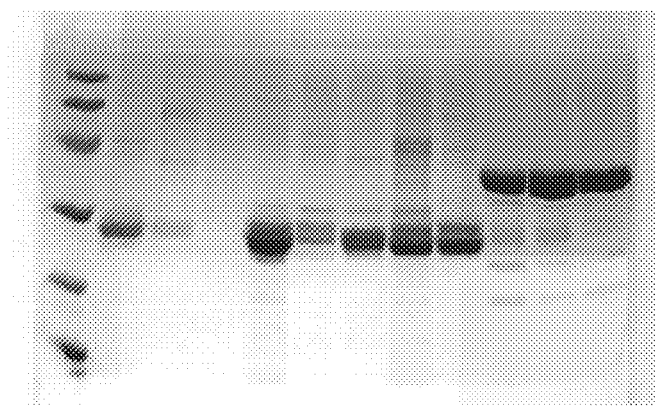
Figure 224:
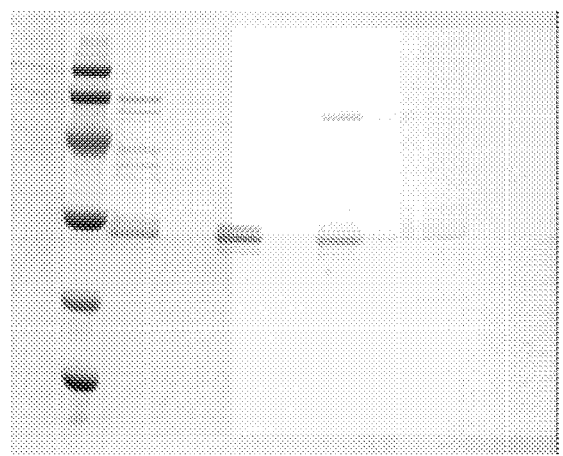
Figure 225:
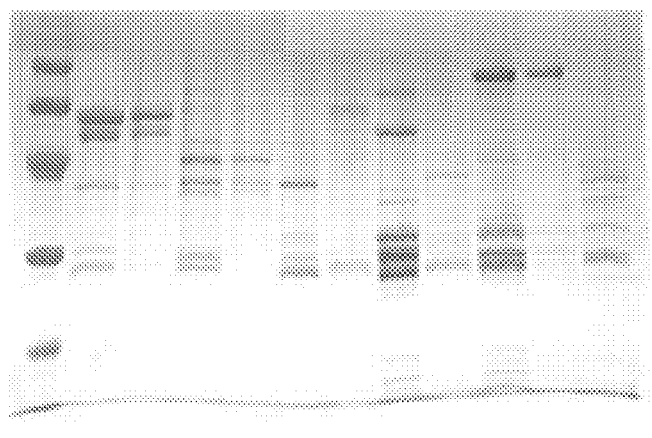
Figure 226:
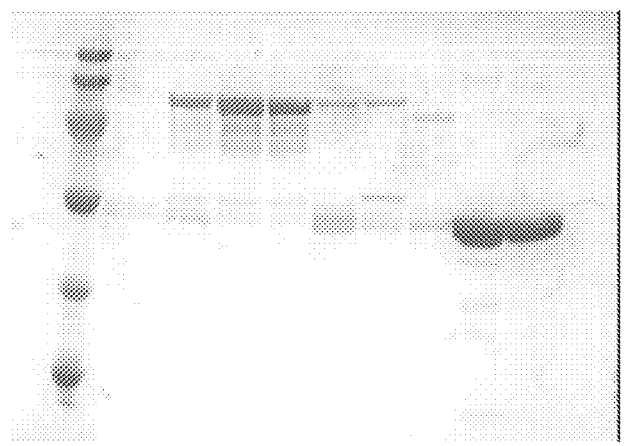
Figure 227:
Figure 228:
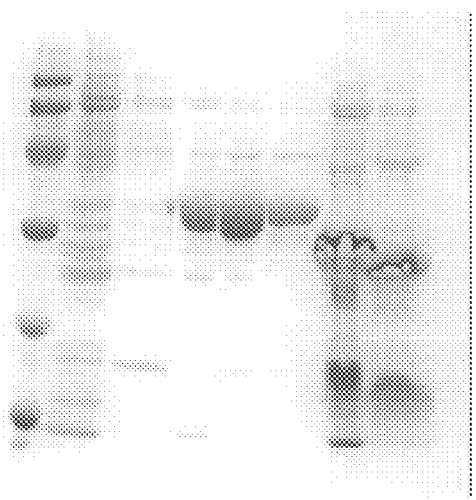
Figure 229:
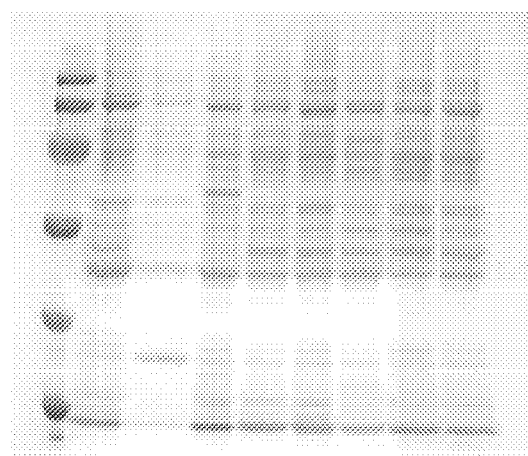
Figure 230:
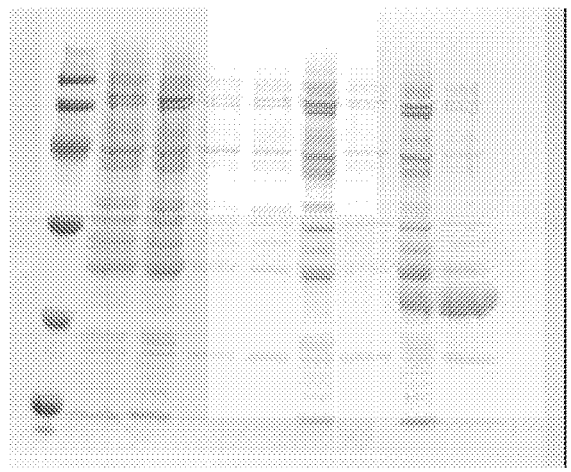
Figure 231:
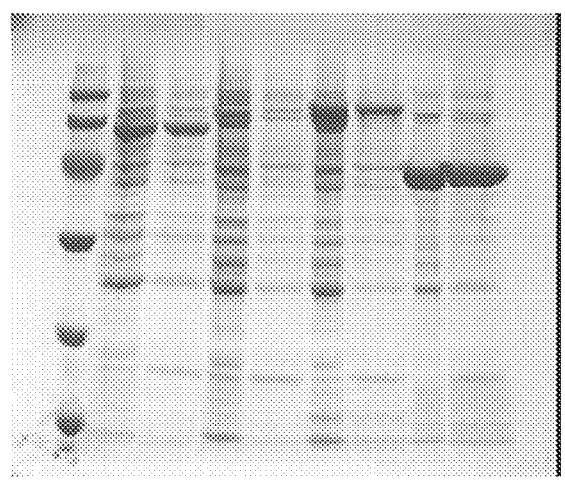
Figure 232:
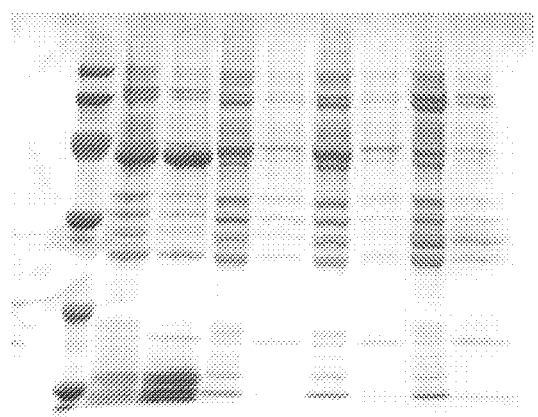
Figure 233:
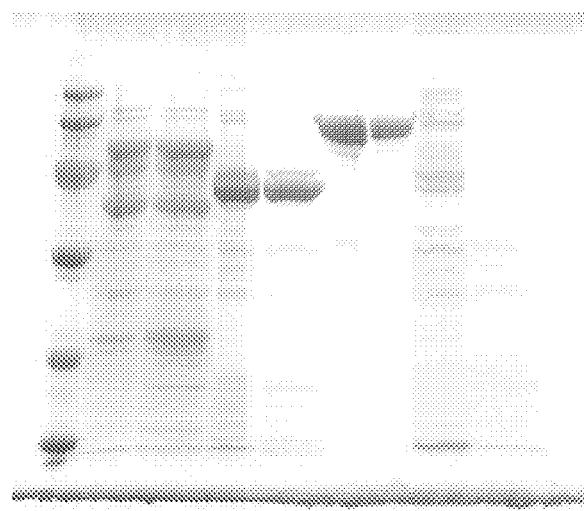
Figure 234:
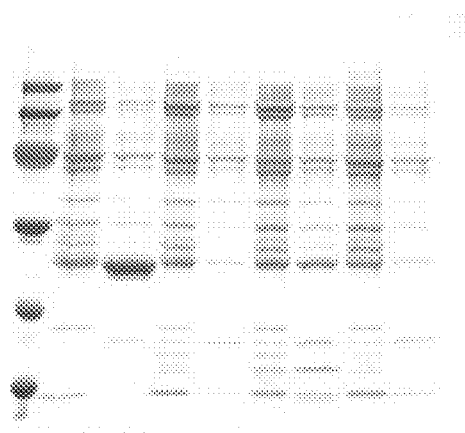
Figure 235:
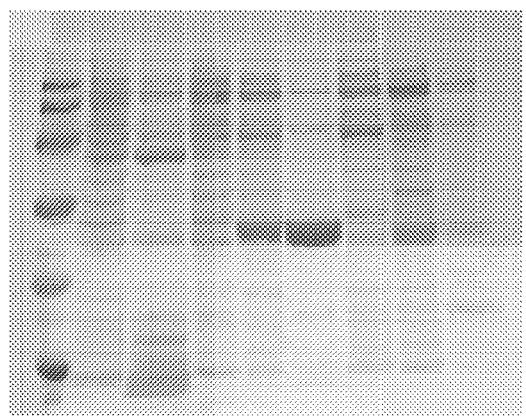
Figure 236:
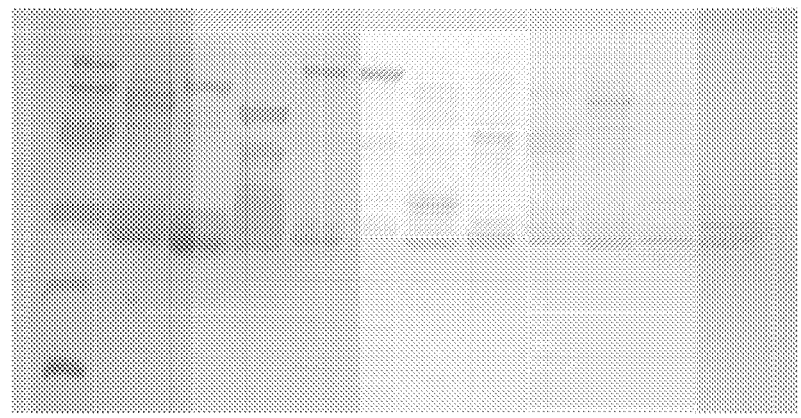
Figure 237:
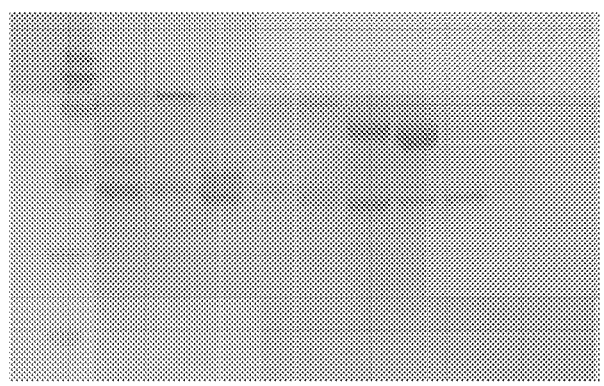
Figure 238:
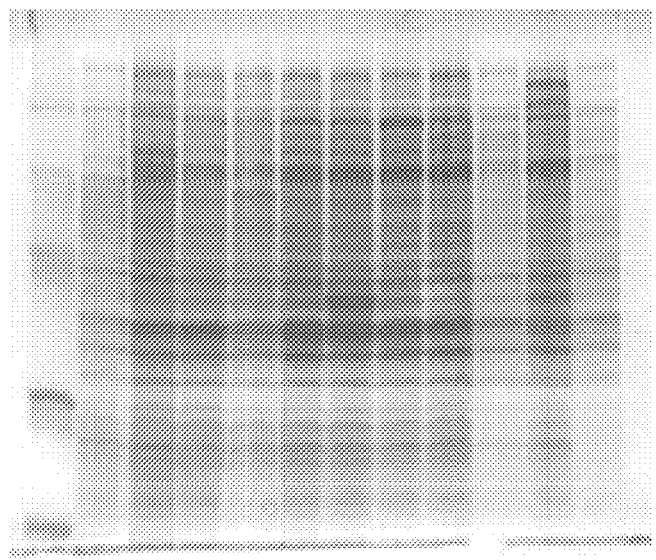
Figure 239:
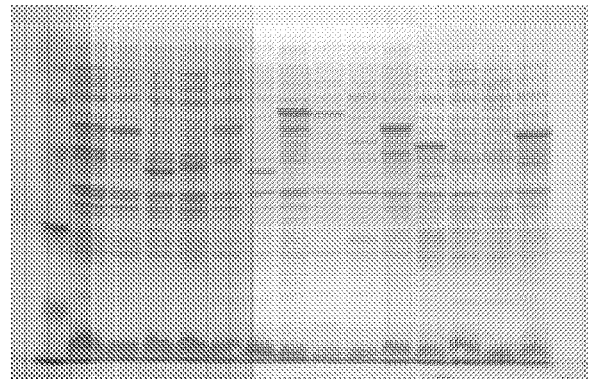
Figure 240:
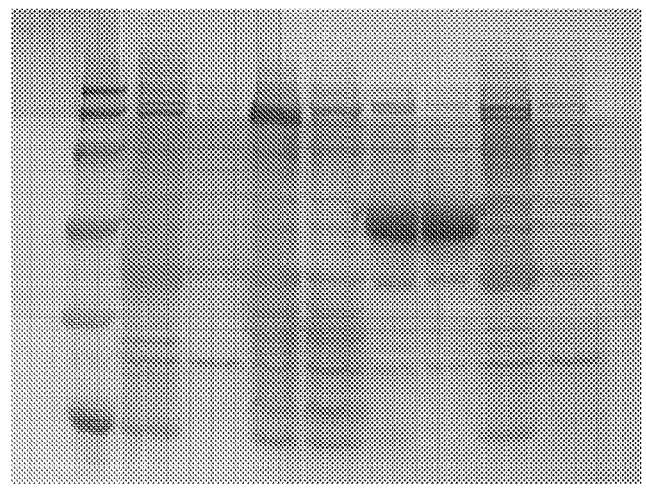
Figure 241:
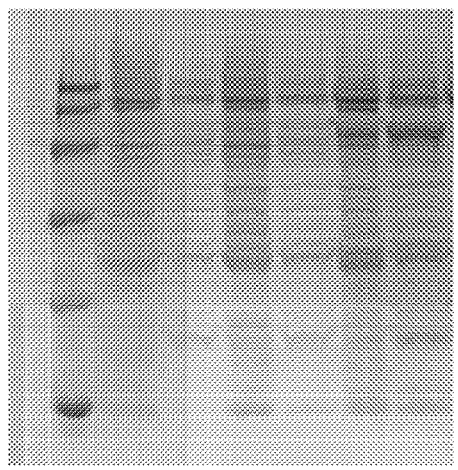
Figure 242:
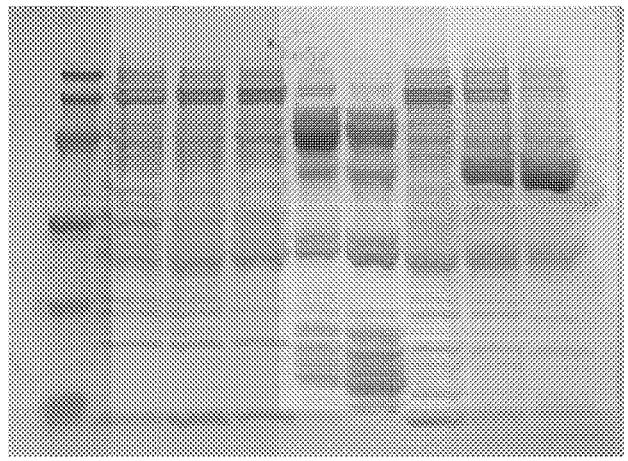
Figure 243:
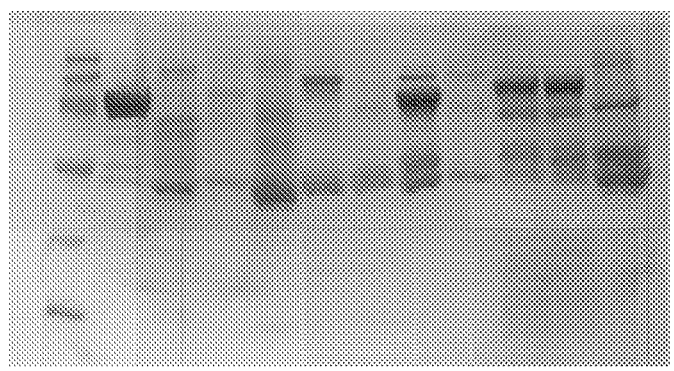
Figure 244:
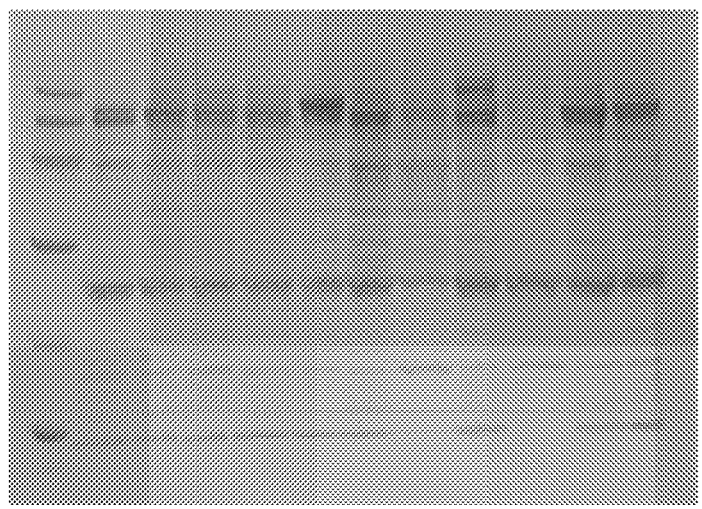

GBS317-GST was purified as shown in FIG. 224, lane 9-10. GBS317-His was purified as shown in FIG. 222, lane 9.

Figure 149:
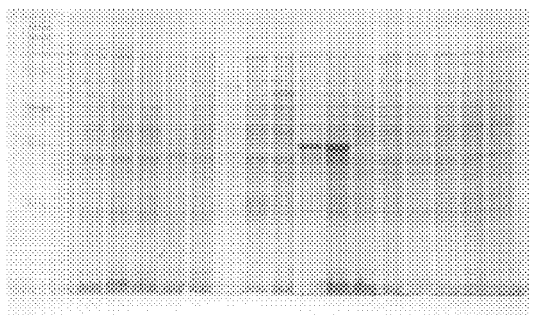
Figure 150:
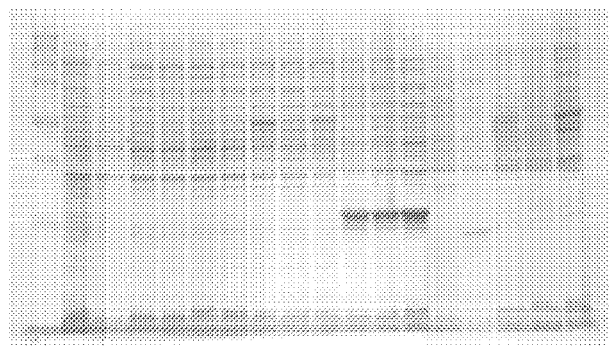
Figure 151:
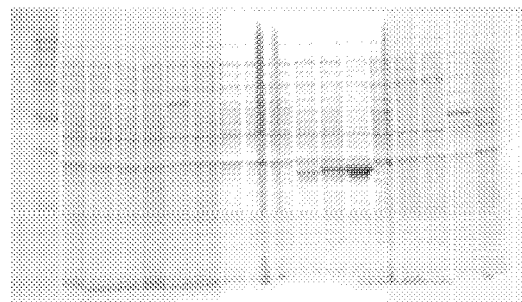
Figure 152:
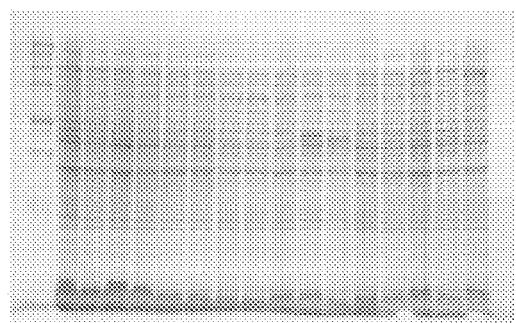
Figure 153:
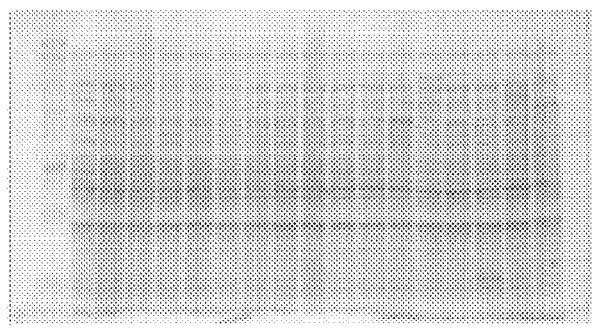
Figure 154:
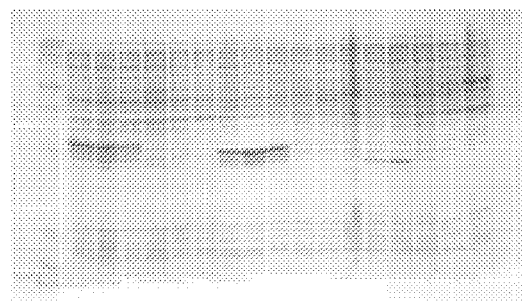
Figure 155:
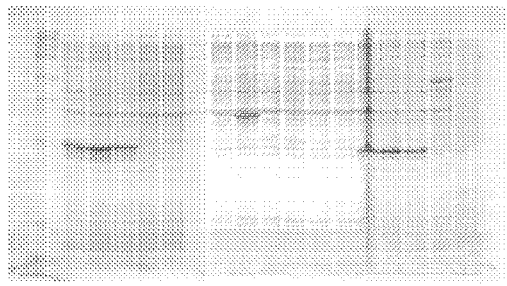
Figure 156:
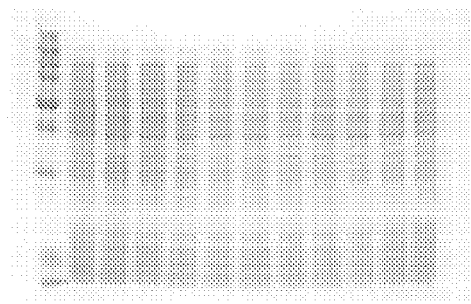
Figure 157:
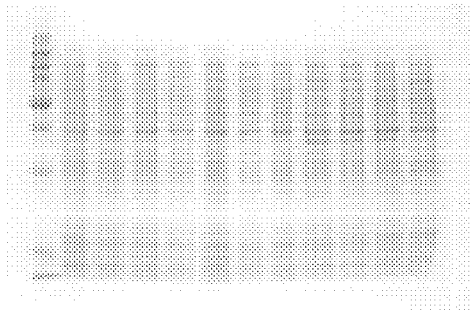
Figure 158:
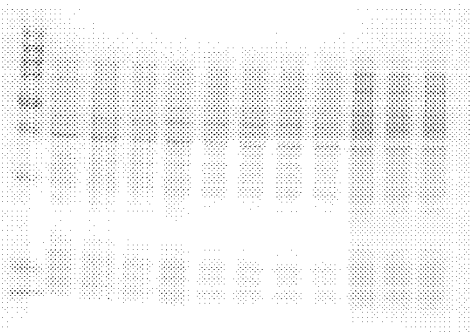

GBS317N was expressed in *E. coli* as a GST-fusion product. SDS-PAGE analysis of total cell extract is shown in FIG. 149 (lane 2-4; MW 116 kDa).

Figure 166:
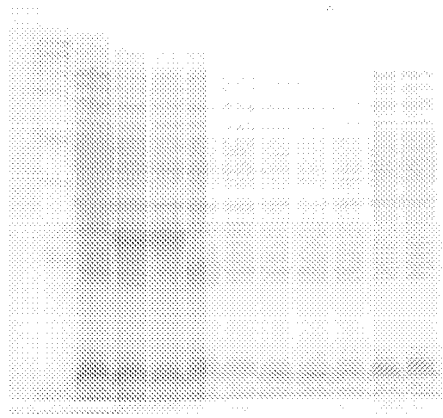
Figure 167:
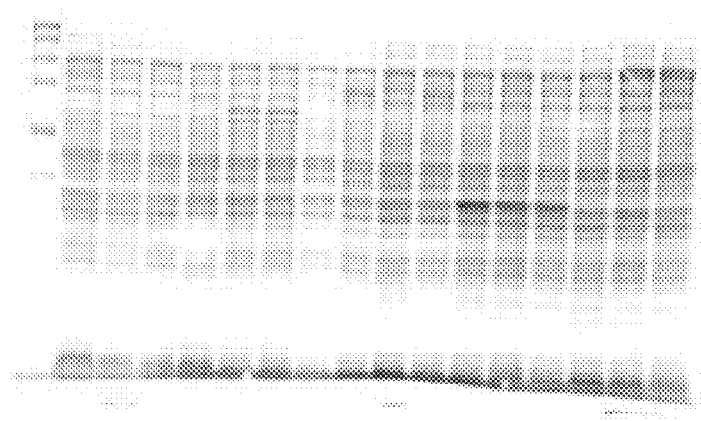
Figure 168:
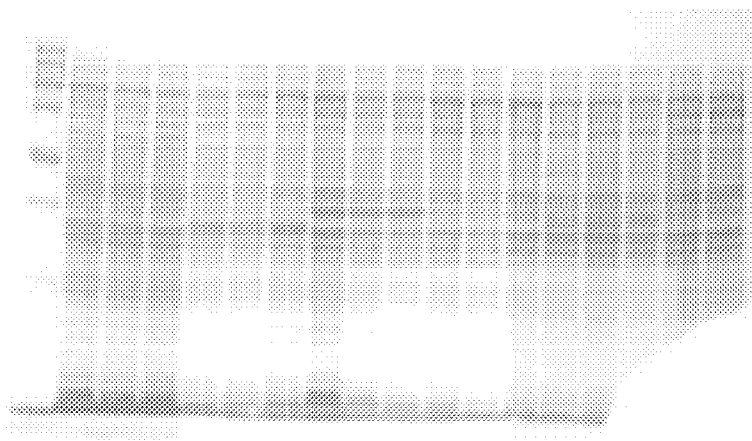
Figure 169:
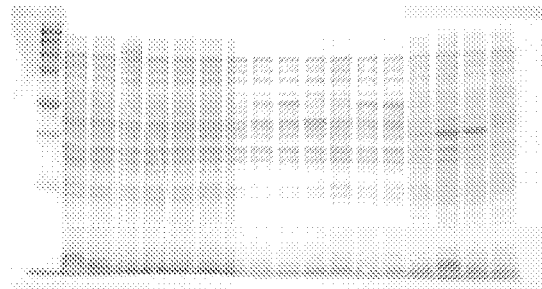
Figure 170:
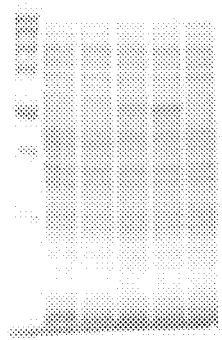
Figure 171:
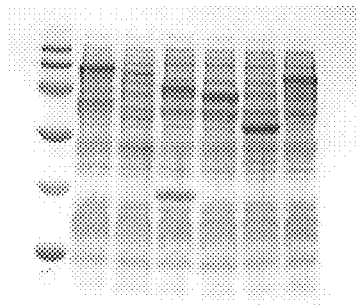
Figure 172:
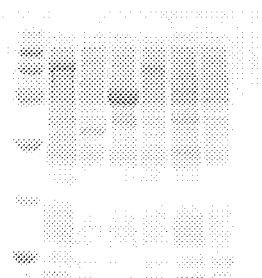
Figure 173:
Figure 174:
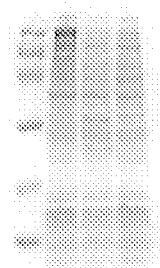
Figure 175:
Figure 176:
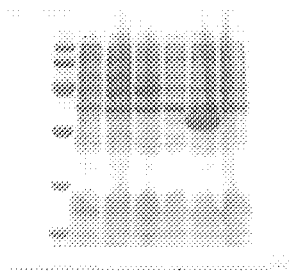
Figure 177:
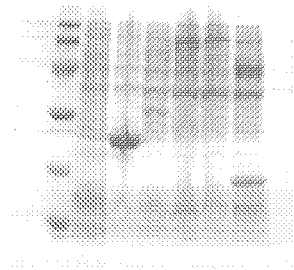
Figure 178:
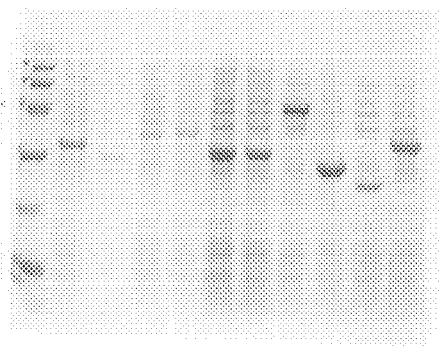
Figure 179:
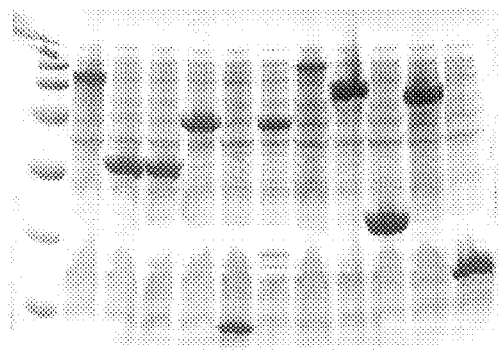
Figure 180:
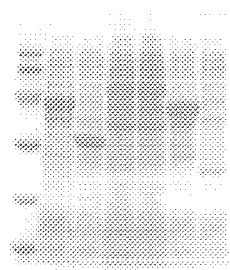
Figure 181:
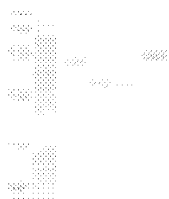
Figure 182:
Figure 183:
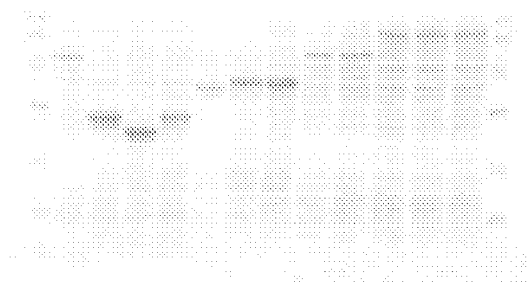
Figure 184:
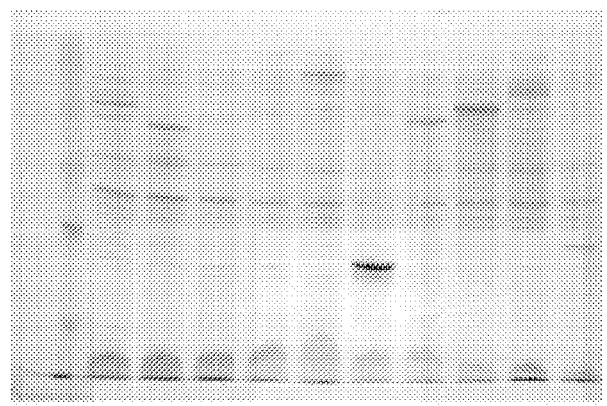
Figure 185:
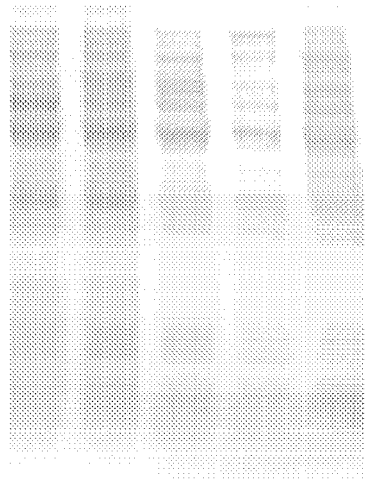
Figure 186:
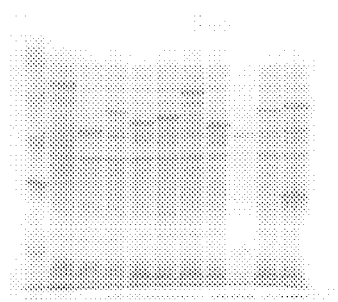

GBS317C was expressed in *E. coli* as a GST-fusion product. SDS-PAGE analysis of total cell extract is shown in FIG. 166 (lane 6-8; MW 92 kDa).

Figure 187:
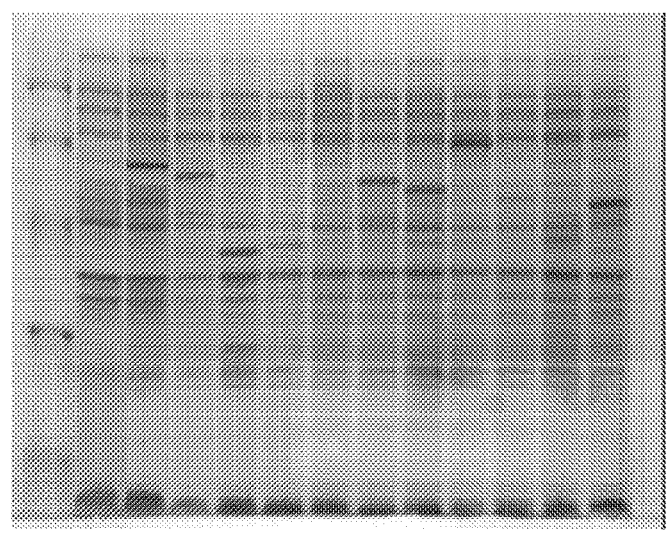
Figure 245:
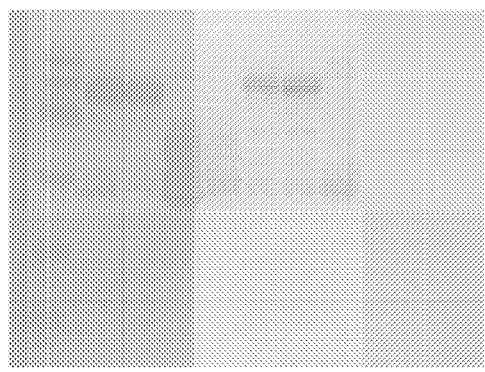
Figure 246:
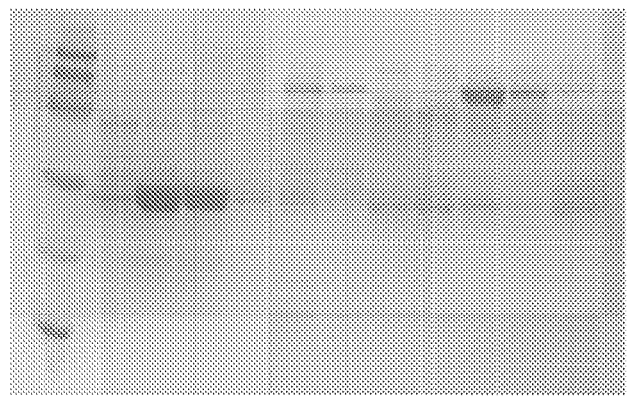
Figure 247:
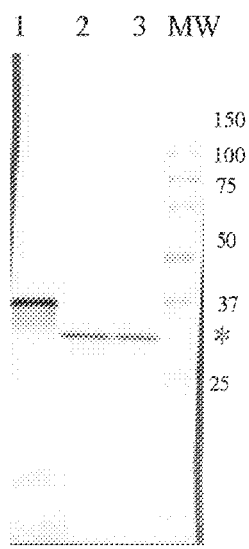
Figure 259A:
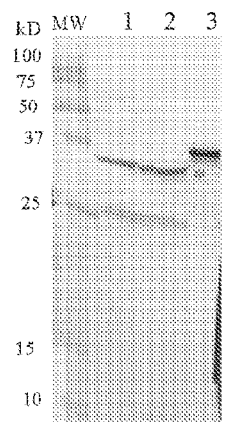
Figure 259B:
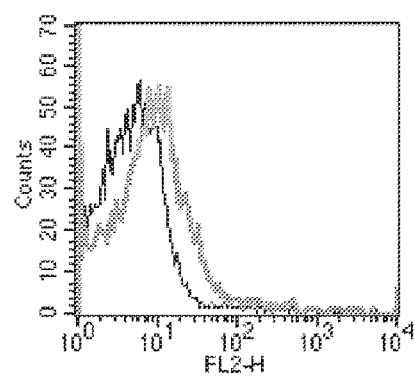
Figure 260:
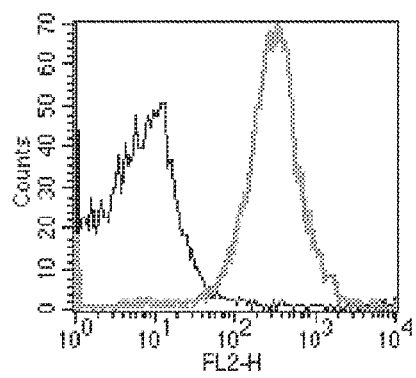
Figure 261:
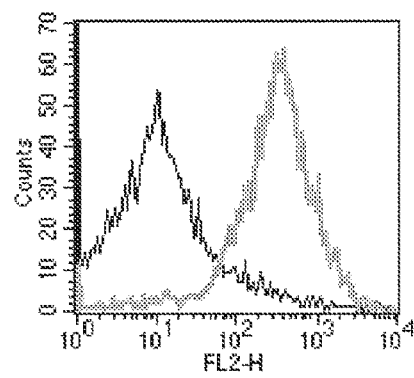
Figure 262:
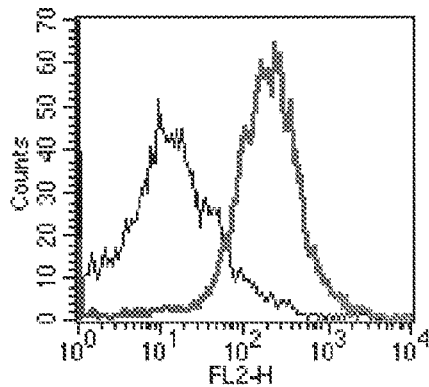
Figure 263:
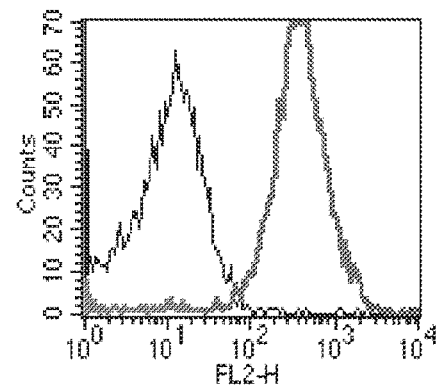
Figure 264:
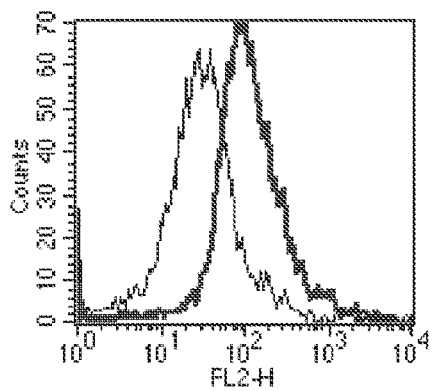
Figure 265:
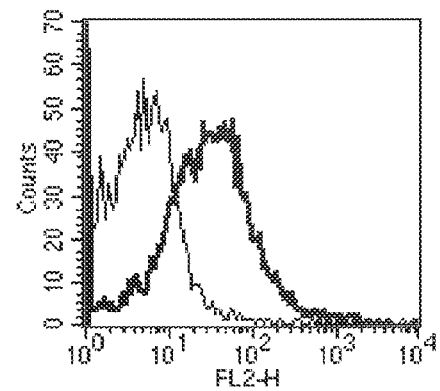
Figure 266:
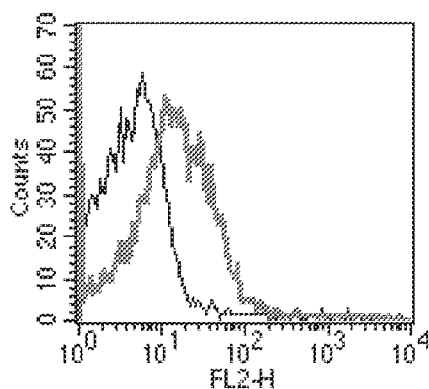
Figure 267:
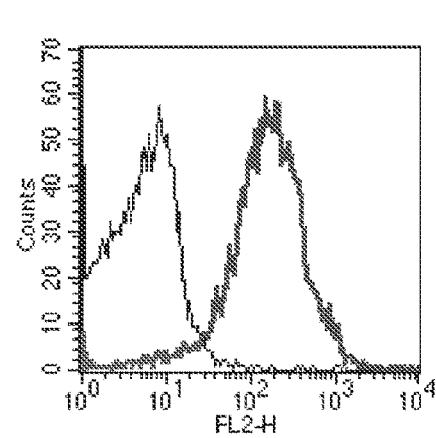
Figure 268:
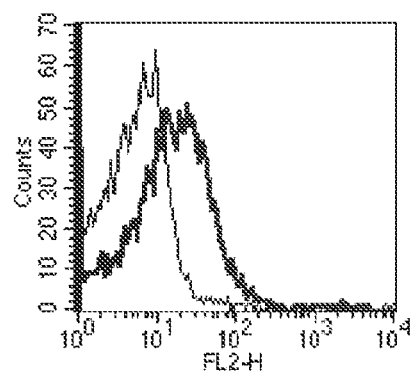
Figure 269:
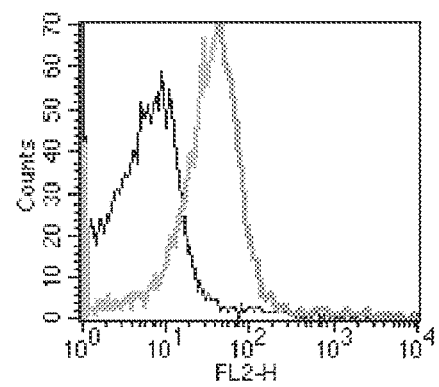
Figure 270:
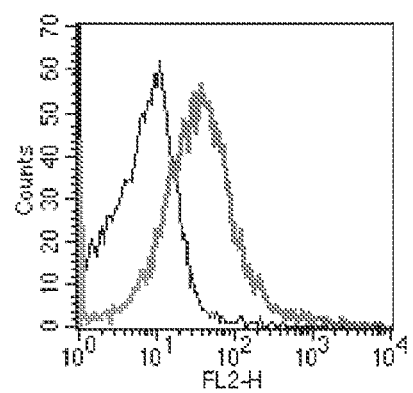
Figure 271:
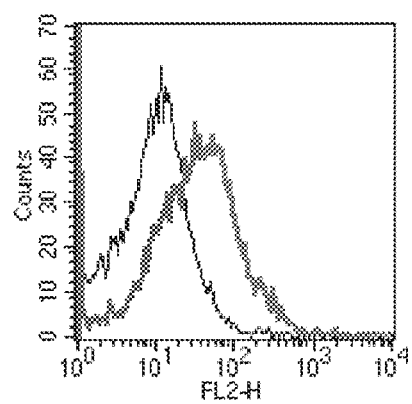
Figure 272:
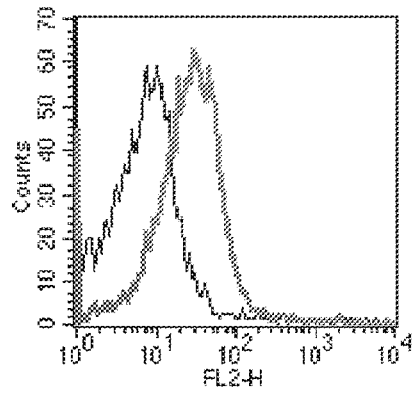
Figure 273:
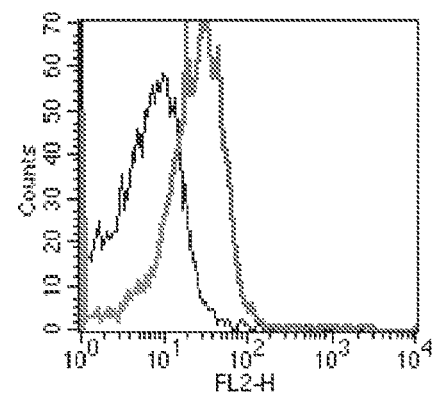
Figure 274:
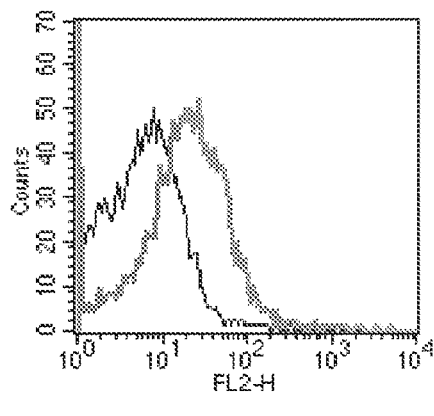
Figure 275:
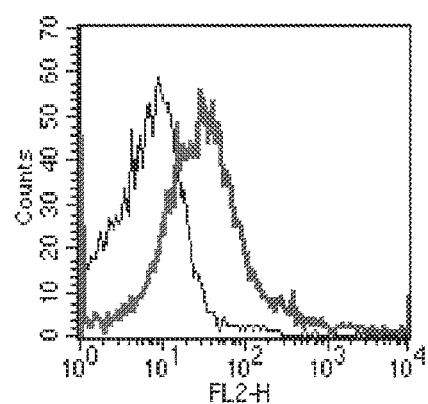
Figure 276:
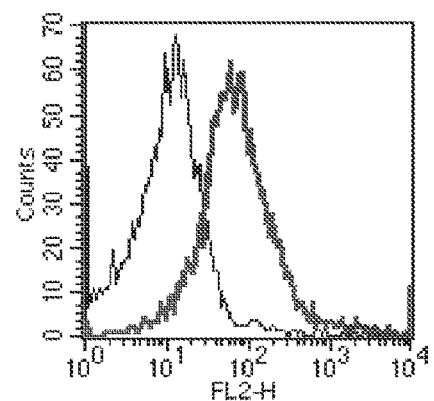
Figure 277:
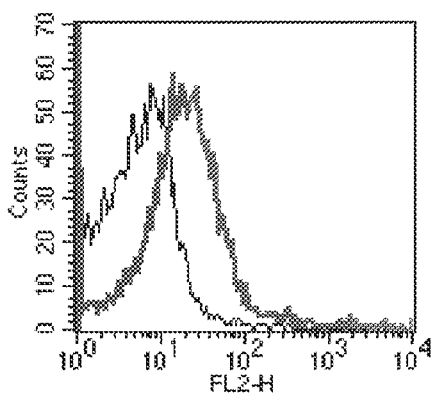
Figure 278:
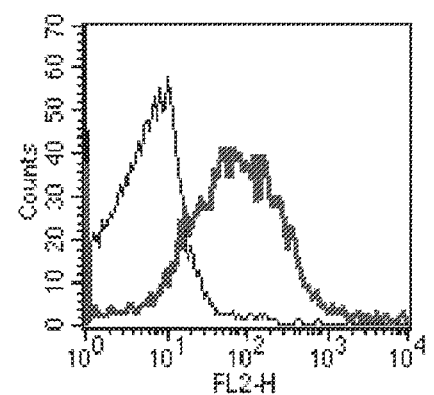
Figure 279:
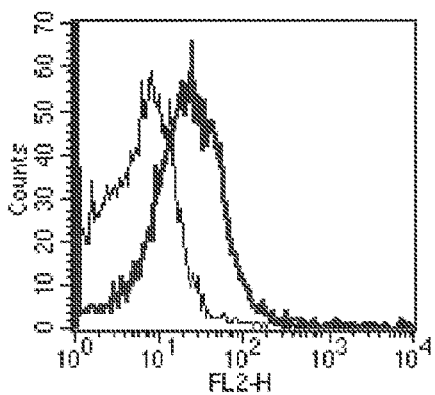
Figure 280:
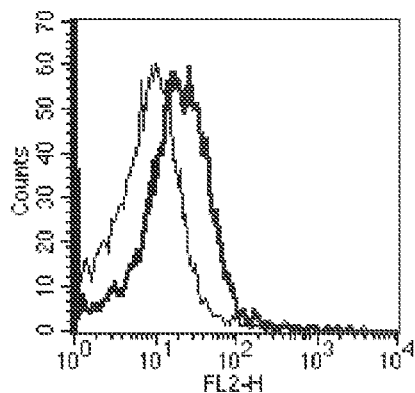
Figure 281:
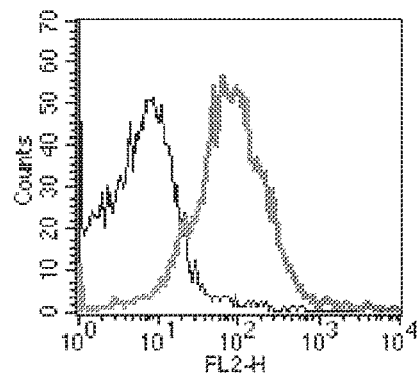
Figure 282:
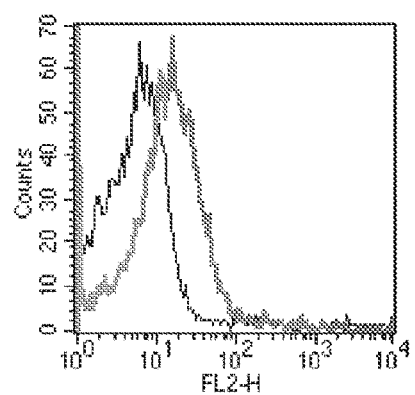
Figure 283:
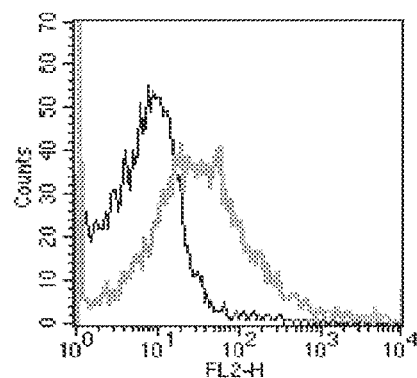
Figure 284:
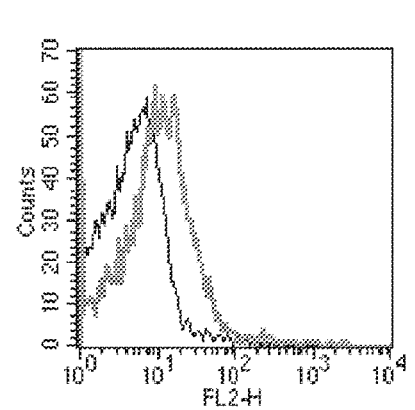
Figure 285:
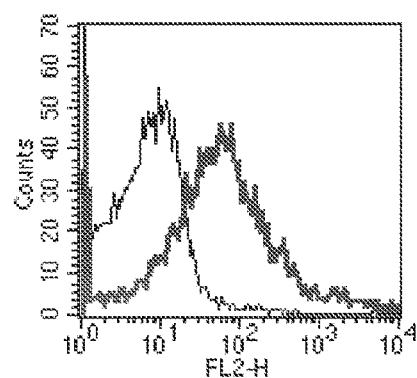
Figure 286:
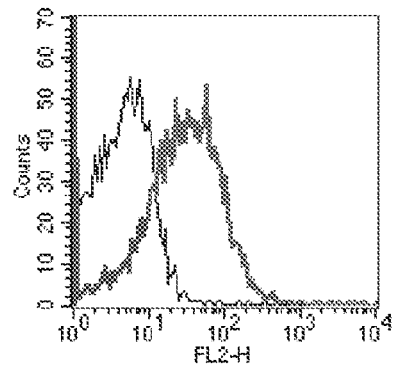
Figure 287:
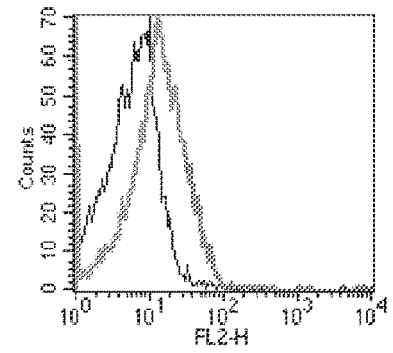
Figure 288:
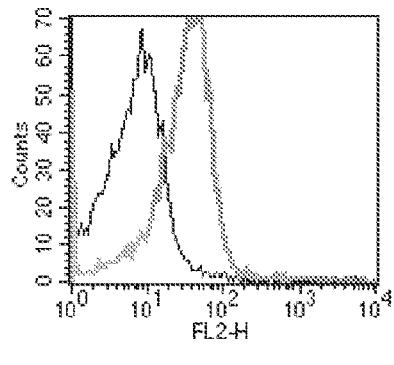
Figure 289:
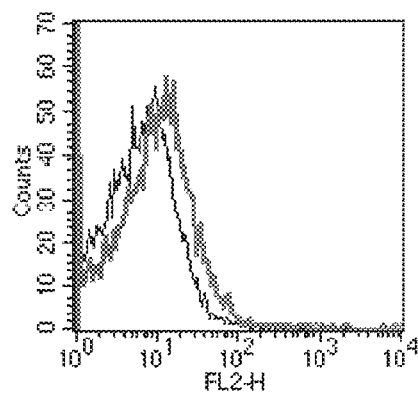
Figure 290:
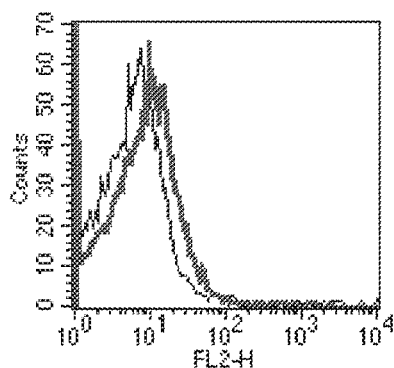
Figure 291:
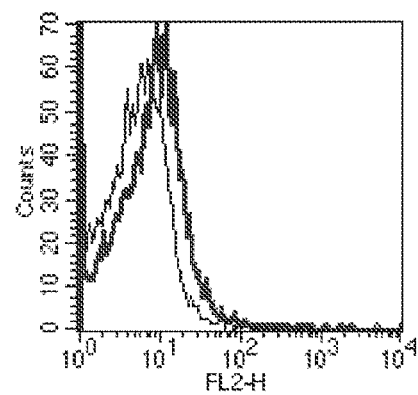
Figure 292:
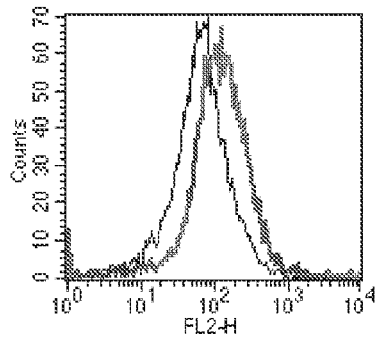
Figure 293:
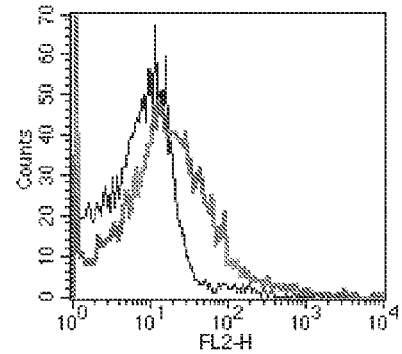
Figure 294:
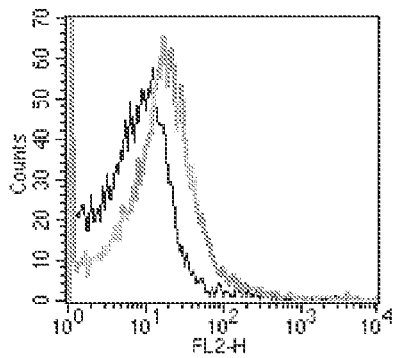
Figure 295:
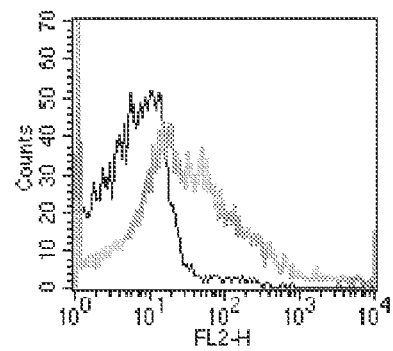
Figure 296:
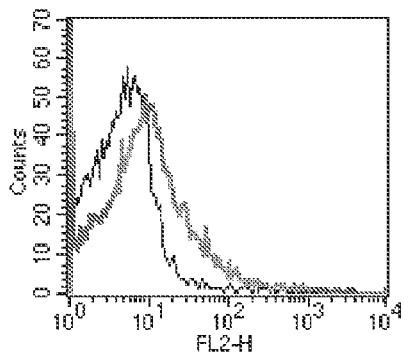
Figure 297:
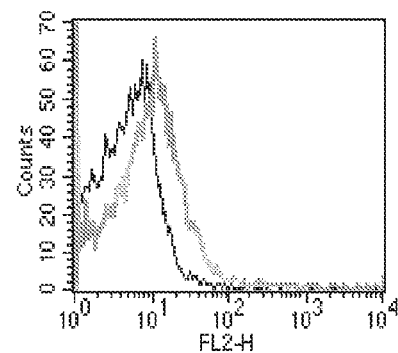
Figure 298:
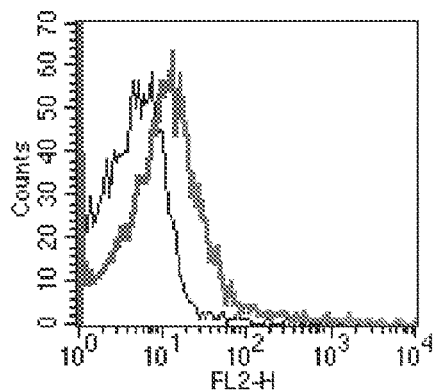
Figure 299:
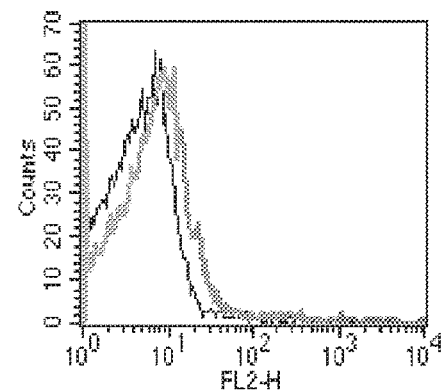
Figure 300:
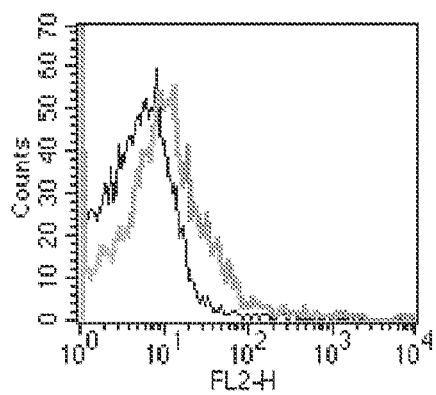
Figure 301:
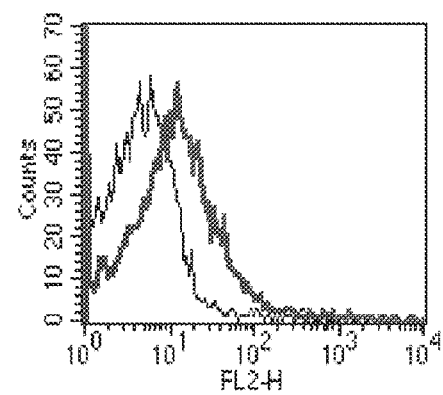
Figure 302:
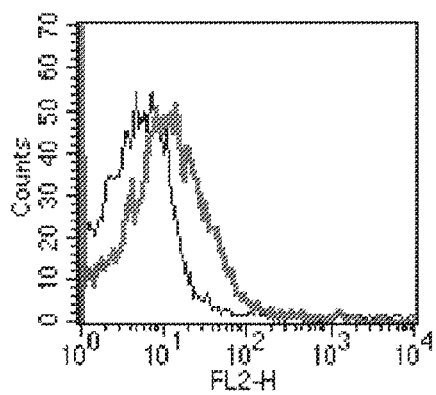
Figure 303:
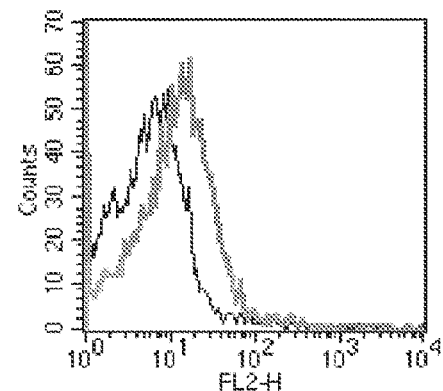
Figure 304:
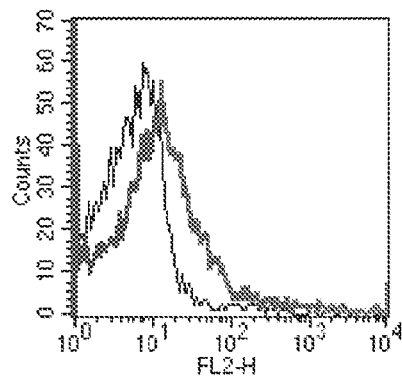
Figure 305:
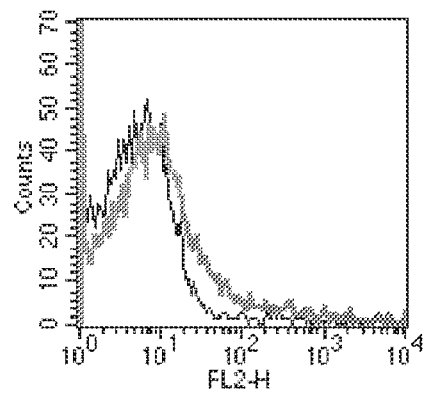
Figure 306:
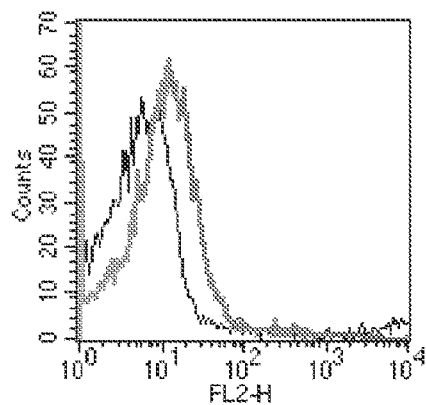
Figure 307:
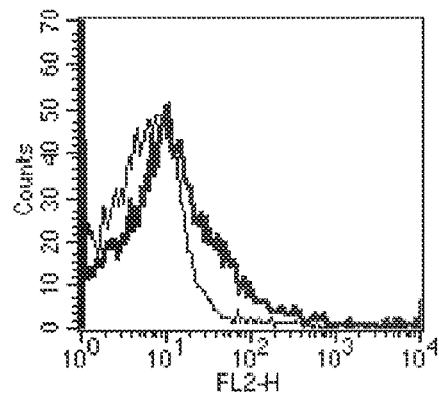
Figure 308:
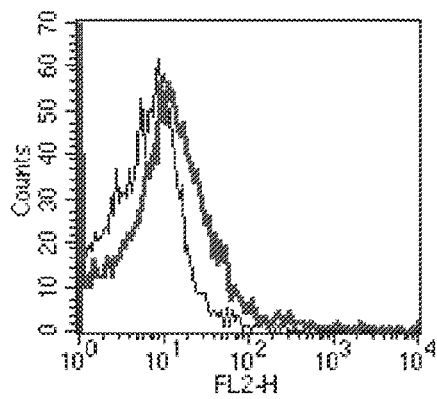
Figure 309:
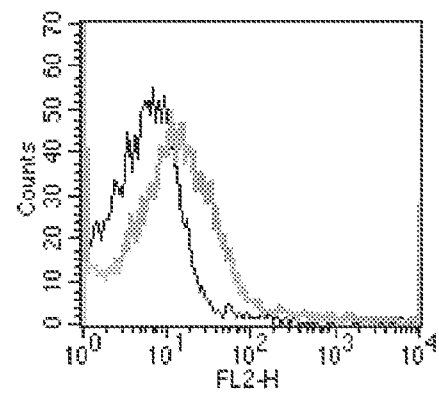
Figure 310:
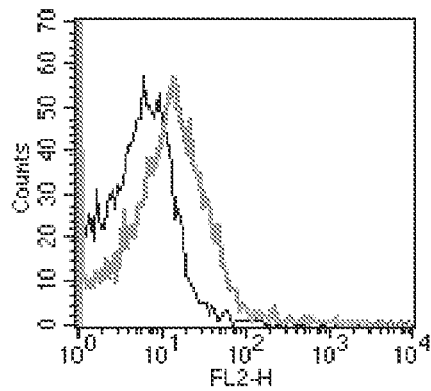
Figure 311:
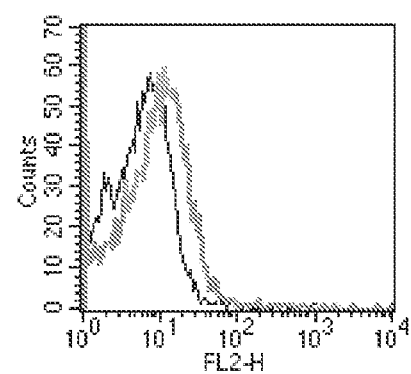
Figure 312:
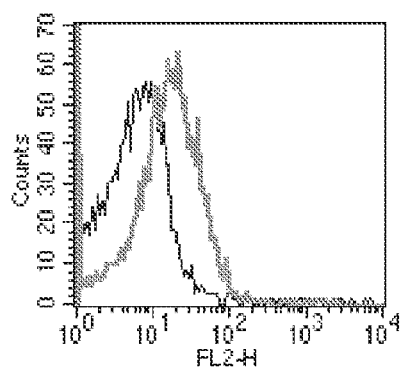
Figure 313:
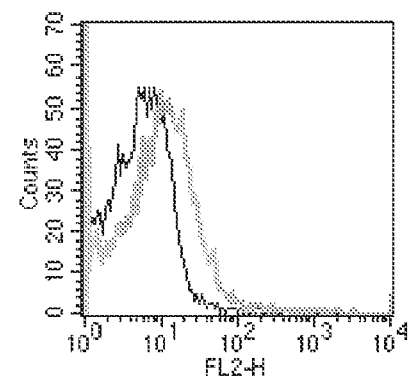
Figure 314:
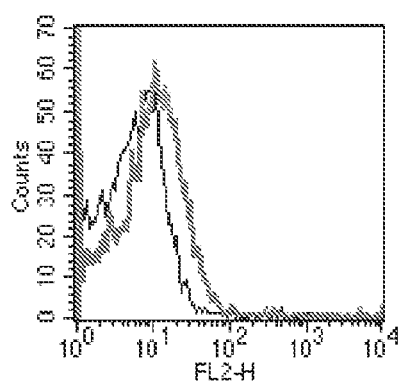
Figure 315:
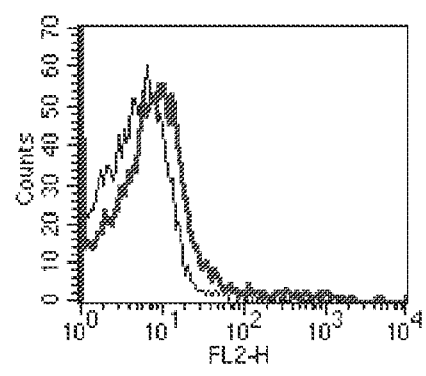
Figure 316:
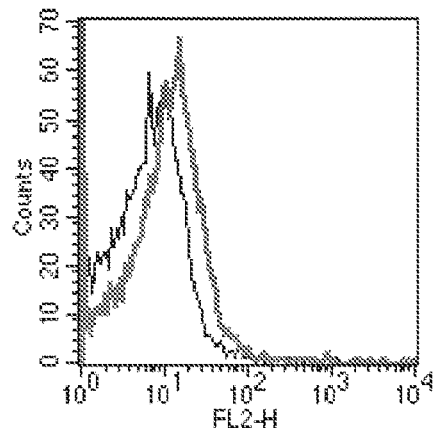
Figure 317:
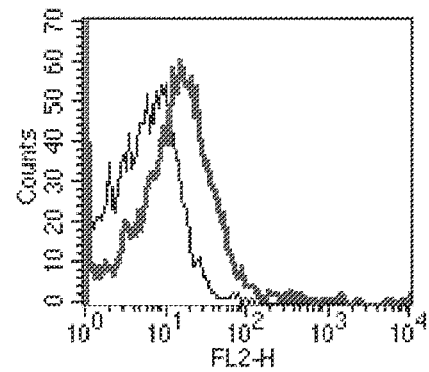
Figure 318:
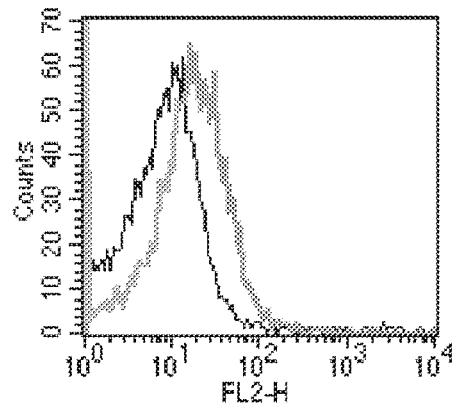
Figure 319:
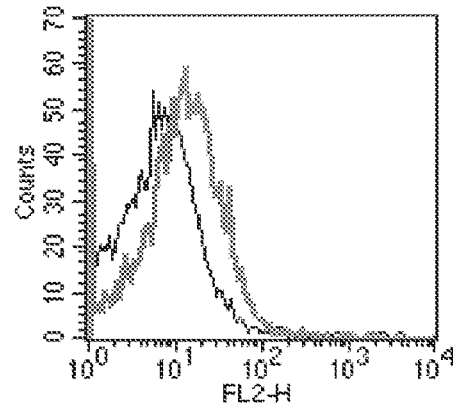

GBS317dN was expressed in *E. coli* as a GST-fusion product. SDS-PAGE analysis of total cell extract is shown in FIG. 187 (lane 7; MW 116 kDa). Purified GBS317dN-GST is shown in FIG. 245, lane 8.

Figure 188:
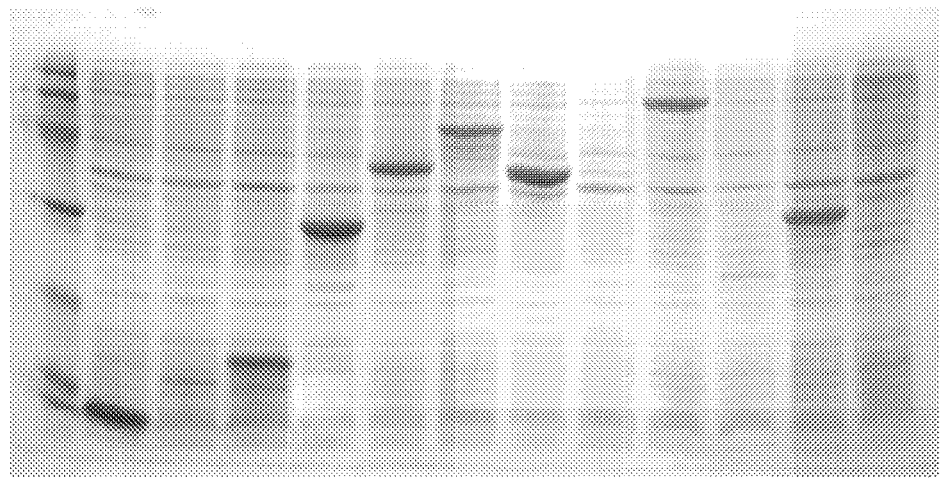
Figure 189:
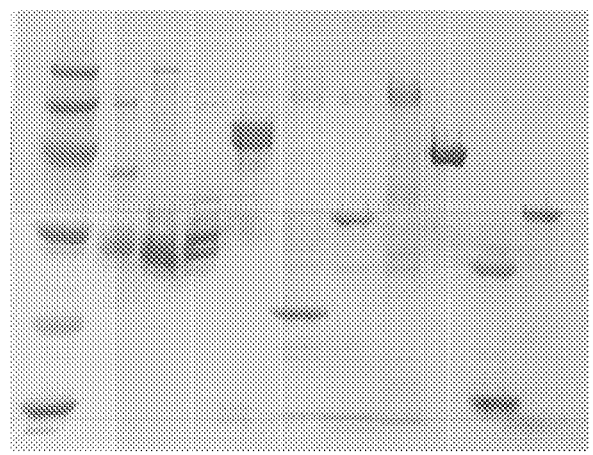
FIGS. 189 to 237 and 240 to 246 show SDS-PAGE analysis of purified GBS proteins of the invention. The left-hand lane contains molecular weight markers. These are 94, 67, 43, 30, 20.1, and 14.4 kDa.
Figure 190:
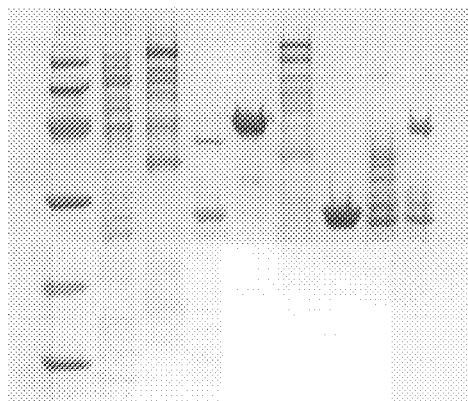
Figure 191:
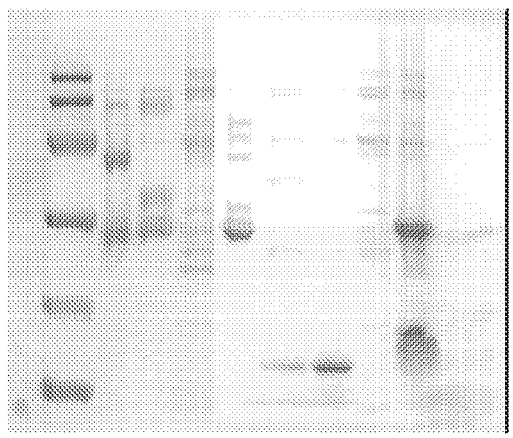
Figure 192:
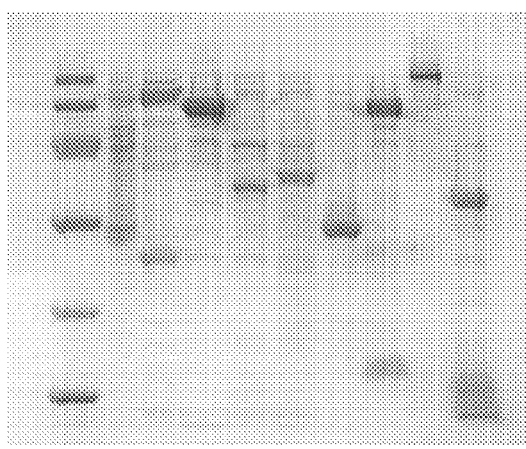
Figure 193:
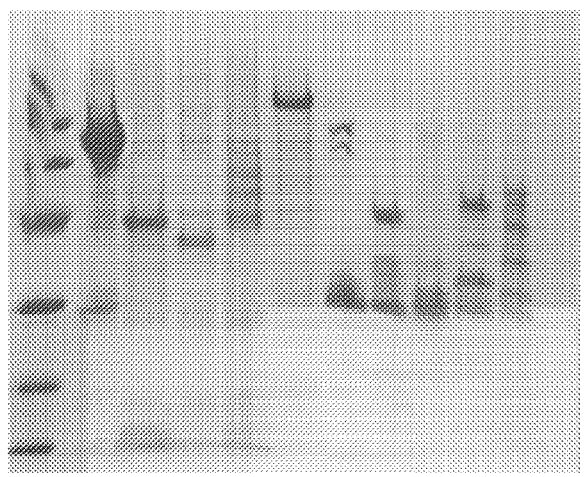
Figure 194:
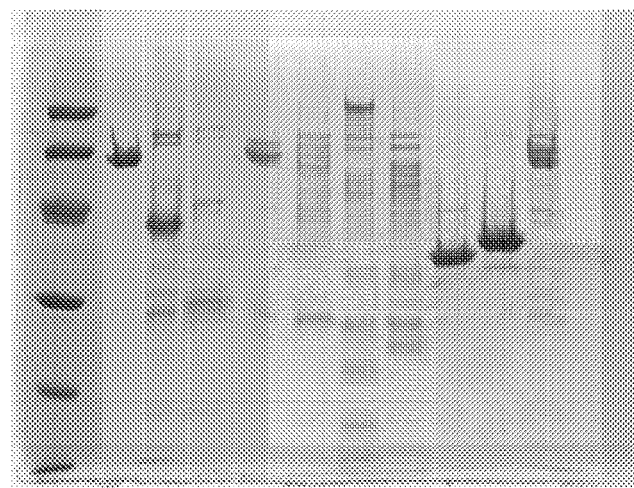
Figure 195:
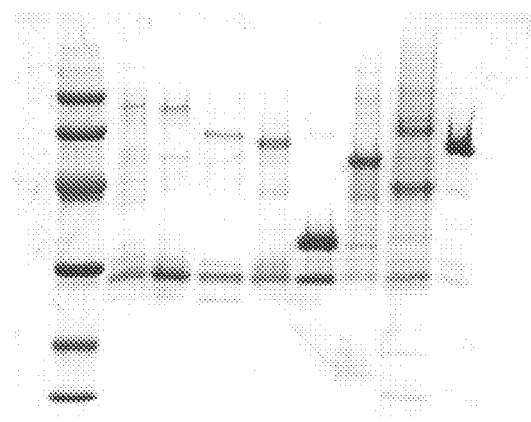
Figure 196:
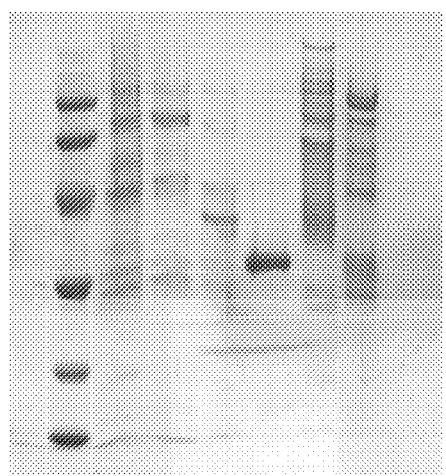
Figure 197:
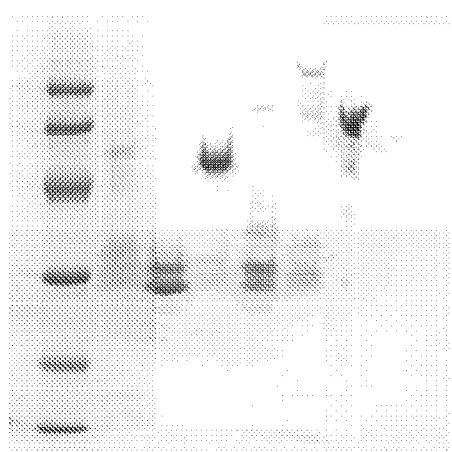
Figure 198:
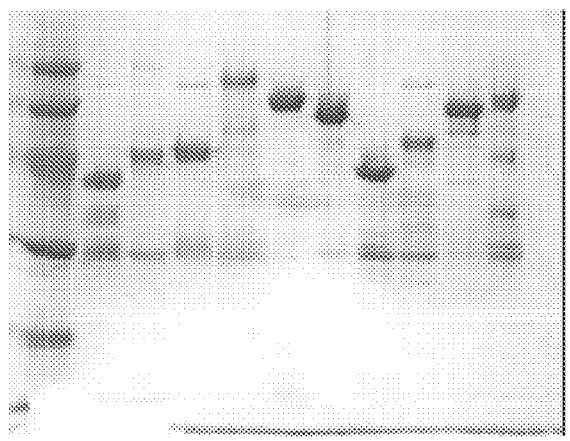
Figure 199:
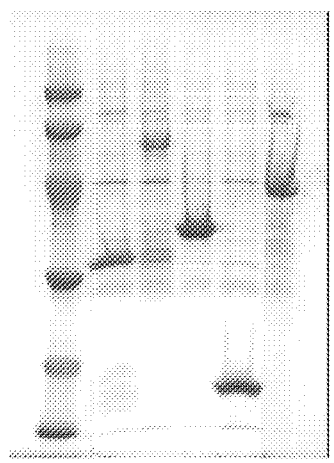
Figure 200:
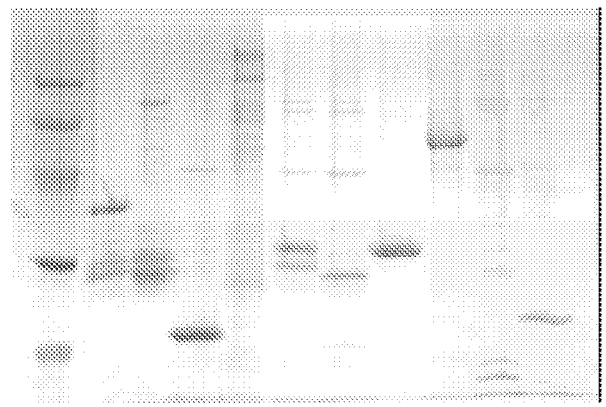
Figure 201:
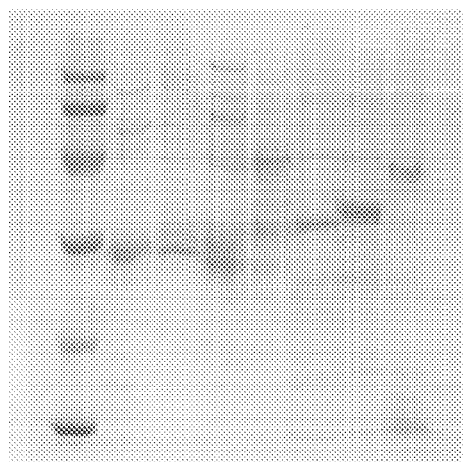
Figure 202:
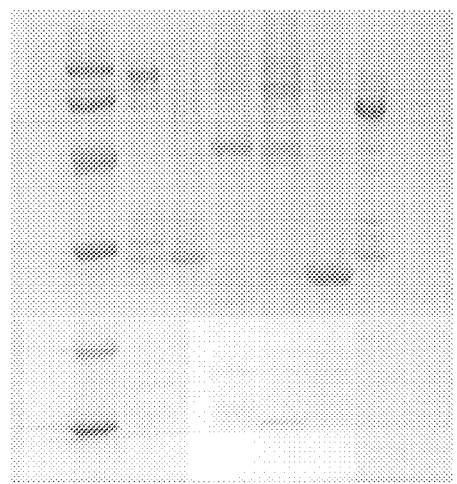
Figure 203:
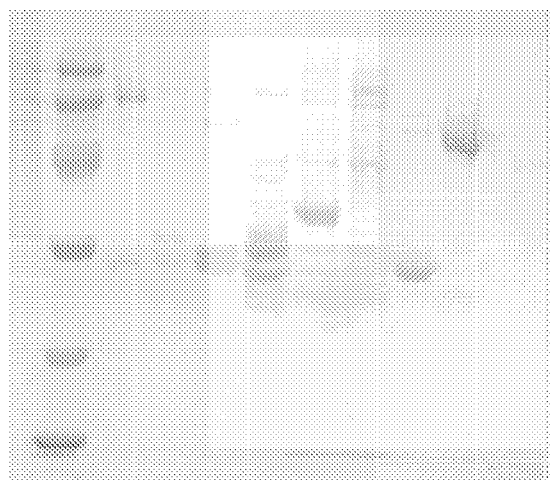
Figure 204:
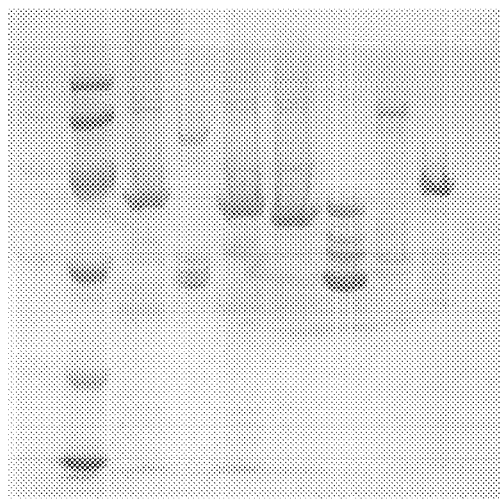
Figure 205:
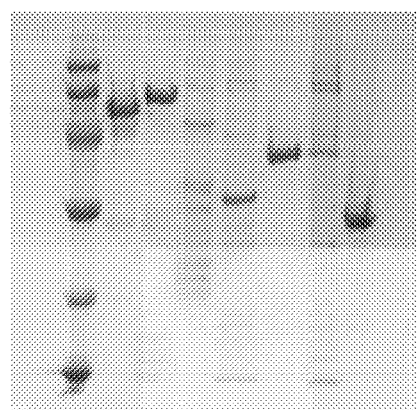
Figure 206:
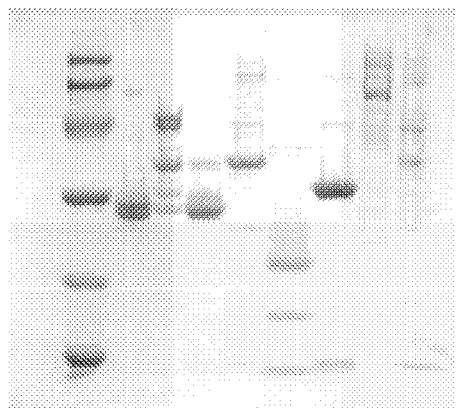
Figure 207:
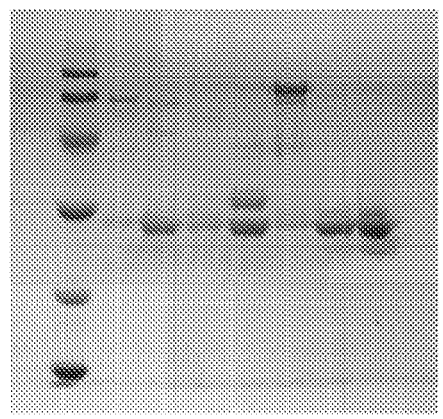
Figure 208:
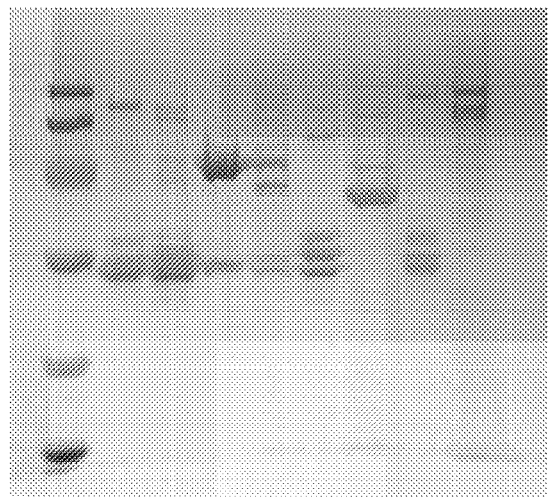
Figure 209:
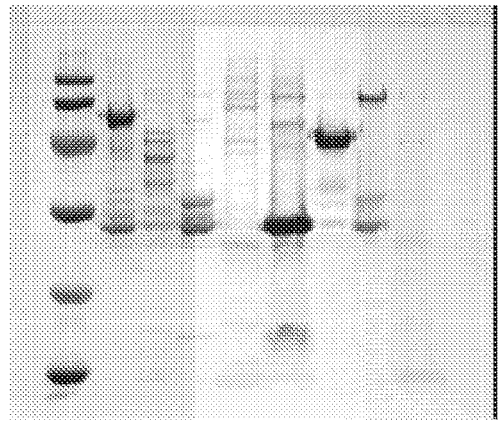
Figure 210:
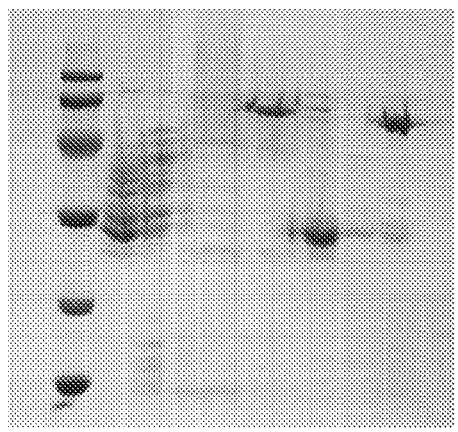
Figure 211:
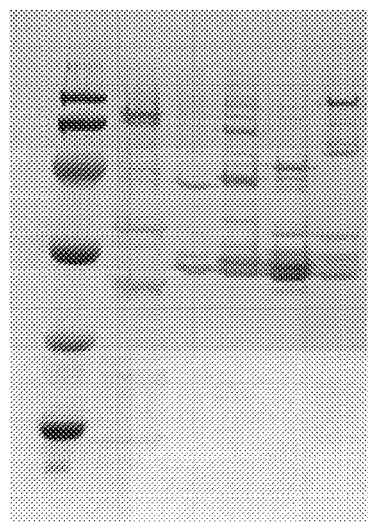
Figure 212:
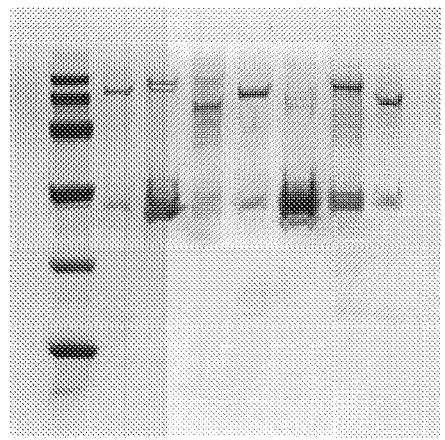
Figure 213:
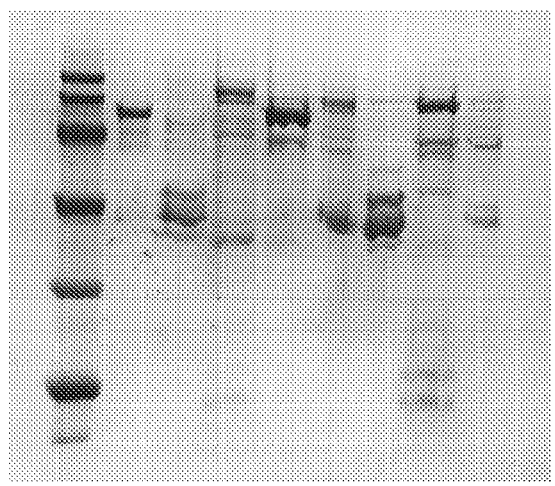
Figure 214:
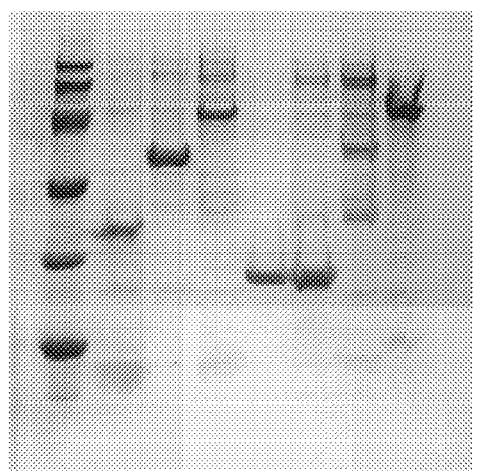
Figure 215:
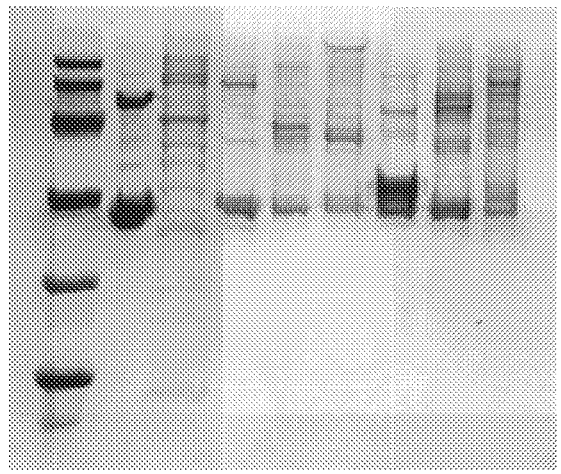
Figure 216:
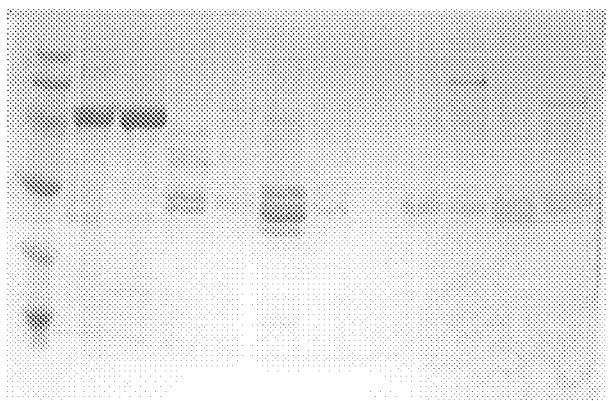
Figure 217:
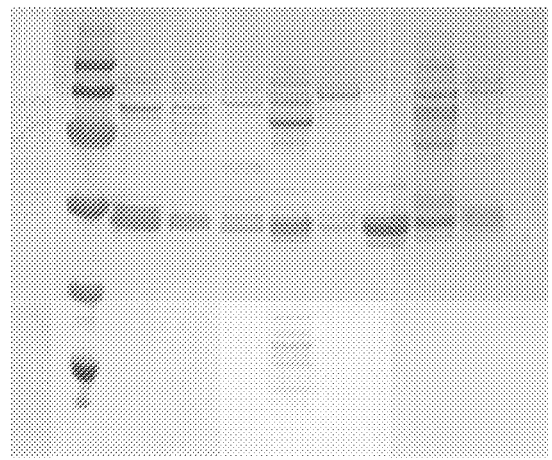
Figure 218:
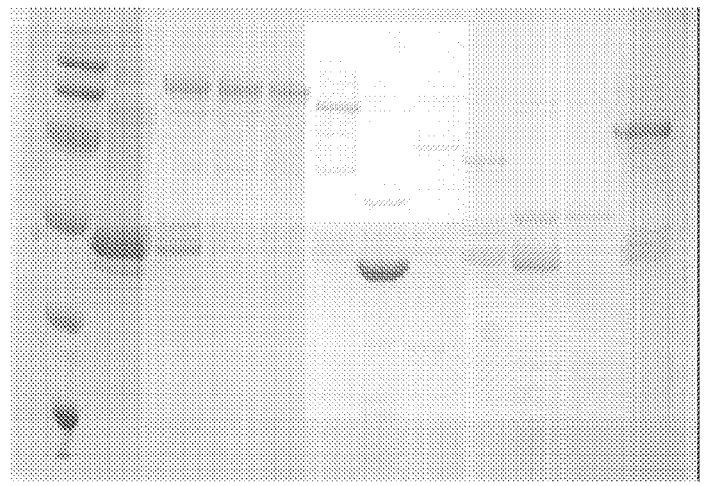
Figure 219:
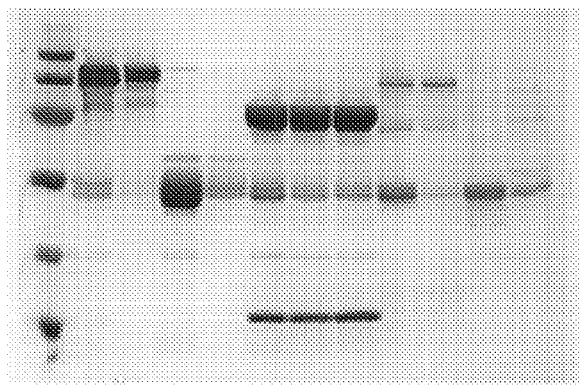
Figure 220:
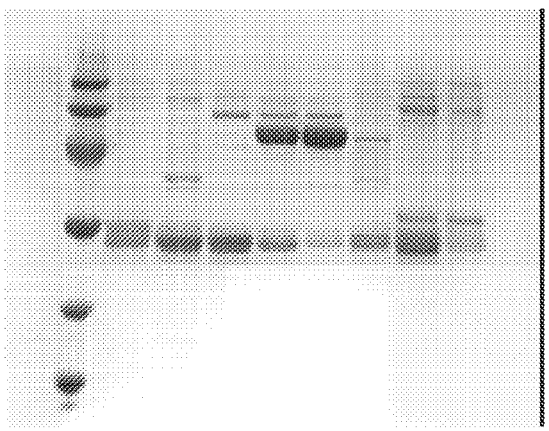
Figure 221:
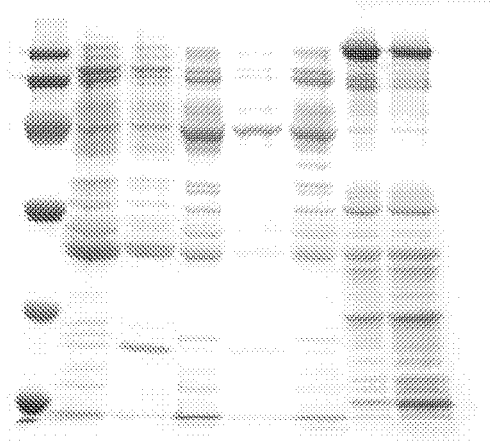

GBS317C was expressed in *E. coli* as a GST-fusion product. SDS-PAGE analysis of total cell extract is shown in FIG. 188 (lane 13; MW 92 kDa). Purified GBS317dC-GST is shown in FIG. 245, lane 9.

Based on this analysis, it was predicted that these proteins and their epitopes could be useful antigens for vaccines or diagnostics.

TABLE I

THEROETICAL MOLECULAR WEIGHTS FOR GBS PROTEINS

| GBS # | expected mol. weight (dalton) | | |
|---|---|---|---|
| | GST-fusion | His-fusion | Native |
| 1 | 78425 | 53460 | 49720 |
| 2 | 40035 | 15070 | 11330 |
| 3 | 90305 | 65340 | 61600 |
| 4 | 43115 | 18150 | 14410 |
| 5 | 158835 | 133870 | 130130 |
| 6 | 39265 | 14300 | 10560 |
| 7 | 44985 | 20020 | 16280 |
| 8 | 56315 | 31350 | 27610 |
| 9 | 50265 | 25300 | 21560 |

TABLE I-continued

THEORETICAL MOLECULAR WEIGHTS FOR GBS PROTEINS

| GBS # | GST-fusion | His-fusion | Native |
|---|---|---|---|
| 10 | 96465 | 71500 | 67760 |
| 11 | 91515 | 66550 | 62810 |
| 11d | 85905 | 60940 | 57200 |
| 12 | 64455 | 39490 | 35750 |
| 13 | 40475 | 15510 | 11770 |
| 14 | 33325 | 8360 | 4620 |
| 15 | 44765 | 19800 | 16060 |
| 16 | 73475 | 48510 | 44770 |
| 17 | 46745 | 21780 | 18040 |
| 18 | 54335 | 29370 | 25630 |
| 19 | 46085 | 21120 | 17380 |
| 20 | 47625 | 22660 | 18920 |
| 21 | 56535 | 31570 | 27830 |
| 21 long | 66435 | 41470 | 37730 |
| 22 | 60055 | 35090 | 31350 |
| 23 | 60165 | 35200 | 31460 |
| 24 | 58405 | 33440 | 29700 |
| 25 | 50265 | 25300 | 21560 |
| 26 | 118245 | 93280 | 89540 |
| 28 | 63795 | 38830 | 35090 |
| 29 | 50595 | 25630 | 21890 |
| 30 | 44215 | 19250 | 15510 |
| 31 | 63795 | 38830 | 35090 |
| 31d | 58735 | 33770 | 30030 |
| 32 | 40585 | 15620 | 11880 |
| 33 | 71495 | 46530 | 42790 |
| 34 | 69295 | 44330 | 40590 |
| 35 | 56535 | 31570 | 27830 |
| 36 | 59065 | 34100 | 30360 |
| 37 | 46965 | 22000 | 18260 |
| 38 | 61815 | 36850 | 33110 |
| 39 | 65225 | 40260 | 36520 |
| 41 | 75235 | 50270 | 46530 |
| 42 | 46745 | 21780 | 18040 |
| 43 | 58955 | 33990 | 30250 |
| 44 | 52355 | 27390 | 23650 |
| 45 | 43555 | 18590 | 14850 |
| 46 | 59835 | 34870 | 31130 |
| 47 | 84255 | 59290 | 55550 |
| 48 | 86455 | 61490 | 57750 |
| 48d | 106695 | 81730 | 77990 |
| 49 | 59615 | 34650 | 30910 |
| 50 | 94155 | 69190 | 65450 |
| 51 | 47075 | 22110 | 18370 |
| 52 | 55435 | 30470 | 26730 |
| 53 | 110215 | 85250 | 81510 |
| 54 | 73365 | 48400 | 44660 |
| 55 | 36295 | 11330 | 7590 |
| 56 | 34865 | 9900 | 6160 |
| 57 | 51145 | 26180 | 22440 |
| 58 | 128805 | 103840 | 100100 |
| 59 | 99215 | 74250 | 70510 |
| 60 | 63575 | 38610 | 34870 |
| 61 | 68085 | 43120 | 39380 |
| 62 | 105485 | 80520 | 76780 |
| 63 | 64125 | 39160 | 35420 |
| 64 | 112745 | 87780 | 84040 |
| 65 | 72485 | 47520 | 43780 |
| 66 | 49715 | 24750 | 21010 |
| 67 | 120335 | 95370 | 91630 |
| 68 | 131225 | 106260 | 102520 |
| 68d | 103065 | 78100 | 74360 |
| 69 | 53895 | 28930 | 25190 |
| 70 | 74465 | 49500 | 45760 |
| 70d | 59725 | 34760 | 31020 |
| 71 | 56755 | 31790 | 28050 |
| 72 | 75565 | 50600 | 46860 |
| 73 | 72815 | 47850 | 44110 |
| 74 | 131225 | 106260 | 102520 |
| 74d | 95475 | 70510 | 66770 |
| 75 | 114725 | 89760 | 86020 |
| 76 | 198875 | 173910 | 170170 |
| 77 | 78535 | 53570 | 49830 |
| 78 | 48835 | 23870 | 20130 |
| 79 | 58185 | 33220 | 29480 |
| 79d | 50815 | 25850 | 22110 |
| 80 | 81835 | 56870 | 53130 |
| 81 | 89205 | 64240 | 60500 |
| 82 | 40475 | 15510 | 11770 |
| 83 | 62585 | 37620 | 33880 |
| 84 | 122645 | 97680 | 93940 |
| 85 | 70175 | 45210 | 41470 |
| 86 | 84035 | 59070 | 55330 |
| 87 | 44435 | 19470 | 15730 |
| 88 | 73365 | 48400 | 44660 |
| 89 | 143325 | 118360 | 114620 |
| 90 | 93495 | 68530 | 64790 |
| 91 | 88325 | 63360 | 59620 |
| 92 | 193595 | 168630 | 164890 |
| 93 | 95585 | 70620 | 66880 |
| 94 | 77435 | 52470 | 48730 |
| 95 | 60605 | 35640 | 31900 |
| 96 | 57195 | 32230 | 28490 |
| 97 | 138375 | 113410 | 109670 |
| 98 | 82055 | 57090 | 53350 |
| 99 | 60715 | 35750 | 32010 |
| 100 | 53015 | 28050 | 24310 |
| 101 | 59395 | 34430 | 30690 |
| 102 | 40695 | 15730 | 11990 |
| 103 | 56975 | 32010 | 28270 |
| 104 | 120005 | 95040 | 91300 |
| 105 | 179735 | 154770 | 151030 |
| 105dNterm | 127265 | 102300 | 98560 |
| 105dCterm | 81285 | 56320 | 52580 |
| 106 | 85795 | 60830 | 57090 |
| 107 | 89535 | 64570 | 60830 |
| 108 | 64565 | 39600 | 35860 |
| 109 | 75125 | 50160 | 46420 |
| 109d | 70725 | 45760 | 42020 |
| 110 | 53895 | 28930 | 25190 |
| 111/190 | 60165 | 35200 | 31460 |
| 112 | 63905 | 38940 | 35200 |
| 113 | 59175 | 34210 | 30470 |
| 114 | 51915 | 26950 | 23210 |
| 115 | 98225 | 73260 | 69520 |
| 116 | 73475 | 48510 | 44770 |
| 117 | 47515 | 22550 | 18810 |
| 118 | 42235 | 17270 | 13530 |
| 119 | 109225 | 84260 | 80520 |
| 120 | 71385 | 46420 | 42680 |
| 121 | 65115 | 40150 | 36410 |
| 122 | 46855 | 21890 | 18150 |
| 123 | 68305 | 43340 | 39600 |
| 124 | 54115 | 29150 | 25410 |
| 125 | 57305 | 32340 | 28600 |
| 126 | 56865 | 31900 | 28160 |
| 127 | 80845 | 55880 | 52140 |
| 128 | 39925 | 14960 | 11220 |
| 129 | 43775 | 18810 | 15070 |
| 130 | 82275 | 57310 | 53570 |
| 130d | 63245 | 38280 | 34540 |
| 131 | 89755 | 64790 | 61050 |
| 132 | 49055 | 24090 | 20350 |
| 133 | 54445 | 29480 | 25740 |
| 134 | 42015 | 17050 | 13310 |
| 135 | 65225 | 40260 | 36520 |
| 136 | 54885 | 29920 | 26180 |
| 137 | 63465 | 38500 | 34760 |
| 138 | 40145 | 15180 | 11440 |
| 139 | 38165 | 13200 | 9460 |
| 140 | 43445 | 18480 | 14740 |
| 141 | 49935 | 24970 | 21230 |
| 142 | 79745 | 54780 | 51040 |
| 143 | 33545 | 8580 | 4840 |
| 144 | 49165 | 24200 | 20460 |
| 145 | 63025 | 38060 | 34320 |

TABLE I-continued

THEROETICAL MOLECULAR WEIGHTS FOR GBS PROTEINS

| GBS # | GST-fusion | His-fusion | Native |
|---|---|---|---|
| 146 | 107025 | 82060 | 78320 |
| 147 | 156965 | 132000 | 128260 |
| 148 | 41905 | 16940 | 13200 |
| 149 | 62365 | 37400 | 33660 |
| 150 | 54665 | 29700 | 25960 |
| 151 | 50412 | 25447 | 21707 |
| 151L | 50045 | 25080 | 21340 |
| 152 | 45535 | 20570 | 16830 |
| 153 | 46965 | 22000 | 18260 |
| 154 | 101525 | 76560 | 72820 |
| 155 | 62585 | 37620 | 33880 |
| 156 | 61265 | 36300 | 32560 |
| 157 | 74025 | 49060 | 45320 |
| 158 | 52025 | 27060 | 23320 |
| 159 | 41025 | 16060 | 12320 |
| 160 | 82825 | 57860 | 54120 |
| 161 | 95365 | 70400 | 66660 |
| 162 | 42015 | 17050 | 13310 |
| 163 | 69405 | 44440 | 40700 |
| 164 | 42345 | 17380 | 13640 |
| 165 | 43555 | 18590 | 14850 |
| 166 | 38055 | 13090 | 9350 |
| 167 | 50375 | 25410 | 21670 |
| 168 | 32555 | 7590 | 3850 |
| 169 | 43445 | 18480 | 14740 |
| 170 | 64015 | 39050 | 35310 |
| 170d | 59945 | 34980 | 31240 |
| 171 | 49825 | 24860 | 21120 |
| 172 | 62365 | 37400 | 33660 |
| 173 | 96795 | 71830 | 68090 |
| 174 | 45095 | 20130 | 16390 |
| 175 | 59175 | 34210 | 30470 |
| 176 | 55435 | 30470 | 26730 |
| 177 | 66215 | 41250 | 37510 |
| 178 | 62365 | 37400 | 33660 |
| 179 | 58515 | 33550 | 29810 |
| 180 | 37615 | 12650 | 8910 |
| 181 | 63685 | 38720 | 34980 |
| 182 | 90085 | 65120 | 61380 |
| 182d | 87225 | 62260 | 58520 |
| 183 | 57855 | 32890 | 29150 |
| 184 | 46415 | 21450 | 17710 |
| 185 | 40695 | 15730 | 11990 |
| 186 | 85685 | 60720 | 56980 |
| 187 | 56205 | 31240 | 27500 |
| 188 | 61595 | 36630 | 32890 |
| 189 | 60165 | 35200 | 31460 |
| 191 | 116705 | 91740 | 88000 |
| 192 | 69625 | 44660 | 40920 |
| 193 | 98005 | 73040 | 69300 |
| 194 | 49385 | 24420 | 20680 |
| 195 | 81065 | 56100 | 52360 |
| 195L | 147615 | 122650 | 118910 |
| 195L N-term | 91405 | 66440 | 62700 |
| 196 | 69515 | 44550 | 40810 |
| 197 | 99325 | 74360 | 70620 |
| 198 | 73805 | 48840 | 45100 |
| 199 | 158285 | 133320 | 129580 |
| 200 | 132325 | 107360 | 103620 |
| 201 | 74538 | 49573 | 45833 |
| 202 | 157295 | 132330 | 128590 |
| 203 | 61705 | 36740 | 33000 |
| 204 | 39705 | 14740 | 11000 |
| 205 | 55985 | 31020 | 27280 |
| 206 | 56645 | 31680 | 27940 |
| 207 | 44765 | 19800 | 16060 |
| 208 | 59725 | 34760 | 31020 |
| 209 | 62145 | 37180 | 33440 |
| 209d | 56425 | 31460 | 27720 |
| 210 | 60935 | 35970 | 32230 |
| 210d | 53675 | 28710 | 24970 |
| 211 | 64895 | 39930 | 36190 |
| 212 | 60825 | 35860 | 32120 |
| 213 | 45205 | 20240 | 16500 |
| 214 | 38935 | 13970 | 10230 |
| 215 | 45205 | 20240 | 16500 |
| 216 | 91515 | 66550 | 62810 |
| 217 | 36075 | 11110 | 7370 |
| 218 | 81065 | 56100 | 52360 |
| 219 | 56535 | 31570 | 27830 |
| 220 | 54555 | 29590 | 25850 |
| 220 | 50155 | 25190 | 21450 |
| 221 | 41465 | 16500 | 12760 |
| 222 | 47405 | 22440 | 18700 |
| 223 | 42895 | 17930 | 14190 |
| 224 | 45865 | 20900 | 17160 |
| 225 | 56645 | 31680 | 27940 |
| 226 | 44875 | 19910 | 16170 |
| 227 | 46195 | 21230 | 17490 |
| 228 | 46525 | 21560 | 17820 |
| 229 | 35855 | 10890 | 7150 |
| 230 | 51915 | 26950 | 23210 |
| 231 | 60935 | 35970 | 32230 |
| 231d | 58735 | 33770 | 30030 |
| 232 | 41795 | 16830 | 13090 |
| 233 | 35635 | 10670 | 6930 |
| 234 | 43115 | 18150 | 14410 |
| 235 | 58295 | 33330 | 29590 |
| 235d | 48395 | 23430 | 19690 |
| 236 | 46525 | 21560 | 17820 |
| 237 | 44215 | 19250 | 15510 |
| 238 | 59725 | 34760 | 31020 |
| 239 | 63905 | 38940 | 35200 |
| 240 | 51475 | 26510 | 22770 |
| 241 | 45095 | 20130 | 16390 |
| 242 | 43225 | 18260 | 14520 |
| 243 | 119455 | 94490 | 90750 |
| 244 | 48065 | 23100 | 19360 |
| 245 | 48615 | 23650 | 19910 |
| 246 | 49605 | 24640 | 20900 |
| 246d | 45975 | 21010 | 17270 |
| 247 | 58955 | 33990 | 30250 |
| 248 | 92505 | 67540 | 63800 |
| 248d | 70835 | 45870 | 42130 |
| 249 | 103835 | 78870 | 75130 |
| 250 | 136505 | 111540 | 107800 |
| 251 | 52135 | 27170 | 23430 |
| 252 | 51695 | 26730 | 22990 |
| 253 | 74245 | 49280 | 45540 |
| 254 | 59615 | 34650 | 30910 |
| 255 | 69075 | 44110 | 40370 |
| 256 | 47845 | 22880 | 19140 |
| 257 | 60495 | 35530 | 31790 |
| 258 | 67975 | 43010 | 39270 |
| 259 | 79415 | 54450 | 50710 |
| 260 | 48175 | 23210 | 19470 |
| 261 | 55765 | 30800 | 27060 |
| 262 | 75345 | 50380 | 46640 |
| 263 | 63465 | 38500 | 34760 |
| 264 | 47185 | 22220 | 18480 |
| 265 | 56315 | 31350 | 27610 |
| 266 | 51365 | 26400 | 22660 |
| 267 | 88655 | 63690 | 59950 |
| 268 | 50265 | 25300 | 21560 |
| 269 | 60495 | 35530 | 31790 |
| 270 | 59285 | 34320 | 30580 |
| 271 | 56315 | 31350 | 27610 |
| 272 | 118355 | 93390 | 89650 |
| 272d | 98885 | 73920 | 70180 |
| 273 | 70945 | 45980 | 42240 |
| 274 | 56205 | 31240 | 27500 |
| 275 | 47515 | 22550 | 18810 |
| 276 | 147945 | 122980 | 119240 |
| 277 | 87005 | 62040 | 58300 |
| 277d | 75675 | 50710 | 46970 |
| 278 | 52245 | 27280 | 23540 |

TABLE I-continued

THEORETICAL MOLECULAR WEIGHTS FOR GBS PROTEINS

| GBS # | GST-fusion | His-fusion | Native |
|---|---|---|---|
| 279 | 79415 | 54450 | 50710 |
| 280 | 88655 | 63690 | 59950 |
| 281 | 74465 | 49500 | 45760 |
| 281d | 71495 | 46530 | 42790 |
| 282 | 44765 | 19800 | 16060 |
| 283 | | 20240 | 16500 |
| 284 | 67645 | 42680 | 38940 |
| 285 | 57525 | 32560 | 28820 |
| 286 | 41355 | 16390 | 12650 |
| 287 | 61045 | 36080 | 32340 |
| 287d | 57085 | 32120 | 28380 |
| 288 | 53675 | 28710 | 24970 |
| 288d | 51035 | 26070 | 22330 |
| 289 | 65005 | 40040 | 36300 |
| 289 long | 71825 | 46860 | 43120 |
| 290 | 47405 | 22440 | 18700 |
| 291 | 63795 | 38830 | 35090 |
| 292 | 103505 | 78540 | 74800 |
| 293 | 115935 | 90970 | 87230 |
| 293d N-term | 73805 | 48840 | 45100 |
| 293d C-term | 70835 | 45870 | 42130 |
| 294 | 75785 | 50820 | 47080 |
| 295 | 89425 | 64460 | 60720 |
| 296 | 60385 | 35420 | 31680 |
| 297 | 100205 | 75240 | 71500 |
| 298 | 54335 | 29370 | 25630 |
| 299 | 62255 | 37290 | 33550 |
| 300 | 130895 | 105930 | 102190 |
| 301 | 54885 | 29920 | 26180 |
| 302 | 80075 | 55110 | 51370 |
| 303 | 53235 | 28270 | 24530 |
| 304 | 75125 | 50160 | 46420 |
| 305 | 78645 | 53680 | 49940 |
| 306 | 67975 | 43010 | 39270 |
| 307 | 86675 | 61710 | 57970 |
| 308 | 59285 | 34320 | 30580 |
| 309 | 62695 | 37730 | 33990 |
| 310 | 58845 | 33880 | 30140 |
| 311 | 76445 | 51480 | 47740 |
| 312 | 64785 | 39820 | 36080 |
| 313 | 65995 | 41030 | 37290 |
| 314 | 52135 | 27170 | 23430 |
| 315 | 51695 | 26730 | 22990 |
| 316 | 41795 | 16830 | 13090 |
| 317 | 179295 | 154330 | 150590 |
| 317d N-term | 115935 | 90970 | 87230 |
| 317d C-term | 92160 | 67402 | 63360 |
| 318 | 70065 | 45100 | 41360 |
| 319 | 61925 | 36960 | 33220 |
| 320 | 57965 | 33000 | 29260 |
| 321 | 83705 | 58740 | 55000 |
| 322 | 76628 | 51663 | 47923 |
| 323 | 86345 | 61380 | 57640 |
| 324 | 86345 | 61380 | 57640 |
| 325 | 82605 | 57640 | 53900 |
| 326 | 91515 | 66550 | 62810 |
| 326L | 172695 | 147730 | 143990 |
| 326L N-term | 113955 | 88990 | 85250 |
| 327 | 279175 | 254210 | 250470 |
| 327d N-term | 139915 | 114950 | 111210 |
| 327d C-term | 167965 | 143000 | 139260 |
| 328 | 97602 | 72637 | 68897 |
| 329 | 113955 | 88990 | 85250 |
| 330 | 83595 | 58630 | 54890 |
| 331 | 60825 | 35860 | 32120 |
| 332 | 75675 | 50710 | 46970 |
| 333 | 63465 | 38500 | 34760 |
| 333d | 57965 | 33000 | 29260 |
| 334 | 38275 | 13310 | 9570 |
| 335 | 43555 | 18590 | 14850 |
| 336 | 67645 | 42680 | 38940 |
| 337 | 75235 | 50270 | 46530 |
| 338 | 54995 | 30030 | 26290 |
| 339 | 76665 | 51700 | 47960 |
| 339d | 72925 | 47960 | 44220 |
| 340 | 86565 | 61600 | 57860 |
| 341 | 38385 | 13420 | 9680 |
| 342 | 61595 | 36630 | 32890 |
| 343 | 60385 | 35420 | 31680 |
| 344 | 55875 | 30910 | 27170 |
| 345 | 40585 | 15620 | 11880 |
| 346 | 53895 | 28930 | 25190 |
| 347 | 55325 | 30360 | 26620 |
| 348 | 58405 | 33440 | 29700 |
| 349 | 98335 | 73370 | 69630 |
| 350 | 53895 | 28930 | 25190 |
| 351 | 82165 | 57200 | 53460 |
| 352 | 111315 | 86350 | 82610 |
| 352d | 105485 | 80520 | 76780 |
| 353 | 55325 | 30360 | 26620 |
| 354 | 42345 | 17380 | 13640 |
| 355 | 52135 | 27170 | 23430 |
| 356 | 59065 | 34100 | 30360 |
| 357 | 40255 | 15290 | 11550 |
| 358 | 60495 | 35530 | 31790 |
| 359 | 78865 | 53900 | 50160 |
| 360 | 73695 | 48730 | 44990 |
| 361 | 109005 | 84040 | 80300 |
| 362 | 125945 | 100980 | 97240 |
| 362d N-term | 63355 | 38390 | 34650 |
| 362d C-term | 91295 | 66330 | 62590 |
| 363 | 53125 | 28160 | 24420 |
| 364 | 75015 | 50050 | 46310 |
| 365 | 102075 | 77110 | 73370 |
| 366 | 68415 | 43450 | 39710 |
| 367 | 76885 | 51920 | 48180 |
| 368 | 44765 | 19800 | 16060 |
| 369 | 142115 | 117150 | 113410 |
| 370 | 94595 | 69630 | 65890 |
| 371 | 65555 | 40590 | 36850 |
| 372 | 55105 | 30140 | 26400 |
| 373 | 50265 | 25300 | 21560 |
| 374 | 57525 | 32560 | 28820 |
| 375 | 66875 | 41910 | 38170 |
| 376 | 48065 | 23100 | 19360 |
| 377 | 73805 | 48840 | 45100 |
| 378 | 58955 | 33990 | 30250 |
| 379 | 68855 | 43890 | 40150 |
| 380 | 47405 | 22440 | 18700 |
| 381 | 66875 | 41910 | 38170 |
| 382 | 50815 | 25850 | 22110 |
| 383 | 57085 | 32120 | 28380 |
| 384 | 77985 | 53020 | 49280 |
| 385 | 75675 | 50710 | 46970 |
| 386 | 39485 | 14520 | 10780 |
| 387 | 54555 | 29590 | 25850 |
| 388 | 45645 | 20680 | 16940 |
| 389 | 43005 | 18040 | 14300 |
| 390 | 62255 | 37290 | 33550 |
| 391 | 54775 | 29810 | 26070 |
| 392 | 71385 | 46420 | 42680 |
| 393 | 55765 | 30800 | 27060 |
| 394 | 59725 | 34760 | 31020 |
| 395 | 72375 | 47410 | 43670 |
| 396 | 34865 | 9900 | 6160 |
| 397 | 113625 | 88660 | 84920 |
| 397d | 100865 | 3740 | 72160 |
| 398 | 56755 | 31790 | 28050 |
| 399 | 55435 | 30470 | 26730 |
| 400 | 74135 | 49170 | 45430 |
| 401 | 59395 | 34430 | 30690 |
| 402 | 78095 | 53130 | 49390 |
| 403 | 64455 | 39490 | 35750 |
| 404 | 61595 | 36630 | 32890 |
| 405 | 45975 | 21010 | 17270 |
| 406 | 36955 | 11990 | 8250 |

TABLE I-continued

THEORETICAL MOLECULAR WEIGHTS FOR GBS PROTEINS

| GBS # | expected mol. weight (dalton) | | |
|---|---|---|---|
|  | GST-fusion | His-fusion | Native |
| 407 | 82715 | 57750 | 54010 |
| 407d | 71715 | 46750 | 43010 |
| 408 | 45315 | 20350 | 16610 |
| 409 | 70395 | 45430 | 41690 |
| 409d | 59600 | 34842 | 30800 |
| 410 | 62475 | 37510 | 33770 |
| 411 | 41355 | 16390 | 12650 |
| 412 | 35965 | 11000 | 7260 |
| 413 | 59175 | 34210 | 30470 |
| 414 | 50375 | 25410 | 21670 |
| 415 | 46195 | 21230 | 17490 |
| 416 | 42455 | 17490 | 13750 |
| 417 | 77985 | 53020 | 49280 |
| 418 | 42125 | 17160 | 13420 |
| 419 | 47515 | 22550 | 18810 |
| 420 | 67755 | 42790 | 39050 |
| 421 | 62915 | 37950 | 34210 |
| 422 | 60165 | 35200 | 31460 |
| 423 | 74245 | 49280 | 45540 |
| 424 | 89975 | 65010 | 61270 |
| 424 | 77325 | 52360 | 48620 |
| 425 | 116045 | 91080 | 87340 |
| 426 | 83815 | 58850 | 55110 |
| 427 | 41135 | 16170 | 12430 |
| 428 | 55325 | 30360 | 26620 |
| 429 | 59175 | 34210 | 30470 |
| 430 | 53785 | 28820 | 25080 |
| 431 | 54005 | 29040 | 25300 |
| 432 | 65665 | 40700 | 36960 |
| 433 | 40915 | 15950 | 12210 |
| 434 | 44545 | 19580 | 15840 |
| 642 | 91845 | 66880 | 63140 |
| 643 | 78975 | 54010 | 50270 |
| 644 | 49605 | 24640 | 20900 |
| 645 | 59725 | 34760 | 31020 |
| 646 | 61595 | 36630 | 32890 |
| 647 | 55875 | 30910 | 27170 |
| 648 | 59835 | 34870 | 31130 |
| 649 | 76115 | 51150 | 47410 |
| 650 | 51475 | 26510 | 22770 |
| 651 | 53345 | 28380 | 24640 |
| 652 | 49715 | 24750 | 21010 |
| 653 | 44655 | 19690 | 15950 |
| 654 | 51255 | 26290 | 22550 |
| 655 | 65995 | 41030 | 37290 |
| 656 | 57525 | 32560 | 28820 |
| 657 | 62805 | 37840 | 34100 |
| 658 | 60165 | 35200 | 31460 |
| 659 | 60275 | 35310 | 31570 |
| 660 | 71495 | 46530 | 42790 |
| 661 | 60605 | 35640 | 31900 |
| 662 | 62695 | 37730 | 33990 |
| 663 | 89535 | 64570 | 60830 |
| 664 | 45315 | 20350 | 16610 |
| 665 | 41135 | 16170 | 12430 |
| 666 | 47075 | 22110 | 18370 |
| 667 | 53162 | 28197 | 24457 |
| 668 | 43555 | 18590 | 14850 |
| 669 | 48505 | 23540 | 19800 |
| 670 | 45315 | 20350 | 16610 |
| 671 | 36940 | 12182 | 8140 |
| 672 | 40130 | 15372 | 11330 |
| 673 | 41450 | 16692 | 12650 |
| 674 | 45300 | 20542 | 16500 |
| 675 | 55970 | 31212 | 27170 |
| 676 | 65650 | 40892 | 36850 |
| 677 | 54320 | 29562 | 25520 |
| 678 | 77750 | 52992 | 48950 |
| 679 | 60480 | 35722 | 31680 |
| 680 | 64440 | 39682 | 35640 |
| 681 | 93040 | 68282 | 64240 |
| 682 | 84790 | 60032 | 55990 |
| 683 | 15950 | 44655 | 19690 |
| 684 | 11880 | 40585 | 15620 |
| 685 | 16280 | 44985 | 20020 |
| 686 | 21340 | 50045 | 25080 |
| 687 | 9350 | 38055 | 13090 |
| 689 | 55105 | 3740 | 26400 |

TABLE II

PRIMERS USED TO AMPLIFY GBSnnn PROTEINS
Forward primers begin 5'-GGGGACAAGTTTGTACAAAAAAGCAGGC-3' and continue with the sequences
indicated in the table below; reverse primers begin 5'-GGGGACCACTTTGTACAAGAAAGCTGGGTT-3'
and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 1 | TCTCAATCTCATATTGTTTCAG | ATTTTTAGACATCATAGACA |
| 2 | TCTAATTACATTATTACATTTTTG | GGGAATGCCTACAAA |
| 3 | TCTGATACTAGTTCAGGAATATC | TTTTTTACTATACTTTTTGT |
| 4 | TCTGATACAAGTGATAAGAATACT | TTCCTTTTTAGGCTTACT |
| 5 | TCTATTTTTCTTCATAGTCCAC | ATTAGCTTCATTTGTCAG |
| 6 | TCTGAATGGGTGTTATTAACTC | AGTTTCTTCTTTAAAATCAT |
| 7 | TCTACAAATTCTTATTTTAGCAA | CTCTGAAGCTGTAAAACC |
| 8 | TCTGTATCAGTTCAGGCGT | TTTATCAATGTTTGAAACG |
| 9 | TCTGCTGCTCTAGGACAAC | TAGTAAATCAAGTTTTTGCA |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492. The reverse primer sequences are SEQ IDs 11493-12017.

| GBS | Forward | Reverse |
|---|---|---|
| 10 | TCTTTTGTTGTTGCCTTATT | ATCCCTTCTATTTTCGA |
| 11 | TCTCCACCTATGGAACGT | ATGTAGTGACGTTTCTGTG |
| 11d | TCTCAGAAAGTCTATCGGG | ATGTAGTGACGTTTCTGTG |
| 12 | TCTAGTGAGAAGAAAGCAAAT | ATTGGGTGTAAGCATT |
| 13 | TCTTCTTGGAATTATTGGAG | CTTAACTCTACCCGTCC |
| 14 | TCTGCAATGATTGTAACCAT | TTTTCTCTTATTAAAGAATT |
| 15 | TCTGCATCTTATACCGTGAA | ATACCAGCCGTTACTATT |
| 16 | TCTGCCGAGAAGGATAAA | TTTAGCTGCTTTTTTAATG |
| 17 | TCTGTTTATAAAGTTATTCAAAA | AAATACTACATTTACAGGTG |
| 18 | TCTAAGCCTAACAGTCAACA | TTGGTTATTCTCCTTTAAT |
| 19 | TCTGATGATAACTTTGAAATGC | ATTATATTTTGGATATTTC |
| 20 | TCTGCAGTGATTGCAAGTC | GGGCTTTTCTTAAAAA |
| 21 | TGTGCTGCATCAAAC | GTTGGCATCCCTTTT |
| 21 Long + A527 | TGTGCTGCATCAAAC | CTTTTGATGGGATTGG |
| 22 | TGTACTAAACAAAGCCAG | TTGATTTAACGATTTGA |
| 23 | TGTCAATTAACCGATAC | TTTATCTCCTCTAAAATAATG |
| 24 | TGCTCAAATGATTCAT | CTTTGATAAGTCAGACCA |
| 25 | TCTAAAAGTTCACAAGTTACTACT | GTAACCCCAAGCTGAT |
| 26 | TCTAGTCATTATTCCATAAAATT | TGATTTTGCAATATCAA |
| 28 | TCTAATCATATGCTGATTGAG | TTTTTGTAATTTAAGTACTAA |
| 29 | TCAGTTTGGATGTTAAC | TTCTTTTATATTAAGAGCTT |
| 30 | TCAACAAATGCAGATG | ATTCGGATAAATGTAGC |
| 31 | TGTTTTGTCATTATTGATAG | TCCATTTTTATCCTCAC |
| 31d | TCTCTAACTTGGTTTTTATTAGA | TCCATTTTTATCCTCAC |
| 32 | TCTGGTTTAAAAGTGACTGAA | ATGACCTCTACTTTCCA |
| 33 | TCTCATCATTTAGGTAAGGAA | CTTGTAATCACTTGGAC |
| 34 | TCTGTTAGTAATCGCTACAATC | ATTAATCATGGTATTGGT |
| 35 | TCTAATCAAGAAGTTTCAGC | CCATTGTGGAATATCA |
| 36 | TCTCGAGTTTTAGCGGATA | TTTGTAAAGCAGTTCTT |
| 37 | TCTGTATTATTTTACCAATCACA | ATCATTCATATGATCTCTAGA |
| 38 | TTAGGAGTGGTAGTTCAT | ATTTTGATTGATTCTACTC |
| 39 | TTTTTATTGTTAGTATTAGC | TTTTGTTTTTTTCAAATA |
| 41 | TCTGTTTATCTAGCGGTTAGA | ATCTTCAACGTCCTCC |
| 42 | TATAACAGTTTAGTTAGAAGTC | AAAGTCAAAGGAAACTT |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 43 | TTTAAAGGGTTTACATATT | TTCTTTATCTAATTTATAATAG |
| 44 | TTTAATACAATTGGTCG | TTGCAATGTTTTTTCT |
| 45 | TCTATGGAAAAAATTAGGATT | TAAACTTTGGATAATCTGT |
| 46 | TCTAGAGATGAGCAAGAAATA | GTTGAAATTTTGATATGA |
| 47 | TCTCAACAGATAGGTCTTTATAA | CTCCTTTACTATATAGCTAACT |
| 48 | TTTCTCTATAATTACTTCAAT | TTGTTTGTGAAGTAAAAC |
| 49 | TCTAATAAGGCATTATTAGAGG | TGATAATATCTCCATATTTT |
| 50 | TCTACACATTTAGTTGACTTAAC | GCATTGGCGCCATA |
| 51 | TCTAGTAAACAACACATTTATCTA | TTCTACACGACTTTTATTC |
| 52 | TCTCAAGAAACTCATCAGTTG | AAGACCTCCTCGAGAT |
| 53 | TCTGCAGAAGACATTGTTACA | TGTTTTTTCTTTCTGTTG |
| 54 | TATAATTTTTCGACTAATGA | TGGATTAGTTTGACCTG |
| 55 | TCTGACACAGTGTCTTATCCT | TTTATCGTAAGCACTTAGG |
| 56 | TCTGTGGAGCAAGTGGCCA | CTCCTTCCAGGCATCG |
| 57 | TCTCAAGAACTAAGTAACTTTGA | GTAAAAGTATCTTAAATAGTCA |
| 58 | TCTACTGAAACGTTTGAAGG | TGCCATTCCTCCTCT |
| 59 | TCTGATGAAGCAACAACTAA | TGTTACCTTTTTATTTTCT |
| 60 | TCTAATAAAGATAATCAAAAAACT | TTTTTCATGCGATTGA |
| 61 | TGTTTCTTTTTTATTCCA | GAGACGTTTCTTATACCTT |
| 62 | TATTACTTTGATGGTAGTTT | TGTACCATATGTTCTCTCT |
| 63 | TCTGTTCAATCATTAGCAAA | AAAAGTTGGACTACTTTC |
| 64 | TTTAAAGGTAATAAGAAGTTG | TCGTTTTCCACCC |
| 64d | TCTAGTCAAGTTGACTCTGTTA | TCGTTTTCCACCC |
| 65 | TCTCAAAACCAGGTGACTG | ATTTGGGTAAATATAGTAAA |
| 66 | TTAAGATTTTATAACAACGA | TTTACGACTAACCTCAAC |
| 67 | TCTAATGTTTTAGGGGAAA | AATTCCTTTTGGTGG |
| 68 | TCCCAAAAGACTTTTG | GGCAGAATACACCTTC |
| 68d | TCCCAAAAGACTTTTG | GGCTGACGTCGACGCA |
| 69 | TCTAAAGTTTTAGCCTTTGA | AACTCTCTTAATATATTCTTCT |
| 70 | TCTGAAATGGCTTTAG | GTCTTTTTCAATATTCTGT |
| 70d | TCTACTAACTTATTGAGTAGAATCA | GTCTTTTTCAATATTCTGT |
| 71 | TGTAGCTCAAAATCTCAT | CTTCTCCTTAGGAGTAACG |
| 72 | TCTAGTTTATCTATTAAAGATGCC | ATTATTATCAATTAATAACTCTT |
| 73 | TCTATCAAGAGGCGGTAA | GTCAAACATACTTCCAAA |
| 74 | TCTAAAGAGGATAAAAAGCTAG | TTTCGTCGTATAAGCA |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 74d | TCTAGTGTTTCAGGTAGTAGTG | TTTCGTCGTATAAGCA |
| 75 | TCTAAAAAATTAAAACACTCAA | TGTCCTCATTTTTTCAG |
| 76 | TCTGATGAAGTTACAACTTCAG | AATACTTGCTGGAACAG |
| 77 | TTATTCCAAAGTAAAATAAA | GTCTTTCTTCAATTTTGG |
| 78 | TCTCATAACCATCACTCAGAACACATGT | GTCGTGATTTTTATGAGT |
| 79 | TCTCCCAAGAATAGGATAAA | CCCAAACTGGCATAAC |
| 79d | TCTAGTCAGTATGAGTCACAGA | CCCAAACTGGCATAAC |
| 80 | TCTGCAGAAGTGTCACAAGA | TGAAGGACGTTTGTTG |
| 81 | TCTTTTGATGGATTTTT | TTTTTTTAGTTTAAGGCTA |
| 82 | TCTACAAATGAAAAACGAAC | GTCCACCTTCCGAT |
| 83 | TCTGAAATTAAACTCAAAAATATT | AACATTGTTTTTCCTTTC |
| 84 | TCTCATACTCAAGAACACAAAA | ATGGTGATGATGACCT |
| 85 | TCTCCTAAGAAGAAATCAGATAC | ATTAACATTTTGAGGGT |
| 86 | TCTGCAGAACTAACTCTTTTAA | TTTTGCAAAATCAACA |
| 87 | TCTGCGGATACATATAATAACTA | GAATAAATAACTGTATTTTTT |
| 88 | TCTTACCAAAAAATGACG | ATTTTCATTAATTTCCTCT |
| 89 | TCTGAAGAGCTTACCAAAAC | GATAGCTAATTGGTCTGT |
| 90 | TCTAGATATACAAATGGAAATTT | TAAAAGATGAGCTTCTCG |
| 91 | TCTAAAAAAGGACAAGTAAATG | AATTTCAATATAGCGACG |
| 92 | TCTGATTCTGTCATAAATAAGC | CTTGTTTGTCTTTACCTT |
| 93 | TCTGAATTTTCACGAGAAA | ATTATCCTTCAAAGCTG |
| 94 | TACCAATTAGGTAGCTATAA | TGTGTCATATAATGTAACCA |
| 95 | TCTGTTAATACAAAAACACTTCT | TGATCTTAATTTTCGAG |
| 96 | TCTGGTCAGTCTAAAAATGAAG | CCAAACAGGTTGATCT |
| 97 | TCTAGCCAGGAGGTATATG | ATTTACATCAGACTGTGAC |
| 98 | TCTGAAACTATTAATCCAGAAA | TTTATGGCCAATAACA |
| 99 | TCTACAAGTATGAACCATCAA | TTTTTTAGTAGTTGTCAATT |
| 100 | TCTAAGGGGCCAAAAGTAG | GTAAGCTGAATTTTCGA |
| 101 | TCTATTACTTTAGAAAAATTTATAGA | ACGAGAGTGGTTATTGG |
| 102 | TCTGCCTTTTACTTTGGCA | TTTCTTCACTCTTTCTAGAG |
| 103 | TCTATTTTTTCCTTGATCAT | CGGCCAGTTTTTTCTT |
| 104 | TCTGGTGAAACCCAAGATA | AACACCTGGTGGGCGT |
| 105 | TTAACAATTCATGGACC | ACTATTTCTAATTGCTCTG |
| 105d | TTAACAATTCATGGACC | TGGTCCCGGTGCGCCA |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 105d | TCTCAAGGACCTCCCGGTG | ACTATTTCTAATTGCTCTG |
| 106 | TCTCAAAATCAAAATTCACA | CTTAGCAGATTCATCCC |
| 107 | TCTCTGGAGCCTTTTATTT | TTTACTATTTGAAAATTGG |
| 108 | TCTGGTAATCGTTCAGATAAG | TTTCATAGGAACTTGTATT |
| 109 | TCTATCCAGCAGATCAACT | GTCCACACCTGCGACT |
| 109d | TCTAAACGGGTTCGCTATG | GTCCACACCTGCGACT |
| 110 | TCTGTAAAATTAGTATTCGCAC | TTTACCTAAGTAATATTCTGA |
| 111.19 | TCTGTTAGCGTTGATAAGGC | TCCCCGTCTTTTTGT |
| 112 | TCTACAATTAAAAATCTCACTG | GTCGTAATCATAAAAGCC |
| 113 | TCTAGTAAAATCAAAATTGTAACG | TTCATAACGAACCATAAC |
| 114 | TCTAATCTTTTAATTATGGGTT | TTTGAGTTCTAGCAACG |
| 115 | TTTCAATACTATTTAAAAGG | TTTTTTATCTTCTTCTTGC |
| 116 | TCTACCGAGGAGCCATTAA | TTTTAAAACCTGGTAAAC |
| 117 | TCTGAACAATCACAAAAAACA | TCAGCTCGTACTGTTT |
| 118 | TCTATGGTGACGGTGCTGG | GTCCTCCTCAATTGGT |
| 119 | TCTAGTCAGCCGGTAGGGG | CTCTTTTATACGCGATG |
| 120 | TCTGGTGGAGCATTTGCTA | GTTATTTGCTCGTTGTT |
| 121 | TCTAATAAAGATAATCAAAAAACT | TTTCTCAAATGTTTTCAT |
| 122 | TCTGCTGCCACCAAGAAAG | TTTCAAATGATCTACAGC |
| 123 | TCTACAACAAATGTAATGGC | GGCTAGTGTCTGTCCG |
| 124 | TCAATGAATTTTTCATTT | ACCATCTATTTTTACCCC |
| 125 | TCTACAAAATATCAGCGAATG | AGAACCCGCACTCTCA |
| 126 | TCTACTAAGCAAGCAATGTC | GAACGCAACGGCTGCT |
| 127 | TCTACAAAAGAATATCAAAATTAT | TTTCATATCAAAAACTATCG |
| 128 | TCGACTAATTCGTTAAA | TTCTTTATCTCTTAATGCTT |
| 129 | TTTGAAATAGTATTGGAAA | CACAACAGTTATTTTTCA |
| 130 | TCTATATTTTCTATTTTTATTATGT | AGGCCCTTCTGAGTAG |
| 130d | TCTAAAAAACAACTTCACAAC | AGGCCCTTCTGAGTAG |
| 131 | TCTAAACAGATATTGAAATAGC | AAATAATCCAATGGCTG |
| 132 | TCTATTAAATATTATCATTTGCA | CTTTTCAAGCTTTTTCC |
| 133 | TCTGCTTTACGGAACCTTG | AAAATGATCAGTTTGAGG |
| 134 | TCTACTATTTCTCAACAACAATAC | TTTTTGGCTTAAGAAAG |
| 135 | TCTGAAAAAAGAGTAGTTCAAC | CTTACGATACATTTTAAATTG |
| 136 | TCTAATCAATTATCAGAAATCA | TTCTTTTTTTACTTTAGCG |
| 137 | TCTCAAGAGTATAAAACAAAAGAG | CCATTGCAATCCAGCA |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 138 | TCTGCTGTATTTACACTCGTC | ATGTTTATGGCTTGCT |
| 139 | TCTGGCGGCAAGATAAAAT | TTTTTGATAAATCCCC |
| 140 | TCTGATGGGTTAAAGAATAATG | ATATGTGTATTCATCCTTT |
| 141 | TCTGATGTTGTAATTAGTGGAG | TACTTCTATTTTTCCATCTG |
| 142 | TTCGAATTAAGAGAAAGA | GTAATGCAATAAATCAAAA |
| 143 | TCTAGCTTTTTAGTGATTTCA | GGATTTTAGTTTCGCA |
| 144 | TATACGCATAGTGGAAC | CCCATTGATTTCGTCG |
| 145 | TCTGTTATTATCAGGGGCG | TACCTCTTTCAATACCAC |
| 146 | TCTGTTAGTCGTTCTCCGA | ATTACCGTTAGGTACTGTA |
| 147 | TCTGAGGAGCAAGAATTAAA | GGTATGGTTAACAGAATC |
| 148 | TCTATTCTAACAAAAGCAAGT | ATATACCCTAGACTTTTGA |
| 149 | TCTAGTGGGCGTTCATGGA | AGGAGTTTTATTGATGATAT |
| 150 | TCTGATACCCCTAATCAACTA | AAATGATTGTGGAAAAA |
| 151 | TGCAGGAGCTGTCCGC | ATCAAAGAAGTTGACATTG |
| 151 Long | TCTGTCCGCATTGGTAAAG | ATCAAAGAAGTTGACATTG |
| 152 | TCTAACTGCTTAGAAAATGAA | GTTAGATAAATTAACCAGTG |
| 153 | TCTAACAACTCCAGCA | CCCTTTGCTTCGTTGT |
| 154 | TCTGGAAAGGTCAGTGCAG | TTCCACAAGTCCGATT |
| 155 | TCTATTTTATTTTCAGATGAAC | TTGTTTGATTCGTCCT |
| 156 | TCTGCATCAGATGTTCAGA | ACTACCAAACTGCTGG |
| 157 | TCTAGTGACGTTGACAAATA | TTGTGTATTTTTAGTTAGGT |
| 158 | TCTATGACCATTTACTTCAATA | GTGGATAAAATTCGAAA |
| 159 | TCTCAAACTATTTTGACGC | CAGACTGACTAGGAGCT |
| 160 | TCTGATGAATATCTACGTGTCG | GACTTGTAATTGATTCGC |
| 161 | TCTGATGAGGTGGACTATAACA | GAAGGCACCACCACCT |
| 162 | TCTATTTTCTTGCTCTTAGTTG | GTTGTATAGATGAGTTAATCTG |
| 163 | TCTGAAACTGTCATTCAACTTG | ACGGTTTTAAAGAATG |
| 164 | TATTTTTAACAACAAAAA | TTTTTCTTTATCTTCTGTG |
| 165 | TCTCCAATTTTTATTGGTTT | CGATTTTGTAAGAGCTT |
| 166 | TCTGCATCTTATACCGTGAA | CGACGAAGCTATTTCT |
| 167 | TCTACAATTTATATTGCTTGG | TAAGGCTTGCATTTTG |
| 168 | TCTGTTGGATTGATGTTGG | TTTTCCTAAAAATTTTCC |
| 169 | TGGAAACAAATCACAG | GGCATCTCCTAGCTTT |
| 170 | TCTGCAATAGTTTTTACTTTTTT | TGATAAAGGTAGTTCTACAC |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 170d | TCTGGTTCTTATCATTTAACAA | TGATAAAGGTAGTTCTACAC |
| 171 | TCTGCTAGACCCAAACAGT | TTTTAGATGTTTTGTGG |
| 172 | TACACTCATATTGTTGAAAA | ATGATTGATAATTTTAAGC |
| 173 | TCTAATAGTACTGAGACAAGTGC | TGCTTTTTGATATGCC |
| 174 | TCTGCTTATGTCGTCAATTT | TAAAATAAAGTTCAGAAAAG |
| 175 | TCTGAATTACCTTCGTTTATC | TTTCTCCCTTGACTTTC |
| 176 | TCTAAACATCCGATACTTAATG | CTTTTTCTCAGATGCTT |
| 177 | TCTAATTATCCTTTTGCGA | GACATTGAAACGGAAT |
| 178 | TCTGGACTACGCGGAGTAT | TTTTATCAATGATGTTGA |
| 179 | TCTGCTATTGGAGCAGCTG | CATATGACGCAAACGC |
| 180 | TCTGATAAAGAAGGGATAGAGG | AGCCTCTTTTCTTGTT |
| 181 | TCTAAAGAAAAATCACAAACTG | ACGATTATCAACAAAGTT |
| 182 | TCTCAAAATAATAAAAAAGTAAAA | CATTCTTTTAAATACAAATC |
| 182d | TCTCAAAATAATAAAAAAGTAAAA | GGGTTTGAAAGTTTTC |
| 183 | TCAAATGGTCAATCTAGC | TTTAACTTTAATTACTGGAAT |
| 184 | TCTAAGGATTCAAAAATCCC | TTTTTTAATAAGCTTCGA |
| 185 | TCTGGGCAACCATCTACAT | TTTTTTGTAAACTTCCTG |
| 186 | TCTCATTCACAGGATAGCA | CTTAGATACATTGTTTTTTC |
| 187 | TCTGGACGAGGAGAAGTATC | CTTTCTTTTCTTACTTGC |
| 188 | TCACAATCTTCTCAAAA | TTTATTATTTTTAATACTTGAA |
| 189 | TCTGATAAGTCAGCAAACCC | CTTCAACTGTTGATAGAGC |
| 191 | TCTATCACGACATTACAGACT | TCCTTTAGCAGGAGCT |
| 192 | TCTAGATATTTAACTGCTGGT | GTTATACATGTTGTCTGAAG |
| 193 | TCTATAAAATATCAAGATGATTTT | CCAAATAATAACACGTTT |
| 194 | TTAGAAGTCAGAGAGCAG | GCTATCCCTTTCCAAT |
| 195 | TCTATTATGGAGACGGGTA | TGTATTTTAATTTGTTTTC |
| 195L | TCTTTGAATAATAAAGGTGTCG | TGTATTTTTAATTTGTTTTC |
| 195LN | TCTTTGAATAATAAAGGTGTCG | CAAACTTTTAACATTTAATG |
| 196 | TCTATTTCCTCAAATTTTTACG | ATAGTGTAAGCTACCAGC |
| 197 | TCTAATTTTTATAAGCTCTTG | GTCATCATATTCCTGAAA |
| 198 | TCTGCGCTTAAAGAATTAA | TGTTCGGCGTAAGATT |
| 199 | TTTTTAAAAGAAATTGAAA | ATTGGTCATTTCTTGAG |
| 200 | TTTCGTAAATATAATTTTGA | AACAGATTATTGGTTGG |
| 201 | TCTAGCGATACCTTTAATTTT | AGACTCATCAACTTTTTCT |
| 202 | TCTATGCTGATTAAGTCGC | GAACCCTGAAGGGTAG |

TABLE II-continued

PRIMERS USED TO AMPLIFY GBSnnn PROTEINS
Forward primers begin 5'-GGGGACAAGTTTGTACAAAAAAGCAGGC-3' and continue with the sequences
indicated in the table below; reverse primers begin 5'-GGGGACCACTTTGTACAAGAAAGCTGGGTT-3'
and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 203 | TGTGGTAAAACTGGACT | CCAATTGTATTTTTCAAC |
| 204 | TCTAAGACAGGAGCACCCGT | ATTTATACTACCTGTTGAATC |
| 205 | TGCGAGTCAATTGAGC | TTTAAATTTGTAGTCTTTAATA |
| 206 | TCTACAAATACTTTGAAAAAGA | CTCTTTTACTTTTCCAAAA |
| 207 | TCTAATTTATTTAAACGTTCCT | CCCTCCCTTAAGAGAA |
| 208 | TCTAAAAAGCGGCTAGTCA | TTGACGATGTTGCATC |
| 209 | TCTGGACAAAAATCAAAAATA | TTTCGAATTATTGTGACT |
| 209d | TCTGGACAAAAATCAAAAATA | GTATTGTTGTTGCCTG |
| 210 | TCTGGAGGAAAATTTCAGAA | TTTTTGATTTCCCTTTC |
| 210d | TCTACCTCATATCCTTTTATTT | TTTATAGTGTGTTGCAA |
| 211 | TGTGGACATCGTGGTG | TTTGCTAGGAACTTTGA |
| 212 | TCTAAGACTAAAAAAATCATCA | TGATTCAATTCCTTTTC |
| 213 | TCTAAACACACCAGTAAAGAA | TTTTTCCTCTACTTTCTTA |
| 214 | TCTAAAAATAAAAAAATCTTATTT | TTTGCTCACCTCCACA |
| 215 | TTAATAAAAGGATTATTGTCA | CAATAACTTCTGTAAAATAAA |
| 216 | TCTGCTCGTTTAATACCACA | TTCACCCTTAAAATAATT |
| 217 | TCTAACACTAACATCCCTAGC | TGCATTTTTCCCTTCT |
| 218 | TCTAGAGGGAAGGTTATTTAC | CTCCAGTAAAGTATTAGTATTT |
| 219 | TCTATCAATAAAGTAACAGCTCA | GTGAGGTTTTGGTAATT |
| 220 | TCTAGAACACTATTTAGAATGATAT | TGCATATAAGTTTTTTAGC |
| 220d | TACTATGCGAATCACAG | TGCATATAAGTTTTTTAGC |
| 221 | TCTAGTTTAGCATTGCAAAT | CTCATCTAAAGTGCTATCC |
| 222 | TCTACATTTTATAAAAGACGG | CTCGTATTTAGGCAACT |
| 223 | TCTAAGAAAATACGAAGCTATAC | ATTGGATATGCCATAAA |
| 224 | TCTGGAGGAAATGAAATATTA | GACTTTTTGATGTTTACTTT |
| 225 | TCTGGTATGTCTAATAAGGAAAT | TTCTTTACTATAAACATCTTCA |
| 226 | TCTAACAAACTTATTACAGAAAA | AGCATTTAAAGTTGAATGT |
| 227 | TCTGTTTCATATGAAAAAGTCC | GTTAGTCTCTTCAAGATCA |
| 228 | TCTAGTAGAGGTATTTTTTTACAA | AAGACCTACCGCCCAA |
| 229 | TCTGAACGTCGGGTAAGTC | TACTTCTTTCTCTTTCAATT |
| 230 | TTTTTAATCGATTTTATTT | CTTAGTGTTCCGATATGA |
| 231 | TCATTAATTATTCTTACGGT | TCTTGTTTTAAGAGCAGA |
| 231d | TCTTTATACGTTGTTAAACA | TCTTGTTTTAAGAGCAGA |
| 232 | TGGCTAAGTAAGCATGAG | ATCATGTTTTCCCTCAA |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 233 | TTCCCAGCTAGCTGTC | ATCTGATATATCCGTTTTAT |
| 234 | TCTATAGAAATTGCTGTATTAATT | TTTTTTGTCTCCTTTTTTA |
| 235 | TCTATTCGATTTCTTATTCTTG | AAAGACACGATAAACATAAG |
| 235d | TCTGACTCAACCACAGTCTC | AAAGACACGATAAACATAAG |
| 236 | TCTGCAGACCTTACAAGTCA | ATTTGCAACTTCTTGTATA |
| 237 | TCTATTGTATTTGCTATTGCA | TTTAAAAGTATCCTTAAATAAG |
| 238 | TCTGATATTTTTCAGCTATTGA | CTTCCTCCTCAATAGTTG |
| 239 | TCTGTTAGTGCTGCTATTGAA | TTCTCCTCCCCCATTA |
| 240 | TCTAAGAAGCTTACTTTTATTTG | ATCCAAACGAGTGAAAT |
| 241 | TCAAAAGGATATTCAAGA | AGGTGTTGTTGTATTTTC |
| 242 | TCTCATAATATATTAAGATTTTAGG | CTTTCTAAGTTTATTAAACATA |
| 243 | TCTATTCTTGGTCAAGATGT | GGCATCTGTTACCTTG |
| 244 | TCTCATGAAAATGTTAAAAAAG | AAACAACTCCATTATTTTT |
| 245 | TCTAAGTCAACGGTAACAAA | TAAACGTTGAAGAGCAT |
| 246 | AGGAAACGTTTTTCCT | CTTATCATATCTTGTTAAATCA |
| 246d | TCTAACCATAAGGGAAAAGTA | CTTATCATATCTTGTTAAATCA |
| 247 | TCTGCTAAACAATTAATTGGT | TTGCCATGGGTTATAG |
| 248 | TCTTTGATGGTGTTGTTATTC | AGAATTAAAATTTTCATGC |
| 248d | TCTAAAACTTATTTGTCAAATG | AGAATTAAAATTTTCATGC |
| 249 | TGGGCTTACCATACTG | TTTTTTAGATGTTTTATGTG |
| 250 | TCTGGCCTTAATCTTAAGC | CTCTTTTACTTTAGCTTCA |
| 251 | TCTCAATATTTTTTGAAACAAG | TTTCAAACTCCAGCCA |
| 252 | TTTATTTCAGGTTATATCAA | GGAGTGCCTTTCTACT |
| 253 | TCTGAAAATTGGAAGTTTGC | TTCATATCGTAAAGCATC |
| 254 | TCTATTGAAAAGGGAGTTG | ATCGTCAACCTTAACG |
| 255 | TCTATTGTTGGTAGAGAAATCA | TTTTACTTGACGTCTCAC |
| 256 | TATCATGTAAAAATTGATCA | GTCTTCCATTAATATTCCC |
| 257 | TCTGATTTTTTATACAAAGGAGG | CCAATTATTTTGAAAGTTC |
| 258 | TCTGAACGTTATACAGATAAAATG | ATTTTTTTGAATAATATAATCC |
| 259 | TCTCTTTCTCGTAAAAAAGAG | TTTATTATCAGAAAAGGC |
| 260 | TCTACTCTTGTCTTAGTTGTTTAT | ATTCAAAAAATTTTTCAA |
| 261 | TCTATAAAGAAAGCTGAAAATC | CGAAACGTCAGGTAAA |
| 262 | TCTATAAAAAATGCTATAGCATA | ACTTATTTTTGATAATATTTCTT |
| 263 | TCTCAGCCTTCTAAACTACTTC | ATCAGCATTTCTACGAA |
| 264 | TCTGATTTGTTTAGCATGTTG | ATGTAGACTCCTAATGATTT |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 265 | TCTCTTGCTTCCCTGATTT | TTTACTGTTCCTTTCGC |
| 266 | TCTCATCAATCAAATCATTATC | GAGATTAATTTGATTATATTTT |
| 267 | TCTATCTTTATTATCGGACAA | AACATCATTTCCTCCC |
| 268 | TCTAAAGAATTTATTAAAGAATGG | GTTGATAGTTCCAAAACG |
| 269 | TCTGCAGATGATGGTGGTT | TAAATGTGTTCCTACTAAATT |
| 270 | TTAAATGATGCAATAACAA | CATCAATAGCCGAGCTG |
| 271 | TTGCTGGATTATCCTC | TTTATTTTCCAAATGACA |
| 272 | TCTGTATTTATGGCAAATAAGA | TTCACTCGGAGTTGGAG |
| 272d | TCTATGAGTTCTCTGGAAGTT | TTCACTCGGAGTTGGAG |
| 273 | TCTGGTGTCCTCAACTCTG | AATGTAAATGACAAAGGTA |
| 274 | TCTGTTCATGATTTTGGTGA | GTTTTTTAATGGTTTGC |
| 275 | TCTGGGGTTTGGTTTTATA | TTTATCATAAGCATCTAGAC |
| 276 | TCTCAATCAGACATTAAAGCA | CTGATCTCTTGTTGATGC |
| 277 | TCTATTTGGAGGGGGAAA | AAGCAGGGGAGCAATA |
| 277d | TCTACCAAATTTGACTGGG | AAGCAGGGGAGCAATA |
| 278 | TCTGTTACGTTTTTCTTAT | CTGAGCAACACCTGTC |
| 279 | TCTAAAAAGAAAAGTTTAATTAGC | GGCAATTTTGTGGCAA |
| 280 | TTTGATTTTTTTAAGAAAA | TTGCTTAGTTAATGGCT |
| 281 | TCTAAGAAATTAATTATAGGTATTT | AGGCGTTGAATATAATTC |
| 281d | TCTGGTTTTTCGTTTTTGA | AGGCGTTGAATATAATTC |
| 282 | TCTCTATTCTCAGATGAAACAA | CTTTTCAACTCCAAACA |
| 283 | TCTGTTAAATTAAAATCGTTACTG | GAGTTGTCTTTTTTTGTC |
| 284 | TCTATGCAACGATTAGGAC | GCAATCACAATTGACAT |
| 285 | TTAGGTGAAAGCAAATC | CTTTGTCTGCTTCACTT |
| 286 | TCTGGAGGATTTTATATGAAAG | TTGTATCTTCTCCTGACC |
| 287 | TCTGCACACACACCTACTAGT | TTGGTTAATCGTCTTG |
| 287d | TCTAACAATCGTTCAAAGC | TTGGTTAATCGTCTTG |
| 288 | TCTAAAAAGTTTTTAAAAGTTTT | TTTAGTTACTTTCATAAATGG |
| 288d | TGGAATAATCATCAGTCA | TTTAGTTACTTTCATAAATGG |
| 289 | TCTCAATCTAAAGGGCAAA | ATATAATTCCTCTAAAACTAGC |
| 289L | TCTCAATCTAAAGGGCAAA | CCACTTCAAATTAACTAAC |
| 290 | TATTACTTATCAAAAGAAAAGG | ATTCCTTGAACACGAA |
| 291 | TCTCAAGTATTAAATGACAATGG | GTGCCATTCATTCTCT |
| 292 | TTGAATCGTAAAAAAGG | TTGTCCTGTGAACTGTG |

TABLE II-continued

PRIMERS USED TO AMPLIFY GBSnnn PROTEINS
Forward primers begin 5'-GGGGACAAGTTTGTACAAAAAAGCAGGC-3' and continue with the sequences
indicated in the table below; reverse primers begin 5'-GGGGACCACTTTGTACAAGAAAGCTGGGTT-3'
and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 293 | TCTATGGGTCTAGCAACAA | AGGGTTTATTTGTTGAAG |
| 293d N-term | TCTATGGGTCTAGCAACAA | TCCTGATTTATCCACTG |
| 293d C-term | TCTGTTACAGCTAAACACGG | AGGGTTTATTTGTTGAAG |
| 294 | TCTGGTCATTTTAGTGAAAAA | CAAAATACCTAAGCTAGC |
| 295 | TCTAGCGACATAAAAATCAT | ACGAACTTCCATAACC |
| 296 | TCTAAAGGTATTATTTTAGCG | GGCTTCTCCAATCAAA |
| 297 | TCTATTCAGATTGGCAAATT | TTGAGTTAATGGATTGTT |
| 298 | TCTACTAAATTTATTGTTGATTCA | TAGCGTTATTTCACTGTG |
| 299 | TTTGAAATACTTAAACCTG | TTTCTCCGCCCAGTCA |
| 300 | TCTGCTTCTACAAATAATGTTTC | CCGTTTATTCTTTCTACTG |
| 301 | TCTGTAATTAATATTGAGCAAGC | CATATCTGTTGCATCAAT |
| 302 | TCTGAAATCAACACTGAAATAG | AACTGGCTTTTTAGTCAG |
| 303 | TCTACAAGGCATATAAAAATTTC | TTTATTATTTAATTCTTCAATA |
| 304 | TCTAACGAAATCAAATGCCC | GTCTTTTAGAGCATCGA |
| 305 | TCTGGACGAGTAATGAAAACA | CTCTCCTCTAAGACTTTCG |
| 306 | TCTGGGAAAAAAATTGTTTT | TCCTTTTGTTACTTTTGC |
| 307 | TCTAAATTTACAGAACTTAACTTAT | TTTATCGCCTTTGTTG |
| 308 | ATGACACAGATGAATTTTA | ATGTTCAGGTTCTCCG |
| 309 | TTGCAACTTGGAATTG | TTCCATTATCTTCAAGTTA |
| 310 | TCTGCTAAAGAGAGGGTAGAT | CTCTTCTTCATTTTTCTTA |
| 311 | TCAATTATTACTGATGTTTAC | TTTTTTTAAGTTGTAGAATG |
| 312 | TCTACTGCAACTAAACAACAT | GTTTTTTGATGCTTCTTG |
| 313 | TCTAAACGTATTGCTGTTTTA | TTTACTACTTTGGTTGGC |
| 314 | TCTAAATTTTATCTTGTTAGACAC | GTGTGTCATTTTGACCT |
| 315 | TCTATAGGGGATTATTCAGTAA | TCCTTCAAGATCATTTAA |
| 316 | TCTACTGAACGAACATTCGA | ACCTCCTTTTCTTTCATT |
| 317 | TCTAATAAGCCATATTCAATAG | ATCTTCTCCTAACTTACCC |
| 317d N-term | TCTAATAAGCCATATTCAATAG | ACTAGCTAGATTCTTAACGC |
| 317d C-term | TCTGACTTGAATGGCAATAT | ATCTTCTCCTAACTTACCC |
| 318 | TCTATTGATTTATTATTTCTATTG | GCCTCTTTCTCCAAAT |
| 319 | TTAAAACATTTTGGTAGTAA | ATGTCCTGTTATATCTTCTT |
| 320 | TCTACTATTTATGACCAAATTG | GCGTTGAATAATGGTT |
| 321 | TCTAAAAATAAAAAAGATCAGTT | TATTTCTTTAGTTTCTTCAA |
| 322 | TCTCAAGAAACAGATACGACG | TAATAAAAATTATATAAGAACCT |
| 323 | TCTGGTAATGAGTCAAAGAAC | TTCTGTCTTATAAGCATAAG |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 324 | TCTGGAAGTAAATCAGCTTC | TTTTTTATAAGCATGTGTA |
| 325 | TCTGCTTGGCAACTTGTTC | ATGAGACATAAGGTCTTG |
| 326 | TCTGGCATCTCAGACTTACC | GTTGGAGCTCCTACTG |
| 326L | TCTAAATTCAAATCTGGGG | GTTGGAGCTCCTACTG |
| 326L N-term | TCTAAATTCAAATCTGGGG | CATTTCTTTGGTTAAAGC |
| 327 | TCTGGAGGGAAAATGAATC | TATCTCGAGTGCTATTTG |
| 327d N-term | TCTGGAGGGAAAATGAATC | CTCTTCATCGACATAGTAA |
| 327d C-term | TCTGGCAACTTCAAAGCAT | TATCTCGAGTGCTATTTG |
| 328 | TCTGACCAAGTCGGTGTCC | ATTTTACAGTAGTGGAGTTT |
| 329 | TCTAAATCAAAGACCTCTTCTA | TGTCCTCATTTTTTCA |
| 330 | TCTAATAAACGCGTAAAAATC | TTTAACAGTACGAACACG |
| 331 | TCTACCAGAACAGTAGCAAT | CCCCCTGTTTTTAAAAT |
| 332 | TCTACAAAAAACCTGTTATTAA | ACCCTCATATGATTCC |
| 333 | TCTATTGATATACAAAAAATAAAA | TTTAAAATAATGATACATCTC |
| 333d | TCTGGATCATTGAGGGCAA | TTTAAAATAATGATACATCTC |
| 334 | TCTAATTTAGTAAAAGTGAATAGTG | TAACCCCGTCTCAACA |
| 335 | TCTGAAGAAGAAAAATATTTTGA | TATTTTCGTTTTCTCAAA |
| 336 | TCTCAGGTTGAAGTTGACTTA | TTTCTCCAAATAATCTCTC |
| 337 | TCTGAAACAGATTCGTTTGTA | CCTACTTTTAGTTTTAGAAGA |
| 338 | TCTGCTATAATAGACAAAAAG | GAAATCATAGCTTCCC |
| 339 | TCGAAACCGATTAAGAT | ACCTTTTACTTTTGGTAGT |
| 339d | TCTCAAGTCATGCGCTATG | ACCTTTTACTTTTGGTAGT |
| 340 | TCTGGATTTCTCTATAATTACTTC | TTGTTTGTGAAGTAAAACG |
| 341 | TCTGGAAAACCATTGTTAAC | TAATTTAAAAATTGCATAAA |
| 342 | TCTCAGAAAATTGAAGGTATT | TTTCGTTACCATATCTAGA |
| 343 | TCTGAAATGCAAGTTCAAA | TAAATCATGGAAACTAGC |
| 344 | TCTGCACAACGCAGAATGT | AAAGCCCAACCTTCCG |
| 345 | TCTAAAAACCTGAATTGGG | GTTTCCACGTCCTTTC |
| 346 | TCTAATAAAATAGCTAATACAGAAG | AAGTTTATTCAAATCTGG |
| 347 | TCTATTGATATTCATTCTCATATC | AATGTAATGGTTTTTAATA |
| 348 | TCTACTGGATCTAAAAAATTAGC | AGCTAAAATACCTAACCAG |
| 349 | TCTAAAGATCGCTTATATAATAAA | ATTTTTTAAACGACTCAT |
| 350 | TCTGCAAAAGATATAATTAAGGTT | AGCGGAACGGTGAATA |
| 351 | TCAGAAGATCAAAAACA | ATAATCTAAACTATCAGCTCT |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 352 | TCTACTTTTTTAAAAAGCTAAA | ATCTCCTATTGTAATTTTGA |
| 352d | TCTGGTACAGATAGTAAATTTGG | ATCTCCTATTGTAATTTTGA |
| 353 | TCTACAATGTTAAAAATTGAAA | CACCTCTTTTGTCAGA |
| 354 | TCTATTAAAGAACTAAAAGAATTT | TTTGTTAGCGAGTAAGTC |
| 355 | TCTCGCTCACTACCTT | TTTATCATCCTCCTTAATAA |
| 356 | TCTAAATTCTATATTATTGATGATG | AAACGTTTTACTCTGTAAAA |
| 357 | TTGGAACATTTTTATATTAT | AAATAAGAATGTTAAAAGAGC |
| 358 | TTTTATACAATTGAAGAGC | TTCCCCAAAAATTTCT |
| 359 | TCAAGAAATAATTACGGT | ACGCAGTCCCATTTTC |
| 360 | TCTATAATGAAGGCGGTCT | CTGGCATGAGGTCTCA |
| 361 | TCTAGCGTATATGTTAGTGGA | CCTTTTTTCAATAATAGC |
| 362 | TCTACTAAACCACAGGGGG | ATCTTTAATCTTACCATCC |
| 362d N-term | TCTACTAAACCACAGGGGG | TGCTGCTACTGCAATG |
| 362 C-term | TCTGGTAATGAAGGAAATATCAC | ATCTTTAATCTTACCATCC |
| 363 | TCTCTCGAATTAAAAAATATTG | TAAATTCCTTTGTTGTAATA |
| 364 | TCTAACTATATGGGTATGGGC | ACCATCAGTTGTCACC |
| 365 | TCTGGAACTGCTACATATAGTAGG | TATTGACCAGTGCACG |
| 366 | TGGCTTGACATTATTTT | TTTTTTTGAATTTGTAAAAG |
| 367 | TCTAAGAAATTAAAAATATTCCC | AGAGATTATTTTTATTTTAAAT |
| 368 | TCTAAAATCATTATTCAACGT | TTTATTTTTAGTATCTAAAACG |
| 369 | TCTAGTAGAATGATTCCAGG | TTTAGAAACTCCAAGTATCTC |
| 370 | TCTACCGAATTTAATGACG | GTTAATTTGACTATTGATATATT |
| 371 | TCTAAAGATAGATATATTTTAGCAG | TAAACTCTCAAAAGCTAAAC |
| 372 | TCAGAAAAATATTCCACT | ACGTTCTTCTCTGGCT |
| 373 | TCTGAAATTGGTCAGCAAA | ACTTAAATGGAACAACC |
| 374 | TCTAAGTTCGAAAATATAATATATG | TTTGCCTAAAAAATTAGG |
| 375 | TCTGAAAAAGAAACTATTTTAAGT | GGCTTTCCTCCCTTCA |
| 376 | TCTAAAGAAAAGAAAAATTTGG | TTCATCTTTTTCAATATCA |
| 377 | TCTGGTAATAAACTGATGTATCA | GTGAGAGTGTCTTTGTTT |
| 378 | TCTGAAGATCAACTCACTATATTT | CAGATTTTTAGCTACTTGTC |
| 379 | TCTCAAATTACCCGAGAAG | TCTAGAGCGCTTTATAAG |
| 380 | TCTCTTAAAAGATTACTTACTGAAG | TTTTCTAATAGTTAGAAGCC |
| 381 | TCTCTTGGGATAGCTCACA | TTTTAAATGTGCAGAGA |
| 382 | TCTATAAAGTTTAAATTATTTTTAA | ATTTATAATTTCCTTGGG |
| 383 | TCTATTTTACAGACGAATATACTAT | TCTATAATATCTCTCTAAAGTGA |

TABLE II-continued

PRIMERS USED TO AMPLIFY GBSnnn PROTEINS
Forward primers begin 5'-GGGGACAAGTTTGTACAAAAAAGCAGGC-3' and continue with the sequences
indicated in the table below; reverse primers begin 5'-GGGGACCACTTTGTACAAGAAAGCTGGGTT-3'
and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
| --- | --- | --- |
| 384 | TCTAGAATAATTGTTGTCGG | CCTCGCTAACATATCAC |
| 385 | TCTAATGTAAAAAACGC | AGCTCTTACAGTCTTGC |
| 386 | TCTCTAGTATCAAAGGAGAAAGC | TTGTCTGAGTGACCAA |
| 387 | TCTGGTATGTTGTTAGCA | ATAATATGAAATATGTTGTTCA |
| 388 | TCTCTTATGATAATAAATTCATTCG | TCCGCAGAGTAAAAA |
| 389 | TCTATGAATAGTGAACATAAAATT | TTCATAAATGTGCCAA |
| 390 | TCTAGGGAAACTTACTGGA | TTCATCTCTGCTCACC |
| 391 | TCTAAAAAAGTCATCGATTTAA | TTCTCCTTCAGCTTTTA |
| 392 | TCTATTACATATGATTTCACAAG | GTCATTTTTCTAAAGTTTG |
| 393 | TCTAATAAATCTTGGTTGAGAA | TTTTTGTAGTTGTTTCAAT |
| 394 | TCTCCTATGTTGTCTGTTGG | TTTCATTAGATAACTATTCAGC |
| 395 | TCTACTTATCAAAAAACAGTTG | TATAGACTGAAGATAATTAATTAA |
| 396 | TTTGTCAAAGGGATTT | AAATCGATTAATCAAGTC |
| 397 | TCTAAATTATTTGATAAGTTTATAGA | TCTAAAGTAGTCCTTTAGACTA |
| 397d | TCTAAAACTGCTACAGTTAG | TCTAAAGTAGTCCTTTAGACTA |
| 398 | TATTTAGAACAATTAAAAGAGG | TTTGTCCATAATCATTTC |
| 399 | TCTAAAGTTTTAGTAGTTGATGAT | GGTAGATATGCCTAACATT |
| 400 | TCTAAAATAGTTGAAGGCG | GTTTCCTTCCAAAAAA |
| 401 | TCTGGAATTGAATTTAAAAATG | TCCATGCTTAATAGCC |
| 402 | TCTGGAAAATATTTTGGTACAG | ATCTAAACCAATTTCTGTAC |
| 403 | TCTGAGGTTAGAATGGTAACTC | GTCCACAAAAACGTCT |
| 404 | TCTAAAATAGATGACCTAAGAAA | TAGATGTTCTACGGAGAA |
| 405 | TTGAAAATTCAGTATTATCA | AAAGATGGCAAGCCAT |
| 406 | TCTGATAAAAATAATTTAGAAGACT | TCTCTCTCCACACCATA |
| 407 | TCTAAAATTGACATGAGGAA | CTTACCTCCTGTGGCT |
| 407d | TCTAAAATTGACATGAGGAA | CTTTTGTTGGTTACCTC |
| 408 | TCTAACCACTTACTTAACCTCA | TATTGTTAAATATGATGAAATG |
| 409 | TCTAAGGTAGTAGTAGCTATTGAT | ATGATTATACAAATTGATTAAT |
| 409d | TCTACTGAAGAGAGAAATCCT | ATGATTATACAAATTGATTAAT |
| 410 | TCTGCTTTATTATCAGTTATTGTC | TCCCTCTTCCTTGACA |
| 411 | TCTAAAGACTATATTAACAGAATATT | AACGTTTTGAGCTTT |
| 412 | TCTGGATTTTTTGCACAGC | TTTTGTCTTAAACGTTCT |
| 413 | TCTATTGTTGGTGAACAAGA | TTTAGATAGTCTAGCCATTT |
| 414 | TTAAATCAATATTTTCTGC | ACGGCTTGGGGCAGAG |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 415 | TCTGAGCGAATTCCTGTTC | TACCATTATCCGTGCT |
| 416 | TCTGAAGTCATTCGTGAACA | ACTATTAAACTCCAATGTTA |
| 417 | TCAAAACAATATGATTATATC | GCGCATTGTAACAAAT |
| 418 | TCTAGCAAGCCTAATGTTG | TTTTGGTAAAAGGTCTG |
| 419 | TCTGATTTAAATAATTACATCGC | TCCTGGAAAGTTCATC |
| 420 | TCTAAACGTGAATTACTACTCG | TAGTTTATCTAAAGCGTTC |
| 421 | TCTATACGCCAGTTTTTAAG | TTTATGTATAGAAACAGCAG |
| 422 | TTTTCGAGCGATTTTG | AATGTACATAACAATAGAGAGC |
| 423 | TCTGTAACCAAAGTTGAAGAG | CAACGATCCCAAGAAC |
| 424 | TCTATGAAAGATTTTATTGAATG | GCCATTCTTACCTCCT |
| 424d | TCTATGAAAGATTTTATTGAATG | ACGTTTTTCTGACCG |
| 425 | TCTATAGCCTTTAATAGTTTATTT | TATAAAATAAATTTGAAGATCT |
| 426 | TCTD440ACAGTTTATAATATAAACCATG | ATCATCTTGTACCAACTC |
| 427 | TATTCTTTTGAAGAACTTTT | GCCAATAAATTCACGG |
| 428 | TCTATAAAAATTTTGATCCC | AGTCTGTTTTTTAACAAAAG |
| 429 | TCTAATCATTCCATTGAATC | TGGTTTTAGAACAACTTTA |
| 430 | TTACAAAAAAATATCGG | AATTAAGCTGAAAATGAC |
| 431 | TCTGCGGCTCAATTAGCTG | ATTATATTCTTTTAATTTGTCA |
| 432 | TCTCGTACCTTCAAACCAG | CTTACGACGTCCTGGA |
| 433 | TCTATTAAAGCAACTTTTACTC | GTGTGTCATGACTACTGTAC |
| 434 | TCAATTTTTCAGACAACA | TGAGTAGAGCACAAGC |
| 642 | TCTAGAAAACGTAATGATACATT | GAAACGAATACGTTCTT |
| 643 | TCTGATTGTCAAATTACACCA | ACTACCTACCGTTTTCAC |
| 644 | TCTATTTTTCGTGGTGATAA | TTTGATGGTAACAGTCG |
| 645 | TTTTTTAATATTGAATATCAC | AGAAAGGCGCTCTTCT |
| 646 | TCTAAGGGAGTCCAATATATG | TATCTTTAATAAAGCCCTA |
| 647 | TCTCGTCGCATGAATACCA | CATCCCATAAATTTGTT |
| 648 | TCTATAGAATTTTCAGGGC | CAAGACATTTCTTAAAGC |
| 649 | TCTGCTACTCACTCTAACTCAG | TTTTGTTTTAGCGATG |
| 650 | TGCTCTTCTTCAAATACT | TTTTAAACCATGCTGT |
| 651 | TCTCTAACACCATTTACAAAAG | TTTGTAAAGACCTTCTTT |
| 652 | TCTCAACAAGGTATTATGGATA | TTCCTCGTTTATTAATTT |
| 653 | TCTAAAATTTTAGGTACACCA | AAAGAAAAGATGTGCC |
| 654 | TCTGGAAAAATGGTTAAGAA | CTGTGCAGGCTCAAAT |
| 655 | TCTAAATTCGTCCGAACCGT | AATTGTCCAGTCTAAGTTA |

TABLE II-continued

PRIMERS USED TO AMPLIFY GBSnnn PROTEINS
Forward primers begin 5'-GGGGACAAGTTTGTACAAAAAAGCAGGC-3' and continue with the sequences indicated in the table below; reverse primers begin 5'-GGGGACCACTTTGTACAAGAAAGCTGGGTT-3' and continue with the sequences indicated in the table. The primers for GBS1 are thus:
Fwd: GGGGACAAGTTTGTACAAAAAAGCAGGCTCTCAATCTCATATTGTTTCAG
Rev: GGGGACCACTTTGTACAAGAAAGCTGGGTTATTTTTAGACATCATAGACA
The full forward primer sequences are given in the sequence listing as SEQ IDs 10968-11492.
The reverse primer sequences are SEQ IDs 11493-12017.

| GBS | Forward | Reverse |
|---|---|---|
| 656 | TCTGGTCTTCCAACGCAGC | ATTTAGTGTTATTTCTCCTG |
| 657 | TGCTCAGGTAAAACAT | TTTTTTAAGTGATGATGAA |
| 658 | TCTGAAAGCAAATCTTTGC | CTTTGTCTGCTTCACTT |
| 659 | TGTGCTAATTGGATTG | TTTTGGGGTTACTTTAC |
| 660 | TGTGGAAATGTCGGAG | TTTTGCTGAAATAATGTT |
| 661 | TGTCAGTCAAACCACA | ATCATACGAATGCAAC |
| 662 | TCTGCTAGTTTTTATTTTTCC | TTTTTCATATTTTTTCAAA |
| 663 | TGTGGAAGTAAATCAGC | ATTATTTTTATAAGCATGTG |
| 664 | TCTGTTAAATTAAAATCGTTACTG | GAGTTGTCTTTTTTTGTC |
| 665 | TCTATTGCTGGTCCTAGTG | GATAAGCACTTTCCTTAA |
| 666 | TTATTTTTTGGAAATTGG | GCCTAAAAACCAATCA |
| 667 | TCTGCTGTATTTACACTCGTC | ATGTTTATGGCTTGCT |
| 668 | TTTTATATGAAAGAACAACA | TTGTATCTTCTCCTGACC |
| 669 | TCAATTATTATTGGGTTAA | ATATACCCTAGACTTTTGA |
| 670 | TCTCCTAAATTAACCCTAGTCT | GGCTTTAAAGTTCGATA |
| 671 | TCTAGTCTTGCGAAGGCAG | TTTATCGTAAGCACTTAGG |
| 672 | TCTGTATTTACACTCGTCTTACA | ATGTTTATGGCTTGCTT |
| 673 | TCTGGAGGATTTTATATGAAAG | TTGTATCTTCTCCTGACC |
| 674 | TCTGTTAAATTAAAATCGTTACTG | GAGTTGTCTTTTTTTGTCT |
| 675 | TCTGGTTCATCAGACAAACA | TTCAACTTGATTGCCA |
| 676 | TCTGTAGTTAAAGTTGGTATTAACG | TTTTGCAATTTTTGC |
| 677 | TCTGTATTAGAAGTACATGCTGA | TTTTAATGCTGTTTGAA |
| 678 | TCTGAGACACCAGTAATGGC | TTTTTTAGCTAAGGCTG |
| 679 | TCTGCTAACAAGCAGGATC | TTTTGCTAAACCTTCTG |
| 680 | TCTAATAAGTCCAGTAACTCTAAG | ATTCATATTAACACGATGC |
| 681 | TCTGCTTTTGATGTAATTATGC | TTTGCGTTTTGGAGGG |
| 682 | TCTATTAACTATGAGGTAAAGC | TGCACCTTGATGGCGA |
| 683 | TCTGTAATTGTTGAACTTAGTTTG | CCATAATATTTGATGCTG |
| 684 | TCTCTTAGGAAGTATAAGCAAA | TTCTAATCCTACAGCATG |
| 685 | TCTAAAATTTGTCTGGTTGG | AAAAATTCCTCCTAAATTAA |
| 686 | TCTGACTTTTATGATATCAATCTT | AAAGTTTTGACTATTACTGATAG |
| 687 | TATGCTATTATGCAAAAAG | TGGGGGAGATAGTTATG |
| 688 | TCTGCAATCGTTTCAGCAG | TTGACAGAAAGCTAATTG |

TABLE III

RESULTS FOR in vivo GBS CHALLENGE

| | % survival | |
|---|---|---|
| GBS # | Pre-immune | Post-immune |
| 1 | 18.7 | 22.2 |
| 4gst | 19.4 | 37.2 |
| 4his | 25.0 | 75.0 |
| 8 | 14.3 | 42.1 |
| 10 | 29.1 | 36.0 |
| 15 | 30.0 | 60.9 |
| 16 | 33.3 | 53.8 |
| 18 | 29.4 | 50.0 |
| 21 | 5.9 | 10.0 |
| 22 | 36.8 | 63.1 |
| 24 | 38.5 | 41.4 |
| 25 | 28.6 | 85.7 |
| 32 | 20.0 | 25.0 |
| 35 | 0.0 | 17.6 |
| 45 | 26.7 | 37.5 |
| 48 | 20.0 | 25.0 |
| 52 | 14.2 | 17.3 |
| 53 | 23.8 | 29.2 |
| 54 | 22.7 | 44.0 |
| 55 | 50.0 | 52.9 |
| 57 | 33.3 | 55.6 |
| 58 | 6.7 | 11.8 |
| 62 | 15.8 | 36.4 |
| 63 | 21.4 | 42.9 |
| 65 | 3.7 | 23.3 |
| 67 | 23.5 | 27.8 |
| 71 | 13.3 | 26.7 |
| 73 | 28.6 | 39.1 |
| 80 | 38.8 | 56.5 |
| 84 | 33.3 | 37.5 |
| 85 | 30.8 | 62.5 |
| 90 | 14.3 | 22.7 |
| 94 | 25.0 | 30.0 |
| 95 | 16.7 | 23.1 |
| 98 | 5.9 | 11.1 |
| 100 | 26.9 | 42.9 |
| 103 | 16.7 | 52.9 |
| 106 | 10.0 | 18.2 |
| 110 | 11.1 | 30.0 |
| 113 | 17.6 | 29.4 |
| 114 | 40.0 | 52.2 |
| 117 | 27.8 | 36.8 |
| 119 | 36.4 | 52.2 |
| 139 | 23.1 | 26.7 |
| 150 | 21.6 | 44.4 |
| 153 | 25.0 | 30.0 |
| 155 | 22.6 | 36.8 |
| 157 | 14.3 | 31.8 |
| 158 | 22.6 | 40.0 |
| 163 | 29.6 | 37.9 |
| 164 | 25.0 | 43.8 |
| 173 | 17.9 | 38.7 |
| 176 | 20.0 | 38.9 |
| 177 | 21.7 | 33.3 |
| 181 | 5.0 | 21.7 |
| 186 | 41.2 | 52.6 |
| 188 | 11.8 | 23.5 |
| 189 | 21.4 | 31.6 |
| 195 | 32.1 | 64.7 |
| 206 | 33.3 | 50.0 |
| 211 | 30.8 | 33.3 |
| 232 | 50.0 | 57.1 |
| 233 | 34.8 | 55.2 |
| 236 | 57.1 | 70.6 |
| 243 | 46.7 | 52.9 |
| 263 | 15.4 | 35.7 |
| 273 | 61.5 | 75.0 |
| 276 | 23.8 | 44.4 |
| 296 | 25.0 | 28.6 |
| 297 | 13.3 | 23.5 |
| 298 | 20.0 | 22.2 |
| 302 | 30.0 | 52.2 |
| 304 | 33.3 | 40.9 |
| 305 | 42.1 | 70.0 |
| 316 | 38.5 | 42.9 |
| 318 | 7.1 | 15.8 |

TABLE IV

COMPARISON OF GBSnnn NUMBERING AND SEQ ID NUMBER

| GBS numbering | Sequence listing |
|---|---|
| GBS1 | SEQ ID 3532 & 8736 |
| GBS2 | SEQ ID 4530 & 8818 |
| GBS3 | SEQ ID 6266 & 8958 |
| GBS4 | SEQ ID 2 & 8786 |
| GBS5 | SEQ ID 2598 & 8674 |
| GBS6 | SEQ ID 398 & 8496 |
| GBS7 | SEQ ID 8790 & 9798 |
| GBS8 | SEQ ID 8694 |
| GBS9 | SEQ ID 4540 & 8822 |
| GBS10 | SEQ ID 8718 |
| GBS11 | SEQ ID 5884 & 8930 |
| GBS12 | SEQ ID 8764 & 9692 |
| GBS13 | SEQ ID 8484 |
| GBS14 | SEQ ID 5406 & 8892 |
| GBS15 | SEQ ID 4 & 8710 |
| GBS16 | SEQ ID 944 & 8538 |
| GBS17 | SEQ ID 1770 & 8602 |
| GBS18 | SEQ ID 6860 & 9002 |
| GBS19 | SEQ ID 4422 & 8812 |
| GBS20 | SEQ ID 308 & 8488 |
| GBS21 | SEQ ID 8762 |
| GBS22 | SEQ ID 8584 |
| GBS23 | SEQ ID 8512 |
| GBS24 | SEQ ID 1694 & 8598 |
| GBS25 | SEQ ID 3180 & 8714 |
| GBS26 | SEQ ID 8820 |
| GBS27 | SEQ ID 8774 |
| GBS28 | SEQ ID 8738 |
| GBS29 | SEQ ID 8744 |
| GBS30 | SEQ ID 8860 |
| GBS31 | SEQ ID 8702 |
| GBS32 | SEQ ID 8910 & 10142 |
| GBS33 | SEQ ID 5734 & 8912 |
| GBS34 | SEQ ID 5750 & 8916 |
| GBS35 | SEQ ID 8908 |
| GBS36 | SEQ ID 8542 |
| GBS37 | SEQ ID 8564 |
| GBS38 | SEQ ID 2122 & 8642 |
| GBS39 | SEQ ID 8480 |
| GBS40 | SEQ ID 8654 |
| GBS41 | SEQ ID 1176 & 8562 |
| GBS42 | SEQ ID 4856 & 8850 |
| GBS43 | SEQ ID 672 & 8520 |
| GBS44 | SEQ ID 9000 |
| GBS45 | SEQ ID 9018 |
| GBS46 | SEQ ID 1834 & 8608 |
| GBS47 | SEQ ID 8588 |
| GBS48 | SEQ ID 8594 & 8596 |
| GBS49 | SEQ ID 8494 & 9490 |
| GBS50 | SEQ ID 1236 & 8566 |
| GBS51 | SEQ ID 5410 |
| GBS52 | SEQ ID 3920 |
| GBS53 | SEQ ID 8586 |
| GBS54 | SEQ ID 3442 |
| GBS55 | SEQ ID 9020 & 10338 |
| GBS56 | SEQ ID 2510 & 8668 |
| GBS57 | SEQ ID 8854 |
| GBS58 | SEQ ID 8664 |
| GBS59 | SEQ ID 3744 |
| GBS60 | SEQ ID 8760 |
| GBS61 | SEQ ID 8776 |

TABLE IV-continued

COMPARISON OF GBSnnn NUMBERING AND SEQ ID NUMBER

| GBS numbering | Sequence listing |
|---|---|
| GBS62 | SEQ ID 2244 |
| GBS63 | SEQ ID 390 |
| GBS64 | SEQ ID 374 |
| GBS65 | SEQ ID 8544 |
| GBS66 | SEQ ID 3028 |
| GBS67 | SEQ ID 3746 |
| GBS68 | SEQ ID 4012 |
| GBS69 | SEQ ID 4916 |
| GBS70 | SEQ ID 3718 |
| GBS71 | SEQ ID 8906 |
| GBS72 | SEQ ID 1348 |
| GBS73 | SEQ ID 220 |
| GBS74 | SEQ ID 5872 |
| GBS75 | SEQ ID 8926 |
| GBS76 | SEQ ID 5862 |
| GBS77 | SEQ ID 3256 |
| GBS78 | SEQ ID 3262 |
| GBS79 | SEQ ID 3264 |
| GBS80 | SEQ ID 8780 |
| GBS81 | SEQ ID 2706 |
| GBS82 | SEQ ID 2898 |
| GBS83 | SEQ ID 8772 |
| GBS84 | SEQ ID 4182 |
| GBS85 | SEQ ID 216 |
| GBS86 | SEQ ID 2978 |
| GBS87 | SEQ ID 3452 |
| GBS88 | SEQ ID 5694 |
| GBS89 | SEQ ID 2682 |
| GBS90 | SEQ ID 8476 |
| GBS91 | SEQ ID 8938 |
| GBS92 | SEQ ID 8964 & 10238 |
| GBS93 | SEQ ID 2848 |
| GBS94 | SEQ ID 1592 |
| GBS95 | SEQ ID 2224 |
| GBS96 | SEQ ID 2130 |
| GBS97 | SEQ ID 800 |
| GBS98 | SEQ ID 8746 |
| GBS99 | SEQ ID 4240 |
| GBS100 | SEQ ID 8782 |
| GBS101 | SEQ ID 6902 |
| GBS102 | SEQ ID 6894 |
| GBS103 | SEQ ID 6 |
| GBS104 | SEQ ID 8778 |
| GBS105 | SEQ ID 1400 |
| GBS106 | SEQ ID 8502 |
| GBS107 | SEQ ID 6026 |
| GBS108 | SEQ ID 8532 |
| GBS109 | SEQ ID 4116 |
| GBS110 | SEQ ID 6832 |
| GBS111 | SEQ ID 8842 |
| GBS112 | SEQ ID 8904 |
| GBS113 | SEQ ID 300 |
| GBS114 | SEQ ID 8968 |
| GBS115 | SEQ ID 5164 |
| GBS116 | SEQ ID 5152 |
| GBS117 | SEQ ID 8962 |
| GBS118 | SEQ ID 2508 |
| GBS119 | SEQ ID 8814 |
| GBS120 | SEQ ID 8874 |
| GBS121 | SEQ ID 3826 |
| GBS122 | SEQ ID 9006 |
| GBS123 | SEQ ID 6310 |
| GBS124 | SEQ ID 260 |
| GBS125 | SEQ ID 3872 |
| GBS126 | SEQ ID 6736 |
| GBS127 | SEQ ID 8816 |
| GBS128 | SEQ ID 752 |
| GBS129 | SEQ ID 8990 |
| GBS130 | SEQ ID 9004 |
| GBS131 | SEQ ID 6198 |
| GBS132 | SEQ ID 8730 |
| GBS133 | SEQ ID 474 |
| GBS134 | SEQ ID 9008 |
| GBS135 | SEQ ID 8882 |
| GBS136 | SEQ ID 1188 |
| GBS137 | SEQ ID 3960 |
| GBS138 | SEQ ID 9052 |
| GBS139 | SEQ ID 884 |
| GBS140 | SEQ ID 8632 |
| GBS141 | SEQ ID 1768 |
| GBS142 | SEQ ID 8600 |
| GBS143 | SEQ ID 9054 |
| GBS144 | SEQ ID 2238 |
| GBS145 | SEQ ID 8700 |
| GBS146 | SEQ ID 8696 |
| GBS147 | SEQ ID 8526 |
| GBS148 | SEQ ID 9010 |
| GBS149 | SEQ ID 8732 |
| GBS150 | SEQ ID 3736 |
| GBS151 | SEQ ID 3188 |
| GBS152 | SEQ ID 3952 |
| GBS153 | SEQ ID 3904 |
| GBS154 | SEQ ID 4024 |
| GBS155 | SEQ ID 8796 |
| GBS156 | SEQ ID 4646 |
| GBS157 | SEQ ID 4812 |
| GBS158 | SEQ ID 5504 |
| GBS159 | SEQ ID 8628 |
| GBS160 | SEQ ID 8924 |
| GBS161 | SEQ ID 8922 |
| GBS162 | SEQ ID 168 |
| GBS163 | SEQ ID 224 |
| GBS164 | SEQ ID 1102 |
| GBS165 | SEQ ID 3672 |
| GBS166 | SEQ ID 8712 |
| GBS167 | SEQ ID 4214 |
| GBS168 | SEQ ID 9016 |
| GBS169 | SEQ ID 4346 |
| GBS170 | SEQ ID 8982 |
| GBS171 | SEQ ID 6720 |
| GBS172 | SEQ ID 6704 |
| GBS173 | SEQ ID 8788 |
| GBS174 | SEQ ID 6150 |
| GBS175 | SEQ ID 62 |
| GBS176 | SEQ ID 8478 |
| GBS177 | SEQ ID 8876 |
| GBS178 | SEQ ID 6078 |
| GBS179 | SEQ ID 8848 |
| GBS180 | SEQ ID 3062 |
| GBS181 | SEQ ID 1924 |
| GBS182 | SEQ ID 3774 |
| GBS183 | SEQ ID 4796 |
| GBS184 | SEQ ID 1978 |
| GBS185 | SEQ ID 1046 |
| GBS186 | SEQ ID 8470 |
| GBS187 | SEQ ID 844 |
| GBS188 | SEQ ID 3410 |
| GBS189 | SEQ ID 6986 |
| GBS190 | SEQ ID 8842 |
| GBS191 | SEQ ID 1814 |
| GBS192 | SEQ ID 8618 |
| GBS193 | SEQ ID 2382 |
| GBS194 | SEQ ID 3912 |
| GBS195 | SEQ ID 8 |
| GBS196 | SEQ ID 4944 |
| GBS197 | SEQ ID 5486 |
| GBS198 | SEQ ID 8896 |
| GBS199 | SEQ ID 1162 |
| GBS200 | SEQ ID 8936 |
| GBS201 | SEQ ID 4550 |
| GBS202 | SEQ ID 8666 |
| GBS203 | SEQ ID 6478 |
| GBS204 | SEQ ID 1996 |
| GBS205 | SEQ ID 18 |
| GBS206 | SEQ ID 8552 |
| GBS207 | SEQ ID 3822 |
| GBS208 | SEQ ID 3916 |
| GBS209 | SEQ ID 3918 |
| GBS210 | SEQ ID 3738 |
| GBS211 | SEQ ID 4680 |

TABLE IV-continued

COMPARISON OF GBSnnn NUMBERING AND SEQ ID NUMBER

| GBS numbering | Sequence listing |
|---|---|
| GBS212 | SEQ ID 8750 |
| GBS213 | SEQ ID 8500 |
| GBS214 | SEQ ID 8498 |
| GBS215 | SEQ ID 9022 |
| GBS216 | SEQ ID 8606 |
| GBS217 | SEQ ID 9024 |
| GBS218 | SEQ ID 8652 |
| GBS219 | SEQ ID 8646 |
| GBS220 | SEQ ID 2730 |
| GBS221 | SEQ ID 9028 |
| GBS222 | SEQ ID 3842 |
| GBS223 | SEQ ID 8794 |
| GBS224 | SEQ ID 9026 |
| GBS225 | SEQ ID 8834 |
| GBS226 | SEQ ID 4966 |
| GBS227 | SEQ ID 5030 |
| GBS228 | SEQ ID 5050 |
| GBS229 | SEQ ID 9056 |
| GBS230 | SEQ ID 1296 |
| GBS231 | SEQ ID 5810 |
| GBS232 | SEQ ID 5830 |
| GBS233 | SEQ ID 4722 |
| GBS234 | SEQ ID 1106 |
| GBS235 | SEQ ID 8560 |
| GBS236 | SEQ ID 6162 |
| GBS237 | SEQ ID 8706 |
| GBS238 | SEQ ID 4246 |
| GBS239 | SEQ ID 8980 |
| GBS240 | SEQ ID 8986 |
| GBS241 | SEQ ID 9030 |
| GBS242 | SEQ ID 9032 |
| GBS243 | SEQ ID 8678 |
| GBS244 | SEQ ID 6554 |
| GBS245 | SEQ ID 8994 |
| GBS246 | SEQ ID 6864 |
| GBS247 | SEQ ID 8856 |
| GBS248 | SEQ ID 454 |
| GBS249 | SEQ ID 8620 |
| GBS250 | SEQ ID 8634 |
| GBS251 | SEQ ID 2258 |
| GBS252 | SEQ ID 8648 |
| GBS253 | SEQ ID 2526 |
| GBS254 | SEQ ID 2710 |
| GBS255 | SEQ ID 2966 |
| GBS256 | SEQ ID 3424 |
| GBS257 | SEQ ID 3550 |
| GBS258 | SEQ ID 3752 |
| GBS259 | SEQ ID 8756 |
| GBS260 | SEQ ID 4162 |
| GBS261 | SEQ ID 1530 |
| GBS262 | SEQ ID 8572 |
| GBS263 | SEQ ID 1616 |
| GBS264 | SEQ ID 8824 |
| GBS265 | SEQ ID 4554 |
| GBS266 | SEQ ID 4652 |
| GBS267 | SEQ ID 4980 |
| GBS268 | SEQ ID 5038 |
| GBS269 | SEQ ID 5534 |
| GBS270 | SEQ ID 1998 |
| GBS271 | SEQ ID 8570 |
| GBS272 | SEQ ID 22 |
| GBS273 | SEQ ID 5994 |
| GBS274 | SEQ ID 774 |
| GBS275 | SEQ ID 2308 |
| GBS276 | SEQ ID 8942 |
| GBS277 | SEQ ID 8954 |
| GBS278 | SEQ ID 8524 |
| GBS279 | SEQ ID 6292 |
| GBS280 | SEQ ID 6254 |
| GBS281 | SEQ ID 4458 |
| GBS282 | SEQ ID 4444 |
| GBS283 | SEQ ID 9034 |
| GBS284 | SEQ ID 6456 & 8974 |
| GBS285 | SEQ ID 8802 |
| GBS286 | SEQ ID 9036 |
| GBS287 | SEQ ID 5354 |
| GBS288 | SEQ ID 5374 |
| GBS289 | SEQ ID 8616 |
| GBS290 | SEQ ID 8680 |
| GBS291 | SEQ ID 8530 |
| GBS292 | SEQ ID 8998 |
| GBS293 | SEQ ID 8582 |
| GBS294 | SEQ ID 8604 |
| GBS295 | SEQ ID 2722 |
| GBS296 | SEQ ID 2658 |
| GBS297 | SEQ ID 3024 |
| GBS298 | SEQ ID 8704 |
| GBS299 | SEQ ID 3268 |
| GBS300 | SEQ ID 4170 |
| GBS301 | SEQ ID 8576 |
| GBS302 | SEQ ID 8670 |
| GBS303 | SEQ ID 8554 |
| GBS304 | SEQ ID 5846 |
| GBS305 | SEQ ID 208 |
| GBS306 | SEQ ID 212 |
| GBS307 | SEQ ID 8992 |
| GBS308 | SEQ ID 8880 |
| GBS309 | SEQ ID 3386 |
| GBS310 | SEQ ID 286 |
| GBS311 | SEQ ID 3964 |
| GBS312 | SEQ ID 4660 |
| GBS313 | SEQ ID 4090 |
| GBS314 | SEQ ID 8556 |
| GBS315 | SEQ ID 1766 |
| GBS316 | SEQ ID 2000 |
| GBS317 | SEQ ID 4210 |
| GBS318 | SEQ ID 8548 |
| GBS319 | SEQ ID 892 |
| GBS320 | SEQ ID 916 |
| GBS321 | SEQ ID 8846 |
| GBS322 | SEQ ID 8540 |
| GBS323 | SEQ ID 2102 |
| GBS324 | SEQ ID 8490 |
| GBS325 | SEQ ID 8900 |
| GBS326 | SEQ ID 8630 |
| GBS327 | SEQ ID 5856 |
| GBS328 | SEQ ID 6016 |
| GBS329 | SEQ ID 8928 |
| GBS330 | SEQ ID 8792 |
| GBS331 | SEQ ID 922 |
| GBS332 | SEQ ID 1004 |
| GBS333 | SEQ ID 1786 |
| GBS334 | SEQ ID 1784 |
| GBS335 | SEQ ID 1782 |
| GBS336 | SEQ ID 1886 |
| GBS337 | SEQ ID 2010 |
| GBS338 | SEQ ID 8638 |
| GBS339 | SEQ ID 2080 |
| GBS340 | SEQ ID 8594 & 8596 |
| GBS341 | SEQ ID 2280 |
| GBS342 | SEQ ID 2266 |
| GBS343 | SEQ ID 8644 |
| GBS344 | SEQ ID 8662 |
| GBS345 | SEQ ID 2442 |
| GBS346 | SEQ ID 2768 |
| GBS347 | SEQ ID 2766 |
| GBS348 | SEQ ID 8658 |
| GBS349 | SEQ ID 2360 |
| GBS350 | SEQ ID 8698 |
| GBS351 | SEQ ID 2970 |
| GBS352 | SEQ ID 8692 |
| GBS353 | SEQ ID 3454 |
| GBS354 | SEQ ID 8754 |
| GBS355 | SEQ ID 8752 |
| GBS356 | SEQ ID 8724 |
| GBS357 | SEQ ID 8720 |
| GBS358 | SEQ ID 3184 |
| GBS359 | SEQ ID 3948 |
| GBS360 | SEQ ID 3926 |
| GBS361 | SEQ ID 8770 |

TABLE IV-continued

COMPARISON OF GBSnnn NUMBERING AND SEQ ID NUMBER

| GBS numbering | Sequence listing |
|---|---|
| GBS362 | SEQ ID 8768 |
| GBS363 | SEQ ID 3816 |
| GBS364 | SEQ ID 1452 |
| GBS365 | SEQ ID 1398 |
| GBS366 | SEQ ID 8574 |
| GBS367 | SEQ ID 1340 |
| GBS368 | SEQ ID 1598 |
| GBS369 | SEQ ID 4822 |
| GBS370 | SEQ ID 8844 |
| GBS371 | SEQ ID 4926 |
| GBS372 | SEQ ID 4956 |
| GBS373 | SEQ ID 5062 |
| GBS374 | SEQ ID 8878 |
| GBS375 | SEQ ID 326 |
| GBS376 | SEQ ID 5380 |
| GBS377 | SEQ ID 5468 |
| GBS378 | SEQ ID 5570 |
| GBS379 | SEQ ID 8918 |
| GBS380 | SEQ ID 156 |
| GBS381 | SEQ ID 8934 |
| GBS382 | SEQ ID 8610 |
| GBS383 | SEQ ID 4738 |
| GBS384 | SEQ ID 8836 |
| GBS385 | SEQ ID 1094 |
| GBS386 | SEQ ID 9038 |
| GBS387 | SEQ ID 8558 |
| GBS388 | SEQ ID 9040 |
| GBS389 | SEQ ID 8516 |
| GBS390 | SEQ ID 8952 |
| GBS391 | SEQ ID 8522 |
| GBS392 | SEQ ID 6220 |
| GBS393 | SEQ ID 8966 |
| GBS394 | SEQ ID 8960 |
| GBS395 | SEQ ID 6276 |
| GBS396 | SEQ ID 8468 |
| GBS397 | SEQ ID 6262 |
| GBS398 | SEQ ID 8806 |
| GBS399 | SEQ ID 1960 |
| GBS400 | SEQ ID 3154 |
| GBS401 | SEQ ID 3170 |
| GBS402 | SEQ ID 4236 |
| GBS403 | SEQ ID 8798 |
| GBS404 | SEQ ID 8800 |
| GBS405 | SEQ ID 8508 |
| GBS406 | SEQ ID 8506 |
| GBS407 | SEQ ID 6484 |
| GBS408 | SEQ ID 9042 |
| GBS409 | SEQ ID 6678 |
| GBS410 | SEQ ID 4064 |
| GBS411 | SEQ ID 9044 |
| GBS412 | SEQ ID 9046 |
| GBS413 | SEQ ID 272 |
| GBS414 | SEQ ID 8946 |
| GBS415 | SEQ ID 8944 |
| GBS416 | SEQ ID 6044 |
| GBS417 | SEQ ID 1874 |
| GBS418 | SEQ ID 5146 |
| GBS419 | SEQ ID 2638 |
| GBS420 | SEQ ID 2104 |
| GBS421 | SEQ ID 2108 |
| GBS422 | SEQ ID 714 |
| GBS423 | SEQ ID 6884 |
| GBS424 | SEQ ID 4874 |
| GBS425 | SEQ ID 3978 |
| GBS426 | SEQ ID 3976 |
| GBS427 | SEQ ID 6958 |
| GBS428 | SEQ ID 3398 |
| GBS429 | SEQ ID 3402 |
| GBS430 | SEQ ID 8840 |
| GBS431 | SEQ ID 8902 |
| GBS432 | SEQ ID 8534 |
| GBS433 | SEQ ID 2558 |
| GBS434 | SEQ ID 8590 |
| GBS435 | SEQ ID 484 |
| GBS436 | SEQ ID 8472 |
| GBS437 | SEQ ID 466 |
| GBS438 | SEQ ID 362 |
| GBS439 | SEQ ID 900 |
| GBS440 | SEQ ID 8536 |
| GBS441 | SEQ ID 936 |
| GBS442 | SEQ ID 940 |
| GBS443 | SEQ ID 998 |
| GBS444 | SEQ ID 1776 |
| GBS445 | SEQ ID 8634 |
| GBS446 | SEQ ID 2048 |
| GBS447 | SEQ ID 1654 |
| GBS448 | SEQ ID 8592 |
| GBS449 | SEQ ID 1634 |
| GBS450 | SEQ ID 1630 |
| GBS451 | SEQ ID 2098 |
| GBS452 | SEQ ID 2062 |
| GBS453 | SEQ ID 8636 |
| GBS454 | SEQ ID 1734 |
| GBS455 | SEQ ID 1690 |
| GBS456 | SEQ ID 1684 |
| GBS457 | SEQ ID 8656 |
| GBS458 | SEQ ID 8650 |
| GBS459 | SEQ ID 2152 |
| GBS460 | SEQ ID 2148 |
| GBS461 | SEQ ID 2394 |
| GBS462 | SEQ ID 2778 |
| GBS463 | SEQ ID 8688 |
| GBS464 | SEQ ID 8684 |
| GBS465 | SEQ ID 8682 |
| GBS466 | SEQ ID 2694 |
| GBS467 | SEQ ID 2350 |
| GBS468 | SEQ ID 8660 |
| GBS469 | SEQ ID 2998 |
| GBS470 | SEQ ID 2988 |
| GBS471 | SEQ ID 2924 |
| GBS472 | SEQ ID 2910 |
| GBS473 | SEQ ID 2882 |
| GBS474 | SEQ ID 2878 |
| GBS475 | SEQ ID 2856 |
| GBS476 | SEQ ID 8690 |
| GBS477 | SEQ ID 3112 |
| GBS478 | SEQ ID 3432 |
| GBS479 | SEQ ID 3460 |
| GBS480 | SEQ ID 3504 |
| GBS481 | SEQ ID 8734 |
| GBS482 | SEQ ID 8740 |
| GBS483 | SEQ ID 3606 |
| GBS484 | SEQ ID 3562 |
| GBS485 | SEQ ID 3552 |
| GBS486 | SEQ ID 3762 |
| GBS487 | SEQ ID 3756 |
| GBS488 | SEQ ID 3732 |
| GBS489 | SEQ ID 3730 |
| GBS490 | SEQ ID 3704 |
| GBS491 | SEQ ID 3698 |
| GBS492 | SEQ ID 3252 |
| GBS493 | SEQ ID 3244 |
| GBS494 | SEQ ID 3238 |
| GBS495 | SEQ ID 8722 |
| GBS496 | SEQ ID 8716 |
| GBS497 | SEQ ID 3876 |
| GBS498 | SEQ ID 3858 |
| GBS499 | SEQ ID 8758 |
| GBS500 | SEQ ID 4022 |
| GBS501 | SEQ ID 4106 |
| GBS502 | SEQ ID 1406 |
| GBS503 | SEQ ID 8580 |
| GBS504 | SEQ ID 4578 |
| GBS505 | SEQ ID 4566 |
| GBS506 | SEQ ID 8832 |
| GBS507 | SEQ ID 8830 |
| GBS508 | SEQ ID 4644 |
| GBS509 | SEQ ID 8828 |
| GBS510 | SEQ ID 8826 |
| GBS511 | SEQ ID 4892 |

TABLE IV-continued

COMPARISON OF GBSnnn NUMBERING AND SEQ ID NUMBER

| GBS numbering | Sequence listing |
| --- | --- |
| GBS512 | SEQ ID 4970 |
| GBS513 | SEQ ID 4974 |
| GBS514 | SEQ ID 8862 |
| GBS515 | SEQ ID 8864 |
| GBS516 | SEQ ID 8866 |
| GBS517 | SEQ ID 8868 |
| GBS518 | SEQ ID 9012 |
| GBS519 | SEQ ID 5068 |
| GBS520 | SEQ ID 8870 |
| GBS521 | SEQ ID 5228 |
| GBS522 | SEQ ID 322 |
| GBS523 | SEQ ID 8492 |
| GBS524 | SEQ ID 8894 |
| GBS525 | SEQ ID 5430 |
| GBS526 | SEQ ID 5414 |
| GBS527 | SEQ ID 5524 |
| GBS528 | SEQ ID 8898 |
| GBS529 | SEQ ID 5670 |
| GBS530 | SEQ ID 5630 |
| GBS531 | SEQ ID 5588 |
| GBS532 | SEQ ID 1324 |
| GBS533 | SEQ ID 8914 |
| GBS534 | SEQ ID 8550 |
| GBS535 | SEQ ID 8568 |
| GBS536 | SEQ ID 1288 |
| GBS537 | SEQ ID 5798 |
| GBS538 | SEQ ID 8920 |
| GBS539 | SEQ ID 158 |
| GBS540 | SEQ ID 8482 |
| GBS541 | SEQ ID 184 |
| GBS542 | SEQ ID 9048 |
| GBS543 | SEQ ID 8932 |
| GBS544 | SEQ ID 5880 |
| GBS545 | SEQ ID 44 |
| GBS546 | SEQ ID 9014 |
| GBS547 | SEQ ID 12 |
| GBS548 | SEQ ID 8614 |
| GBS549 | SEQ ID 8612 |
| GBS550 | SEQ ID 4720 |
| GBS551 | SEQ ID 4710 |
| GBS552 | SEQ ID 1086 |
| GBS553 | SEQ ID 1088 |
| GBS554 | SEQ ID 1138 |
| GBS555 | SEQ ID 8748 |
| GBS556 | SEQ ID 5968 |
| GBS557 | SEQ ID 774 |
| GBS558 | SEQ ID 1192 |
| GBS559 | SEQ ID 1196 |
| GBS560 | SEQ ID 1268 |
| GBS561 | SEQ ID 8518 |
| GBS562 | SEQ ID 8676 |
| GBS563 | SEQ ID 2296 |
| GBS564 | SEQ ID 2300 |
| GBS565 | SEQ ID 8950 |
| GBS566 | SEQ ID 694 |
| GBS567 | SEQ ID 680 |
| GBS568 | SEQ ID 6300 |
| GBS569 | SEQ ID 8956 |
| GBS570 | SEQ ID 8972 |
| GBS571 | SEQ ID 8970 |
| GBS572 | SEQ ID 3300 |
| GBS573 | SEQ ID 3304 |
| GBS574 | SEQ ID 8726 |
| GBS575 | SEQ ID 8810 |
| GBS576 | SEQ ID 4418 |
| GBS577 | SEQ ID 8808 |
| GBS578 | SEQ ID 4382 |
| GBS579 | SEQ ID 4378 |
| GBS580 | SEQ ID 1932 |
| GBS581 | SEQ ID 8622 |
| GBS582 | SEQ ID 8624 |
| GBS583 | SEQ ID 1962 |
| GBS584 | SEQ ID 8708 |
| GBS585 | SEQ ID 8672 |
| GBS586 | SEQ ID 6444 |
| GBS587 | SEQ ID 8976 |
| GBS588 | SEQ ID 8804 |
| GBS589 | SEQ ID 8514 |
| GBS590 | SEQ ID 8510 |
| GBS591 | SEQ ID 630 |
| GBS592 | SEQ ID 8504 |
| GBS593 | SEQ ID 514 |
| GBS594 | SEQ ID 8978 |
| GBS595 | SEQ ID 6738 |
| GBS596 | SEQ ID 6712 |
| GBS597 | SEQ ID 6686 |
| GBS598 | SEQ ID 6674 |
| GBS599 | SEQ ID 6662 |
| GBS600 | SEQ ID 8988 |
| GBS601 | SEQ ID 8578 |
| GBS602 | SEQ ID 8948 |
| GBS603 | SEQ ID 6132 |
| GBS604 | SEQ ID 5282 |
| GBS605 | SEQ ID 5302 |
| GBS606 | SEQ ID 8884 |
| GBS607 | SEQ ID 5314 |
| GBS608 | SEQ ID 8886 |
| GBS609 | SEQ ID 8888 |
| GBS610 | SEQ ID 8890 |
| GBS611 | SEQ ID 6028 |
| GBS612 | SEQ ID 8474 |
| GBS613 | SEQ ID 5092 |
| GBS614 | SEQ ID 8872 |
| GBS615 | SEQ ID 6052 |
| GBS616 | SEQ ID 8940 |
| GBS617 | SEQ ID 1824 |
| GBS618 | SEQ ID 6600 |
| GBS619 | SEQ ID 6608 |
| GBS620 | SEQ ID 6620 |
| GBS621 | SEQ ID 864 |
| GBS622 | SEQ ID 8640 |
| GBS623 | SEQ ID 8996 |
| GBS624 | SEQ ID 9050 |
| GBS625 | SEQ ID 2812 |
| GBS626 | SEQ ID 8858 |
| GBS627 | SEQ ID 8852 |
| GBS628 | SEQ ID 8784 |
| GBS629 | SEQ ID 6950 |
| GBS630 | SEQ ID 4502 |
| GBS631 | SEQ ID 4492 |
| GBS632 | SEQ ID 4488 |
| GBS633 | SEQ ID 8728 |
| GBS634 | SEQ ID 3066 |
| GBS635 | SEQ ID 8838 |
| GBS636 | SEQ ID 4772 |
| GBS637 | SEQ ID 8626 |
| GBS638 | SEQ ID 8984 |
| GBS639 | SEQ ID 8546 |
| GBS640 | SEQ ID 6780 |
| GBS641 | SEQ ID 900 |
| GBS642 | 1312 |
| GBS643 | 1772 |
| GBS644 | 1956 |
| GBS645 | 2726 |
| GBS646 | 3348 |
| GBS647 | 3770 |
| GBS648 | 4934 |
| GBS649 | 5076 |
| GBS650 | 5446 |
| GBS651 | 5602 |
| GBS652 | 5610 |
| GBS653 | 5760 |
| GBS654 | 6096 |
| GBS655 | 6656 |
| GBS656 | 9324 |
| GBS657 | 10782 |
| GBS658 | 8802 |
| GBS659 | 9344 |
| GBS660 | 9410 |
| GBS661 | 9428 |

TABLE IV-continued

COMPARISON OF GBSnnn NUMBERING AND SEQ ID NUMBER

| GBS numbering | Sequence listing |
|---|---|
| GBS662 | 9286 |
| GBS663 | 9294 |
| GBS664 | 9034 |
| GBS665 | 10546 |
| GBS666 | 10610 |
| GBS667 | 9052 |
| GBS668 | 9036 |
| GBS669 | 9010 |
| GBS670 | 10730 |
| GBS671 | 9020 |
| GBS672 | 9052 |
| GBS673 | 9036 |
| GBS674 | 9034 |
| GBS675 | 10634 |
| GBS676 | 10692 |
| GBS677 | 10746 |
| GBS678 | 9330 |
| GBS679 | 9404 |
| GBS680 | 6668 |
| GBS681 | 4264 |
| GBS682 | 6762 |
| GBS683 | 9290 |
| GBS684 | 9614 |
| GBS685 | 10454 |
| GBS686 | 2774 |
| GBS687 | 4620 |
| GBS688 | 10224 |

TABLE V

NUCLEOTIDES DELETED IN EXPRESSION OF GBSnnn PROTEINS

| GBS | Deleted nucleotides |
|---|---|
| 11d | 1-153 |
| 31d | 1-129 |
| 64d | 1-165 |
| 68d | 2029-2796 |
| 70d | 1-402 |
| 74d | 1-975 |
| 79d | 1-201 |
| 105dN | 2689-4119 |
| 105dC | 1-2688 |
| 105d | 1-2688 |
| 109d | 1-120 |
| 130d | 1-518 |
| 170d | 1-111 |
| 182d | 1596-1674 |
| 195C | 1-1710 |
| 195N | 1711-3243 |
| 209d | 757-912 |
| 210d | 1-99 & 777-879 |
| 220d | 1-120 |
| 231d | 1-54 |
| 235d | 1-270 |
| 246d | 1-75 |
| 248d | 1-591 |
| 272d | 1-531 |
| 277d | 1-318 |
| 281d | 1-54 |
| 287d | 1-108 |
| 288d | 1-72 |
| 293C | 1-1229 |
| 293N | 1230-2379 |
| 317N | 1729-4107 |
| 317C | 1-2379 |
| 326N | 1707-2652 |
| 326dN | 2326-3927 |
| 327N | 3034-6831 |
| 327C | 1-3033 |
| 333d | 1-150 |
| 339d | 1-111 |
| 352d | 1-158 |
| 362N | 1707-2652 |
| 362C | 1-1706 |
| 397d | 1-348 |
| 399d | 1-111 |
| 407d | 1174-1473 |
| 409d | 1-297 |
| 424d | 1327-1671 |

TABLE VI

PREDICTED FUNCTIONS FOR CERTAIN SEQ IDS

| SEQ ID | Function |
|---|---|
| 6 | manganese ABC transporter, ATP-binding protein (psaB) |
| 12 | iron (chelated) ABC transporter, permease protein (psaC) |
| 18 | peptidyl-prolyl cis-trans isomerase, cyclophilin-type |
| 26 | chorismate binding enzyme (pabB) |
| 30 | probable transposase (insertion sequence IS861) |
| 42 | peptidase, M20/M25/M40 family |
| 44 | drug transporter |
| 50 | ribosomal protein L11 (rplK) |
| 54 | ribosomal protein L1 (rplA) |
| 62 | peptide ABC transporter, permease protein |
| 66 | peptide ABC transporter, permease protein |
| 78 | uridylate kinase (pyrH) |
| 84 | ribosome recycling factor (frr) |
| 104 | PhoH family protein (phoH) |
| 110 | MutT/nudix family protein superfamily |
| 116 | tetracenomycin polyketide synthesis O-methyltransferase TcmP |
| 134 | phosphopantetheine adenylyltransferase (coaD) |
| 140 | PDZ domain protein |
| 144 | 5-nucleotidase family protein |
| 156 | VanZF-related protein |
| 158 | ABC transporter, ATP-binding/permease protein |
| 162 | ABC transporter, ATP-binding/permease protein |
| 168 | BioY family protein |
| 180 | acetyl-CoA acetyltransferase |

TABLE VI-continued

PREDICTED FUNCTIONS FOR CERTAIN SEQ IDS

| SEQ ID | Function |
| --- | --- |
| 188 | endonuclease III (nth) |
| 196 | glucokinase (gki) |
| 200 | rhodanese family protein |
| 204 | elongation factor Tu family protein (typA) |
| 216 | cell division protein DivIB |
| 220 | cell division protein FtsA (ftsA) |
| 224 | cell division protein FtsZ (ftsZ) |
| 236 | ylmH protein (ylmH) |
| 240 | cell division protein DivIVA (divIVA) |
| 244 | isoleucyl-tRNA synthetase (ileS) |
| 252 | MutT/nudix family protein |
| 256 | ATP-dependent Clp protease, ATP-binding subunit ClpE (clpE) |
| 274 | exodeoxyribonuclease VII, large subunit (xseA) |
| 278 | exodeoxyribonuclease VII, small subunit (xseB) |
| 282 | geranyltranstransferase (ispA) |
| 286 | hemolysin A |
| 290 | transcriptional repressor |
| 296 | DNA repair protein RecN (recN) |
| 300 | degV family protein (degV) |
| 322 | peptide ABC transporter, permease protein (oppC) |
| 326 | peptide ABC transporter, ATP-binding protein (oppD) |
| 328 | peptide ABC transporter, ATP-binding protein (oppF) |
| 348 | 4-diphosphocytidyl-2C-methyl-D-erythritol kinase (ispE) |
| 352 | adc operon repressor AdcR (adcR) |
| 356 | zinc ABC transporter, ATP-binding protein (adcC) |
| 370 | tyrosyl-tRNA synthetase (tyrS) |
| 374 | penicillin-binding protein 1B (pbp1B) |
| 378 | DNA-directed RNA polymerase, beta subunit (rpoB) |
| 382 | dna-directed rna polymerase beta' chain |
| 390 | competence protein CglA (cglA) |
| 406 | acetate kinase (ackA) |
| 410 | transcriptional regulator |
| 418 | pyrroline-5-carboxylate reductase (proC) |
| 422 | glutamyl-aminopeptidase (pepA) |
| 432 | thioredoxin family protein |
| 436 | tRNA binding domain protein (pheT) |
| 440 | methyltransferase |
| 442 | single-strand DNA-binding protein, authentic point mutation (ssbB) |
| 454 | GAF domain protein (lytS) |
| 466 | IrgB protein (IrgB) |
| 474 | oligopeptide ABC transporter, permease protein |
| 476 | peptide ABC transporter, ATP-binding protein |
| 480 | peptide ABC transporter, ATP-binding protein (oppF) |
| 484 | PTS system, IIABC components (treB) |
| 488 | alpha amylase family protein (treC) |
| 494 | transcriptional regulator, BglG family |
| 506 | transcriptional regulator, BglG family |
| 508 | PTS system, IIB component |
| 514 | PTS system, IIC component |
| 518 | transketolase, N-terminal subunit (tktA) |
| 528 | ribosomal protein S15 (rpsO) |
| 546 | cysteinyl-tRNA synthetase (cysS) |
| 554 | RNA methyltransferase, TrmH family, group 3 |
| 562 | DegV family protein (degV) |
| 572 | ribosomal protein S9 (rpsI) |
| 576 | integrase, phage family |
| 580 | transcriptional regulator |
| 596 | recombination protein |
| 626 | transcriptional regulator MutR |
| 630 | transporter |
| 640 | amino acid ABC transporter, permease protein (opuBB) |
| 642 | glycine betaine/L-proline transport ATP binding subunit (proV) |
| 654 | lectin, alpha subunit precursor |
| 662 | transcriptional regulator |
| 664 | acetyltransferase, GNAT family |
| 666 | acetyltransferase, GNAT family (rimJ) |
| 670 | acetyltransferase, GNAT family |
| 676 | transcriptional regulator, tetR family domain protein |
| 680 | ABC transporter efflux protein, DrrB family |
| 690 | IS1381, transposase OrfA/OrfB, truncation |
| 714 | magnesium transporter, CorA family |
| 718 | oxidoreductase, Gfo/ldh/MocA family |
| 722 | valyl-tRNA synthetase (valS) |
| 730 | acetyltransferase, GNAT family |
| 746 | methyltransferase |
| 750 | bacteriophage L54a, integrase |

TABLE VI-continued

PREDICTED FUNCTIONS FOR CERTAIN SEQ IDS

| SEQ ID | Function |
|---|---|
| 754 | DNA-damage-inducible protein J |
| 774 | cation efflux system protein |
| 778 | oxidoreductase, aldo/keto reductase family |
| 784 | alcohol dehydrogenase, zinc-containing |
| 804 | ribonucleoside-diphosphate reductase, alpha subunit (nrdE) |
| 808 | nrdI protein (nrdI) |
| 812 | Ribonucleotide reductases |
| 824 | elaA protein (elaA) |
| 828 | RNA methyltransferase, TrmA family |
| 832 | RecX family protein |
| 840 | -identity (jag) |
| 844 | membrane protein, 60 kDa (yidC) |
| 856 | UTP-glucose-1-phosphate uridylyltransferase (galU) |
| 864 | rhomboid family protein |
| 884 | MORN motif family |
| 892 | transcriptional regulator |
| 896 | adenylosuccinate lyase (purB) |
| 908 | phosphoribosylaminoimidazole carboxylase, catalytic subunit (purE) |
| 912 | phosphoribosylamine--glycine ligase (purD) |
| 916 | phosphosugar-binding transcriptional regulator |
| 920 | acetyl xylan esterase |
| 922 | ROK family protein (gki) |
| 926 | N-acetylneuraminate lyase (nanA) |
| 936 | sugar ABC transporter, permease protein |
| 940 | sugar ABC transporter, permease protein (msmF) |
| 952 | LysM domain protein, authentic frameshift |
| 956 | zoocin A endopeptidase |
| 962 | acetyltransferase, GNAT family family |
| 964 | phosphoribosylglycinamide formyltransferase (purN) |
| 968 | phosphoribosylformylglycinamidine cyclo-ligase (purM) |
| 972 | amidophosphoribosyltransferase (purF) |
| 980 | phosphoribosylformylglycinamidine synthase |
| 984 | phosphoribosylaminoimidazole-succinocarboxamide synthase (purC) |
| 1042 | oligoendopeptidase F (pepF) |
| 1060 | ebsC protein |
| 1068 | hydrolase, haloacid dehalogenase-like family |
| 1076 | riboflavin synthase, beta subunit (ribH) |
| 1082 | riboflavin biosynthesis protein RibD (ribD) |
| 1086 | Mn2+/Fe2+ transporter, NRAMP family |
| 1094 | peptidase, U32 family |
| 1116 | HPr(Ser) kinase/phosphatase (hprK) |
| 1130 | oxidoreductase |
| 1148 | signal recognition particle-docking protein FtsY (ftsY) |
| 1152 | Cof family protein |
| 1156 | Cof family protein |
| 1172 | vicX protein (vicX) |
| 1176 | sensory box sensor histidine kinase (vicK) |
| 1180 | DNA-binding response regulator (vicR) |
| 1184 | amino acid ABC transporter, ATP-binding protein |
| 1188 | amino acid ABC transporter, amino acid-binding protein (fliY) |
| 1192 | amino acid ABC transporter, permease protein |
| 1196 | amino acid ABC transporter, permease protein |
| 1208 | DNA-binding response regulator (vicR) |
| 1210 | threonyl-tRNA synthetase (thrS) |
| 1214 | glycosyl transferase, group 1 |
| 1218 | glycosyl transferase, group 1 (cpoA) |
| 1222 | alpha-amylase (amy) |
| 1230 | proline dipeptidase (pepQ) |
| 1238 | haloacid dehalogenase-like hydrolase superfamily |
| 1244 | mannonate dehydratase (uxuA) |
| 1248 | glucuronate isomerase |
| 1254 | transcriptional regulator, GntR family |
| 1268 | sodiumgalactoside symporter family protein |
| 1270 | D-isomer specific 2-hydroxyacid dehydrogenase family protein |
| 1282 | transcriptional regulator, LysR family |
| 1290 | ABC transporter, ATP-binding protein (potA) |
| 1296 | DedA family protein |
| 1308 | MutT/nudix family protein family |
| 1310 | phosphoserine phosphatase SerB (serB) |
| 1312 | septation ring formation regulator EzrA |
| 1320 | hydrolase, haloacid dehalogenase-like family (gph) |
| 1340 | sensor histidine kinase (vncS) |
| 1348 | transmembrane protein Vexp3 (vex3) |
| 1352 | ABC transporter, ATP-binding protein (vex2) |
| 1358 | transmembrane protein Vexp1 (vex1) |
| 1366 | transposase |

TABLE VI-continued

PREDICTED FUNCTIONS FOR CERTAIN SEQ IDS

| SEQ ID | Function |
|---|---|
| 1374 | integrase, phage family |
| 1390 | holin 2 |
| 1398 | minor structural protein |
| 1400 | host specificity protein |
| 1404 | minor structural protein |
| 1406 | PblA |
| 1486 | homeobox protein drg11 |
| 1488 | reverse transcriptase |
| 1496 | p22 erf-like protein |
| 1498 | gp157 |
| 1500 | tropomyosin 2 |
| 1512 | gp49 homologous |
| 1526 | transcriptional regulator-related protein |
| 1566 | chorismate mutase |
| 1572 | PTS system component |
| 1576 | PTS system, IIB component |
| 1580 | PTS system IIA component |
| 1584 | lactose phosphotransferase system repressor (lacR) |
| 1594 | adhesion lipoprotein (lmb) |
| 1602 | GTP pyrophosphokinase (relA) |
| 1606 | 2',3'-cyclic-nucleotide 2'-phosphodiesterase (cpdB) |
| 1616 | iron ABC transporter, iron-binding protein |
| 1620 | DNA-binding response regulator |
| 1630 | PTS system component |
| 1634 | PTS system component (manM) |
| 1638 | PTS system component (manL) |
| 1642 | PTS system component |
| 1658 | response regulator BlpR (blpR) |
| 1676 | phosphate transport system regulatory protein PhoU |
| 1680 | phosphate ABC transporter, ATP-binding protein (pstB) |
| 1684 | phosphate ABC transporter, permease protein (pstA) |
| 1690 | phosphate ABC transporter, permease protein (pstC) |
| 1694 | probable hemolysin precursor |
| 1704 | ribosomal protein L11 methyltransferase (prmA) |
| 1710 | transcriptional regulator, MerR family (skgA) |
| 1714 | acetyltransferase, GNAT family |
| 1716 | MutT/nudix family protein |
| 1722 | spermidine N1-acetyltransferase |
| 1726 | ATPase, AAA family |
| 1736 | ABC transporter domain protein |
| 1738 | Helix-turn-helix domain protein |
| 1748 | integrase, phage family |
| 1756 | Helix-turn-helix domain protein |
| 1762 | bacteriophage L54a, integrase |
| 1768 | LPXTG-motif cell wall anchor domain protein |
| 1776 | membrane protein |
| 1778 | conjugal transfer protein |
| 1780 | IS1381, transposase OrfA/OrfB, truncation |
| 1802 | transcriptional regulator (rstR-1) |
| 1806 | transcriptional regulator |
| 1808 | FtsK/SpoIIIE family protein |
| 1814 | aggregation substance |
| 1818 | mercuric reductase |
| 1822 | transcriptional regulator, MerR family |
| 1824 | Mn2+/Fe2+ transporter, NRAMP family |
| 1830 | ABC transporter, ATP-binding protein (epiF) |
| 1848 | Helix-turn-helix domain protein |
| 1850 | type 2 phosphatidic acid phosphatase(PAP2), family |
| 1858 | Abortive infection protein family |
| 1868 | aminotransferase, class-V |
| 1874 | glutathione reductase (gor) |
| 1882 | chorismate synthase (aroC) |
| 1886 | 3-dehydroquinate synthase (aroB) |
| 1900 | sulfatase family protein |
| 1914 | ABC transporter, ATP-binding protein |
| 1920 | smf protein (Smffamily) |
| 1924 | transferrin receptor |
| 1928 | iron compound ABC transporter, ATP-binding protein |
| 1932 | iron compound ABC transporter, permease protein |
| 1942 | acetyltransferase, CysE/LacA/LpxA/NodL family |
| 1952 | GTP-binding protein |
| 1958 | carbon starvation protein A |
| 1960 | response regulator (lytR) |
| 1962 | GAF domain protein (lytS) |
| 2000 | extracellular protein |
| 2004 | diarrheal toxin (yukA) |

TABLE VI-continued

PREDICTED FUNCTIONS FOR CERTAIN SEQ IDS

| SEQ ID | Function |
| --- | --- |
| 2024 | carbamoyl-phosphate synthase, large subunit (carB) |
| 2028 | carbamoyl-phosphate synthase, small subunit (carA) |
| 2032 | aspartate carbamoyltransferase (pyrB) |
| 2036 | dihydroorotase, multifunctional complex type (pyrC) |
| 2040 | orotate phosphoribosyltransferase (pyrE) |
| 2048 | membrane protein |
| 2062 | phosphate ABC transporter, permease protein (pstA-2) |
| 2064 | phosphate ABC transporter, ATP-binding protein (pstB) |
| 2070 | phosphate transport system regulatory protein PhoU |
| 2072 | aminopeptidase N (pepN) |
| 2076 | DNA-binding response regulator (arlR) |
| 2080 | sensor histidine kinase (arlS) |
| 2088 | signal recognition particle protein (ffh) |
| 2102 | peptide ABC transporter, peptide-binding protein |
| 2104 | integrase/recombinase, phage integrase family |
| 2108 | sensor histidine kinase |
| 2112 | DNA-binding response regulator (vicR) |
| 2118 | ABC transporter, ATP-binding protein |
| 2122 | nisin-resistance protein |
| 2130 | lipoprotein |
| 2136 | gid protein (gid) |
| 2140 | transcriptional regulator, GntR family |
| 2142 | GMP synthase (guaA) |
| 2152 | branched-chain amino acid ABC transporter, permease protein (livM) |
| 2154 | branched-chain amino acid ABC transporter, ATP-binding protein (livG) |
| 2156 | branched-chain amino acid ABC transporter, ATP-binding protein (livF) |
| 2160 | acetoin utilization protein AcuB |
| 2174 | DNA polymerase III, delta prime subunit (holB) |
| 2186 | copper homeostasis protein (cutC) |
| 2190 | phosphoserine aminotransferase (serC) |
| 2202 | methylated-DNA--protein-cysteine S-methyltransferase (ogt) |
| 2208 | exodeoxyribonuclease III (xth) |
| 2214 | PTS system, IIC component |
| 2224 | tellurite resistance protein TehB (tehB) |
| 2246 | icaA protein |
| 2250 | acetyltransferase, GNAT family |
| 2258 | oxidoreductase, short chain dehydrogenase/reductase family (fabG) |
| 2266 | oxidoreductase, Gfo/Idh/MocA family family |
| 2268 | glyoxalase family protein |
| 2272 | UDP-N-acetylglucosamine pyrophosphorylase (glmU) |
| 2276 | MutT/nudix family protein |
| 2284 | 5-methylthioadenosine/S-adenosylhomocysteine nucleosidase (mtf) |
| 2296 | phosphatidate cytidylyltransferase (cdsA) |
| 2300 | membrane-associated zinc metalloprotease |
| 2308 | autolysin (flgJ) |
| 2312 | DNA polymerase III, alpha subunit, Gram-positive type |
| 2320 | nitroreductase family protein superfamily |
| 2328 | carbohydrate kinase, PfkB family |
| 2336 | oxidoreductase, short chain dehydrogenase/reductase family (fabG) |
| 2338 | PTS system, IIA component (manL) |
| 2342 | glucuronyl hydrolase |
| 2346 | PTS system, IIB component (manL) |
| 2350 | PTS system, IIC component (manM) |
| 2364 | sugar binding transcriptional regulator RegR (regR) |
| 2368 | polypeptide deformylase (def) |
| 2380 | oxidoreductase, Gfo/Idh/MocA family |
| 2382 | endopeptidase O (pepO) |
| 2394 | Na+/H+ antiporter |
| 2404 | transcriptional regulator |
| 2410 | replication initiation protein RepRC |
| 2412 | bacteriophage L54a, antirepressor |
| 2416 | e11 |
| 2422 | replicative DNA helicase (dnaB) |
| 2432 | GTP-binding protein |
| 2440 | arpR protein |
| 2444 | gene 17 protein |
| 2458 | integrase/recombinase, phage integrase family |
| 2468 | bacteriophage L54a, phage D3 terminase |
| 2472 | protease |
| 2500 | PblB |
| 2504 | sensor histidine kinase |
| 2514 | N-acetylmuramoyl-L-alanine amidase |
| 2518 | KH domain protein |
| 2522 | ribosomal protein S16 (rpsP) |
| 2526 | permease |
| 2528 | ABC transporter, ATP-binding protein |

TABLE VI-continued

PREDICTED FUNCTIONS FOR CERTAIN SEQ IDS

| SEQ ID | Function |
|---|---|
| 2538 | carbamoyl-phosphate synthase, large subunit |
| 2540 | carbamoyl-phosphate synthase, small subunit (carA) |
| 2550 | transcriptional regulator, LysR family |
| 2554 | ribosomal protein L27 (rpmA) |
| 2562 | ribosomal protein L21 (rplU) |
| 2572 | glycerophosphoryl diester phosphodiesterase |
| 2582 | nitroreductase family protein |
| 2586 | dipeptidase (pepV) |
| 2614 | GTP-binding protein HflX (hflX) |
| 2618 | galactose-1-phosphate uridylyltransferase (galT) |
| 2626 | oxidoreductase, short chain dehydrogenase/reductase family |
| 2630 | single-stranded-DNA-specific exonuclease RecJ (recJ) |
| 2638 | adenine phosphoribosyltransferase (apt) |
| 2646 | Bcl-2 family protein |
| 2654 | oxidoreductase, DadA family protein |
| 2658 | glucose-1-phosphate thymidylyltransferase (rfbA) |
| 2664 | dTDP-4-dehydrorhamnose 3,5-epimerase (rfbC) |
| 2682 | hyaluronidase |
| 2686 | mutator MutT protein (mutX) |
| 2690 | MutT/nudix family protein |
| 2694 | membrane protein |
| 2702 | acetolactate synthase (ilvK) |
| 2706 | adherence and virulence protein A (pavA) |
| 2714 | ABC transporter, permease protein (rbsC) |
| 2722 | metallo-beta-lactamase superfamily protein |
| 2734 | ribose 5-phosphate isomerase (rpiA) |
| 2738 | phosphopentomutase (deoB) |
| 2742 | purine nucleoside phosphorylase, family 2 (deoD) |
| 2750 | purine nucleoside phosphorylase (deoD) |
| 2762 | capsular polysaccharide biosynthesis protein Cps4A (cps4A) |
| 2768 | cpsb protein |
| 2770 | cpsc protein |
| 2772 | CpsE |
| 2774 | CpsF |
| 2776 | CpsVG |
| 2778 | CpsVH |
| 2780 | CpsVM |
| 2782 | CpsVN |
| 2784 | glycosyl transferase domain protein |
| 2786 | glycosyl transferase, family 2/glycosyl transferase family 8 |
| 2790 | CpsVK |
| 2794 | CpsL |
| 2796 | neuB protein |
| 2798 | UDP-N-acetylglucosamine 2-epimerase |
| 2800 | hexapeptide transferase family protein |
| 2802 | NeuA |
| 2808 | uracil-DNA glycosylase (ung) |
| 2818 | DNA topoisomerase IV, B subunit (parE) |
| 2822 | DNA topoisomerase IV, A subunit (parC) |
| 2826 | branched-chain amino acid aminotransferase (ilvE) |
| 2842 | glycerol kinase (glpK) |
| 2848 | aerobic glycerol-3-phosphate dehydrogenase (glpD) |
| 2874 | ABC transporter, ATP-binding protein |
| 2882 | PTS system component (bglP) |
| 2886 | glutamate 5-kinase (proB) |
| 2890 | gamma-glutamyl phosphate reductase (proA) |
| 2898 | cell division protein FtsL (ftsL) |
| 2904 | penicillin-binding protein 2X (pbpX) |
| 2910 | phospho-N-acetylmuramoyl-pentapeptide-transferase (mraY) |
| 2914 | ATP-dependent RNA helicase, DEAD/DEAH box family (deaD) |
| 2918 | ABC transporter, substrate-binding protein |
| 2924 | amino acid ABC transporter, permease protein |
| 2928 | amino acid ABC transporter, ATP-binding protein |
| 2932 | thioredoxin reductase (trxB) |
| 2940 | NAD+ synthetase (nadE) |
| 2944 | aminopeptidase C (pepC) |
| 2952 | recombination protein U (recU) |
| 2966 | Uncharacterized protein family UPF0020 family |
| 2974 | autoinducer-2 production protein LuxS (luxS) |
| 2978 | KH domain protein |
| 2986 | ABC transporter, ATP-binding protein |
| 2994 | DNA-binding response regulator (vraR) |
| 3000 | guanylate kinase (gmk) |
| 3004 | DNA-directed RNA polymerase, omega subunit |
| 3008 | primosomal protein N (priA) |
| 3012 | methionyl-tRNA formyltransferase (fmt) |

TABLE VI-continued

PREDICTED FUNCTIONS FOR CERTAIN SEQ IDS

| SEQ ID | Function |
|---|---|
| 3016 | Sun protein (sun) |
| 3020 | protein phosphatase 2C |
| 3032 | sensor histidine kinase |
| 3034 | DNA-binding response regulator (vraR) |
| 3040 | S1 RNA binding domain protein (rpsA) |
| 3044 | pyruvate formate-lyase-activating enzyme |
| 3062 | PTS system, IIB component (celA) |
| 3066 | PTS system, cellobiose-specific IIC component (celB) |
| 3068 | formate acetyltransferase (pfl) |
| 3072 | transaldolase |
| 3080 | cysteine synthase A (cysK) |
| 3088 | comF operon protein 1 (comFA) |
| 3092 | competence protein ComF |
| 3096 | ribosomal subunit interface protein (yfiA) |
| 3104 | tryptophanyl-tRNA synthetase (trpS) |
| 3108 | carbamate kinase (arcC) |
| 3116 | ornithine carbamoyltransferase (argF) |
| 3124 | arginine deiminase (arcA) |
| 3134 | transcriptional regulator, Crp/Fnr family |
| 3138 | inosine-5'-monophosphate dehydrogenase (guaB) |
| 3140 | MutR |
| 3142 | transporter |
| 3146 | recF protein (recF) |
| 3158 | peptidase, M16 family |
| 3166 | ABC transporter, ATP-binding protein |
| 3170 | ABC transporter, ATP-binding protein |
| 3178 | LysM domain protein (lytN) |
| 3180 | immunodominant antigen A (isaA) |
| 3184 | L-serine dehydratase, iron-sulfur-dependent, alpha subunit (sdhA) |
| 3188 | L-serine dehydratase, iron-sulfur-dependent, beta subunit (sdhB) |
| 3202 | DHH subfamily 1 protein |
| 3206 | ribosomal protein L9 (rplI) |
| 3210 | replicative DNA helicase (dnaB) |
| 3216 | ribosomal protein S4 (rpsD) |
| 3224 | transcriptional regulator, TetR family |
| 3236 | membrane protein |
| 3238 | choline transporter (proWX) |
| 3240 | glycine betaine/L-proline transport ATP binding subunit (proV) |
| 3242 | DNA-binding response regulator |
| 3244 | Histidine kinase-, DNA gyrase B-, phytochrome-like ATPase family |
| 3246 | ornithine carbamoyltransferase (argF) |
| 3248 | carbamate kinase (arcC) |
| 3252 | membrane protein |
| 3256 | sensory box histidine kinase VicK |
| 3258 | DNA-binding response regulator |
| 3268 | Helix-turn-helix domain protein |
| 3278 | integrase |
| 3284 | ribosomal protein L33 (rpmG) |
| 3288 | ribosomal protein L32 (rpmF) |
| 3300 | YitT family protein |
| 3304 | YitT family protein |
| 3320 | DNA mismatch repair protein MutS (mutS) |
| 3324 | cold-shock domain family protein-related protein |
| 3336 | drug transporter |
| 3340 | Holliday junction DNA helicase RuvA (ruvA) |
| 3352 | recA protein (recA) |
| 3386 | oxidoreductase, Gfo/Idh/MocA family |
| 3390 | acetyltransferase, GNAT family |
| 3412 | ABC transporter, permease protein (rbsC) |
| 3414 | ABC transporter, ATP-binding protein (nrtC) |
| 3416 | PTS system, mannose-specific IIAB components (manL) |
| 3420 | Cof family protein |
| 3432 | xanthine/uracil permease family protein |
| 3440 | acetyltransferase, GNAT family |
| 3442 | transcriptional regulator (cps4A) |
| 3448 | HIT family protein (hit) |
| 3460 | ABC transporter, permease protein |
| 3472 | Uncharacterized BCR, YhbC family COG0779 superfamily |
| 3484 | ribosomal protein L7A family |
| 3496 | esterase |
| 3500 | transcriptional repressor, CopY (copY) |
| 3504 | cation-transporting ATPase, E1-E2 family |
| 3508 | cation-binding protein-related protein |
| 3520 | DNA polymerase I (polA) |
| 3534 | DNA-binding response regulator (saeR) |
| 3536 | sensor histidine kinase (saeS) |

TABLE VI-continued

PREDICTED FUNCTIONS FOR CERTAIN SEQ IDS

| SEQ ID | Function |
|---|---|
| 3562 | drug resistance transporter, EmrB/QacA subfamily |
| 3566 | peptidase M24 family protein |
| 3570 | peptidase M24 family protein (pepQ) |
| 3572 | cytidine/deoxycytidylate deaminase family protein |
| 3584 | translation elongation factor P (efp) |
| 3592 | N utilization substance protein B (nusB) |
| 3596 | sugar-binding transcriptional regulator, LacI family (scrR) |
| 3600 | sucrose-6-phosphate dehydrogenase (scrB) |
| 3606 | PTS system IIABC components (scrA) |
| 3610 | fructokinase (scrK) |
| 3614 | mannose-6-phosphate isomerase, class I (manA) |
| 3622 | phospho-2-dehydro-3-deoxyheptonate aldolase (aroH) |
| 3626 | holo-(acyl-carrier-protein) synthase (acpS) |
| 3630 | alanine racemase (alr) |
| 3634 | autolysin (usp45) |
| 3636 | ATP-dependent DNA helicase RecG (recG) |
| 3642 | shikimate 5-dehydrogenase (aroE) |
| 3652 | Cof family protein |
| 3668 | ferredoxin-related protein |
| 3676 | peptidase t (pepT) |
| 3692 | iron compound ABC transporter, substrate-binding protein |
| 3698 | FecCD transport family protein (sirB) |
| 3704 | iron compound ABC transporter, permease protein (sirB) |
| 3710 | inorganic pyrophosphatase, manganese-dependent (ppaC) |
| 3714 | pyruvate formate-lyase-activating enzyme (pflA) |
| 3718 | CBS domain protein |
| 3730 | acid phosphatase |
| 3736 | LPXTG-motif cell wall anchor domain protein |
| 3738 | LPXTG-site transpeptidase family protein |
| 3742 | LPXTG-site transpeptidase family protein |
| 3744 | cell wall surface anchor family protein |
| 3746 | cell wall surface anchor family protein |
| 3752 | glycosyl transferase, group 1 family protein domain protein |
| 3754 | EpsQ protein |
| 3756 | polysaccharide extrusion protein |
| 3768 | dTDP-glucose 4-6-dehydratase |
| 3782 | glycosyl transferase domain protein |
| 3788 | dTDP-4-dehydrorhamnose reductase (rfbD) |
| 3796 | RNA polymerase sigma-70 factor (rpoD) |
| 3802 | DNA primase (dnaG) |
| 3816 | ABC transporter, ATP-binding protein Vexp2 (vex2) |
| 3818 | permease |
| 3820 | transmembrane protein Vexp3 |
| 3822 | transmembrane protein Vexp3 |
| 3832 | endopeptidase O (pepO) |
| 3834 | endopeptidase O (pepO) |
| 3840 | serine protease, subtilase family |
| 3842 | exotoxin 2 |
| 3844 | CylK |
| 3854 | glycine cleavage system T protein |
| 3856 | CylE |
| 3858 | ABC transporter homolog CylB |
| 3862 | acyl carrier protein homolog AcpC (acpP) |
| 3864 | 3-oxoacyl-(acyl-carrier-protein) reductase (fabG) |
| 3868 | CylD |
| 3876 | membrane protein |
| 3912 | LPXTG-site transpeptidase family protein |
| 3916 | LPXTG-site transpeptidase family protein |
| 3918 | LPXTG-site transpeptidase family protein |
| 3920 | LPXTG-motif cell wall anchor domain protein |
| 3928 | chaperonin, 33 kDa (hslO) |
| 3932 | Tn5252, Orf 10 protein |
| 3934 | transposase OrfAB, subunit B |
| 3948 | psr protein |
| 3952 | shikimate kinase (aroK) |
| 3964 | enolase (eno) |
| 3972 | MutT/nudix family protein |
| 3976 | glycosyl transferase, group 1 |
| 3978 | preprotein translocase, SecA subunit (secA) |
| 3986 | preprotein translocase SecY family protein |
| 3990 | glycosyl transferase, family 8 |
| 3992 | glycosyl transferase, family 2 |
| 3998 | glycosyl transferase, family 8 |
| 4000 | glycosyl transferase, family 2/glycosyl transferase family 8 |
| 4002 | glycosyl transferase, family 8 |
| 4012 | LPXTG-motif cell wall anchor domain protein (clfB) |

TABLE VI-continued

PREDICTED FUNCTIONS FOR CERTAIN SEQ IDS

SEQ ID  Function

| SEQ ID | Function |
|---|---|
| 4016 | transcriptional regulator |
| 4018 | excinuclease ABC, B subunit (uvrB) |
| 4022 | Abortive infection protein family |
| 4024 | amino acid ABC transporter, amino acid-binding protein/permease protein |
| 4026 | amino acid ABC transporter, ATP-binding protein |
| 4034 | GTP-binding protein, GTP1/Obg family (obg) |
| 4042 | aminopeptidase PepS (pepS) |
| 4050 | ribosomal small subunit pseudouridine synthase A (rsuA) |
| 4060 | lactoylglutathione lyase (gloA) |
| 4064 | glycosyl transferase family protein |
| 4072 | alkylphosphonate utilization operon protein PhnA (phnA) |
| 4078 | glucosamine--fructose-6-phosphate aminotransferase (isomerizing) (glmS) |
| 4090 | Phosphofructokinase |
| 4094 | DNA polymerase III, alpha subunit (dnaE) |
| 4098 | transcriptional regulator, GntR family |
| 4102 | ABC transporter, ATP-binding protein |
| 4106 | ABC transporter, ATP-binding protein |
| 4116 | FtsK/SpoIIIE family protein |
| 4122 | Helix-turn-helix domain protein |
| 4152 | Helix-turn-helix domain protein |
| 4158 | excisionase |
| 4160 | transposase |
| 4166 | chloramphenicol acetyltransferase (cat) |
| 4174 | PilB-related protein |
| 4178 | acetyltransferase |
| 4182 | Leucine Rich Repeat domain protein |
| 4190 | nucleoside diphosphate kinase (ndk) |
| 4206 | Protein of unknown function superfamily |
| 4218 | hydrolase, haloacid dehalogenase-like family (pho2) |
| 4226 | oxygen-independent coproporphyrinogen III oxidase |
| 4236 | phosphoglucomutase/phosphomannomutase family protein (femD) |
| 4240 | Gram-positive signal peptide, YSIRK family domain protein |
| 4256 | cobyric acid synthase (cobQ) |
| 4260 | lipoate-protein ligase A (lplA) |
| 4286 | magnesium transporter, CorA family |
| 4294 | exonuclease RexB (rexB) |
| 4302 | phenylalanyl-tRNA synthetase, beta subunit (pheT) |
| 4324 | ATP synthase F1, epsilon subunit (atpC) |
| 4328 | ATP synthase F1, beta subunit (atpD) |
| 4332 | ATP synthase F1, gamma subunit (atpG) |
| 4338 | ATP synthase F1, alpha subunit (atpA) |
| 4342 | ATP synthase F1, delta subunit (atpH) |
| 4346 | ATP synthase F0, B subunit (atpF) |
| 4350 | ATP synthase, F0 subunit A (atpB) |
| 4354 | proton-translocating ATPase, c subunit-related protein |
| 4360 | glycogen synthase (glgA) |
| 4362 | glycogen biosynthesis protein GlgD (glgD) |
| 4366 | 1,4-alpha-glucan branching enzyme (glgB) |
| 4368 | pullulanase |
| 4382 | ribonuclease BN |
| 4396 | acetyltransferase, GNAT family |
| 4398 | UDP-N-acetylglucosamine 1-carboxyvinyltransferase (murA) |
| 4402 | thiamine-phosphate pyrophosphorylase (thiE) |
| 4406 | phosphomethylpyrimidine kinase (thiD) |
| 4410 | transcriptional regulator, Deg family (tenA) |
| 4414 | ABC transporter, ATP-binding protein |
| 4426 | S-adenosylmethionine synthetase (metK) |
| 4440 | DNA polymerase III, gamma and tau subunits (dnaX) |
| 4444 | GAF domain protein |
| 4448 | uridine kinase (udk) |
| 4452 | ATP-dependent RNA helicase, DEAD/DEAH box family |
| 4458 | peptidoglycan GlcNAc deacetylase (pgdA) |
| 4462 | glyceraldehyde-3-phosphate dehydrogenase, NADP-dependent (gapN) |
| 4466 | phosphoenolpyruvate-protein phosphotransferase (ptsI) |
| 4470 | phosphocarrier protein hpr |
| 4474 | NrdH-redoxin-related protein |
| 4478 | ribonucleoside-diphosphate reductase 2, alpha subunit (nrdE) |
| 4498 | glycosyl transferase, family 8 |
| 4504 | alanyl-tRNA synthetase (alaS) |
| 4512 | alkyl hydroperoxide reductase, subunit F (ahpF) |
| 4516 | alkyl hydroperoxide reductase, subunit C (ahpC) |
| 4520 | ribosomal protein S2 (rpsB) |
| 4524 | translation elongation factor Ts (tsf) |
| 4532 | transcriptional regulator CtsR (ctsR) |
| 4536 | ATP-dependent Clp protease, ATP-binding subunit (clpC) |
| 4540 | deoxynucleoside kinase |

TABLE VI-continued

PREDICTED FUNCTIONS FOR CERTAIN SEQ IDS

| SEQ ID | Function |
|---|---|
| 4544 | NifR3/Smm1 family protein |
| 4548 | chaperonin, 33 kDa (hslO) |
| 4558 | glutamate--cysteine ligase (gshA) |
| 4562 | Helix-turn-helix domain, fis-type protein |
| 4566 | perfringolysin O regulator protein (pfoR) |
| 4570 | adenylosuccinate synthetase (purA) |
| 4578 | SgaT protein (sgaT) |
| 4582 | PTS system, IIB component (sgaT) |
| 4586 | PTS system, IIA component (mtlA) |
| 4590 | hexulose-6-phosphate synthase |
| 4594 | hexulose-6-phosphate isomerase |
| 4598 | L-ribulose-5-phosphate 4-epimerase (araD) |
| 4606 | sugar binding transcriptional regulator RegR |
| 4610 | D-isomer specific 2-hydroxyacid dehydrogenase family protein (serA) |
| 4622 | transcriptional regulator, BglG family |
| 4632 | glycine betaine/L-proline transport ATP binding subunit (proV) |
| 4636 | amino acid ABC transporter, permease protein |
| 4644 | Na+/H+ exchanger family protein (kefB) |
| 4648 | glyoxylase family protein |
| 4652 | LPXTG-site transpeptidase family protein |
| 4656 | DNA gyrase, A subunit (gyrA) |
| 4660 | L-lactate dehydrogenase (ldh) |
| 4664 | NADH oxidase (nox) |
| 4680 | lipoprotein (bmpD) |
| 4690 | pantothenate kinase (coaA) |
| 4694 | ribosomal protein S20 (rpsT) |
| 4698 | amino acid ABC transporter, amino acid-binding protein (aatB) |
| 4702 | amino acid ABC transporter, ATP-binding protein |
| 4726 | ribosomal large subunit pseudouridine synthase B (rluB) |
| 4734 | Uncharacterized ACR, COG1354 |
| 4738 | integrase/recombinase, phage integrase family (xerD) |
| 4742 | CBS domain protein |
| 4746 | phosphoesterase |
| 4750 | HAM1 protein |
| 4768 | transcriptional regulator, biotin repressor family |
| 4792 | amino acid ABC transproter, permease protein |
| 4796 | amino acid ABC transporter, substrate-binding protein |
| 4798 | 6-aminohexanoate-cyclic-dimer hydrolase |
| 4800 | transcription elongation factor GreA (greA) |
| 4804 | Uncharacterized BCR, YceG family COG1559 |
| 4812 | UDP-N-acetylmuramate--alanine ligase (murC) |
| 4822 | Snf2 family protein |
| 4828 | GTP-binding protein (b2511) |
| 4832 | primosomal protein DnaI (dnaI) |
| 4844 | sensor histidine kinase (arlS) |
| 4846 | DNA-binding response regulator (arlR) |
| 4852 | heat shock protein HtpX (htpX) |
| 4870 | potassium uptake protein, Trk family |
| 4874 | ABC transporter, ATP-binding protein |
| 4888 | phosphoglycerate kinase (pgk) |
| 4896 | transcriptional regulator, MerR family |
| 4900 | glutamine synthetase, type I (glnA) |
| 4904 | secreted 45 kd protein (usp45) |
| 4908 | metallo-beta-lactamase superfamily protein |
| 4916 | glycoprotease family protein |
| 4926 | glycoprotease family protein (gcp) |
| 4938 | ribosomal protein S14p/S29e (rpsN) |
| 4952 | exonuclease (dnaQ) |
| 4956 | transcriptional regulator, merR family |
| 4958 | cyclopropane-fatty-acyl-phospholipid synthase (cfa) |
| 4970 | 1,4-dihydroxy-2-naphthoate octaprenyltransferase (menA) |
| 4972 | pyridine nucleotide-disulphide oxidoreductase (ndh) |
| 4974 | cytochrome d oxidase, subunit I (cydA) |
| 4976 | cytochrome d ubiquinol oxidase, subunit II (cydB) |
| 4980 | transport ATP-binding protein CydD |
| 4988 | polyprenyl synthetase (ispB) |
| 4990 | X-pro dipeptidyl-peptidase (pepX) |
| 4998 | drug transporter |
| 5002 | universal stress protein family |
| 5004 | glycerol uptake facilitator protein (glpF) |
| 5012 | cppA protein (cppA) |
| 5034 | exodeoxyribonuclease V, alpha subunit (recD) |
| 5038 | Signal peptidase I |
| 5042 | ribonuclease HIII (rnhC) |
| 5062 | transcriptional regulator |
| 5068 | maltose ABC transporter, permease protein (malD) |

TABLE VI-continued

PREDICTED FUNCTIONS FOR CERTAIN SEQ IDS

| SEQ ID | Function |
|---|---|
| 5072 | maltose ABC transporter, permease protein (malC) |
| 5088 | ABC transporter, ATP-binding protein |
| 5092 | ABC transporter, permease protein |
| 5106 | spspoJ protein (spo0J) |
| 5114 | DNA polymerase III, beta subunit (dnaN) |
| 5118 | Diacylglycerol kinase catalytic domain (presumed) protein |
| 5138 | transcription-repair coupling factor (mfd) |
| 5142 | S4 domain protein |
| 5156 | MesJ/Ycf62 family protein |
| 5160 | hypoxanthine phosphoribosyltransferase (hpt) |
| 5164 | cell division protein FtsH (ftsH) |
| 5172 | hydrolase, haloacid dehalogenase-like family (b2690) |
| 5178 | transcriptional regulator, MarR family |
| 5182 | 3-oxoacyl-(acyl-carrier-protein) synthase III (fabH) |
| 5190 | enoyl-(acyl-carrier-protein) reductase (fabK) |
| 5194 | malonyl CoA-acyl carrier protein transacylase (fabD) |
| 5198 | 3-oxoacyl-[acyl-carrier protein] reductase (fabG) |
| 5200 | 3-oxoacyl-(acyl-carrier-protein) synthase II (fabF) |
| 5202 | acetyl-CoA carboxylase, biotin carboxyl carrier protein (accB) |
| 5206 | (3R)-hydroxymyristoyl-(acyl-carrier-protein) dehydratase (fabZ) |
| 5210 | acetyl-CoA carboxylase, biotin carboxylase (accC) |
| 5214 | acetyl-CoA carboxylase, carboxyl transferase, beta subunit (accD) |
| 5218 | acetyl-CoA carboxylase, carboxyl transferase, alpha subunit (accA) |
| 5224 | seryl-tRNA synthetase (serS) |
| 5234 | PTS system, mannose-specific IID component |
| 5246 | ribosomal large subunit pseudouridine synthase, RluD subfamily (rluD) |
| 5254 | GTP pyrophosphokinase (relA) |
| 5266 | ribose-phosphate pyrophosphokinase (prsA) |
| 5270 | aminotransferase, class-V |
| 5274 | DNA-binding protein |
| 5282 | Domain of unknown function |
| 5290 | platelet activating factor |
| 5296 | transcriptional regulator, AraC family |
| 5302 | voltage-gated chloride channel family protein |
| 5318 | spermidine/putrescine ABC transporter, ATP-binding protein (potA) |
| 5320 | UDP-N-acetylenolpyruvoylglucosamine reductase (murB) |
| 5324 | bifunctional folate synthesis protein (folK) |
| 5328 | dihydroneopterin aldolase (folB) |
| 5332 | dihydropteroate synthase (folP) |
| 5336 | GTP cyclohydrolase I (folE) |
| 5344 | rarD protein (rarD) |
| 5348 | homoserine kinase (thrB) |
| 5354 | Polysaccharide deacetylase family (icaB) |
| 5362 | osmoprotectant transporter, BCCT family (opuD) |
| 5384 | thiol peroxidase (psaD) |
| 5388 | hydrolase |
| 5390 | transcriptional regulator, GntR family |
| 5402 | gls24 protein |
| 5424 | uncharacterized domain 1 |
| 5440 | cation efflux family protein |
| 5454 | dihydroorotate dehydrogenase A (pyrDa) |
| 5458 | beta-lactam resistance factor (fibB) |
| 5462 | beta-lactam resistance factor (fibA) |
| 5474 | HD domain protein |
| 5482 | cation-transporting ATPase, E1-E2 family |
| 5486 | fructose-1,6-bisphosphatase (fbp) |
| 5488 | iron-sulfur cluster-binding protein |
| 5492 | peptide chain release factor 2 (prfB) |
| 5496 | cell division ABC transporter, ATP-binding protein FtsE (ftsE) |
| 5504 | carboxymethylenebutenolidase-related protein |
| 5506 | metallo-beta-lactamase superfamily protein |
| 5514 | DNA polymerase III, epsilon subunit/ATP-dependent helicase DinG |
| 5520 | asparaginyl-tRNA synthetase (asnS) |
| 5526 | inosine-uridine preferring nucleoside hydrolase (iunH) |
| 5528 | general stress protein 170 |
| 5534 | Uncharacterised protein family superfamily |
| 5538 | Uncharacterized BCR, COG1481 |
| 5546 | zinc ABC transporter, zinc-binding adhesion liprotein (adcA) |
| 5560 | isochorismatase family protein (entB) |
| 5566 | 3-hydroxybutyryl-CoA dehydrogenase |
| 5572 | pyruvate phosphate dikinase (ppdK) |
| 5574 | glutamyl-tRNA(Gln) amidotransferase, C subunit (gatC) |
| 5580 | glutamyl-tRNA(Gln) amidotransferase, A subunit (gatA) |
| 5594 | GTP-binding protein |
| 5612 | iojap-related protein |
| 5626 | transcriptional regulator SkgA (skgA) |

TABLE VI-continued

PREDICTED FUNCTIONS FOR CERTAIN SEQ IDS

| SEQ ID | Function |
|---|---|
| 5630 | glycerol uptake facilitator protein (glpF) |
| 5634 | dihydroxyacetone kinase family protein |
| 5638 | dihydroxyacetone kinase family protein |
| 5640 | transcriptional regulator, tetR family |
| 5646 | dihydroxyacetone kinase family protein |
| 5654 | glutamine amidotransferase, class I |
| 5666 | peptidase, M20/M25/M40 family |
| 5668 | ABC transporter, ATP-binding protein |
| 5686 | pur operon repressor (purR) |
| 5690 | cmp-binding-factor 1 (cbf1) |
| 5694 | competence-induced protein Ccs50 (ccs50) |
| 5702 | ribulose-phosphate 3-epimerase (rpe) |
| 5710 | rRNA (guanine-N1-)-methyltransferase (rrmA) |
| 5712 | dimethyladenosine transferase (ksgA) |
| 5718 | primase-related protein |
| 5726 | endosome-associated protein |
| 5728 | CG17785 gene product |
| 5734 | dltD protein (dltD) |
| 5738 | D-alanyl carrier protein-related protein |
| 5742 | dltB protein (dltB) |
| 5754 | DNA-binding response regulator (arlR) |
| 5756 | ribosomal protein L34 (rpmH) |
| 5766 | penicillin-binding protein 4 (pbp4) |
| 5770 | intein-containing protein |
| 5774 | NifU family protein |
| 5778 | aminotransferase, class-V |
| 5782 | Uncharacterized protein family (UPF0051) family |
| 5786 | ABC transporter, ATP-binding protein |
| 5790 | glycosyl transferase domain protein (llm) |
| 5794 | transcriptional regulator MecA (mecA) |
| 5798 | undecaprenol kinase |
| 5806 | amino acid ABC transporter, amino acid-binding protein/permease protein |
| 5808 | amino acid ABC transporter, ATP-binding protein |
| 5834 | riboflavin biosynthesis protein RibF (ribF) |
| 5850 | type I restriction-modification system, S subunit |
| 5860 | lipoprotein |
| 5862 | aggregation substance |
| 5866 | ID479 |
| 5896 | type II DNA modification methyltransferase Spn5252IP (spn5252IMP) |
| 5916 | ribosomal protein L10 (rplJ) |
| 5922 | ATP-dependent Clp protease, ATP-binding subunit ClpC (clpC) |
| 5926 | homocysteine S-methyltransferase (mmuM) |
| 5932 | transcriptional regulator, TetR family |
| 5938 | GTP-binding protein (cgpA) |
| 5952 | thymidylate synthase (thyA) |
| 5956 | condensing enzyme, FabH-related |
| 5960 | hydroxymethylglutaryl-CoA reductase, degradative |
| 5976 | FMN-dependent dehydrogenase family protein |
| 5980 | phosphomevalonate kinase |
| 5986 | diphosphomevalonate decarboxylase (mvaD) |
| 5990 | mevalonate kinase (mvk) |
| 6002 | GTP pyrophosphokinase (relA) |
| 6006 | transposase for insertion sequence element is904 |
| 6016 | 5'-nucleotidase family |
| 6018 | polypeptide deformylase (def) |
| 6022 | NADP-specific glutamate dehydrogenase (gdhA) |
| 6026 | ABC transporter, ATP-binding/permease protein |
| 6028 | ABC transporter, ATP-binding/permease protein |
| 6030 | acetyltransferase, GNAT family family |
| 6032 | ABC transporter, ATP-binding protein |
| 6040 | degV family protein (degV) |
| 6056 | carbohydrate kinase, PfkB family (fruB) |
| 6064 | beta-lactam resistance factor (fibB) |
| 6070 | 2-dehydropantoate 2-reductase |
| 6076 | PTS system component |
| 6078 | pyridine nucleotide-disulphide oxidoreductase family protein (trxB) |
| 6082 | tRNA (guanine-N1-)-methyltransferase (trmD) |
| 6092 | c5a peptidase precursor |
| 6100 | ParA |
| 6102 | transposase family protein (orfA) |
| 6116 | Tn5252, relaxase |
| 6120 | Tn5252, Orf 10 protein |
| 6124 | mercuric reductase |
| 6126 | transcriptional regulator, MerR family |
| 6132 | cation transport ATPase, E1-E2 family |
| 6138 | cation-transporting ATPase, E1-E2 family |

TABLE VI-continued

PREDICTED FUNCTIONS FOR CERTAIN SEQ IDS

| SEQ ID | Function |
|---|---|
| 6140 | cation-transporting ATPase, E1-E2 family |
| 6144 | cation-transporting ATPase, E1-E2 family |
| 6146 | transcriptional repressor, CopY (copY) |
| 6150 | cadmium resistance transporter |
| 6158 | membrane protein |
| 6162 | flavoprotein (dfp) |
| 6170 | lipoate-protein ligase A |
| 6174 | FMN oxidoreductase (nemA) |
| 6178 | Bacterial luciferase superfamily |
| 6182 | glycine cleavage system H protein (gcvH) |
| 6186 | Domain of unknown function |
| 6194 | lipoate-protein ligase A (lplA) |
| 6198 | formate--tetrahydrofolate ligase (fhs) |
| 6202 | cardiolipin synthetase (cls) |
| 6220 | aminotransferase, class II (aspB) |
| 6222 | RNA methyltransferase, TrmH family, group 2 |
| 6232 | 60 kda chaperonin |
| 6242 | purine nucleoside phosphorylase (deoD) |
| 6248 | deoxyribose-phosphate aldolase (deoC) |
| 6254 | Lyme disease proteins of unknown function |
| 6258 | ribosomal large subunit pseudouridine synthase, RluD subfamily (rluD) |
| 6262 | penicillin-binding protein 2A (pbp2A) |
| 6266 | pathenogenicity protein |
| 6268 | transcription antitermination protein NusG (nusG) |
| 6272 | glycosyl transferase, family 8 |
| 6276 | glycosyl transferase, family 8 |
| 6284 | sugar transporter family protein |
| 6292 | sensory box histidine kinase |
| 6306 | homocysteine S-methyltransferase (metH) |
| 6310 | glycerol dehydrogenase |
| 6312 | DNA topology modulation protein FlaR |
| 6316 | translation initiation factor IF-1 (infA) |
| 6320 | adenylate kinase (adk) |
| 6326 | ribosomal protein L15 (rplO) |
| 6330 | ribosomal protein L30 (rpmD) |
| 6336 | ribosomal protein S5 (rpsE) |
| 6344 | ribosomal protein L6 (rplF) |
| 6348 | ribosomal protein S8 (rpsH) |
| 6352 | ribosomal protein S14 (rpsN) |
| 6356 | ribosomal protein L5 (rplE) |
| 6360 | ribosomal protein L24 (rplX) |
| 6366 | ribosomal protein L14 (rplN) |
| 6368 | ribosomal protein S17 (rpsQ) |
| 6372 | ribosomal protein L29 (rpmC) |
| 6374 | ribosomal protein L16 (rplP) |
| 6378 | ribosomal protein S3 (rpsC) |
| 6382 | ribosomal protein L22 (rplV) |
| 6386 | ribosomal protein S19 (rpsS) |
| 6390 | ribosomal protein L2 (rplB) |
| 6394 | ribosomal protein L23 (rplW) |
| 6398 | ribosomal protein L4/L1 family (rplD) |
| 6402 | ribosomal protein L3 (rplC) |
| 6408 | ribosomal protein S10 (rpsJ) |
| 6414 | MATE efflux family protein |
| 6418 | threonine synthase (thrC) |
| 6428 | Uncharacterized BCR, COG1636 superfamily |
| 6436 | 4-alpha-glucanotransferase (malQ) |
| 6440 | glycogen phosphorylase family protein (malP) |
| 6444 | glycerol-3-phosphate transporter (glpT) |
| 6452 | rhodanese family protein |
| 6458 | ammonium transporter |
| 6464 | DNA repair protein RadA (radA) |
| 6472 | oxidoreductase, pyridine nucleotide-disulfide, class I |
| 6478 | ribose ABC transporter, periplasmic D-ribose-binding protein (rbsB) |
| 6484 | ribose ABC transporter, ATP-binding protein (rbsA) |
| 6486 | ribose ABC transporter protein (rbsD) |
| 6488 | ribokinase (rbsK) |
| 6498 | ABC transporter, ATP-binding protein |
| 6502 | DNA-binding response regulator (vicR) |
| 6506 | argininosuccinate synthase (argG) |
| 6508 | argininosuccinate lyase (argH) |
| 6514 | bacteriophage L54a, repressor protein |
| 6528 | soluble transducer HtrXIII |
| 6542 | probable transposase (insertion sequence IS861) |
| 6544 | ABC transporter, ATP-binding/permease protein |
| 6550 | ABC transporter, ATP-binding/permease protein |

TABLE VI-continued

PREDICTED FUNCTIONS FOR CERTAIN SEQ IDS

| SEQ ID | Function |
|---|---|
| 6560 | Serine hydroxymethyltransferase |
| 6568 | HemK protein (hemK) |
| 6572 | peptide chain release factor 1 (prfA) |
| 6576 | thymidine kinases |
| 6580 | 4-oxalocrotonate tautomerase (dmpI) |
| 6588 | oxidoreductase |
| 6594 | oxidoreductase |
| 6600 | formate/nitrite transporter family protein |
| 6608 | xanthine permease (pbuX) |
| 6612 | xanthine phosphoribosyltransferase (xpt) |
| 6616 | guanosine monophosphate reductase (guaC) |
| 6620 | drug resistance transporter, EmrB/QacA subfamily |
| 6622 | oxidoreductase |
| 6624 | Kup system potassium uptake protein (kup) |
| 6636 | O-methyltransferase |
| 6642 | oligoendopeptidase F (pepF) |
| 6646 | competence protein CoiA (coiA) |
| 6650 | major facilitator superfamily protein superfamily |
| 6652 | ribosomal small subunit pseudouridine synthase A (rsuA) |
| 6658 | glucosamine-6-phosphate isomerase (nagB) |
| 6662 | nodulin-related protein, truncation |
| 6664 | S-adenosylmethioninetRNA ribosyltransferase-isomerase (queA) |
| 6674 | permease, GntP family |
| 6684 | 6-phospho-beta-glucosidase (bglA) |
| 6686 | PTS system, beta-glucosides-specific IIABC components |
| 6688 | transcription antiterminator LicT (licT) |
| 6704 | esterase |
| 6706 | sugar-binding transcriptional repressor, LacI family |
| 6708 | hydrolase, haloacid dehalogenase-like family |
| 6712 | DNA internalization-related competence protein CamEC/Rec2 |
| 6716 | competence protein CelA (celA) |
| 6720 | acyltransferase family protein |
| 6732 | ATP-dependent RNA helicase DeaD (deaD) |
| 6736 | lipoprotein, YaeC family |
| 6738 | ABC transporter, permease protein |
| 6752 | diacylglycerol kinase (dgkA) |
| 6768 | formamidopyrimidine-DNA glycosylase (mutM) |
| 6776 | epidermin immunity protein F |
| 6788 | glycyl-tRNA synthetase, beta subunit (glyS) |
| 6790 | acyl carrier protein phosphodiesterase |
| 6800 | SsrA-binding protein (smpB) |
| 6822 | D-alanine--D-alanine ligase |
| 6824 | recombination protein RecR (recR) |
| 6830 | penicillin-binding protein 2b |
| 6832 | phosphoglycerate mutase (gpmA) |
| 6836 | triosephosphate isomerase (tpiA) |
| 6856 | phosphoglycerate mutase family protein |
| 6860 | D-alanyl-D-alanine carboxypeptidase family |
| 6864 | autolysin |
| 6868 | heat-inducible transcription repressor HrcA (hrcA) |
| 6872 | heat shock protein GrpE (grpE) |
| 6876 | chaperone protein dnak |
| 6880 | dnaJ protein (dnaJ) |
| 6884 | transcriptional regulator, gntR family domain protein |
| 6888 | tRNA pseudouridine synthase A (truA) |
| 6892 | phosphomethylpyrimidine kinase (thiD) |
| 6910 | galactose-6-phosphate isomerase, LacA subunit (lacA) |
| 6922 | tagatose 1,6-diphosphate aldolase (lacD) |
| 6932 | sugar ABC transporter, ATP-binding protein (msmK) |
| 6936 | glucan 1,6-alpha-glucosidase (dexB) |
| 6940 | UDP-glucose 4-epimerase (galE) |
| 6942 | response regulator (citB) |
| 6950 | citrate carrier protein (citS) |
| 6954 | malate oxidoreductase (tme) |
| 6958 | bacterocin transport accessory protein |
| 6976 | transposase family protein (orfA) |
| 6980 | pXO1-128 |
| 6986 | adhesion lipoprotein (lmb) |
| 6994 | DNA-directed RNA polymerase, alpha subunit (rpoA) |
| 6998 | ribosomal protein L17 (rplQ) |
| 7040 | probable dna-directed rna polymerase delta subunit |
| 7044 | CTP synthase (pyrG) |
| 7058 | bacteriocin transport accessory protein |
| 7074 | translation initiation factor IF-3 (infC) |
| 7100 | adenosine deaminase |
| 8468 | preprotein translocase, SecE subunit |

TABLE VI-continued

PREDICTED FUNCTIONS FOR CERTAIN SEQ IDS

| SEQ ID | Function |
|---|---|
| 8476 | antigen, 67 kDa |
| 8486 | Lipase/Acylhydrolase |
| 8492 | peptide ABC transporter, permease protein (oppB) |
| 8494 | competence protein CglB (cglB) |
| 8502 | peptide ABC transporter, peptide-binding protein |
| 8504 | oxidoreductase |
| 8510 | amino acid ABC transporter, permease protein (opuBB) |
| 8522 | abc transporter atp-binding protein ybhf |
| 8530 | glycerol-3-phosphate dehydrogenase (NAD(P)+) (gpsA) |
| 8538 | sugar ABC transporter, sugar-binding protein |
| 8544 | secreted 45 kd protein (usp45) |
| 8556 | phosphoglycerate mutase family protein |
| 8566 | glycosyl hydrolase, family 3 |
| 8576 | N-acetylmuramoyl-L-alanine amidase |
| 8596 | sensory box histidine kinase (withHAMPandPASd) |
| 8608 | aminoglycoside 6-adenylyltransferase |
| 8622 | iron compound ABC transporter, permease protein (sirB) |
| 8636 | phosphate ABC transporter, permease protein (pstC-2) |
| 8650 | branched-chain amino acid transport system II carrier protein (brnQ) |
| 8658 | PTS system, IID component |
| 8662 | replisome organiser-related protein |
| 8674 | alkaline amylopullulanase |
| 8676 | exfoliative toxin A |
| 8690 | glycerol uptake facilitator protein (glpF) |
| 8698 | ABC transporter, ATP-binding protein |
| 8708 | cobalt transport protein |
| 8730 | integral membrane protein |
| 8734 | yadS protein |
| 8736 | cell wall surface anchor family protein |
| 8748 | polysaccharide biosynthesis protein |
| 8752 | glycosyl transferase domain protein |
| 8764 | endopeptidase O |
| 8770 | beta-ketoacyl-acyl carrier protein synthase II |
| 8772 | ABC transporter, ATP-binding protein |
| 8776 | penicillin-binding protein |
| 8778 | cell wall surface anchor family protein |
| 8780 | cell wall surface anchor family protein |
| 8786 | LPXTG-motif cell wall anchor domain protein |
| 8788 | 6-aminohexanoate-cyclic-dimer hydrolase |
| 8796 | NLP/P60 family protein |
| 8802 | DNA/RNA non-specific endonuclease |
| 8806 | hydroxyethylthiazole kinase (thiM) |
| 8826 | PTS system component |
| 8832 | sugar ABC transporter, permease protein |
| 8836 | potassium uptake protein, Trk family (trkA) |
| 8850 | lemA protein (lemA) |
| 8856 | cobalt transport protein |
| 8884 | spermidine/putrescine ABC transporter, permease protein (potC) |
| 8906 | ABC transporter, substrate-binding protein |
| 8908 | lipoprotein |
| 8916 | sensor histidine kinase |
| 8930 | TrsK-like protein (traK) |
| 8936 | R5 protein |
| 8962 | chromosome assembly protein homolog |
| 8978 | ribose ABC transporter, permease protein (rbsC) |
| 8980 | permease |
| 8982 | sensor histidine kinase (arlS) |
| 8986 | hydrolase, haloacid dehalogenase-like family (gph) |
| 8994 | dephospho-CoA kinase |
| 8996 | oxalateformate antiporter |
| 9004 | sensory box protein |
| 9006 | host cell surface-exposed lipoprotein |
| 9012 | PAP2 family protein |
| 9034 | GtrA family protein |
| 9050 | lipoprotein signal peptidase (lspA) |
| 9280 | alcohol dehydrogenase, zinc-containing (adh) |
| 9284 | trigger factor (tig) |
| 9290 | fructose-bisphosphate aldolase (fba) |
| 9292 | DAK2 domain protein |
| 9296 | oligopeptide ABC transporter, permease protein |
| 9298 | N-acetylglucosamine-6-phosphate deacetylase (nagA) |
| 9300 | transcriptional regulator, DeoR family (lacR) |
| 9302 | PTS system, mannose-specific IIC component (manM) |
| 9306 | Phosphoglucose isomerase |
| 9310 | aspartate--ammonia ligase (asnA) |
| 9312 | amino acid ABC transporter, ATP-binding protein |

TABLE VI-continued

PREDICTED FUNCTIONS FOR CERTAIN SEQ IDS

| SEQ ID | Function |
| --- | --- |
| 9314 | DNA-binding protein HU (hup) |
| 9316 | DHH subfamily 1 protein |
| 9318 | chloride channel |
| 9320 | integrase (int) |
| 9324 | DNA/RNA non-specific endonuclease |
| 9326 | PTS system component |
| 9328 | cell division protein, FtsW/RodA/SpoVE family (ftsW) |
| 9330 | LPXTG-motif cell wall anchor domain protein |
| 9332 | peptide chain release factor 3 (prfC) |
| 9334 | ABC transporter, ATP-binding protein |
| 9336 | superoxide dismutase [mn—fe] |
| 9340 | phenylalanyl-tRNA synthetase, alpha subunit (pheS) |
| 9342 | amino acid ABC transporter, permease protein |
| 9344 | phosphate ABC transporter, phosphate-binding protein (pstS) |
| 9346 | NOL1/NOP2/sun family protein (sun) |
| 9348 | Abortive infection protein family |
| 9350 | permease |
| 9352 | N-acetylmuramoyl-L-alanine amidase domain protein (usp45) |
| 9354 | ABC transporter, ATP-binding protein |
| 9356 | phosphoglucomutase (pgm) |
| 9358 | oxidoreductase, short chain dehydrogenase/reductase family |
| 9360 | phosphate acetyltransferase |
| 9362 | gls24 protein |
| 9364 | ribosomal protein S1 (rpsA) |
| 9368 | dTDP-glucose 4,6-dehydratase (rfbB) |
| 9370 | excinuclease ABC, C subunit (uvrC) |
| 9372 | MATE efflux family protein |
| 9378 | amino acid permease (rocE) |
| 9380 | DNA-binding response regulator TrcR (trcR) |
| 9382 | 16S rRNA processing protein RimM (rimM) |
| 9384 | transcriptional regulator |
| 9388 | ribosomal protein L20 (rplT) |
| 9394 | sugar-binding transcriptional repressor, LacI family (malR) |
| 9396 | proton/peptide symporter family protein |
| 9398 | amino acid permease |
| 9400 | exoribonuclease, VacB/Rnb family (vacB) |
| 9402 | multi-drug resistance efflux pump (pmrA) |
| 9404 | adhesion lipoprotein (psaA) |
| 9406 | iron-dependent transcriptional regulator (sirR) |
| 9412 | amino acid permease |
| 9414 | SpoU rRNA Methylase family protein |
| 9416 | sodium/dicarboxylate symporter (gltP-2) |
| 9418 | branched-chain amino acid transport system II carrier protein (brnQ) |
| 9420 | alcohol dehydrogenase, zinc-containing |
| 9422 | aminotransferase, class I (aspB) |
| 9424 | ribosomal protein S6 (rpsF) |
| 9426 | A/G-specific adenine glycosylase (mutY) |
| 9428 | acid phosphatase (olpA) |
| 9430 | ribosomal protein S12 (rpsL) |
| 9434 | microcin immunity protein McсF (mccF-1) |
| 9436 | undecaprenyl diphosphate synthase (uppS) |
| 9438 | preprotein translocase, YajC subunit (yajC) |
| 9440 | chaperonin, 10 kDa (groES) |
| 9444 | YitT family protein |
| 9446 | serine protease (htrA) |
| 9448 | ribose-phosphate pyrophosphokinase (prsA) |
| 9450 | aromatic amino acid aminotransferase (araT) |
| 9452 | Recombination protein O (recO) |
| 9454 | Abortive infection protein family |
| 9456 | fatty acid/phospholipid synthesis protein PlsX (plsX) |
| 9458 | acyl carrier protein (acpP) |
| 9462 | phosphoribosylaminoimidazole carboxylase, ATPase subunit (purK) |
| 9464 | alcohol dehydrogenase, iron-containing |
| 9466 | ribosomal protein L18 (rplR) |
| 9468 | preprotein translocase, SecY subunit |
| 9470 | transcriptional regulator ComX1 (comX1) |
| 9472 | deoxyuridine 5'-triphosphate nucleotidohydrolase (dut) |
| 9478 | sugar-binding transcriptional regulator, LacI family (rbsR) |
| 9480 | SPFH domain/Band 7 family |
| 9488 | zinc ABC transporter, permease protein (adcB) |
| 9492 | abortive infection protein |
| 9494 | hydrolase, haloacid dehalogenase-like family |
| 9496 | response regulator (lytT) |
| 9500 | transketolase, C-terminal subunit |
| 9502 | polyribonucleotide nucleotidyltransferase (pnp) |
| 9504 | serine O-acetyltransferase (cysE) |

TABLE VI-continued

PREDICTED FUNCTIONS FOR CERTAIN SEQ IDS

| SEQ ID | Function |
|---|---|
| 9508 | ribosomal protein L13 (rplM) |
| 9510 | replication initiation protein |
| 9518 | amino acid ABC transporter, amino acid-binding protein |
| 9522 | glycyl-tRNA synthetase, alpha subunit (glyQ) |
| 9524 | NADH oxidase |
| 9528 | transketolase (tkt) |
| 9534 | penicillin-binding protein 1A (pbp1A) |
| 9536 | cell division protein DivIVA (divIVA) |
| 9538 | sensor histidine kinase |
| 9540 | serine/threonine protein kinase (pknB) |
| 9542 | transcriptional regulator |
| 9544 | PTS system, IIA component (lacF) |
| 9546 | glycerol dehydrogenase (gldA) |
| 9548 | aspartate kinase (thrA) |
| 9550 | enoyl-CoA hydratase/isomerase family protein |
| 9552 | acyl carrier protein (acpP) |
| 9564 | ABC transporter, ATP-binding protein |
| 9566 | N utilization substance protein A (nusA) |
| 9568 | ribosome-binding factor A (rbfA) |
| 9570 | Cof family protein |
| 9572 | CoA binding domain protein (b0965) |
| 9574 | transcriptional regulator, Fur family |
| 9578 | queuine tRNA-ribosyltransferase (tgt) |
| 9580 | ribonuclease P protein component (rnpA) |
| 9582 | serine protease, subtilase family |
| 9584 | glycosyl transferase domain protein |
| 9586 | transcriptional activator, AraC family |
| 9588 | transcriptional regulator, TetR family |
| 9590 | transcriptional regulator, AraC family |
| 9594 | surface protein Rib |
| 9596 | transposase, mutator family |
| 9600 | acetyltransferase, GNAT family |
| 9602 | Transposase, Mutator family |
| 9606 | UDP-sugar hydrolase |
| 9610 | anthranilate synthase component II (trpG) |
| 9612 | biotin synthetase (bioB) |
| 9616 | UDP-N-acetylmuramoylalanine--D-glutamate ligase (murD) |
| 9618 | ylmF protein (ylmF) |
| 9620 | amino acid ABC transporter, permease protein |
| 9622 | phosphoglucomutase (pgm) |
| 9624 | YjeF-related protein, C-terminus |
| 9626 | FemAB family protein (fibA) |
| 9628 | Cof family protein |
| 9630 | cell division ABC transporter, permease protein FtsX (ftsX) |
| 9632 | oxidoreductase, short-chain dehydrogenase/reductase family (fabG) |
| 9634 | aspartate aminotransferase (aspC) |
| 9638 | ribosomal protein L31 (rpmE) |
| 9640 | nrdI protein (nrdI) |
| 9642 | ribosomal protein L19 (rplS) |
| 9644 | bacteriophage L54a, repressor protein |
| 9646 | bacteriophage L54a, antirepressor |
| 9652 | single-strand binding protein (ssb) |
| 9660 | pneumococcal surface protein A |
| 9666 | DNA-binding response regulator (vncR) |
| 9668 | transposase OrfAB, subunit B |
| 9670 | cell division protein, FtsW/RodA/SpoVE family (rodA) |
| 9672 | DNA gyrase, B subunit (gyrB) |
| 9674 | 3-phosphoshikimate 1-carboxyvinyltransferase (aroA) |
| 9676 | RNA methyltransferase, TrmA family |
| 9680 | transcriptional regulator, AraC family |
| 9682 | ABC transporter, ATP-binding protein |
| 9690 | CylJ |
| 9696 | permease |
| 9698 | regulatory protein |
| 9700 | carbohydrate kinase, pfkB family |
| 9702 | beta-glucuronidase |
| 9706 | 3-oxoacyl-(acyl-carrier-protein) reductase |
| 9708 | catabolite control protein A (ccpA) |
| 9712 | ribonuclease III (rnc) |
| 9714 | SMC family, C-terminal domain family |
| 9718 | S1 RNA binding domain protein |
| 9722 | prolipoprotein diacylglyceryl transferase (lgt) |
| 9724 | riboflavin synthase, alpha subunit (ribE) |
| 9728 | lysyl-tRNA synthetase (lysS) |
| 9734 | Transposase subfamily |
| 9738 | translation elongation factor Tu (tuf) |

TABLE VI-continued

PREDICTED FUNCTIONS FOR CERTAIN SEQ IDS

| SEQ ID | Function |
|---|---|
| 9746 | Glutathione S-transferases domain protein |
| 9754 | Ribonucleotide reductases |
| 9756 | biotin--acetyl-CoA-carboxylase ligase |
| 9760 | Uncharacterized protein family SNZ family |
| 9762 | methionine aminopeptidase, type I (map) |
| 9764 | DNA ligase, NAD-dependent (ligA) |
| 9766 | glucose-1-phosphate adenylyltransferase (glgC) |
| 9768 | UDP-N-acetylglucosamine 1-carboxyvinyltransferase (murA) |
| 9770 | acetyltransferase, GNAT family |
| 9772 | exonuclease RexA (rexA) |
| 9774 | tRNA modification GTPase TrmE (trmE) |
| 9776 | ABC transporter, ATP-binding protein |
| 9782 | Mur ligase family protein |
| 9786 | HD domain protein |
| 9788 | translation elongation factor G (fusA) |
| 9796 | pyruvate kinase (pyk) |
| 9798 | Signal peptidase I |
| 9802 | cytidine deaminase (cdd) |
| 9804 | sugar ABC transporter, ATP-binding protein |
| 9806 | sugar ABC transporter, permease protein |
| 9808 | acetyltransferase, GNAT family |
| 9810 | ABC transporter, permease protein |
| 9812 | SatD |
| 9814 | Helix-turn-helix domain, fis-type protein |
| 9816 | phosphate ABC transporter, ATP-binding protein (pstB-1) |
| 9818 | tRNA pseudouridine synthase B (truB) |
| 9820 | Acetyltransferase (GNAT) family |
| 9822 | DNA topoisomerase I (topA) |
| 9824 | ribonuclease HII (rnhB) |
| 9830 | orotidine 5'-phosphate decarboxylase (pyrF) |
| 9832 | aspartate-semialdehyde dehydrogenase (asd) |
| 9836 | pantothenate metabolism flavoprotein (dfp) |
| 9840 | Sua5/YciO/YrdC/YwlC family protein |
| 9844 | thiamine biosynthesis protein ApbE |
| 9846 | Domain of unknown function |
| 9848 | DNA repair protein RadC (radC) |
| 9850 | glycosyl hydrolase, family 1 (bglA) |
| 9852 | Cof family protein (b0844) |
| 9854 | spermidine/putrescine ABC transporter, permease protein (potH) |
| 9856 | folylpolyglutamate synthase (folC) |
| 9858 | homoserine dehydrogenase (hom) |
| 9860 | succinate-semialdehyde dehydrogenase (gabD-1) |
| 9862 | membrane protein |
| 9864 | ATP-dependent DNA helicase PcrA (pcrA) |
| 9866 | uracil permease (uraA) |
| 9868 | sodiumalanine symporter family protein |
| 9878 | capsular polysaccharide biosynthesis protein Cps4B (cps4B) |
| 9880 | transcriptional regulator, LysR family |
| 9882 | CpslaS |
| 9884 | chloride channel protein |
| 9886 | tributyrin esterase (estA) |
| 9888 | ABC transporter, ATP-binding protein (potA) |
| 9890 | alpha-acetolactate decarboxylase (budA) |
| 9892 | TPR domain protein |
| 9896 | metallo-beta-lactamase superfamily protein |
| 9898 | tRNA delta(2)-isopentenylpyrophosphate transferase (miaA) |
| 9902 | glycerophosphoryl diester phosphodiesterase |
| 9904 | transposase OrfAB, subunit B |
| 9906 | IS3-Spn1, transposase |
| 9908 | transposase OrfAB, subunit B (orfB) |
| 9910 | reverse transcriptase |
| 9916 | transposase OrfAB, subunit B |
| 9918 | integrase, phage family (int) |
| 9920 | transcription regulator |
| 9922 | TnpA |
| 9926 | structural gene for ultraviolet resistance (uvra) |
| 9930 | Helicases conserved C-terminal domain protein |
| 9932 | abortive infection bacteriophage resistance protein (abiEi) |
| 9944 | ribosomal protein L7/L12 (rplL) |
| 9948 | ATP-dependent Clp protease, ATP-binding subunit ClpX (clpX) |
| 9950 | dihydrofolate reductase (folA) |
| 9952 | hemolysin |
| 9954 | transcriptional regulator, MarR family |
| 9958 | polyA polymerase family protein |
| 9960 | PTS system, fructose specific IIABC components (fruA-1) |
| 9962 | lactose phosphotransferase system repressor (lacR) |

TABLE VI-continued

PREDICTED FUNCTIONS FOR CERTAIN SEQ IDS

| SEQ ID | Function |
| --- | --- |
| 9964 | choline binding protein D (cbpD) |
| 9968 | pyrimidine operon regulatory protein (pyrR) |
| 9970 | ribosomal large subunit pseudouridine synthase D (rluD) |
| 9972 | thiamine biosynthesis protein ThiI (thiI) |
| 9974 | 3-dehydroquinate dehydratase, type I (aroD) |
| 9976 | iron compound ABC transporter, ATP-binding protein (fepC) |
| 9980 | transcriptional regulator |
| 9982 | glycosyl transferase domain protein |
| 9984 | Cps9H |
| 9988 | 4-diphosphocytidyl-2C-methyl-D-erythritol synthase (ispD) |
| 9990 | licD1 protein (licD1) |
| 9996 | large conductance mechanosensitive channel protein (mscL) |
| 10000 | maltose ABC transporter, maltose-binding protein |
| 10004 | nucleotide sugar synthetase-like protein |
| 10006 | transcriptional regulator |
| 10008 | oxidoreductase, aldo/keto reductase family |
| 10010 | NAD(P)H-flavin oxidoreductase |
| 10016 | transcriptional regulator MutR |
| 10018 | GTP-binding protein Era (era) |
| 10022 | peptide methionine sulfoxide reductase (msrA) |
| 10026 | peptide ABC transporter, ATP-binding protein |
| 10028 | peptide ABC transporter, ATP-binding protein (amiE) |
| 10030 | peptide ABC transporter, peptide-binding protein |
| 10032 | transposase, IS30 family |
| 10034 | transcriptional regulator, LysR family |
| 10036 | spoE family protein (ftsK) |
| 10044 | methionyl-tRNA synthetase (metG) |
| 10046 | D-isomer specific 2-hydroxyacid dehydrogenase family protein (serA) |
| 10048 | acetyltransferase, GNAT family |
| 10050 | phosphoserine aminotransferase (serC) |
| 10054 | thymidylate kinase (tmk) |
| 10060 | branched-chain amino acid ABC transporter, permease protein (livH) |
| 10062 | ATP-dependent Clp protease, proteolytic subunit ClpP (clpP) |
| 10064 | uracil phosphoribosyltransferase (upp) |
| 10066 | potassium uptake protein, Trk family (trkH) |
| 10068 | glutamate racemase (murI) |
| 10070 | membrane protein |
| 10072 | HD domain protein |
| 10074 | Acylphosphatase |
| 10076 | spoIIIJ family protein |
| 10078 | acetyltransferase, GNAT family |
| 10080 | glucose-inhibited division protein B (gidB) |
| 10082 | potassium uptake protein, Trk family |
| 10084 | ABC transporter, permease protein |
| 10088 | isochorismatase family protein |
| 10092 | haloacid dehalogenase-like hydrolase superfamily |
| 10094 | membrane protein |
| 10096 | glutamyl-tRNA(Gln) amidotransferase, B subunit (gatB) |
| 10098 | CBS domain protein protein |
| 10100 | transcriptional regulator (codY) |
| 10102 | universal stress protein family |
| 10104 | L-asparaginase (ansA) |
| 10106 | oxidoreductase, aldo/keto reductase 2 family |
| 10108 | preprotein translocase, SecA subunit (secA) |
| 10112 | excinuclease ABC, A subunit (uvrA) |
| 10114 | magnesium transporter, CorA family (corA) |
| 10116 | thioredoxin (trx) |
| 10118 | MutS2 family protein (mutS2) |
| 10122 | DNA-damage inducible protein P (dinP) |
| 10124 | formate acetyltransferase (pfl) |
| 10126 | transcriptional regulator, Crp family |
| 10128 | transport ATP-binding protein CydC |
| 10138 | ribosomal-protein-alanine acetyltransferase (rimI) |
| 10140 | hydrolase |
| 10144 | D-alanine-activating enzyme (dltA) |
| 10148 | carbohydrate kinase, FGGY family |
| 10150 | transaldolase |
| 10160 | Helix-turn-helix domain protein |
| 10164 | single-strand binding protein (ssb) |
| 10166 | type II DNA modification methyltransferase Spn5252IP (spn5252IMP) |
| 10174 | integrase, phage family |
| 10178 | Cyclic nucleotide-binding domain protein |
| 10180 | transcriptional regulator, MarR family |
| 10182 | prolyl-tRNA synthetase (proS) |
| 10184 | leucine-rich protein |
| 10186 | lacX protein, truncation (lacX) |

TABLE VI-continued

PREDICTED FUNCTIONS FOR CERTAIN SEQ IDS

| SEQ ID | Function |
|---|---|
| 10188 | tagatose-6-phosphate kinase (lacC) |
| 10190 | galactose-6-phosphate isomerase, LacB subunit (lacB) |
| 10192 | neuraminidase |
| 10200 | ABC transporter, ATP-binding protein |
| 10202 | PTS system, IIABC components (ptsG) |
| 10204 | phosphate regulon response regulator PhoB (phoB) |
| 10212 | Uncharacterized ACR, COG2161 subfamily |
| 10216 | abortive phage resistance protein |
| 10222 | TnpA |
| 10226 | acetyltransferase, GNAT family |
| 10230 | ABC transporter domain protein |
| 10236 | branched-chain amino acid transport protein AzlC (azlC) |
| 10240 | DNA-binding response regulator (srrA) |
| 10242 | leucyl-tRNA synthetase (leuS) |
| 10246 | NupC family protein |
| 10248 | transcriptional regulator, GntR family |
| 10252 | glyoxalase family protein |
| 10254 | anaerobic ribonucleoside-triphosphate reductase (nrdD) |
| 10256 | competence-induced protein Ccs4 |
| 10262 | competence/damage-inducible protein CinA (cinA) |
| 10264 | DNA-3-methyladenine glycosylase I (tag) |
| 10268 | DNA mismatch repair protein HexB (hexB) |
| 10270 | arginine repressor (argR) |
| 10272 | arginyl-tRNA synthetase (argS) |
| 10274 | aspartyl-tRNA synthetase (aspS) |
| 10276 | histidyl-tRNA synthetase (hisS) |
| 10280 | AGR_pAT_51p |
| 10286 | hydrolase, alpha/beta hydrolase fold family |
| 10288 | phage infection protein |
| 10290 | Glucose inhibited division protein A (gidA) |
| 10292 | tRNA (5-methylaminomethyl-2-thiouridylate)-methyltransferase (trmU) |
| 10296 | arginine/ornithine antiporter (arcD) |
| 10298 | chromosomal replication initiator protein DnaA (dnaA) |
| 10302 | peptidyl-tRNA hydrolase (pth) |
| 10310 | phosphotyrosine protein phosphatase |
| 10316 | ribosomal protein L36 (rpmJ) |
| 10318 | ribosomal protein S13/S18 (rpsM) |
| 10328 | L-lactate dehydrogenase (ldh) |
| 10330 | ribosomal protein L28 (rpmB) |
| 10362 | RNA polymerase sigma-70 factor, ECF subfamily |
| 10384 | BioY family protein |
| 10386 | AtsA/ElaC family protein |
| 10388 | cytidine/deoxycytidylate deaminase family protein |
| 10394 | phosphorylase, Pnp/Udp family |
| 10396 | transcriptional regulator, MerR family |
| 10402 | methyltransferase (ubiE) |
| 10412 | type IV prepilin peptidase |
| 10416 | ylmG protein (ylmG) |
| 10444 | transposase OrfAB, subunit B |
| 10446 | IS150-like transposase |
| 10452 | Bacterial regulatory proteins, tetR family domain protein |
| 10454 | cell wall surface anchor family protein, authentic frameshift (clfB) |
| 10456 | transposase OrfAB, subunit A (orfA) |
| 10460 | chaperonin, 33 kDa (hslO) |
| 10472 | (3R)-hydroxymyristoyl-(acyl-carrier-protein) dehydratase (fabZ) |
| 10482 | sprT protein |
| 10490 | transcriptional regulator, MarR family |
| 10498 | transcriptional regulator |
| 10504 | glycogen biosynthesis protein GlgD (glgD) |
| 10536 | ribonucleoside-diphosphate reductase, alpha subunit, truncation (nrdD) |
| 10538 | LPXTG-motif cell wall anchor domain |
| 10550 | membrane protein |
| 10554 | arsenate reductase (arsC) |
| 10564 | transposase, authentic frameshift |
| 10570 | transposase OrfAB, subunit A (orfA) |
| 10574 | Tn5252, Orf 9 protein |
| 10580 | IS3-Spn1, transposase |
| 10584 | transcriptional regulator, ArsR family |
| 10628 | ribosomal protein L35 (rpmI) |
| 10630 | cytidylate kinase (cmk) |
| 10636 | MutT/nudix family protein |
| 10644 | preprotein translocase, SecG subunit |
| 10680 | ribosomal protein S18 (rpsR) |
| 10682 | single-strand binding protein (ssb) |
| 10692 | glyceraldehyde 3-phosphate dehydrogenase (gap) |
| 10694 | translation elongation factor G (fusA) |

TABLE VI-continued

PREDICTED FUNCTIONS FOR CERTAIN SEQ IDS

SEQ ID  Function

- 10696  ribosomal protein S7 (rpsG)
- 10704  phosphinothricin N-acetyltransferase (pat)
- 10730  nrdI protein (nrdI)
- 10732  accessory gene regulator protein C (blpH)
- 10744  rhodanese family protein (pspE)
- 10746  cAMP factor
- 10758  competence/damage-inducible protein CinA (cinA)
- 10770  transcriptional regulator, ArgR family (argR)
- 10772  FliP family family
- 10794  peptide ABC transporter, peptide-binding protein
- 10800  ribosomal protein S21 (rpsU)
- 10802  transposase, IS30 family
- 10816  mucin 2 precursor, intestinal
- 10854  SV40-transformed marker protein pG1-related protein
- 10856  SV40-transformed marker protein pG1-related protein
- 10858  SV40-transformed marker protein pG1-related protein
- 10860  SV40-transformed marker protein pG1-related protein
- 10862  SV40-transformed marker protein pG1-related protein
- 10864  SV40-transformed marker protein pG1-related protein
- 10866  SV40-transformed marker protein pG1-related protein
- 10910  transcriptional regulator
- 10920  ribosomal protein S11 (rpsK)
- 10922  elaA protein
- 10926  5-formyltetrahydrofolate cyclo-ligase family protein
- 10938  inositol monophosphatase family protein
- 10940  amino acid ABC transporter, amino acid-binding protein (artI)
- 10944  Holliday junction DNA helicase RuvB (ruvB)
- 10946  D-alanyl-D-alanine carboxypeptidase (dacA)
- 10948  lipoprotein (bmpD)
- 10950  peptidase, U32 family family
- 10952  protease maturation protein
- 10954  glutamyl-tRNA synthetase (gltX)
- 10956  GTP-binding protein LepA (lepA)
- 10960  translation initiation factor if-2
- 10962  phosphoenolpyruvate carboxylase (ppc)
- 10964  calcium E1-E2-type ATPase
- 10966  serine protease, subtilase family

Exemplary Sequences

```
SEQ ID NO: 4209
atgaataagc catattcaat aggccttgac atcggtacta attccgtcgg atggagcatt    60
attacagatg attataaagt acctgctaag aagatgagag ttttagggaa cactgataaa   120
gaatatatta agaagaatct cataggtgct ctgcttttg atggcgggaa tactgctgca    180
gatagacgct tgaagcgaac tgctcgtcgt cgttatacac gtcgtagaaa tcgtattcta   240
tatttacaag aaattttgc agaggaaatg agtaaagttg atgatagttt ctttcatcga    300
ttagaggatt cttttctagt tgaggaagat aagagaggga gcaagtatcc tatctttgca   360
acattgcagg aagagaaaga ttatcatgaa aaattttcga caatctatca tttgagaaaa   420
gaattagctg acaagaaaga aaaagcagac cttcgtctta tttatattgc tctagctcat   480
atcattaaat ttagagggca tttcctaatt gaggatgata gctttgatgt caggaataca   540
gacatttcaa aacaatatca agatttttta gaaatcttta atacaacttt tgaaaataat   600
gatttgttat ctcaaaacgt tgacgtagag gcaatactaa cagataagat tagcaagtct   660
gcgaagaaag atcgtatttt agcgcagtat cctaaccaaa aatctactgg cattttgca    720
gaattttga aattgattgt cggaaatcaa gctgacttca agaaatattt caatttggag    780
gataaaacgc cgcttcaatt cgctaaggat agctacgatg agatttaga aaatcttctt    840
ggacagattg gtgatgaatt tgcagactta ttctcagcag cgaaaaagtt atatgatagt   900
gtccttttgt ctgcattct tacagtaatc gacctcagta ccaaggcgcc actttcagct   960
tctatgattc agcgttatga tgaacataga gaggacttga aacagttaaa acaattcgta  1020
aaagcttcat tgccggaaaa atatcaagaa atatttgctg attcatcaaa agatggctac  1080
gctggttata ttgaaggtaa aactaatcaa gaagcttttt ataaatacct gtcaaaattg  1140
ttgaccaagc aagaagatag cgagaatttt cttgaaaaaa tcaagaatga agatttcttg  1200
agaaaacaaa ggacctttga taatggctca attccacacc aagtccattt gacagagctg  1260
aaagctatta tccgccgtca atcagaatac tatcccttct tgaaagagaa tcaagatagg  1320
attgaaaaaa tccttacctt tagaattcct tattatatcg ggccactagc acgtgagaag  1380
agtgattttg catggatgac tcgcaaaaca gatgacagta ttcgaccttg gaattttgaa  1440
gacttggttg ataaagaaaa atctgcggaa gcttttatcc atcgtatgac caacaatgat  1500
ttttatcttc ctgaagaaaa agttttacca aagcatagtc ttatttatga aaaatttacg  1560
gtctataatg agttgactaa ggttagatat aaaaatgagc aagtgagac ttattttttt   1620
gatagcaata ttaaacaaga aatctttgat ggagtattca aggaacatcg taaggtatcc  1680
aagaagaagt tgctagattt tctggctaaa gaatatgagg agtttaggat agtagatgtt  1740
attggtctag ataagaaaa taagctttc aacgcctcat tgggaactta ccacgatctc    1800
gaaaaaatac tagacaaaga ttttctagat aatccagata atgagtctat tctggaagat  1860
```

| Exemplary Sequences |
| --- |

```
atcgtccaaa ctctaacatt atttgaagac agagaaatga ttaagaagcg tcttgaaaac  1920
tataaagatc tttttacaga gtcacaacta aaaaaactct atcgtcgtca ctatactggc  1980
tggggacgat tgtctgctaa gttaatcaat ggtattcgag ataaagagag tcaaaaaaca  2040
atcttggact atcttattga tgatggtaga tctaatcgca actttatgca gttgataaat  2100
gatgatggtc tatctttcaa atcaattatc agtaaggcac aggctggtag tcattcagat  2160
aatctaaaag aagttgtagg tgagcttgca ggtagccctg ctattaaaaa gggaattcta  2220
caaagtttga aaattgttga tgagcttgtt aaagtcatgg gatacgaacc tgaacaaatt  2280
gtggttgaga tggcgcgtga gaatcaaaca acaaatcaag gtcgtcgtaa ctctcgacaa  2340
cgctataaac ttcttgatga tggcgttaag aatctagcta gtgacttgaa tggcaatatt  2400
ttgaaagaat atcctacgga taatcaagcg ttgcaaaatg aaagactttt cctttactac  2460
ttacaaaacg gaagagatat gtatacaggg gaagctctag atattgacaa tttaagtcaa  2520
tatgatattg accacattat tcctcaagct ttcataaaag atgattctat tgataatcgt  2580
gttttggtat catctgctaa aaatcgtgga aagtcagatg atgttcctag ccttgaaatt  2640
gtaaaagatt gtaaagtttt ctggaaaaaa ttacttgatg ctaagttaat gagtcagcgt  2700
aagtatgata atttgactaa ggcagagcgc ggaggcctaa cttccgatga taaggcaaga  2760
tttatccaac gtcagttggt tgagacacga caaattacca agcatgttgc ccgtatcttg  2820
gatgaacgct ttaataatga gcttgatagt aaaggtagaa ggatccgcaa agttaaaatt  2880
gtaaccttga agtcaaattt ggtttcaaat ttccgaaaag aatttggatt ctataaaatt  2940
cgtgaagtta acaattatca ccatgcacat gatgcctatc ttaatgcagt agttgctaaa  3000
gctattctaa ccaaatatcc tcagttagag ccagaatttg tctacggcga ctatccaaaa  3060
tataatagtt acaaaacgcg taaatccgct acagaaaagc tatttttcta ttcaaatatt  3120
atgaacttct ttaaaactaa ggtaactttta gcggatggaa ccgttgttgt aaaagatgat  3180
attgaagtta ataatgatac gggtgaaatt gtttgggata aaagaaaca ctttgcgaca  3240
gttagaaaag tcttgtcata ccctcagaac aatatcgtga agaagacaga gattcagaca  3300
ggtggtttct ctaaggaatc aatcttggcg catggtaact cagataagtt gattccaaga  3360
aaaacgaagg atatttattt agatcctaag aaatatggag gttttgatag tccgatagta  3420
gcttactctg ttttagttgt agctgatatc aaaaagggta agcacaaaa actaaaaaca  3480
gttacggaac ttttaggaat taccatcatg gagaggtcca gatttgagaa aaatccatca  3540
gctttccttg aatcaaaagg ctatttaaat attagggctg ataaactaat tattttgccc  3600
aagtatagtc tgttcgaatt agaaaatggg cgtcgtcgat tacttgctag tgctggtgaa  3660
ttacaaaaag gtaatgagct agccttacca acacaattta tgaagttctt ataccttgca  3720
agtcgttata atgagtcaaa aggtaaacca gaggagttg agaagaaaca agaatttgta  3780
aatcaacatg tctcttattt tgatgacatc cttcaattaa ttaatgattt ttcaaaacga  3840
gttattctag cagatgctaa tttagagaaa atcaataagc tttaccaaga taataaggaa  3900
aatatatcag tagatgaact tgctaataat attatcaatc tatttacttt taccagtcta  3960
ggagctccag cagctttaa attttttgat aaaatagttg atagaaacg ctatacatca  4020
actaaagaag tacttaattc taccctaatt catcaatcta ttactggact ttatgaaaca  4080
cgtattgatt tgggtaagtt aggagaagat                                  4110
```

SEQ ID NO: 4210
```
Met Asn Lys Pro Tyr Ser Ile Gly Leu Asp Ile Gly Thr Asn Ser Val
1               5                   10                  15
Gly Trp Ser Ile Ile Thr Asp Asp Tyr Lys Val Pro Ala Lys Lys Met
            20                  25                  30
Arg Val Leu Gly Asn Thr Asp Lys Glu Tyr Ile Lys Lys Asn Leu Ile
        35                  40                  45
Gly Ala Leu Leu Phe Asp Gly Gly Asn Thr Ala Ala Asp Arg Arg Leu
    50                  55                  60
Lys Arg Thr Ala Arg Arg Arg Tyr Thr Arg Arg Lys Asn Arg Ile Leu
65                  70                  75                  80
Tyr Leu Gln Glu Ile Phe Ala Glu Glu Met Ser Lys Val Asp Asp Ser
                85                  90                  95
Phe Phe His Arg Leu Glu Asp Ser Phe Leu Val Glu Glu Asp Lys Arg
            100                 105                 110
Gly Ser Lys Tyr Pro Ile Phe Ala Thr Leu Gln Glu Glu Lys Asp Tyr
        115                 120                 125
His Glu Lys Phe Ser Thr Ile Tyr His Leu Arg Lys Lys Leu Ala Asp
    130                 135                 140
Lys Lys Glu Lys Ala Asp Leu Arg Leu Ile Tyr Ile Ala Leu Ala His
145                 150                 155                 160
Ile Ile Lys Phe Arg Gly His Phe Leu Ile Glu Asp Ser Phe Asp
                165                 170                 175
Val Arg Asn Thr Asp Ile Ser Lys Gln Tyr Gln Asp Phe Leu Glu Ile
            180                 185                 190
Phe Asn Thr Thr Phe Glu Asn Asn Asp Leu Leu Ser Gln Asn Val Asp
        195                 200                 205
Val Glu Ala Ile Leu Thr Asp Lys Ile Ser Lys Ser Ala Lys Lys Asp
    210                 215                 220
Arg Ile Leu Ala Gln Tyr Pro Asn Gln Lys Ser Thr Gly Ile Phe Ala
225                 230                 235                 240
Glu Phe Leu Lys Leu Ile Val Gly Asn Gln Ala Asp Phe Lys Lys Tyr
                245                 250                 255
Phe Asn Leu Glu Asp Lys Thr Pro Leu Gln Phe Ala Lys Asp Ser Tyr
            260                 265                 270
Asp Glu Asp Leu Glu Asn Leu Leu Gly Gln Ile Gly Asp Glu Phe Ala
        275                 280                 285
Asp Leu Phe Ser Ala Ala Lys Lys Leu Tyr Asp Ser Val Leu Leu Ser
```

Exemplary Sequences

Gly Ile Leu Thr Val Ile Asp Leu Ser Thr Lys Ala Pro Leu Ser Ala
290 295 300
305
Ser Met Ile Gln Arg Tyr Asp Glu His Arg Glu Asp Leu Lys Gln Leu
310 315 320
325 330 335
Lys Gln Phe Val Lys Ala Ser Leu Pro Glu Lys Tyr Gln Glu Ile Phe
340 345 350
Ala Asp Ser Ser Lys Asp Gly Tyr Ala Gly Tyr Ile Asp Gly Lys Thr
355 360 365
Asn Gln Glu Ala Phe Tyr Lys Tyr Leu Ser Lys Leu Leu Thr Lys Gln
370 375 380
Glu Asp Ser Glu Asn Phe Leu Glu Lys Ile Lys Asn Glu Asp Phe Leu
385 390 395 400
Arg Lys Gln Arg Thr Phe Asp Asn Gly Ser Ile Pro His Gln Val His
405 410 415
Leu Thr Glu Leu Lys Ala Ile Ile Arg Arg Gln Ser Glu Tyr Tyr Pro
420 425 430
Phe Leu Lys Glu Asn Gln Asp Arg Ile Glu Lys Ile Leu Thr Phe Arg
435 440 445
Ile Pro Tyr Tyr Ile Gly Pro Leu Ala Arg Glu Lys Ser Asp Phe Ala
450 455 460
Trp Met Thr Arg Lys Thr Asp Asp Ser Ile Arg Pro Trp Asn Phe Glu
465 470 475 480
Asp Leu Val Asp Lys Glu Lys Ser Ala Glu Ala Phe Ile His Arg Met
485 490 495
Thr Asn Asn Asp Phe Tyr Leu Pro Glu Glu Lys Val Leu Pro Lys His
500 505 510
Ser Leu Ile Tyr Glu Lys Phe Thr Val Tyr Asn Glu Leu Thr Lys Val
515 520 525
Arg Tyr Lys Asn Glu Gln Gly Glu Thr Tyr Phe Phe Asp Ser Asn Ile
530 535 540
Lys Gln Glu Ile Phe Asp Gly Val Phe Lys Glu His Arg Lys Val Ser
545 550 555 560
Lys Lys Lys Leu Leu Asp Phe Leu Ala Lys Glu Tyr Glu Glu Phe Arg
565 570 575
Ile Val Asp Val Ile Gly Leu Asp Lys Glu Asn Lys Ala Phe Asn Ala
580 585 590
Ser Leu Gly Thr Tyr His Asp Leu Glu Lys Ile Leu Asp Lys Asp Phe
595 600 605
Leu Asp Asn Pro Asp Asn Glu Ser Ile Leu Glu Asp Ile Val Gln Thr
610 615 620
Leu Thr Leu Phe Glu Asp Arg Glu Met Ile Lys Lys Arg Leu Glu Asn
625 630 635 640
Tyr Lys Asp Leu Phe Thr Glu Ser Gln Leu Lys Lys Leu Tyr Arg Arg
645 650 655
His Tyr Thr Gly Trp Gly Arg Leu Ser Ala Lys Leu Ile Asn Gly Ile
660 665 670
Arg Asp Lys Glu Ser Gln Lys Thr Ile Leu Asp Tyr Leu Ile Asp Asp
675 680 685
Gly Arg Ser Asn Arg Asn Phe Met Gln Leu Ile Asn Asp Asp Gly Leu
690 695 700
Ser Phe Lys Ser Ile Ile Ser Lys Ala Gln Ala Gly Ser His Ser Asp
705 710 715 720
Asn Leu Lys Glu Val Val Gly Glu Leu Ala Gly Ser Pro Ala Ile Lys
725 730 735
Lys Gly Ile Leu Gln Ser Leu Lys Ile Val Asp Glu Leu Val Lys Val
740 745 750
Met Gly Tyr Glu Pro Glu Gln Ile Val Val Glu Met Ala Arg Glu Asn
755 760 765
Gln Thr Thr Asn Gln Gly Arg Arg Asn Ser Arg Gln Arg Tyr Lys Leu
770 775 780
Leu Asp Gly Val Lys Asn Leu Ala Ser Asp Leu Asn Gly Asn Ile
785 790 795 800
Leu Lys Glu Tyr Pro Thr Asp Asn Gln Ala Leu Gln Asn Glu Arg Leu
805 810 815
Phe Leu Tyr Tyr Leu Gln Asn Gly Arg Asp Met Tyr Thr Gly Glu Ala
820 825 830
Leu Asp Ile Asp Asn Leu Ser Gln Tyr Asp Ile Asp His Ile Ile Pro
835 840 845
Gln Ala Phe Ile Lys Asp Ser Ile Asp Asn Arg Val Leu Val Ser
850 855 860
Ser Ala Lys Asn Arg Gly Lys Ser Asp Asp Val Pro Ser Leu Glu Ile
865 870 875 880
Val Lys Asp Cys Lys Val Phe Trp Lys Lys Leu Leu Asp Ala Lys Leu
885 890 895
Met Ser Gln Arg Lys Tyr Asp Asn Leu Thr Lys Ala Glu Arg Gly Gly
900 905 910

Exemplary Sequences

Leu Thr Ser Asp Asp Lys Ala Arg Phe Ile Gln Arg Gln Leu Val Glu
            915                 920                 925
Thr Arg Gln Ile Thr Lys His Val Ala Arg Ile Leu Asp Glu Arg Phe
        930                 935                 940
Asn Asn Glu Leu Asp Ser Lys Gly Arg Arg Ile Arg Lys Val Lys Ile
945                 950                 955                 960
Val Thr Leu Lys Ser Asn Leu Val Ser Asn Phe Arg Lys Glu Phe Gly
                965                 970                 975
Phe Tyr Lys Ile Arg Glu Val Asn Asn Tyr His His Ala His Asp Ala
            980                 985                 990
Tyr Leu Asn Ala Val Val Ala Lys Ala Ile Leu Thr Lys Tyr Pro Gln
        995                 1000                1005
Leu Glu Pro Glu Phe Val Tyr Gly Asp Tyr Pro Lys Tyr Asn Ser Tyr
    1010                1015                1020
Lys Thr Arg Lys Ser Ala Thr Glu Lys Leu Phe Phe Tyr Ser Asn Ile
1025                1030                1035                1040
Met Asn Phe Phe Lys Thr Lys Val Thr Leu Ala Asp Gly Thr Val Val
                1045                1050                1055
Val Lys Asp Asp Ile Glu Val Asn Asn Asp Thr Gly Glu Ile Val Trp
            1060                1065                1070
Asp Lys Lys Lys His Phe Ala Thr Val Arg Lys Val Leu Ser Tyr Pro
        1075                1080                1085
Gln Asn Asn Ile Val Lys Lys Thr Glu Ile Gln Thr Gly Gly Phe Ser
    1090                1095                1100
Lys Glu Ser Ile Leu Ala His Gly Asn Ser Asp Lys Leu Ile Pro Arg
1105                1110                1115                1120
Lys Thr Lys Asp Ile Tyr Leu Asp Pro Lys Lys Tyr Gly Gly Phe Asp
                1125                1130                1135
Ser Pro Ile Val Ala Tyr Ser Val Leu Val Val Ala Asp Ile Lys Lys
            1140                1145                1150
Gly Lys Ala Gln Lys Leu Lys Thr Val Thr Glu Leu Leu Gly Ile Thr
        1155                1160                1165
Ile Met Glu Arg Ser Arg Phe Glu Lys Asn Pro Ser Ala Phe Leu Glu
    1170                1175                1180
Ser Lys Gly Tyr Leu Asn Ile Arg Ala Asp Lys Leu Ile Ile Leu Pro
1185                1190                1195                1200
Lys Tyr Ser Leu Phe Glu Leu Glu Asn Gly Arg Arg Arg Leu Leu Ala
                1205                1210                1215
Ser Ala Gly Glu Leu Gln Lys Gly Asn Glu Leu Ala Leu Pro Thr Gln
            1220                1225                1230
Phe Met Lys Phe Leu Tyr Leu Ala Ser Arg Tyr Asn Glu Ser Lys Gly
        1235                1240                1245
Lys Pro Glu Glu Ile Glu Lys Lys Gln Glu Phe Val Asn Gln His Val
    1250                1255                1260
Ser Tyr Phe Asp Asp Ile Leu Gln Leu Ile Asn Asp Phe Ser Lys Arg
1265                1270                1275                1280
Val Ile Leu Ala Asp Ala Asn Leu Glu Lys Ile Asn Lys Leu Tyr Gln
                1285                1290                1295
Asp Asn Lys Glu Asn Ile Ser Val Asp Glu Leu Ala Asn Asn Ile Ile
            1300                1305                1310
Asn Leu Phe Thr Phe Thr Ser Leu Gly Ala Pro Ala Ala Phe Lys Phe
        1315                1320                1325
Phe Asp Lys Ile Val Asp Arg Lys Arg Tyr Thr Ser Thr Lys Glu Val
    1330                1335                1340
Leu Asn Ser Thr Leu Ile His Gln Ser Ile Thr Gly Leu Tyr Glu Thr
1345                1350                1355                1360
Arg Ile Asp Leu Gly Lys Leu Gly Glu Asp
                1365                1370

SEQ ID NO: 4211
```
atggataaga aatactcaat aggcttagat atcggcacaa atagcgtcgg atgggcggtg    60
atcactgatg aatataaggt tccgtctaaa aagttcaagg ttctgggaaa tacagaccgc   120
cacagtatca aaaaaaatct tataggggct ctttttatttg acagtggaga gacagcggaa   180
gcgactcgtc tcaaacggac agctcgtaga aggtatacac gtcggaagaa tcgtatttgt   240
tatctacagg agattttttc aaatgagatg gcgaaagtag atgatagttt ctttcatcga   300
cttgaagagt cttttttggt ggaagaagac aagaagcatg aacgtcatcc tatttttgga   360
aatatagtag atgaagttgc ttatcatgag aaatatccaa ctatctatca tctgcgaaaa   420
aaattggtag attctactga taaagcggat ttgcgcttaa tctatttggc cttagcgcat   480
atgattaagt ttcgtggtca ttttttgatt gagggagatt taaatcctga taatagtgat   540
gtggacaaac tatttatcca gttggtacaa acctacaatc aattatttga agaaaaccct   600
attaacgcaa gtggagtaga tgctaaagcg attctttctg cacgattgag taaatcaaga   660
cgattagaaa atctcattgc tcagctcccc ggtgagaaga aaaatggctt atttgggaat   720
ctcattgctt tgtcattggg tttgaccccc aatttttaaat caattttga tttggcagaa   780
gatgctaaat tacagctttc aaaagatact tacgatgatg atttagataa tttattggcg   840
caaattggag atcaatatgc tgatttgttt ttggcagcta agaatttatc agatgctatt   900
ttactttcag atatcctaag agtaaatact gaaataacta aggctcccct atcagcttca   960
atgattaaac gctacgatga acatcatcaa gacttgactc ttttaaaagc tttagttcga  1020
```

Exemplary Sequences

```
caacaacttc cagaaaagta taaagaaatc ttttttgatc aatcaaaaaa cggatatgca  1080
ggttatattg atgggggagc tagccaagaa gaattttata aatttatcaa accaatttta  1140
gaaaaaatgg atggtactga ggaattattg gtgaaactaa atcgtgaaga tttgctgcgc  1200
aagcaacgga cctttgacaa cggctctatt ccccatcaaa ttcacttggg tgagctgcat  1260
gctattttga gaagacaaga agacttttat ccattttaa aagacaatcg tgagaagatt  1320
gaaaaaatct tgacttttcg aattccttat tatgttggtc cattggcgcg tggcaatagt  1380
cgtttttgcat ggatgactcg gaagtctgaa gaaacaatta ccccatggaa ttttgaagaa  1440
gttgtcgata aaggtgcttc agctcaatca tttattgaac gcatgacaaa ctttgataaa  1500
aatcttccaa atgaaaaagt actaccaaaa catagtttgc tttatgagta ttttacggtt  1560
tataacgaat tgacaaaggt caaatatgtt actgaaggaa tgcgaaaacc agcatttctt  1620
tcaggtgaac agaagaaagc cattgttgat ttactcttca aaacaaatcg aaaagtaacc  1680
gttaagcaat taaaagaaga ttatttcaaa aaaatagaat gttttgatag tgttgaaatt  1740
tcaggagttg aagatagatt taatgcttca ttaggtacct accatgattt gctaaaaatt  1800
attaaagata aagattttt ggataatgaa gaaatgaag atatcttaga ggatatttgtt  1860
ttaacattga ccttatttga agatagggag atgattgagg aaagacttaa aacatatgct  1920
caccctcttttg atgataaggt gatgaaacag cttaaacgtc gccgttatac tggttgggga  1980
cgtttgtctc gaaaattgat taatggtatt agggataagc aatctggcaa aacaatatta  2040
gattttttga aatcagatgg ttttgccaat cgcaatttta tgcagctgat ccatgatgat  2100
agtttgacat ttaaagaaga cattcaaaaa gcacaagtgt ctggacaagg cgatagttta  2160
catgaacata ttgcaaattt agctggtagc cctgctatta aaaaaggtat tttacagact  2220
gtaaaagttg ttgatgaatt ggtcaaagta atggggcggc ataagccaga aaatatcgtt  2280
attgaaatgg cacgtgaaaa tcagacaact caaaagggcc agaaaaattc gcgagagcgt  2340
atgaaacgaa tcgaagaagg tatcaaagaa ttaggaagtc agattcttaa agagcatcct  2400
gttgaaaata ctcaattgca aaatgaaaag ctctatctct attatctcca aatggaaga  2460
gacatgtatg tggaccaaga attagatatt aatcgtttaa gtgattatga tgtcgatcac  2520
attgttccac aaagtttcct taagacgat tcaatagaca ataaggtctt aacgcgttct  2580
gataaaaatc gtggtaaatc ggataacgtt ccaagtgaag aagtagtcaa aaagatgaaa  2640
aactattgga gacaacttct aaacgccaag ttaatcactc aacgtaagtt tgataattta  2700
acgaaagctg aacgtggagg tttgagtgaa cttgataaag ctggttttat caaacgccaa  2760
ttggttgaaa ctcgccaaat cactaagcat gtggcacaaa ttttggatag tcgcatgaat  2820
actaaatacg atgaaaatga taaacttatt cgagaggtta aagtgattac cttaaaatct  2880
aaattagttt ctgacttccg aaaagatttc caattctata aagtacgtga gattaacaat  2940
taccatcatg cccatgatgc gtatctaaat gccgtcgttg gaactgcttt gattaagaaa  3000
tatccaaaac ttgaatcgga gtttgtctat ggtgattata aagtttatga tgttcgtaaa  3060
atgattgcta agtctgagca agaaatagc aaagcaaccg caaatatttt ctttactct  3120
aatatcatga acttcttcaa aacagaaatt acacttgcaa atggagagat tcgcaaacgc  3180
cctctaatcg aaactaatgg ggaaactgga gaaattgtct gggataaagg gcgagatttt  3240
gccacagtgc gcaaagtatt gtccatgccc caagtcaata ttgtcaagaa aacagaagta  3300
cagacaggcg gattctccaa ggagtcaatt ttaccaaaaa gaaattcgga caagcttatt  3360
gctcgtaaaa aagactggga tccaaaaaaa tatggtggtt ttgatagtcc aacggtagct  3420
tattcagtcc tagtggttgc taaggtgaaa aaagggaaat cgaagaagtt aaaatccgtt  3480
aaagagttac tagggatcac aattatgaa gagagttcct ttgaaaaaaa tccgattgac  3540
tttttagaag ctaaaggata taggaagtt aaaaaagact taatcattaa actacctaaa  3600
tatagtcttt ttgagttaga aaacggtcgt aaacggatgc tggctagtgc cggagaatta  3660
caaaaggaa atgagctggc tctgccaagc aaatatgtga attttttata tttagctagt  3720
cattatgaaa agttgaaggg tagtccagaa gataacgaac aaaaacaatt gtttgtggag  3780
cagcataagc attatttaga tgagattatt gagcaaatca gtgaatttc taagcgtgtt  3840
attttagcag atgccaattt agataaagtt cttagtgcat ataacaaaca tagagacaaa  3900
ccaatacgtg aacaagcaga aaatattatt cattatttta cgttgacgaa tcttggagct  3960
cccgctgctt ttaaatatt tgatacaaca attgatcgta aacgatatac gtctacaaaa  4020
gaagttttag atgccactct tatccatcaa tccatcactg gtctttatga aacacgcatt  4080
gatttgagtc agctaggagg tgac                                         4104
```

SEQ ID NO: 4212

```
Met Asp Lys Lys Tyr Ser Ile Gly Leu Asp Ile Gly Thr Asn Ser Val
1               5                   10                  15
Gly Trp Ala Val Ile Thr Asp Glu Tyr Lys Val Pro Ser Lys Lys Phe
                20                  25                  30
Lys Val Leu Gly Asn Thr Asp Arg His Ser Ile Lys Lys Asn Leu Ile
            35                  40                  45
Gly Ala Leu Leu Phe Asp Ser Gly Glu Thr Ala Glu Ala Thr Arg Leu
        50                  55                  60
Lys Arg Thr Ala Arg Arg Arg Tyr Thr Arg Arg Lys Asn Arg Ile Cys
65                  70                  75                  80
Tyr Leu Gln Glu Ile Phe Ser Asn Glu Met Ala Lys Val Asp Asp Ser
                85                  90                  95
Phe Phe His Arg Leu Glu Glu Ser Phe Leu Val Glu Glu Asp Lys Lys
                100                 105                 110
His Glu Arg His Pro Ile Phe Gly Asn Ile Val Asp Glu Val Ala Tyr
            115                 120                 125
His Glu Lys Tyr Pro Thr Ile Tyr His Leu Arg Lys Lys Leu Val Asp
        130                 135                 140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
```

Exemplary Sequences

```
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
        210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
                260                 265                 270
Asp Asp Leu Asp Asn Leu Leu Ala Gln Ile Gly Asp Gln Tyr Ala Asp
            275                 280                 285
Leu Phe Leu Ala Ala Lys Asn Leu Ser Asp Ala Ile Leu Leu Ser Asp
        290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
        610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
                660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
        690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
Thr Thr Gln Lys Gly Gln Lys Asn Ser Arg Glu Arg Met Lys Arg Ile
770                 775                 780
Glu Glu Gly Ile Lys Glu Leu Gly Ser Gln Ile Leu Lys Glu His Pro
785                 790                 795                 800
```

Exemplary Sequences

```
Val Glu Asn Thr Gln Leu Gln Asn Glu Lys Leu Tyr Leu Tyr Tyr Leu
                805                 810                 815
Gln Asn Gly Arg Asp Met Tyr Val Asp Gln Glu Leu Asp Ile Asn Arg
            820                 825                 830
Leu Ser Asp Tyr Asp Val Asp His Ile Val Pro Gln Ser Phe Leu Lys
        835                 840                 845
Asp Asp Ser Ile Asp Asn Lys Val Leu Thr Arg Ser Asp Lys Asn Arg
    850                 855                 860
Gly Lys Ser Asp Asn Val Pro Ser Glu Glu Val Lys Lys Met Lys
865                 870                 875             880
Asn Tyr Trp Arg Gln Leu Leu Asn Ala Lys Leu Ile Thr Gln Arg Lys
                885                 890                 895
Phe Asp Asn Leu Thr Lys Ala Glu Arg Gly Gly Leu Ser Glu Leu Asp
            900                 905                 910
Lys Ala Gly Phe Ile Lys Arg Gln Leu Val Glu Thr Arg Gln Ile Thr
        915                 920                 925
Lys His Val Ala Gln Ile Leu Asp Ser Arg Met Asn Thr Lys Tyr Asp
    930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
            980                 985                 990
Val Gly Thr Ala Leu Ile Lys Lys Tyr Pro Lys Leu Glu Ser Glu Phe
        995                 1000                1005
Val Tyr Gly Asp Tyr Lys Val Tyr Asp Val Arg Lys Met Ile Ala Lys
    1010                1015                1020
Ser Glu Gln Glu Ile Gly Lys Ala Thr Ala Lys Tyr Phe Phe Tyr Ser
1025                1030                1035                1040
Asn Ile Met Asn Phe Phe Lys Thr Glu Ile Thr Leu Ala Asn Gly Glu
                1045                1050                1055
Ile Arg Lys Arg Pro Leu Ile Glu Thr Asn Gly Glu Thr Gly Glu Ile
            1060                1065                1070
Val Trp Asp Lys Gly Arg Asp Phe Ala Thr Val Arg Lys Val Leu Ser
        1075                1080                1085
Met Pro Gln Val Asn Ile Val Lys Lys Thr Glu Val Gln Thr Gly Gly
    1090                1095                1100
Phe Ser Lys Glu Ser Ile Leu Pro Lys Arg Asn Ser Asp Lys Leu Ile
1105                1110                1115                1120
Ala Arg Lys Lys Asp Trp Asp Pro Lys Lys Tyr Gly Gly Phe Asp Ser
                1125                1130                1135
Pro Thr Val Ala Tyr Ser Val Leu Val Ala Lys Val Glu Lys Gly
            1140                1145                1150
Lys Ser Lys Lys Leu Lys Ser Val Lys Glu Leu Leu Gly Ile Thr Ile
        1155                1160                1165
Met Glu Arg Ser Ser Phe Glu Lys Asn Pro Ile Asp Phe Leu Glu Ala
    1170                1175                1180
Lys Gly Tyr Lys Glu Val Lys Lys Asp Leu Ile Ile Lys Leu Pro Lys
1185                1190                1195                1200
Tyr Ser Leu Phe Glu Leu Glu Asn Gly Arg Lys Arg Met Leu Ala Ser
                1205                1210                1215
Ala Gly Glu Leu Gln Lys Gly Asn Glu Leu Ala Leu Pro Ser Lys Tyr
            1220                1225                1230
Val Asn Phe Leu Tyr Leu Ala Ser His Tyr Glu Lys Leu Lys Gly Ser
        1235                1240                1245
Pro Glu Asp Asn Glu Gln Lys Gln Leu Phe Val Glu Gln His Lys His
    1250                1255                1260
Tyr Leu Asp Glu Ile Ile Glu Gln Ile Ser Glu Phe Ser Lys Arg Val
1265                1270                1275                1280
Ile Leu Ala Asp Ala Asn Leu Asp Lys Val Leu Ser Ala Tyr Asn Lys
                1285                1290                1295
His Arg Asp Lys Pro Ile Arg Glu Gln Ala Glu Asn Ile Ile His Leu
            1300                1305                1310
Phe Thr Leu Thr Asn Leu Gly Ala Pro Ala Ala Phe Lys Tyr Phe Asp
        1315                1320                1325
Thr Thr Ile Asp Arg Lys Arg Tyr Thr Ser Thr Lys Glu Val Leu Asp
    1330                1335                1340
Ala Thr Leu Ile His Gln Ser Ile Thr Gly Leu Tyr Glu Thr Arg Ile
1345                1350                1355                1360
Asp Leu Ser Gln Leu Gly Gly Asp
                1365
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09738693B2). An electronic copy of the "Sequence Listing" will also be available from the USPTO upon request and payment of the fee set forth in 37 CFR 1.19(b)(3).

The invention claimed is:

1. A fusion polypeptide comprising (i) a polypeptide which has at least 95% sequence identity to SEQ ID NO: 4212 and (ii) a heterologous sequence.

2. The fusion polypeptide of claim 1, wherein the polypeptide of (i) comprises a sequence which has at least 99% sequence identity to SEQ ID NO: 4212.

3. The fusion polypeptide of claim 2, wherein the polypeptide of (i) comprises the sequence of SEQ ID NO: 4212.

4. The fusion polypeptide of claim 1, wherein the heterologous sequence of the fusion polypeptide comprises a histidine tag, a glutathione S-transferase (GST) tag, a signal sequence, or a leader sequence.

5. A composition comprising (a) a fusion polypeptide of claim 1, and (b) a pharmaceutically acceptable vehicle.

* * * * *

UNITED STATES PATENT AND TRADEMARK OFFICE
CERTIFICATE OF CORRECTION

PATENT NO. : 9,738,693 B2  
APPLICATION NO. : 15/166010  
DATED : August 22, 2017  
INVENTOR(S) : John Telford et al.

Page 1 of 4

It is certified that error appears in the above-identified patent and that said Letters Patent is hereby corrected as shown below:

On the Title Page

Page 3, Item (56) in Glaser, replace "Moicrobiol" with --Microbiol--.

Page 4, Item (56) in Orefici, replace "Lancefiled Group B" with --Lancefield Group B--;
In Paoletti, replace "streptoccoccus" with --streptococcus--;
In Takami, replace "NP.244022.1" with --NP_244022.1--.

In the Specification

Column 6, Lines 22-23, replace "a host cell of to the invention" with --a host cell of the invention--;
Line 49, replace "formation of an antibody-antigen complexes" with --formation of antibody-antigen complexes--.

Column 9, Line 60, replace "A further examples would" with --A further example would--.

Column 10, Line 59, replace "metallotheionin gene" with --metallothionein gene--.

Column 11, Line 51, replace "transcription terminater" with --transcription terminator--.

Column 16, Lines 47-48, replace "splicosome machinery" with --spliceosome machinery--.

Column 17, Line 21, replace "*Lycopersion*" with --*Lycopersicon*--;
Line 23, replace "*Hererocallis*" with --*Hemerocallis*--;
Line 25, replace "*Browaalia*" with --*Browallia*--.

Column 18, Line 25, replace "g-laotamase (bla)" with --b-lactamase (bla)--;
Line 63, replace "the 3' and of" with --the 3' end of--.

Signed and Sealed this
Tenth Day of September, 2019

Andrei Iancu
*Director of the United States Patent and Trademark Office*

CERTIFICATE OF CORRECTION (continued)
U.S. Pat. No. 9,738,693 B2

Column 23, Line 24, "Enter a high or low copy number vector may be selected" with --Either a high or low copy number vector may be selected--.

Column 24, Line 10, replace "*Pichia guillermondii*" with --*Pichia guilliermondii*--;
    Line 11, replace "Gregg" with --Cregg--;
    Line 30, replace "Gregg" with --Cregg--.

Column 27, Line 23, replace "monoleate" with --monooleate--.

Column 29, Lines 62-63, replace "Bovine Leukemia, Virus" with --Bovine Leukemia Virus--.

Column 31, Line 24, replace "Middleberg" with --Middelberg--.

Column 33, Line 29, replace "and WO92/11033" with --and WO92/11033.--;
    Line 31, replace "A polynucleotide composition can comprises" with --A polynucleotide composition can comprise--;
    Line 59, replace "hematopoetic" with --hematopoietic--.

Column 34, Line 20, replace "asioloorosomucoid" with --asialoorosomucoid--;
    Line 25, replace "polyethlylene" with --polyethylene--;
    Line 30, replace "poly(lactide-co-glycolide)" with --poly(lactide-co-glycolide).--;
    Line 52, replace "NH-2,3-dioleyloxy)propyll-N,N,N-triethyl-ammonium" with --N[1-2,3-dioleyloxy)propyl]-N,N,N-triethyl-ammonium--.

Column 35, Line 1, replace "dioleoylphoshatidyl" with --dioleoylphosphatidyl--;
    Line 6, replace "multilammelar" with --multilamellar--;
    Lines 29-30, replace "if lipoproteins are including with" with --if lipoproteins are included with--;
    Lines 37-38, replace "AI, AII, AIV; CI, CII, CII" with --AI, AII, AIV, CI, CII, CII--.

Column 36, Line 25, replace "nucleic aid" with --nucleic acid--;
    Line 30, replace "purtrescine" with --putrescine--;
    Line 31, replace "The dimensions and of the physical properties of" with --The dimensions and the physical properties of--.

Column 38, Line 14, replace "for a probe with is" with --for a probe which is--;
    Lines 58-59, replace "with the a streptococcus sequence" with --with a *streptococcus* sequence--.

Column 40, Lines 63-64, replace "a signal sequences is" with --a signal sequence is--.

Column 41, Line 43, replace "(attB×attP" with --(attB × attP--;
    Line 49, replace "(attL×attR" with --(attL × attR--;
    Line 62, replace "N-laurylsarcosine" with --N-lauroylsarcosine--.

CERTIFICATE OF CORRECTION (continued)
U.S. Pat. No. 9,738,693 B2

Column 43, Line 21, replace "(attB×attP" with --(attB × attP--;
    Line 33, replace "(attL×attR" with --(attL × attR--.

Column 46, Line 17, replace "of -1.5 ml" with --of ~1.5 ml--.

Column 47, Line 1, replace "R-Phicoerytrin" with --R-Phycoerythrin--.

Column 48, Line 26, replace "Ito VI" with --I to VI--;
    Line 45, replace "hyopthetical" with --hypothetical--;
    In Query 475, replace
"RPWNFEDLVDKEKSAEAFIHRMINNDFYLPEEKVLPKHSLIYEKFIVYNELTKV--RYKN" with
--RPWNFEDLVDKEKSAEAFIHRMTNNDFYLPEEKVLPKHSLIYEKFIVYNELTKV--RYKN--;
    In Sbjct 329, replace
"FIEFKKYKEFIKALGEHNLSQDD- - - -LNEIAKDIILIKDEIKLKKALAKYD--LNQNQI" with
--FIEFKKYKEFIKALGEHNLSQDD- - - -LNEIAKDITLIKDEIKLKKALAKYD--LNQNQI--.

Column 49, in Query 769, replace
"QIINQGR- - - -RNSRQRYKLLDDG- - -VKNLASDLNG-NILKEYPIDNQALQNERLFLYY" with
--QTTNQGR- - - -RNSRQRYKLLDDG- - -VKNLASDLNG-NILKEYPTDNQALQNERLFLYY--.

Column 52, Line 54, in Table I, replace "THEROETICAL" with --THEORETICAL--.

Column 53, Line 3, in Table I-continued, replace "THEROETICAL" with --THEORETICAL--.

Column 54, Line 3, in Table I-continued, replace "THEROETICAL" with --THEORETICAL--.

Column 55, Line 3, in Table I-continued, replace "THEROETICAL" with --THEORETICAL--.

Column 56, Line 3, in Table I-continued, replace "THEROETICAL" with --THEORETICAL--.

Column 57, Line 3, in Table I-continued, replace "THEROETICAL" with --THEORETICAL--.

Column 58, Line 3, in Table I-continued, replace "THEROETICAL" with --THEORETICAL--.

Column 59, Line 3, in Table I-continued, replace "THEROETICAL" with --THEORETICAL--.

Column 60, Line 3, in Table I-continued, replace "THEROETICAL" with --THEORETICAL--.

Column 109, in 2266, replace "Gfo/Idh/MocA family family" with --Gfo/Idh/MocA family--.

Column 119, in 4792, replace "amino acid ABC transproter" with --amino acid ABC transporter--.

CERTIFICATE OF CORRECTION (continued)
U.S. Pat. No. 9,738,693 B2

Column 121, in 5546, replace "liprotein" with --lipoprotein--.

Column 127, in 6958, replace "bacterocin" with --bacteriocin--.

Column 137, in 10076, replace "spoIllJ" with --spoIIIJ--;
    In 10098, replace "CBS domain protein protein" with --CBS domain protein--.

Column 141, in 10772, replace "FliP family family" with --FliP family--;
    In 10950, replace "peptidase, U32 family family" with --peptidase U32 family--.